US012753165B2

(12) United States Patent
Hudkins et al.

(10) Patent No.: US 12,753,165 B2
(45) Date of Patent: Oct. 6, 2026

(54) AMINOPYRIMIDINE COMPOUNDS

(71) Applicant: TYRA BIOSCIENCES, INC., Carlsbad, CA (US)

(72) Inventors: Robert L. Hudkins, Virginia Beach, VA (US); Daniel C. Bensen, Carlsbad, CA (US)

(73) Assignee: TYRA BIOSCIENCES, INC., Carlsbad, CA (US)

(*) Notice: Subject to any disclaimer, the term of this patent is extended or adjusted under 35 U.S.C. 154(b) by 965 days.

(21) Appl. No.: 17/788,334

(22) PCT Filed: Dec. 30, 2020

(86) PCT No.: PCT/US2020/067417

§ 371 (c)(1),
(2) Date: Jun. 23, 2022

(87) PCT Pub. No.: WO2021/138392

PCT Pub. Date: Jul. 8, 2021

(65) Prior Publication Data

US 2023/0115945 A1 Apr. 13, 2023

Related U.S. Application Data

(60) Provisional application No. 62/968,461, filed on Jan. 31, 2020, provisional application No. 62/954,899, filed on Dec. 30, 2019.

(51) Int. Cl.

| | |
|---|---|
| ***C07D 403/04*** | (2006.01) |
| ***A61P 35/00*** | (2006.01) |
| ***C07D 401/14*** | (2006.01) |

(52) U.S. Cl.

CPC ............ *C07D 403/04* (2013.01); *A61P 35/00* (2018.01); *C07D 401/14* (2013.01)

(58) Field of Classification Search

None

See application file for complete search history.

(56) References Cited

U.S. PATENT DOCUMENTS

| | | | |
|---|---|---|---|
| 4,775,612 | A | 10/1988 | Abe et al. |
| 4,940,703 | A | 7/1990 | Baker et al. |
| 5,041,453 | A | 8/1991 | Huang et al. |
| 5,461,146 | A | 10/1995 | Lewis et al. |
| 5,792,778 | A | 8/1998 | De et al. |
| 5,859,041 | A | 1/1999 | Liverton et al. |
| 6,063,930 | A | 5/2000 | Dinsmore et al. |
| 6,200,968 | B1 | 3/2001 | Dickason et al. |
| 6,329,412 | B1 | 12/2001 | Goldstein et al. |
| 6,391,872 | B1 | 5/2002 | Marfat |
| 6,562,817 | B1 | 5/2003 | Tanimoto et al. |
| 6,579,983 | B1 | 6/2003 | Batchelor et al. |
| 6,600,037 | B1 | 7/2003 | Davis et al. |
| 6,660,729 | B1 | 12/2003 | Dickason et al. |
| 6,689,778 | B2 | 2/2004 | Bemis et al. |
| 6,716,978 | B2 | 4/2004 | Marfat |
| 6,746,729 | B1 | 6/2004 | Cherkaoui et al. |
| 6,953,857 | B2 | 10/2005 | Nazare et al. |
| 6,969,714 | B2 | 11/2005 | Breault et al. |
| 6,982,274 | B2 | 1/2006 | Oinuma et al. |
| 6,995,144 | B2 | 2/2006 | Ozaki et al. |
| 7,008,954 | B1 | 3/2006 | Arimura et al. |
| 7,018,999 | B2 | 3/2006 | Aimone et al. |
| 7,067,665 | B2 | 6/2006 | Nazare et al. |
| 7,186,716 | B2 | 3/2007 | Wei et al. |
| 7,244,739 | B2 | 7/2007 | Cheng et al. |
| 7,265,108 | B2 | 9/2007 | Ozaki et al. |
| 7,276,502 | B2 | 10/2007 | Brenchley et al. |
| 7,429,609 | B2 | 9/2008 | Ohi et al. |
| 7,456,191 | B2 | 11/2008 | Luecking et al. |
| 7,485,638 | B2 | 2/2009 | Newcombe et al. |
| 7,541,376 | B2 | 6/2009 | Oinuma et al. |
| 7,615,562 | B2 | 11/2009 | Bollbuck et al. |
| 7,635,698 | B2 | 12/2009 | Rosse et al. |
| 7,776,890 | B2 | 8/2010 | Oinuma et al. |
| 7,781,442 | B2 | 8/2010 | Cheng et al. |
| 7,795,246 | B2 | 9/2010 | Dickason et al. |
| 7,799,808 | B2 | 9/2010 | Cheng et al. |
| 7,825,128 | B2 | 11/2010 | Luecking et al. |
| 7,834,036 | B2 | 11/2010 | Wood et al. |
| 7,880,002 | B2 | 2/2011 | Carson et al. |
| 7,910,741 | B2 | 3/2011 | Nishizawa et al. |
| 7,915,274 | B2 | 3/2011 | Ozaki et al. |
| 7,968,543 | B2 | 6/2011 | James et al. |
| 8,008,481 | B2 | 8/2011 | Ericsson et al. |
| 8,017,629 | B2 | 9/2011 | Cheng et al. |

(Continued)

FOREIGN PATENT DOCUMENTS

| | | |
|---|---|---|
| CN | 103420906 A | 12/2013 |
| CN | 103664878 A | 3/2014 |

(Continued)

OTHER PUBLICATIONS

Carlson et al., Systematically Mitigating the p38a Activity of Triazole-based BET Inhibitors, ACS Med. Chem. Lett., vol. 10, No. 9, 2019, pp. 1296-1301.

Fricker et al., Substituting c-Jun N-terminal kinase-3 (JNK3) ATP-binding site amino acid residues with their p38 counterparts affects binding of JNK- and p38-selective inhibitors, Archives of Biochemistry and Biophysics, vol. 438, Issue 2, 2005, pp. 195-205.

Frings et al., Sulfoximines from a Medicinal Chemist's Perspective: Physicochemical and in vitro Parameters Relevant for Drug Discovery, Eur. J. Med. Chem., vol. 126, 2017, pp. 225-245.

International Patent Application No. PCT/US2020/067415; Int'l Written Opinion and Search Report; dated Apr. 20, 2021; 9 pages.

(Continued)

*Primary Examiner* — Samantha L Shterengarts

(74) *Attorney, Agent, or Firm* — BakerHostetler

(57) ABSTRACT

Disclosed herein are aminopyrimidine compounds that inhibit FGFR and methods of treating diseases and/or conditions (e.g., cancer) with the aminopyrimidine compounds disclosed herein.

23 Claims, No Drawings

(56) References Cited

U.S. PATENT DOCUMENTS 8,119,680 B2 2/2012 Cheng et al.
8,143,404 B2 3/2012 Takaoka et al.
8,168,788 B2 5/2012 Carson et al.
8,211,429 B2 7/2012 Watts et al.
8,277,830 B2 10/2012 De et al.
8,309,550 B2 11/2012 Luo et al.
8,324,231 B2 12/2012 Koltun et al.
8,329,737 B2 12/2012 Styles et al.
8,338,439 B2 12/2012 Singh et al.
8,338,458 B2 12/2012 Meinke et al.
8,399,006 B2 3/2013 De et al.
8,399,455 B2 3/2013 Rosse et al.
8,410,276 B2 4/2013 Takaoka et al.
8,426,417 B2 4/2013 Caruso et al.
8,450,335 B2 5/2013 Singh et al.
8,455,516 B2 6/2013 Gochin et al.
8,481,279 B2 7/2013 Rikova et al.
8,546,433 B2 10/2013 Hitoshi et al.
8,598,374 B2 12/2013 Shi et al.
8,604,207 B2 12/2013 Takaoka et al.
8,609,679 B2 12/2013 Singh et al.
8,642,587 B2 2/2014 Lange et al.
8,648,197 B2 2/2014 Carson et al.
8,669,289 B2 3/2014 Li
8,710,222 B2 4/2014 Singh et al.
8,722,903 B2 5/2014 Buchstaller et al.
8,735,412 B2 5/2014 Lcking et al.
8,759,337 B2 6/2014 Asberom et al.
8,791,136 B2 7/2014 Goff et al.
8,795,660 B2 8/2014 Watts et al.
8,809,370 B2 8/2014 Goff et al.
8,883,793 B2 11/2014 Chen et al.
8,957,073 B2 2/2015 Allen et al.
8,962,618 B2 2/2015 Reddy et al.
8,975,235 B2 3/2015 Buckman et al.
8,980,921 B2 3/2015 Goff et al.
8,987,303 B2 3/2015 Goff et al.
9,000,175 B2 4/2015 Thotapally et al.
9,016,221 B2 4/2015 Brennan et al.
9,040,547 B2 5/2015 Cheng et al.
9,089,574 B2 7/2015 Gavegnano et al.
9,109,227 B2 8/2015 Valmier
9,120,779 B2 9/2015 Li et al.
9,140,689 B2 9/2015 Byron et al.
9,155,723 B2 10/2015 Jain et al.
9,212,181 B2 12/2015 Singh et al.
9,216,172 B2 12/2015 Kohno et al.
9,248,185 B2 2/2016 Rubin et al.
9,254,288 B2 2/2016 Pollock
9,266,856 B2 2/2016 Goff et al.
9,296,737 B2 3/2016 Singh et al.
9,315,848 B2 4/2016 Haick et al.
9,340,489 B2 5/2016 Atzrodt et al.
9,340,566 B2 5/2016 Reddy et al.
9,351,943 B2 5/2016 Mcleay
9,402,901 B2 8/2016 Binder
9,415,118 B2 8/2016 Batt et al.
9,464,065 B2 10/2016 Schultz et al.
9,476,050 B2 10/2016 Westermarck et al.
9,498,532 B2 11/2016 Batt et al.
9,517,238 B2 12/2016 Rochman et al.
9,523,130 B2 12/2016 Rikova et al.
9,546,162 B2 1/2017 Donde et al.
9,550,000 B2 1/2017 Robinson et al.
9,550,770 B2 1/2017 Qian et al.
9,617,256 B2 4/2017 Moser et al.
9,663,496 B2 5/2017 Irving et al.
9,669,068 B2 6/2017 Shaw
9,676,802 B2 6/2017 Qiu et al.
9,695,178 B2 7/2017 Zhang
9,718,803 B2 8/2017 Allen et al.
9,724,421 B2 8/2017 Denys et al.
9,730,877 B2 8/2017 Christiano et al.
9,732,055 B2 8/2017 Li et al.
9,782,417 B2 10/2017 Rubin et al.
9,782,418 B2 10/2017 Lee et al.
9,801,853 B2 10/2017 Grandori et al.
9,840,516 B2 12/2017 Li et al.
9,884,900 B2 2/2018 Kumar et al.
9,890,147 B2 2/2018 Siegel et al.
9,908,884 B2 3/2018 Gray et al.
9,918,972 B2 3/2018 Civin et al.
9,931,347 B2 4/2018 Cowley et al.
9,931,400 B2 4/2018 Jeong et al.
9,931,401 B2 4/2018 Urano et al.
9,938,264 B2 4/2018 Crews et al.
9,951,064 B2 4/2018 Bryan et al.
9,968,608 B2 5/2018 Khattar et al.
9,987,276 B2 6/2018 Singh et al.
10,000,814 B2 6/2018 Cronin et al.
10,010,548 B2 7/2018 Singh et al.
10,034,891 B2 7/2018 Reddy et al.
10,045,979 B2 8/2018 Long et al.
10,094,834 B2 10/2018 Westermarck et al.
10,100,042 B2 10/2018 Chen et al.
10,124,003 B2 11/2018 Sootome
10,166,237 B2 1/2019 Schultz et al.
10,172,868 B2 1/2019 Qian et al.
10,180,626 B2 1/2019 Fujiwara et al.
10,208,017 B2 2/2019 Hommes et al.
10,246,424 B2 4/2019 Li et al.
10,294,207 B2 5/2019 Choi et al.
10,308,648 B2 6/2019 Ciblat et al.
10,329,270 B2 6/2019 Qiu et al.
10,351,527 B2 7/2019 Rennie et al.
10,377,742 B2 8/2019 Goff et al.
10,414,757 B2 9/2019 Li et al.
10,414,875 B2 9/2019 Cannas et al.
10,463,661 B2 11/2019 Long et al.
10,519,133 B2 12/2019 Chen et al.
10,544,106 B2 1/2020 Qian et al.
10,550,121 B2 2/2020 Gray et al.
10,550,326 B2 2/2020 Wittek et al.
10,562,883 B2 2/2020 Hommes et al.
10,596,172 B2 3/2020 Singh et al.
10,633,338 B2 4/2020 Rennie et al.
10,653,701 B2 5/2020 Qian et al.
10,662,174 B2 5/2020 Wang et al.
10,709,718 B2 7/2020 Reddy et al.
10,736,897 B2 8/2020 Li et al.
10,781,218 B2 9/2020 Wu et al.
10,828,300 B2 11/2020 Singh et al.
10,829,458 B2 11/2020 Li et al.
10,870,651 B2 12/2020 Gray et al.
10,941,134 B2 3/2021 Goff et al.
10,959,966 B2 3/2021 Su et al.
11,040,976 B2 6/2021 Maianti et al.
11,059,795 B2 7/2021 Zhou et al.
11,124,628 B2 9/2021 Zhang et al.
11,351,168 B1 6/2022 Singh et al.
2002/0049220 A1 4/2002 Revesz et al.
2002/0169154 A1 11/2002 Ruggeri et al.
2003/0087899 A1 5/2003 Aimone et al.
2003/0149061 A1 8/2003 Nishihara et al.
2003/0212269 A1 11/2003 Davis et al.
2003/0232391 A1 12/2003 Prescott et al.
2004/0014776 A1 1/2004 Breault et al.
2004/0171630 A1 9/2004 Kim et al.
2004/0220176 A1 11/2004 Dickason et al.
2004/0235876 A1 11/2004 Davis et al.
2005/0004150 A1 1/2005 Brenchley et al.
2005/0049246 A1 3/2005 Bemis et al.
2005/0171134 A1 8/2005 Davis et al.
2005/0176760 A1 8/2005 Cezanne et al.
2005/0203151 A1 9/2005 Malecha et al.
2005/0282880 A1 12/2005 Oinuma et al.
2006/0004033 A1 1/2006 Breault et al.
2006/0058250 A1 3/2006 Denmeade et al.
2006/0094674 A1 5/2006 Neel et al.
2007/0043048 A1 2/2007 Bollbuck et al.
2007/0135401 A1 6/2007 Dziki et al.
2007/0135485 A1 6/2007 Gillig et al.
2007/0135628 A1 6/2007 Dziki et al.
2007/0185069 A1 8/2007 Plum et al.

(56) References Cited

U.S. PATENT DOCUMENTS

| | | | |
|---|---|---|---|
| 2007/0244140 | A1 | 10/2007 | Hu et al. |
| 2008/0021013 | A1 | 1/2008 | Dobrzanski et al. |
| 2008/0066741 | A1 | 3/2008 | Lemahieu et al. |
| 2008/0299215 | A1 | 12/2008 | Czarnik |
| 2009/0047246 | A1 | 2/2009 | Beigelman et al. |
| 2009/0048282 | A1 | 2/2009 | Hauze et al. |
| 2009/0054358 | A1 | 2/2009 | Small et al. |
| 2009/0155352 | A1 | 6/2009 | Drager et al. |
| 2009/0156475 | A1 | 6/2009 | Rikova et al. |
| 2009/0203691 | A1 | 8/2009 | Oinuma et al. |
| 2009/0203709 | A1 | 8/2009 | Steinberg et al. |
| 2009/0209496 | A1 | 8/2009 | Chaplin et al. |
| 2009/0226431 | A1 | 9/2009 | Habib |
| 2009/0227650 | A1 | 9/2009 | Bierlmaier et al. |
| 2009/0275567 | A1 | 11/2009 | Jones et al. |
| 2009/0312319 | A1 | 12/2009 | Ren et al. |
| 2010/0048533 | A1 | 2/2010 | Dziki et al. |
| 2010/0048534 | A1 | 2/2010 | Dziki et al. |
| 2010/0075965 | A1 | 3/2010 | Ni et al. |
| 2010/0135983 | A1 | 6/2010 | Hyde et al. |
| 2010/0135984 | A1 | 6/2010 | Hyde et al. |
| 2010/0136094 | A1 | 6/2010 | Hyde et al. |
| 2010/0136095 | A1 | 6/2010 | Hyde et al. |
| 2010/0136096 | A1 | 6/2010 | Hyde et al. |
| 2010/0136097 | A1 | 6/2010 | Hyde et al. |
| 2010/0137246 | A1 | 6/2010 | Hyde et al. |
| 2010/0137247 | A1 | 6/2010 | Hyde et al. |
| 2010/0143459 | A1 | 6/2010 | Liepold et al. |
| 2010/0179318 | A1 | 7/2010 | Stoner |
| 2010/0298255 | A1 | 11/2010 | Ballesteros et al. |
| 2011/0009421 | A1 | 1/2011 | Setoh et al. |
| 2011/0070232 | A1 | 3/2011 | Lepage et al. |
| 2011/0129463 | A1 | 6/2011 | Erez et al. |
| 2011/0130374 | A1 | 6/2011 | Erez et al. |
| 2011/0245210 | A1 | 10/2011 | Greig et al. |
| 2011/0263541 | A1 | 10/2011 | Luo et al. |
| 2011/0294784 | A1 | 12/2011 | Asberom et al. |
| 2012/0039805 | A1 | 2/2012 | Lisanti et al. |
| 2012/0040977 | A1 | 2/2012 | Li et al. |
| 2012/0135952 | A1 | 5/2012 | Kim et al. |
| 2012/0157500 | A1 | 6/2012 | Tao |
| 2012/0244116 | A1 | 9/2012 | Hiwase et al. |
| 2012/0245156 | A1 | 9/2012 | Nguyen |
| 2013/0028978 | A1 | 1/2013 | Mao et al. |
| 2013/0079348 | A1 | 3/2013 | Velicelebi et al. |
| 2013/0129675 | A1 | 5/2013 | Priebe et al. |
| 2013/0131034 | A1 | 5/2013 | Follmann et al. |
| 2013/0156764 | A1 | 6/2013 | Levis et al. |
| 2013/0209452 | A1 | 8/2013 | Rikova et al. |
| 2013/0252924 | A1 | 9/2013 | Penninger et al. |
| 2013/0266666 | A1 | 10/2013 | Moneo et al. |
| 2013/0267515 | A1 | 10/2013 | Sawyer et al. |
| 2013/0288915 | A1 | 10/2013 | Seligmann et al. |
| 2013/0310340 | A1 | 11/2013 | Payan et al. |
| 2013/0310379 | A1 | 11/2013 | Albrecht et al. |
| 2013/0338161 | A1 | 12/2013 | Hitoshi et al. |
| 2014/0004516 | A1 | 1/2014 | Sattler et al. |
| 2014/0065142 | A1 | 3/2014 | Roschke et al. |
| 2014/0135377 | A1 | 5/2014 | Westermarck et al. |
| 2014/0213538 | A1 | 7/2014 | Buckman et al. |
| 2014/0221404 | A1 | 8/2014 | Kohno et al. |
| 2014/0235558 | A1 | 8/2014 | Kim et al. |
| 2014/0235559 | A1 | 8/2014 | Kim et al. |
| 2014/0303163 | A1 | 10/2014 | Luo |
| 2014/0343128 | A1 | 11/2014 | Bentires-Alj et al. |
| 2014/0349969 | A1 | 11/2014 | Penninger et al. |
| 2014/0357557 | A1 | 12/2014 | Cole et al. |
| 2014/0364420 | A1 | 12/2014 | Carson et al. |
| 2015/0050274 | A1 | 2/2015 | Elenitoba-Johnson et al. |
| 2015/0056193 | A1 | 2/2015 | Crosby et al. |
| 2015/0073036 | A1 | 3/2015 | Hawryluk et al. |
| 2015/0087673 | A1 | 3/2015 | Hitoshi et al. |
| 2015/0093355 | A1 | 4/2015 | Hiwase et al. |
| 2015/0148345 | A1 | 5/2015 | Lannutti et al. |
| 2015/0155494 | A1 | 6/2015 | Wei et al. |
| 2015/0177246 | A1 | 6/2015 | Shibata et al. |
| 2015/0203502 | A1 | 7/2015 | Cheng et al. |
| 2015/0204877 | A1 | 7/2015 | Westermarck et al. |
| 2015/0209369 | A1 | 7/2015 | Westermarck et al. |
| 2015/0210765 | A1 | 7/2015 | Roschke et al. |
| 2015/0218652 | A1 | 8/2015 | Doebele et al. |
| 2015/0297598 | A1 | 10/2015 | Friedman et al. |
| 2015/0366866 | A1 | 12/2015 | Ali et al. |
| 2016/0009785 | A1 | 1/2016 | Lipson et al. |
| 2016/0045498 | A1 | 2/2016 | Ernst et al. |
| 2016/0046678 | A1 | 2/2016 | Roschke et al. |
| 2016/0128974 | A1 | 5/2016 | Jain et al. |
| 2016/0158353 | A1 | 6/2016 | Kielian |
| 2016/0166571 | A1 | 6/2016 | Janes et al. |
| 2016/0235812 | A1 | 8/2016 | Bruhn et al. |
| 2016/0243150 | A1 | 8/2016 | Wood et al. |
| 2016/0251696 | A1 | 9/2016 | Georgopoulos et al. |
| 2016/0272707 | A1 | 9/2016 | Levine et al. |
| 2016/0279135 | A1 | 9/2016 | Lannutti et al. |
| 2016/0289663 | A1 | 10/2016 | Kiyokawa et al. |
| 2016/0304613 | A1 | 10/2016 | Watts et al. |
| 2016/0304616 | A1 | 10/2016 | Hiwase et al. |
| 2016/0317499 | A1 | 11/2016 | Nakanishi et al. |
| 2016/0317660 | A1 | 11/2016 | Mcleay |
| 2016/0355503 | A1 | 12/2016 | Zhou et al. |
| 2017/0008964 | A1 | 1/2017 | Batt et al. |
| 2017/0042891 | A1 | 2/2017 | Hitoshi et al. |
| 2017/0071877 | A1 | 3/2017 | Kim et al. |
| 2017/0087156 | A1 | 3/2017 | Allen et al. |
| 2017/0096409 | A1 | 4/2017 | Singh et al. |
| 2017/0106003 | A1 | 4/2017 | Berenson |
| 2017/0106095 | A1 | 4/2017 | Batt et al. |
| 2017/0114415 | A1 | 4/2017 | Doebele et al. |
| 2017/0136021 | A1 | 5/2017 | Einav et al. |
| 2017/0143725 | A1 | 5/2017 | Sawyer et al. |
| 2017/0157275 | A1 | 6/2017 | Panyam et al. |
| 2017/0172920 | A1 | 6/2017 | Li et al. |
| 2017/0205395 | A1 | 7/2017 | Ballesteros et al. |
| 2017/0246174 | A1 | 8/2017 | Amatangelo et al. |
| 2017/0248616 | A1 | 8/2017 | Sarraf |
| 2017/0258922 | A1 | 9/2017 | Kinoh et al. |
| 2017/0281566 | A1 | 10/2017 | Ciceri et al. |
| 2017/0296669 | A1 | 10/2017 | Denys et al. |
| 2017/0349953 | A1 | 12/2017 | Lovejoy et al. |
| 2017/0362328 | A1 | 12/2017 | Hiwase et al. |
| 2017/0369780 | A1 | 12/2017 | Adlem et al. |
| 2018/0044672 | A1 | 2/2018 | Zehendner et al. |
| 2018/0050085 | A1 | 2/2018 | Kumar et al. |
| 2018/0057898 | A1 | 3/2018 | Tabibiazar et al. |
| 2018/0086764 | A1 | 3/2018 | Gelman et al. |
| 2018/0117061 | A1 | 5/2018 | Lee et al. |
| 2018/0117148 | A1 | 5/2018 | Holman |
| 2018/0117168 | A1 | 5/2018 | Cole et al. |
| 2018/0127426 | A1 | 5/2018 | Kinsella et al. |
| 2018/0153858 | A1 | 6/2018 | Grandori et al. |
| 2018/0162807 | A1 | 6/2018 | Dixon et al. |
| 2018/0185372 | A1 | 7/2018 | Schinazi et al. |
| 2018/0185382 | A1 | 7/2018 | Narla et al. |
| 2018/0200213 | A1 | 7/2018 | Kelley et al. |
| 2018/0201614 | A1 | 7/2018 | Bunker et al. |
| 2018/0214449 | A1 | 8/2018 | Kim et al. |
| 2018/0222886 | A1 | 8/2018 | Chen et al. |
| 2018/0256678 | A1 | 9/2018 | Khodarev et al. |
| 2018/0263992 | A1 | 9/2018 | Richardson et al. |
| 2018/0289717 | A1 | 10/2018 | Keilhack et al. |
| 2018/0305331 | A1 | 10/2018 | Rzymski et al. |
| 2018/0305334 | A1 | 10/2018 | Larsen et al. |
| 2019/0011435 | A1 | 1/2019 | Cagan et al. |
| 2019/0015417 | A1 | 1/2019 | Sootome |
| 2019/0055444 | A1 | 2/2019 | Fujiwara et al. |
| 2019/0177617 | A1 | 6/2019 | Adlem et al. |
| 2019/0298691 | A1 | 10/2019 | Valmier |
| 2019/0300480 | A1 | 10/2019 | Rennie et al. |
| 2019/0375743 | A1 | 12/2019 | Hudson et al. |
| 2020/0102321 | A1 | 4/2020 | Li et al. |
| 2020/0123117 | A1 | 4/2020 | Zhou et al. |
| 2020/0165224 | A1 | 5/2020 | Li et al. |
| 2020/0172495 | A1 | 6/2020 | Qian et al. |
| 2020/0181118 | A1 | 6/2020 | Malhotra et al. |

(56) References Cited

U.S. PATENT DOCUMENTS

| | | | |
|---|---|---|---|
| 2020/0181123 | A1 | 6/2020 | Li et al. |
| 2020/0247792 | A1 | 8/2020 | Burris et al. |
| 2020/0361913 | A1 | 11/2020 | Chen et al. |
| 2020/0392083 | A1 | 12/2020 | Jiang et al. |
| 2021/0009582 | A1 | 1/2021 | Vechorkin et al. |
| 2021/0101908 | A1 | 4/2021 | Wu et al. |
| 2021/0106588 | A1 | 4/2021 | Vechorkin et al. |
| 2021/0187902 | A1 | 6/2021 | Fujiwara et al. |
| 2021/0198213 | A1 | 7/2021 | Zhou et al. |
| 2021/0220408 | A1 | 7/2021 | Boitano et al. |
| 2021/0317127 | A1 | 10/2021 | Li et al. |
| 2021/0359226 | A1 | 11/2021 | Ko et al. |
| 2022/0015338 | A1 | 1/2022 | Zhang et al. |
| 2022/0016146 | A1 | 1/2022 | Wei et al. |
| 2022/0045293 | A1 | 2/2022 | Kim et al. |
| 2022/0079928 | A1 | 3/2022 | Lou et al. |
| 2022/0259201 | A1 | 8/2022 | Su et al. |
| 2022/0273665 | A1 | 9/2022 | Mcgovern et al. |

FOREIGN PATENT DOCUMENTS

| | | | | |
|---|---|---|---|---|
| CN | 105712998 | A | 6/2016 | |
| CN | 108276352 | A | 7/2018 | |
| CN | 109438447 | A | 3/2019 | |
| CN | 111039942 | A | 4/2020 | |
| CN | 112079830 | A | 12/2020 | |
| CN | 112409331 | A | 2/2021 | |
| CN | 112812014 | A | 5/2021 | |
| EP | 0768312 | A2 | 4/1997 | |
| EP | 1011648 | A2 | 6/2000 | |
| EP | 1046631 | A1 | 10/2000 | |
| EP | 1102758 | A1 | 5/2001 | |
| EP | 1187816 | A1 | 3/2002 | |
| EP | 1224180 | A2 | 7/2002 | |
| EP | 1351958 | A1 | 10/2003 | |
| EP | 1389100 | A2 | 2/2004 | |
| EP | 1439174 | A1 | 7/2004 | |
| EP | 1597251 | A2 | 11/2005 | |
| EP | 1605946 | A2 | 12/2005 | |
| EP | 1615898 | A1 | 1/2006 | |
| EP | 1663223 | A2 | 6/2006 | |
| EP | 1685137 | A2 | 8/2006 | |
| EP | 1778224 | A2 | 5/2007 | |
| EP | 1968607 | A1 | 9/2008 | |
| EP | 2170839 | A1 | 4/2010 | |
| EP | 2205244 | A1 | 7/2010 | |
| EP | 2387395 | A1 | 11/2011 | |
| EP | 2433124 | A1 | 3/2012 | |
| EP | 2447359 | A1 | 5/2012 | |
| EP | 2456444 | A1 | 5/2012 | |
| EP | 2547698 | A1 | 1/2013 | |
| EP | 2646000 | A1 | 10/2013 | |
| EP | 2723450 | A2 | 4/2014 | |
| EP | 2740742 | A1 | 6/2014 | |
| EP | 2830662 | A1 | 2/2015 | |
| EP | 2872631 | A1 | 5/2015 | |
| EP | 2890986 | A1 | 7/2015 | |
| EP | 2918589 | A1 | 9/2015 | |
| EP | 2935331 | A1 | 10/2015 | |
| EP | 3111931 | A1 | 1/2017 | |
| EP | 3254698 | A1 | 12/2017 | |
| EP | 3333157 | A1 | 6/2018 | |
| EP | 3722282 | A1 | 10/2020 | |
| JP | 62-135830 | A | 6/1987 | |
| JP | 62-135834 | A | 6/1987 | |
| JP | 62-135835 | A | 6/1987 | |
| JP | 62-136650 | A | 6/1987 | |
| JP | 62-136651 | A | 6/1987 | |
| JP | 62-136654 | A | 6/1987 | |
| JP | 5763937 | B2 | 8/2015 | |
| KR | 10-1648141 | B1 | 8/2016 | |
| KR | 10-2032418 | B1 | 10/2019 | |
| KR | 10-2127006 | B1 | 6/2020 | |
| WO | 99/08668 | A2 | 2/1999 | |
| WO | 00/08004 | A1 | 2/2000 | |
| WO | 01/53268 | A2 | 7/2001 | |
| WO | 01/76582 | A1 | 10/2001 | |
| WO | 02/00651 | A2 | 1/2002 | |
| WO | 02/55484 | A1 | 7/2002 | |
| WO | 03035638 | A1 | 5/2003 | |
| WO | 2004/074244 | A2 | 9/2004 | |
| WO | 2005/066156 | A1 | 7/2005 | |
| WO | 2006/038594 | A1 | 4/2006 | |
| WO | 2007/044085 | A2 | 4/2007 | |
| WO | 2007/050124 | A1 | 5/2007 | |
| WO | 2007/058626 | A1 | 5/2007 | |
| WO | 2007/149427 | A2 | 12/2007 | |
| WO | 2008/008650 | A1 | 1/2008 | |
| WO | 2008/155140 | A1 | 12/2008 | |
| WO | 2009/061446 | A1 | 5/2009 | |
| WO | 2009/158571 | A1 | 12/2009 | |
| WO | 2010/048149 | A2 | 4/2010 | |
| WO | 2010/075273 | A1 | 7/2010 | |
| WO | 2010/081443 | A2 | 7/2010 | |
| WO | 2010/083465 | A1 | 7/2010 | |
| WO | 2010/088518 | A2 | 8/2010 | |
| WO | 2010/108051 | A2 | 9/2010 | |
| WO | 2010/129053 | A2 | 11/2010 | |
| WO | 2010/129509 | A1 | 11/2010 | |
| WO | 2010/135468 | A1 | 11/2010 | |
| WO | 2011/008302 | A1 | 1/2011 | |
| WO | 2011/056764 | A1 | 5/2011 | |
| WO | 2011/094890 | A1 | 8/2011 | |
| WO | 2011/097300 | A1 | 8/2011 | |
| WO | 2011/109217 | A2 | 9/2011 | |
| WO | 2011/115937 | A1 | 9/2011 | |
| WO | 2012/025811 | A1 | 3/2012 | |
| WO | 2012/073188 | A1 | 6/2012 | |
| WO | 2012/126181 | A1 | 9/2012 | |
| WO | 2012/146933 | A1 | 11/2012 | |
| WO | 2012/146936 | A1 | 11/2012 | |
| WO | 2013/019058 | A2 | 2/2013 | |
| WO | 2013/149194 | A1 | 10/2013 | |
| WO | 2013/167743 | A1 | 11/2013 | |
| WO | 2014/029016 | A1 | 2/2014 | |
| WO | 2014/040555 | A1 | 3/2014 | |
| WO | 2014/087018 | A1 | 6/2014 | |
| WO | 2014/105810 | A1 | 7/2014 | |
| WO | 2014/152716 | A1 | 9/2014 | |
| WO | 2014/182521 | A1 | 11/2014 | |
| WO | 2015/039006 | A1 | 3/2015 | |
| WO | 2015/103527 | A1 | 7/2015 | |
| WO | 2015/170266 | A1 | 11/2015 | |
| WO | 2016/025641 | A1 | 2/2016 | |
| WO | 2016/040449 | A1 | 3/2016 | |
| WO | WO-2016059086 | A1 * | 4/2016 | ........... A61K 31/506 |
| WO | 2016/066582 | A1 | 5/2016 | |
| WO | 2016/081364 | A1 | 5/2016 | |
| WO | 2016/089208 | A2 | 6/2016 | |
| WO | 2016/112637 | A1 | 7/2016 | |
| WO | 2016/123086 | A1 | 8/2016 | |
| WO | 2016/135046 | A1 | 9/2016 | |
| WO | 2016/144637 | A1 | 9/2016 | |
| WO | 2016/160617 | A2 | 10/2016 | |
| WO | 2016/160833 | A1 | 10/2016 | |
| WO | 2016/168612 | A1 | 10/2016 | |
| WO | 2016/172199 | A1 | 10/2016 | |
| WO | 2016/179605 | A1 | 11/2016 | |
| WO | 2017/051188 | A1 | 3/2017 | |
| WO | 2017/083592 | A1 | 5/2017 | |
| WO | 2017/120600 | A1 | 7/2017 | |
| WO | 2017/143014 | A1 | 8/2017 | |
| WO | 2017/168454 | A2 | 10/2017 | |
| WO | 2017/175238 | A1 | 10/2017 | |
| WO | 2017/197301 | A1 | 11/2017 | |
| WO | 2017/201089 | A1 | 11/2017 | |
| WO | 2017/211937 | A1 | 12/2017 | |
| WO | 2017/214463 | A1 | 12/2017 | |
| WO | 2017/216584 | A1 | 12/2017 | |
| WO | 2018/005737 | A1 | 1/2018 | |
| WO | 2018/013918 | A2 | 1/2018 | |
| WO | 2018/039557 | A1 | 3/2018 | |
| WO | 2018/052120 | A1 | 3/2018 | |
| WO | 2018/053142 | A2 | 3/2018 | |

(56) References Cited

FOREIGN PATENT DOCUMENTS

| | | | |
|---|---|---|---|
| WO | 2018/058098 | A1 | 3/2018 |
| WO | 2018/085275 | A1 | 5/2018 |
| WO | 2018/126192 | A1 | 7/2018 |
| WO | 2018/144773 | A1 | 8/2018 |
| WO | 2019/018795 | A1 | 1/2019 |
| WO | 2019/101182 | A1 | 5/2019 |
| WO | 2019/101183 | A1 | 5/2019 |
| WO | 2019/141250 | A1 | 7/2019 |
| WO | 2019/209948 | A1 | 10/2019 |
| WO | 2020/028706 | A1 | 2/2020 |
| WO | 2020/081572 | A1 | 4/2020 |
| WO | 2020/113759 | A1 | 6/2020 |
| WO | 2020/131627 | A1 | 6/2020 |
| WO | 2020/231990 | A1 | 11/2020 |
| WO | 2020/236524 | A1 | 11/2020 |
| WO | 2020/243457 | A1 | 12/2020 |
| WO | 2021/104305 | A1 | 6/2021 |
| WO | 2021/127333 | A1 | 6/2021 |
| WO | 2021/127337 | A1 | 6/2021 |
| WO | 2021/155253 | A1 | 8/2021 |
| WO | 2021/161230 | A1 | 8/2021 |
| WO | 2021/183970 | A1 | 9/2021 |
| WO | 2022/015979 | A1 | 1/2022 |
| WO | 2022/147246 | A1 | 7/2022 |
| WO | 2022/182972 | A1 | 9/2022 |

OTHER PUBLICATIONS

International Patent Application No. PCT/US2020/067417; Int'l Preliminary Report on Patentability; dated Jul. 14, 2022; 9 pages.

International Patent Application No. PCT/US2020/067417; Int'l Search Report and the Written Opinion; dated Apr. 20, 2021; 14 pages.

Kang et al., DBM1285 Suppresses Tumor Necrosis Factor a Production by Blocking p38 Mitogen-Activated Protein Kinase/Mitogen-Activated Protein Kinase-Activated Protein Kinase 2 Signaling Pathway, Journal of Pharmacology and Experimental Therapeutics, vol. 334, No. 2, 2010, pp. 657-664.

Lücking, Sulfoximines: A Neglected Opportunity in Medicinal Chemistry, Angew. Chem. Int. Ed. Engl., vol. 52, No. 36, 2013, pp. 9399-9408.

Matralis et al., Development of Chemical Entities Endowed with Potent Fast-Killing Properties against Plasmodium falciparum Malaria Parasites, J. Med. Chem., vol. 62, No. 20, 2019, pp. 9217-9235.

Shirahashi Hiromitsu et al: "The discovery of novel 3-aryl-indazole derivatives as peripherally restricted pan-Trk inhibitors for the treatment of pain", Bioorganic & Medicinal Chemistry Letters, Elsevier, Amsterdam, NL, vol. 29, No. 16, Jun. 17, 2019 (Jun. 17, 2019) , pp. 2320-2326, XP085759046,.

Siemeister et al., Bay 1000394, a Novel Cyclin-Dependent Kinase Inhibitor, with Potent Antitumor Activity in Mono- and in Combination Treatment upon Oral Application, Mol. Cancer Ther., vol. 11, No. 10, 2012, pp. 2265-2273.

Sirvent et al., Novel Pieces for the Emerging Picture of Sulfoximines in Drug Discovery: Synthesis and Evaluation of Sulfoximine Analogues of Marketed Drugs and Advanced Clinical Candidates, ChemMedChem, vol. 12, No. 7, 2017, pp. 487-501.

* cited by examiner

AMINOPYRIMIDINE COMPOUNDS

CROSS-REFERENCE TO RELATED APPLICATIONS

This application is the National Stage Application of International Patent Application No. PCT/US2020/067417, filed Dec. 30, 2020, which claims the benefit of U.S. Provisional Application No. 62/954,899, filed Dec. 30, 2019, and U.S. Provisional Application No. 62/968,461, filed Jan. 31, 2020, the entireties of which are incorporated by reference herein.

FIELD

Disclosed herein are sulfoximine substituted aminopyrimidine compounds, including pharmaceutical compositions that include one or more aminopyrimidine sulfoximine.

BACKGROUND

Various approaches have been employed in the past to block the activity of various tyrosine kinases. These kinase inhibitors are often small molecules. These small molecules can be used to target these kinases to block the development, growth or spread of cancer.

Fibroblast growth factors (FGFs) and their receptors (FGFRs) regulate a wide range of physiologic cellular processes, such as embryonic development, differentiation, proliferation, survival, migration, and angiogenesis. The FGF family comprises 18 secreted ligands (FGFs) which are readily sequestered to the extracellular matrix by heparin sulfate proteoglycans (HPSGs). For signal propagation, FGFs are released from the extracellular matrix by proteases or specific FGF-binding proteins, with the liberated FGFs subsequently binding to a cell surface FGF-receptor (FGFR) in a ternary complex consisting of FGF, FGFR and HPSG (Beenken, A., Nat. Rev. Drug Discov. 2009; 8:235-253).

FGFR signaling components are frequently altered in human cancer, and several preclinical models have provided compelling evidence for the oncogenic potential of aberrant FGFR signaling in carcinogenesis, thereby validating FGFR signaling as an attractive target for cancer treatment.

Compounds that inhibit FGFR are needed.

SUMMARY

Several embodiments disclosed herein pertain to aminopyrimidine sulfoximine compounds, their use as kinase inhibitors, their methods of manufacture, and their methods of use as therapeutics for treating kinase-related disease states (e.g., cancer). In several embodiments, the aminopyrimidine sulfoximine compound comprises a sulfoximine and an aminopyrimidine. Several embodiments comprise or consist essentially of a sulfoximine compound of the disclosure (or any other structure disclosed herein), their pharmaceutically acceptable salts, enantiomers, methods of manufacture, and/or their methods of use in treating disease states. In several embodiments, by using one or more compounds of the disclosure (or any other structure disclosed herein) to inhibit a kinase in a subject, a disease state can be treated. In several embodiments, the disease state is cancer. In several embodiments, the kinase is a wild-type kinase. In several embodiments, the kinase is a mutant or variant kinase whose activity is not influenced by other standard kinase inhibitors.

DETAILED DESCRIPTION

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

Several embodiments disclosed herein provide compounds useful in treating diseases caused by dysregulated protein kinase activity. Several embodiments also provide methods of treating diseases utilizing these compounds or pharmaceutical compositions comprising these compounds. In several embodiments, the compounds are sulfoximine compounds. In several embodiments, the sulfoximine functionalities are bound to a core aryl structure. In several embodiments, the core aryl structure is a heteroaryl. In several embodiments, the heteroaryl sulfoximine is an aminopyrimidine. In several embodiments, the heteroaryl sulfoximine compound has a structure as represented by one of the formulas, as shown below. In several embodiments, the disclosed heteroaryl sulfoximines can be used in methods of treating cancer.

(I)

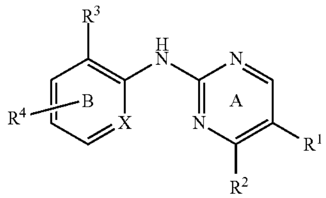

(IA)

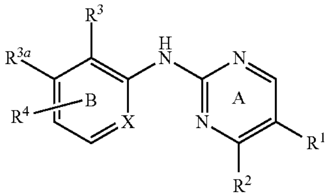

(IB)

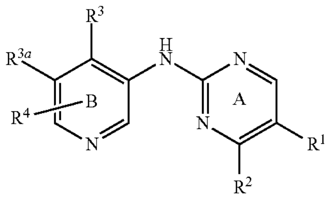

(II)

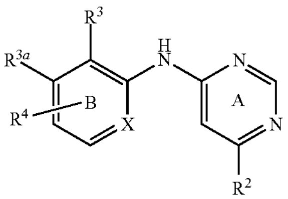

-continued (IIA)

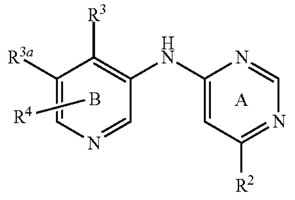

As used herein, any "R" group(s) such as, without limitation, $R^1$, $R^2$, $R^3$, etc., represent substituents that can be attached to the indicated atom. An R group may be substituted or unsubstituted. If two "R" groups are described as being "taken together" the R groups and the atoms they are attached to can form a cycloalkyl, aryl, heteroaryl or heterocycle. For example, without limitation, if $R^{1a}$ and $R^{1b}$ of an $NR^{1a}R^{1b}$ group are indicated to be "taken together," it means that they are covalently bonded to one another to form a ring:

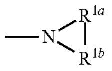

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from hydroxy, halogen, an amino, a mono-substituted amino group, and a di-substituted amino group.

As used herein, "$C_a$ to $C_b$" or $C_{a-b}$ in which "a" and "b" are integers refer to the number of carbon atoms in a moiety as described herein. For example, "a" and "b" refer to the number of carbon atoms in an alkyl, alkenyl or alkynyl group, or the number of carbon atoms in the ring of a, e.g., cycloalkyl, aryl, or heteroaryl group. That is, the alkyl, alkenyl, alkynyl, ring of the cycloalkyl, ring of the aryl, or the ring of the heteroaryl can contain from "a" to "b", inclusive, carbon atoms. Thus, for example, a "$C_1$ to $C_4$ alkyl" group or a "$C_{1-4}$alkyl" group refers to all alkyl groups having from 1 to 4 carbons (e.g., 1, 2, 3, or 4), that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. A "$C_1$ to $C_6$ alkyl" group refers to all alkyl groups having from 1 to 6 carbons (e.g., 1, 2, 3, 4, 5, or 6). If no "a" and "b" are designated with regard to an alkyl, alkenyl, alkynyl, cycloalkyl, aryl, or heteroaryl group, the broadest range described in these definitions is to be assumed.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl. In several embodiments, "Me" is methyl (e.g., $CH_3$).

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by , followed by the number of carbon atoms, followed by a "*". For example,

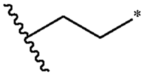 [SMILES: *CC*]

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond.

As used herein, "alkenyl" refers to an alkyl group that contains in the straight or branched hydrocarbon chain one or more double bonds. An alkenyl group may be unsubstituted or substituted.

The term "alkynyl" refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The term "haloalkyl" refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl ($—CF_3$), chloromethyl ($—CH_2Cl$), and the like.

The term "hydroxyalkyl" refers to an alkyl group wherein one or more of the hydrogen atoms has been replaced with one or more OH moieties.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, pyrrolo[2,3-b]pyridine, pyrrolo[2,3-c]pyridine, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. Heteroaryl rings may also be defined to include bridge head nitrogen atoms. For example but not limited to: pyrazolo[1,5-a]pyridine, imidazo[1,2-a]pyridine, pyrazolo[1,5-a]pyrimidine. A heteroaryl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s), or as otherwise noted herein. A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "heterocycloalkyl," "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocycloalkyl," "heterocyclyl," or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, the term "amino" refers to a $—NH_2$ group.

As used herein, the term "hydroxy" refers to a —OH group.

As used herein, the terms "ester" and "C-carboxy" refer to a "—C(═O)OR" group in which R can be the same as defined with respect to O-carboxy. An ester and C-carboxy may be substituted or unsubstituted.

As used herein, the term "halogen atom" or "halogen" refers to any one of the radio-stable atoms of column 7 of the Periodic Table of the Elements, such as, fluorine, chlorine, bromine and iodine.

As used herein, "alkoxy" and "alkylthio" (or thioalkoxy) refer to alkyl groups attached to the remainder of a molecule via an oxygen atom or a sulfur atom, respectively.

As used herein, the term "sulfoximine" refers to a functional group having a sulfur atom with a double bond to each of an oxygen atom and a nitrogen atom, where the sulfur atom is additionally bonded to two other R groups (which may or may not be different atoms of the same molecule) and where the nitrogen is bonded to one other R group. When the two R groups bonded to sulfur are different, the sulfur atom has an asymmetric center.

The term "pharmaceutically acceptable salt" refers to a salt of a compound that does not cause significant irritation to an organism to which it is administered and does not abrogate the biological activity and properties of the compound. In several embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)-methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. It is also understood that, in any compound described herein, all isotopes of the included atoms are envisioned. For example, any instance of hydrogen, may include hydrogen-1 (protium), hydrogen-2 (deuterium), hydrogen-3 (tritium) or other isotopes; any instance of carbon may include carbon-12, carbon-13, carbon-14, or other isotopes; any instance of oxygen may include oxygen-16, oxygen-17, oxygen-18, or other isotopes; any instance of fluorine may include one or more of fluorine-18, fluorine-19, or other isotopes; any instance of sulfur may include one or more of sulfur-32, sulfur-34, sulfur-35, sulfur-36, or other isotopes.

The term "gatekeeper mutation" when used herein denotes mutations in a kinase enzyme that modulate the accessibility of the kinase ATP-binding pocket.

The term "target sequence" or "target nucleic acid sequence" shall be given its ordinary meaning and shall also include and also refer to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence. In several embodiments, the target sequence is one or more of the particular sequences for FGFR mutants provided herein (such as Tables 0.1 or 0.2).

As used herein, the term "kinase inhibitor" means any compound, molecule or composition that inhibits or reduces the activity of a kinase. The inhibition can be achieved by, for example, blocking phosphorylation of the kinase (e.g., competing with adenosine triphosphate (ATP), a phosphorylating entity), by binding to a site outside the active site, affecting its activity by a conformational change, or by depriving kinases of access to the molecular chaperoning systems on which they depend for their cellular stability, leading to their ubiquitylation and degradation.

As used herein, "subject," "host," "patient," and "individual" are used interchangeably and shall be given its ordinary meaning and shall also refer to an organism that has FGFR proteins. This includes mammals, e.g., a human, a non-human primate, ungulates, canines, felines, equines, mice, rats, and the like. The term "mammal" includes both human and non-human mammals. In some aspects, the "subject," "host," "patient," or "individual" is human.

"Diagnosis" as used herein shall be given its ordinary meaning and shall also include determination of a subject's susceptibility to a disease or disorder, determination as to whether a subject is presently affected by a disease or disorder, prognosis of a subject affected by a disease or disorder (e.g., identification of cancer or cancerous states, stages of cancer, or responsiveness of cancer to therapy), and use of therametrics (e.g., monitoring a subject's condition to provide information as to the effect or efficacy of therapy).

The term "sample" or "biological sample" shall be given its ordinary meaning and also encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment," "treating," "treat" and the like shall be given its ordinary meaning and shall also include herein to generally refer to obtaining a desired pharmacologic and/or physiologic effect. "Treatment" as used herein shall be given its ordinary meaning and shall also cover any treatment of a disease in a mammal, particularly a human, and includes: (a) inhibiting the disease symptom, e.g., arresting its development; and/or (b) relieving the disease symptom, e.g., causing regression of the disease or symptom.

The terms "cancer," "neoplasm," and "tumor" are used interchangeably herein, shall be given its ordinary meaning and shall also refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells. As used herein, "FGFR related cancer" denotes those cancers that involve an increased activity in a mutant FGFR kinase, for example, the continued activation of FGFR.

"Cancerous phenotype" shall be given its ordinary meaning and shall also generally refer to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc. In several embodiments, a subject is identified as a potential recipient if they have a cancerous phenotype. In several embodiments, a subject is identified as a potential recipient if they exhibit a new cancerous phenotype when they are already on a cancer therapy (other than a compound as disclosed herein (e.g., the disclosure).

The term "control" refers shall be given its ordinary meaning and shall also include a sample or standard used for comparison with a sample which is being examined, processed, characterized, analyzed, etc. In several embodiments, the control is a sample obtained from a healthy patient or a non-tumor tissue sample obtained from a patient diagnosed with a tumor. In several embodiments, the control is a historical control or standard reference value or range of values. In several embodiments, the control is a comparison to a wild-type FGFR arrangement or scenario.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the general description and the following detailed description are exemplary and explanatory only and are not restrictive. The term "and/or" denotes that the provided possibilities can be used together or be used in the alternative. Thus, the term "and/or" denotes that both options exist for that set of possibilities.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds of the Disclosure

Several embodiments pertain to aminopyrimidine sulfoximine compounds. In several embodiments, the amino pyrimidine sulfoximine is a compound having the structure of any of the formula depicted, below (or a pharmaceutically acceptable salt thereof):

(I)

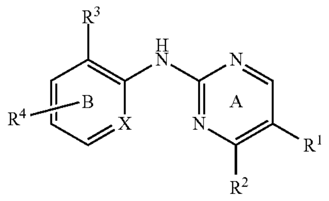

(IA)

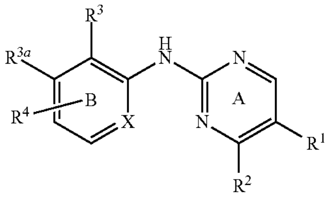

(IB)

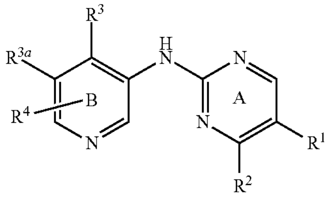

(II)

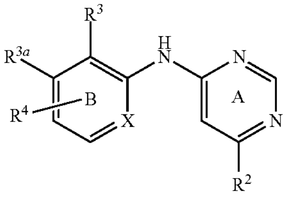

(IIA)

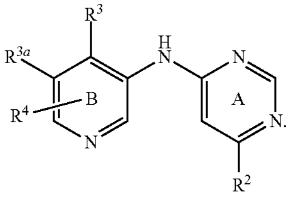

According to the disclosure, $R^1$ is selected from the group consisting of —H, —F, —Cl, —Br, —CN, —$CF_3$, —$CH_3$, and —C(O)$NH_2$; In some aspects, $R^1$ is H, F, Cl, Br, $C_{1-6}$ alkyl, (e.g., methyl, ethyl, iso-propyl), CN, $C_{1-6}$haloalkyl (e.g., trifluoromethyl), —C(O)$NH_2$, —C(O)$NHC_{1-6}$alkyl, or —C(O)N($C_{1-6}$alkyl). In some aspects, $R^1$ is H. In some aspects, $R^1$ is F.

In some aspects, $R^1$ is Cl. In some aspects, $R^1$ is Br. In some aspects, $R^1$ is $C_{1-6}$alkyl, for example methyl, ethyl, iso-propyl, and the like. In some aspects, $R^1$ is $C_{1-6}$haloalkyl, for example, trifluoromethyl. In some aspects, $R^1$ is —C(O)$NH_2$. In some aspects, $R^1$ is C(O)$NHC_{1-6}$alkyl, for example, C(O)$NHCH_3$ or C(O)$NHCH_2CH_3$. In some aspects, $R^1$ is —C(O)N($C_{1-6}$alkyl)$_2$, for example, C(O)N$(CH_3)_2$, C(O)N$(CH_2CH_3)_2$, or C(O)N$(CH_3)(CH_2CH_3)$ According to the disclosure, $R^2$ is a heteroaryl comprising 5-10 atoms optionally substituted with $R^5$. In some aspects, $R^2$ is a heteroaryl comprising 5-10 atoms. For example, in some aspects, $R^2$ is an indolyl, an indazolyl, a pyrrolopyridine, a quinolinyl, a quinazolinyl, or a pyrrolopyridinyl. In some aspects, $R^2$ is an indolyl. In some aspects, $R^2$ is an indazolyl. In some aspects, $R^2$ is a quinolinyl. In some aspects, $R^2$ is a quinazolinyl. In some aspects, $R^2$ is a pyrrolopyridinyl. In some aspects, $R^2$ is a heteroaryl comprising 5-10 atoms substituted with one, two, three, or four independently selected $R^5$. In some aspects, $R^2$ is a heteroaryl comprising 5-10 atoms substituted with one $R^5$. In some aspects, $R^2$ is a heteroaryl comprising 5-10 atoms substituted with two independently selected $R^5$. In some aspects, $R^2$ is a heteroaryl comprising 5-10 atoms substituted with three independently selected $R^5$. In some aspects, $R^2$ is a heteroaryl comprising 5-10 atoms substituted with four independently selected $R^5$. In some aspects, $R^2$ is an indolyl substituted with one, two, three, or four independently selected $R^5$. In some aspects, $R^2$ is an indazolyl substituted with one, two, three, or four independently selected $R^5$. In some aspects, $R^2$ is a quinolinyl substituted with one, two, three, or four independently selected $R^5$. In some aspects, $R^2$ is a quinazolinyl substituted with one, two, three, or four independently selected $R^5$. In some aspects, $R^2$ is a pyrrolopyridinyl substituted with one, two, three, or four independently selected $R^5$.

According to the disclosure, X is selected from —CH— and N. In some aspects, X is —CH—. In other aspects, X is N.

According to the disclosure, $R^3$ is selected from the group consisting of —H, —F, —Cl, —Br, —$CF_3$, $OCF_3$, optionally substituted $C_1$-$C_3$-alkyl, —$OR^6$, CN, —N$(R^7)_2$, —NHCO—($C_1$-$C_6$-alkyl) where $C_1$-$C_6$-alkyl is optionally substituted, —NHCOCH═$CH_2$, and —NHCOCH═$CHCH_2N(Me)_2$.

In some aspects, $R^3$ is H, F, Cl, Br, $OC_{1-6}$alkyl (e.g., $OCH_3$, Oet, OiPr, OiBu), $C_{1-6}$alkyl (e.g., methyl, ethyl, isopropyl), $C_{3-6}$-cycloalkyl (e.g., cyclopropyl, cyclobutyl), $C_{1-6}$haloalkyl (e.g., $CF_3$), $OC_{1-6}$haloalkyl (e.g., $OCF_3$), $NO_2$, $NH_2$, —NHC(O)—($C_1$-$C_6$-alkyl), NHC(O)CH═$CH_2$, NHC(O)$CR^{10}$═$CH_2$, $C_{1-6}$alk-NHC(O)$CR^{10}$═$CHR^{10}$, —NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), —NHCOCH═$CHCH_2N(Me)_2$, $NHSO_2CH$═$CH_2$, or O($C_{1-6}$alk)heterocycloalkyl. In some aspects, $R^3$ is H. In some aspects, $R^3$ is F. In some aspects, $R^3$ is Cl. In some aspects, $R^3$ is Br. In some aspects, $R^3$ is $OC_{1-6}$alkyl (e.g., $OCH_3$, Oet, OiPr, OiBu). In some aspects, $R^3$ is $C_{1-6}$alkyl (e.g., methyl, ethyl, isopropyl). In some aspects, $R^3$ is $C_{3-6}$-cycloalkyl. In some aspects, $R^3$ is $C_{1-6}$haloalkyl (e.g., $CF_3$). In some aspects, $R^3$ is $OC_{1-6}$haloalkyl (e.g., $OCF_3$). In some aspects, $R^3$ is $NO_2$. In some aspects, $R^3$ is $NH_2$. In some aspects, $R^3$ is —NHCO—($C_1$-$C_6$-alkyl). In some aspects, $R^3$ is NHC(O)CH═$CH_2$. In some aspects, $R^3$ is NHC(O)$CR^{10}$═$CHR^{10}$ (e.g., NHC(O)CF═$CH_2$, NHC(O)CH═CFH, NHC(O)CCl═$CH_2$, NHC(O)CH═CClH, NHC(O)C$(CH_3)$═$CH_2$, NHC(O)CH═C$(CH_3)$)). In some aspects, $R^3$ is —NHCOCH═$CHCH_2N(Me)_2$. In some aspects, $R^3$ is $NHSO_2CH$═$CH_2$. In some aspects, $R^3$ is O($C_{1-6}$alk)heterocycloalkyl.

According to the disclosure, $R^{3a}$ is selected from the group consisting of —H, —F, —Cl, —Br, —$CF_3$, $OCF_3$, optionally substituted $C_1$-$C_3$-alkyl, —$OR^6$, CN, —N$(R^7)_2$, —NHCO—($C_1$-$C_6$-alkyl) where $C_1$-$C_6$-alkyl is optionally substituted, —NHCOCH═$CH_2$, and —NHCOCH═$CHCH_2N(Me)_2$. In some aspects, $R^{3a}$ is H, F, Cl, Br, $OC_{1-6}$alkyl (e.g., $OCH_3$, Oet, OiPr, OiBu), $C_{1-6}$alkyl (e.g., methyl, ethyl, isopropyl), $C_{3-6}$-cycloalkyl (e.g., cyclopropyl, cyclobutyl), $C_{1-6}$haloalkyl (e.g., $CF_3$), $OC_{1-6}$haloalkyl (e.g., $OCF_3$), $NO_2$, $NH_2$, —NHC(O)—($C_1$-$C_6$-alkyl), NHC(O)CH═$CH_2$, NHC(O)$CR^{10}$═$CH_2$, —NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), —NHCOCH═$CHCH_2N(Me)_2$, $NHSO_2CH$═$CH_2$, or O($C_{1-6}$alk)heterocycloalkyl. In some aspects, $R^{3a}$ s H. In some aspects, $R^{3a}$ is F. In some aspects, $R^{3a}$ is Cl. In some aspects, $R^{3a}$ is Br. In some aspects, $R^{3a}$ is $OC_{1-6}$alkyl (e.g., $OCH_3$, OEt, OiPr, OiBu). In some aspects, $R^{3a}$ is $C_{1-6}$alkyl (e.g., methyl, ethyl, isopropyl). In some aspects, $R^{3a}$ is $C_{3-6}$-cycloalkyl. In some aspects, $R^{3a}$ is $C_{1-6}$haloalkyl (e.g., $CF_3$). In some aspects, $R^{3a}$ is $OC_{1-6}$haloalkyl (e.g., $OCF_3$). In some aspects, $R^{3a}$ is $NO_2$. In some aspects, $R^3$ is $NH_2$. In some aspects, $R^{3a}$ is —NHCO—($C_1$-$C_6$-alkyl). In some aspects, $R^{3a}$ is NHC(O)CH═$CH_2$. In some aspects, $R^{3a}$ is NHC(O)$CR^{10}$═$CHR^{10}$ (e.g., NHC(O)CF═$CH_2$, NHC(O)CH═CFH, NHC(O)CCl═$CH_2$, NHC(O)CH═CClH, NHC(O)C$(CH_3)$═$CH_2$, NHC(O)CH═C$(CH_3)$)). In some aspects, $R^{3a}$ is —NHCOCH═$CHCH_2N(Me)_2$. In some aspects, $R^{3a}$ is $NHSO_2CH$═$CH_2$. In some aspects, $R^{3a}$ is O($C_{1-6}$alk)heterocycloalkyl.

In some aspects, $R^3$ and $R^{3a}$ are both H. In some aspects, $R^{3a}$ is H and $R^3$ is F, Cl, Br, $OC_{1-6}$alkyl (e.g., $OCH_3$, Oet, OiPr, OiBu), $C_{1-6}$alkyl (e.g., methyl, ethyl, isopropyl), $C_{3-6}$-cycloalkyl (e.g., cyclopropyl, cyclobutyl), $C_{1-6}$haloalkyl (e.g., $CF_3$), $OC_{1-6}$haloalkyl (e.g., $OCF_3$), $NO_2$, $NH_2$, —NHC(O)—($C_1$-$C_6$-alkyl), NHC(O)CH═$CH_2$, NHC(O)$CR^{10}$═$CH_2$, —NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), —NHCOCH═$CHCH_2N(Me)_2$, $NHSO_2CH$═$CH_2$, or O($C_{1-6}$alk)heterocycloalkyl. In some aspects, $R^3$ is H and $R^{3a}$ is F, Cl, Br, $OC_{1-6}$alkyl (e.g., $OCH_3$, Oet, OiPr, OiBu), $C_{1-6}$alkyl (e.g., methyl, ethyl, isopropyl), $C_{3-6}$-cycloalkyl (e.g., cyclopropyl, cyclobutyl), $C_{1-6}$haloalkyl (e.g., $CF_3$), $OC_{1-6}$haloalkyl (e.g., $OCF_3$), $NO_2$, $NH_2$, —NHC(O)—($C_1$-$C_6$-alkyl), NHC(O)CH═$CH_2$, NHC(O)$CR^{10}$═$CH_2$, —NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), —NHCOCH═$CHCH_2N(Me)_2$, $NHSO_2CH$═$CH_2$, or O($C_{1-6}$alk)heterocycloalkyl.

According to the disclosure, $R^5$ is independently selected from the group consisting of —F, —Cl, —$OR^6$, —N$(R^7)_2$, —CN, —$CF_3$, —$OCF_3$, —NHCO—($C_1$-$C_3$-alkyl) where $C_1$-$C_3$-alkyl is optionally substituted, —NHCOCH═$CH_2$, —$NHCOCR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), —NHCOCH═$CHCH_2N(Me)_2$, —$(CH_2)_n$NHCOCH═$CH_2$, —$(CH_2)_n$NHCOCH═C $HCH_2N(Me)_2$; or $NHSO_2CH$═$CH_2$. In some aspects, each $R^5$ is F, Cl, Br, $C_{1-6}$alkyl (e.g., methyl, ethyl, ipropyl), $C_{3-6}$-cycloalkyl (e.g., cyclopropyl, cyclobutyl), $OC_{1-6}$alkyl (e.g., $OCH_3$, OEt, OiPr, OiBu), $C(O)C_{1-6}$alkyl, hydroxy$C_{1-6}$alkyl, $NH_2$, NHC(O)CH═$CH_2$, $C_{1-6}$alk-NHC(O)CH═$CH_2$, NHC(O)CH═CH—$C_{1-6}$alk-$NH_2$, NHC(O)CH═CH—$C_{1-6}$alk-$NHC_{1-6}$alkyl, NHC(O)CH═CH—$C_{1-6}$alk-N($C_{1-6}$alkyl)$_2$, NHC(O)$C_{1-6}$alkyl, or NHC(O)$C_{3-6}$cycloalkyl. In some aspects, at least one $R^5$ is F. In some aspects, at least one $R^5$ is Cl. In some aspects, at least one $R^5$ is Br. In some aspects, at least one $R^5$ is $C_{1-6}$alkyl (e.g., methyl, ethyl, ipropyl). In some aspects, at least one $R^5$ is $C_{3-6}$-cycloalkyl. In some aspects, at least one $R^5$ is —NHCOC$R^{10}$═CH$R^{10}$ (e.g., NHC(O)CF═$CH_2$, NHC(O)CH═CFH, NHC(O)CCl═$CH_2$, NHC(O)CH═CClH, NHC(O)C($CH_3$)═$CH_2$, NHC(O)CH═C($CH_3$)), In some aspects, at least one $R^5$ is $OC_{1-6}$alkyl (e.g., $OCH_3$, OEt, OiPr, OiBu). In some aspects, at least one $R^5$ is $C(O)C_{1-6}$alkyl. In some aspects, at least one $R^5$ is hydroxy$C_{1-6}$alkyl. In some aspects, at least one $R^5$ is $NH_2$. In some aspects, at least one $R^5$ is NHC(O)CH═$CH_2$. In some aspects, In some aspects, at least one $R^5$ is $C_{1-6}$alk-NHC(O)CH═$CH_2$ (e.g., —$CH_2$NHC(O)CH═$CH_2$). In some aspects, at least one $R^5$ is NHC(O)CH═CH—$C_{1-6}$alk-$NH_2$. In some aspects, at least one $R^5$ is NHC(O)CH═CH—$C_{1-6}$alk-$NHC_{1-6}$alkyl. In some aspects, at least one $R^5$ is NHC(O)CH═CH—$C_{1-6}$alk-N($C_{1-6}$alkyl)$_2$. In some aspects, at least one $R^5$ is NHC(O)$C_{1-6}$alkyl. In some aspects, at least one $R^5$ is NHC(O)$C_{3-6}$cycloalkyl. In some aspects, at least one $R^5$ is $NHSO_2CH$═$CH_2$.

According to the disclosure, each instance of $R^6$ is selected from the group consisting of —H, optionally substituted $C_1$-$C_6$-alkyl, optionally substituted $C_1$-$C_6$-alkenyl, —$(CH_2)_n$—$C_3$-$C_6$-cycloalkyl, and —$(CH_2)_n$heteroaryl. In some aspects, at least one $R^6$ is H. In some aspects, at least one $R^6$ is optionally substituted $C_1$-$C_6$-alkyl. In some aspects, at least one $R^6$ is optionally substituted $C_1$-$C_6$-alkenyl. In some aspects, at least one $R^6$ is —$(CH_2)_n$—$C_3$-$C_6$-cycloalkyl. In some aspects, at least one $R^6$ is —$(CH_2)_n$heteroaryl.

According to the disclosure, each instance of $R^7$ is independently selected from the group consisting of —H, optionally substituted —$C_1$-$C_6$-alkyl, —$(CH_2)_n$—$C_3$-$C_6$-cycloalkyl, —$(CH_2)_n$-heteroaryl. In some aspects, at least one $R^7$ is H. In some aspects, at least one $R^7$ is optionally substituted —$C_1$-$C_6$-alkyl. In some aspects, at least one $R^7$ is —$(CH_2)_n$—$C_3$-$C_6$-cycloalkyl. In some aspects, at least one $R^7$ is —$(CH_2)_n$-heteroaryl.

According to the disclosure, each instance of n is an integer equal to 0, 1, 2, 3, or 4. In some aspects, n is 0. In some aspects, n is 1. In some aspects, n is 2. In some aspects, n is 3. In some aspects, n is 4.

According to the disclosure, $R^4$ is positioned at any one of the 3, 4, or 5 positions of Ring B. According to the disclosure, $R^4$ is positioned at any available position of Ring B.

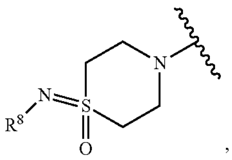,
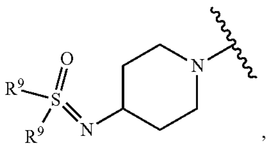,
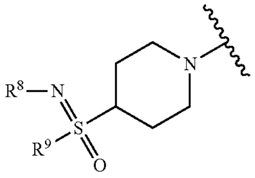,
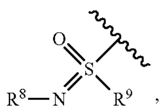,

-continued

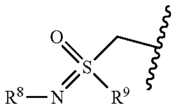,
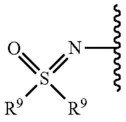, and
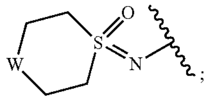;

According to the disclosure, W is selected from the group consisting of —$CH_2$—, —C(O)—, —CH(OH)— and —N($R^8$)—. In some aspects, W is $CH_2$. In some aspects, W is —C(O)—. In some aspects, W is —CH(OH)—. In some aspects, W is —N($R^8$)—.

According to the disclosure, $R^8$ is selected from the group consisting of —H, optionally substituted $C_1$-$C_6$-alkyl, optionally substituted $C_1$-$C_6$-alkenyl, and —$C_3$-$C_6$-cycloalkyl. According to the disclosure, $R^8$ is H. According to the disclosure, $R^8$ is optionally substituted $C_1$-$C_6$-alkyl. According to the disclosure, $R^8$ is optionally substituted $C_1$-$C_6$-alkenyl. According to the disclosure, $R^8$ is $C_3$-$C_6$-cycloalkyl.

According to the disclosure, each instance of $R^9$ is independently selected from the group consisting of optionally substituted $C_1$-$C_6$-alkyl, optionally substituted $C_1$-$C_6$-alkenyl, and $C_3$-$C_6$-cycloalkyl. In some aspects, at least one $R^9$ is optionally substituted $C_1$-$C_6$-alkyl. In some aspects, at least one $R^9$ is optionally substituted $C_1$-$C_6$-alkenyl. In some aspects, at least one $R^9$ is $C_3$-$C_6$-cycloalkyl.

According to the disclosure, optionally substituted alkyl or optionally substituted alkenyl can optionally be substituted with hydroxy, halogen, $C_1$-$C_3$-alkoxy, $C_1$-$C_3$-alkylthio, —CN, $C_3$-$C_6$-cycloalkyl, $C_1$-$C_3$-hydroxyalkyl, $C_2$-$C_6$ alkenyl, $C_2$-$C_6$-alkynyl, —$CF_3$, —$OCF_3$, or —$NR_7R_8$. In some aspects, substituted alkyl or substituted alkenyl can be substituted with hydroxy, halogen, $C_1$-$C_3$-alkoxy, $C_1$-$C_3$-alkylthio, —CN, $C_3$-$C_6$-cycloalkyl, $C_1$-$C_3$-hydroxyalkyl, $C_2$-$C_6$ alkenyl, $C_2$-$C_6$-alkynyl, —$CF_3$, —$OCF_3$, or —$NR_7R_8$.

In several embodiments, the $R^4$ is bonded to the B ring of the compounds of the disclosure at any one of the following positions (e.g., the 3, 4, or 5 positions of Ring B):

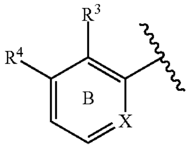
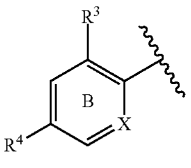
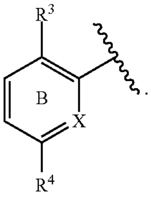.

In several embodiments, $R^2$ is selected from the group consisting of indole, indazole, quinoline, quinazoline, and pyrrolopyridine, each of which may be substituted with $R^5$:

indole

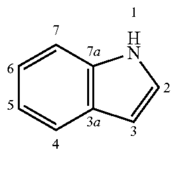

-continued indazole

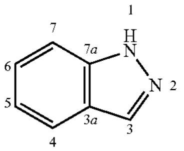

quinoline

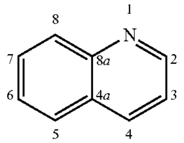

quinazoline

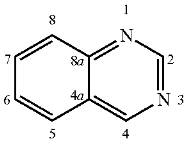

pyrrolopyridine

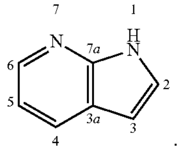

In several embodiments, where $R^2$ is indole, the indole may be bonded to the A ring and/or any instance of one or more $R^5$ groups at any one of the 1, 2, 3, 4, 5, 6, or 7 positions of the indole ring. In several embodiments, where $R^2$ is indazole, the indazole may be bonded to the A ring and/or any instance one or more $R^5$ groups at any one of the 1, 2, 3, 4, 5, 6, or 7 positions of the indazole ring. In several embodiments, where $R^2$ is quinoline, the quinoline may be bonded to the A ring and/or one or more $R^5$ groups at, independently, any one of the 1, 2, 3, 4, 5, 6, 7, or 8 positions of the quinoline ring. In several embodiments, where $R^2$ is quinazoline, the quinazoline may be bonded to the A ring and/or one or more $R^5$ groups at, independently, any one of the 1, 2, 3, 4, 5, 6, 7, or 8 positions of the quinazoline ring.

In several embodiments, the amino pyrimidine sulfoximine is a compound having the structure of Formula (I) (or a pharmaceutically acceptable salt thereof):

(I)

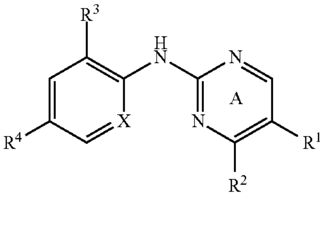

where each variable is as described elsewhere herein.

In several embodiments, the amino pyrimidine sulfoximine is a compound having the structure of Formula (IA) (or a pharmaceutically acceptable salt thereof):

(IA)

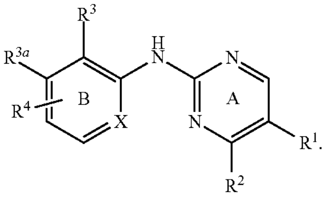

In several embodiments, the amino pyrimidine sulfoximine is a compound having the structure of Formula (IB) (or a pharmaceutically acceptable salt thereof):

(IB)

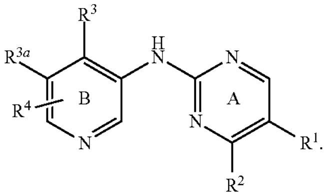

In several embodiments, the amino pyrimidine sulfoximine is a compound having the structure of Formula (II) (or a pharmaceutically acceptable salt thereof):

(II)

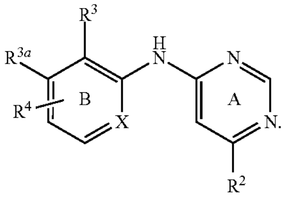

In several embodiments, the amino pyrimidine sulfoximine is a compound having the structure of Formula (II) (or a pharmaceutically acceptable salt thereof):

(IIA)

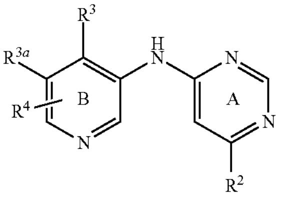

where each variable is as described elsewhere herein.

In some aspects, $R^4$ is

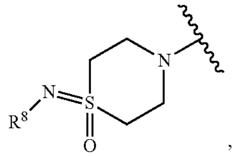

, with the following moieties being particularly preferred:

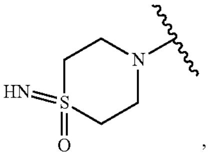 , 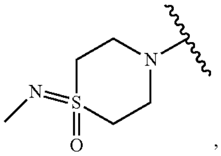 ,

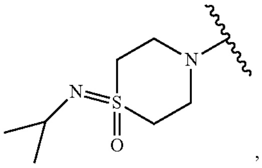 , 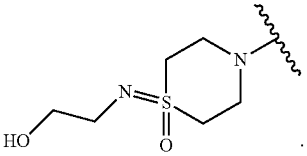 .

In some aspects, $R^4$ is

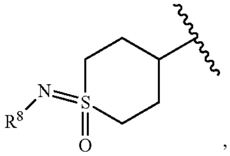 , with the following moieties being particularly preferred:

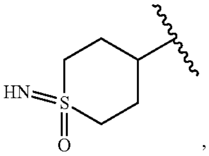 , 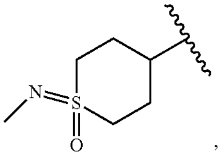 ,

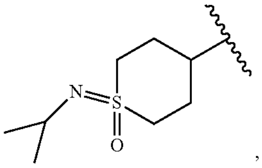 , 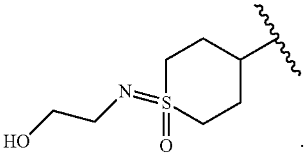 .

In some aspects, $R^4$ is

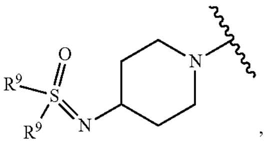 , with the following moieties being particularly preferred:

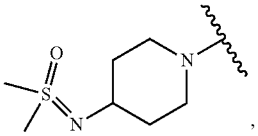 , 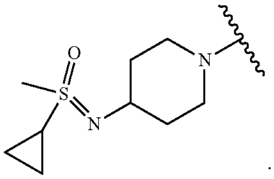 .

In some aspects, $R^4$ is

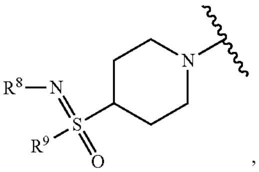 , with the following moieties being particularly preferred:

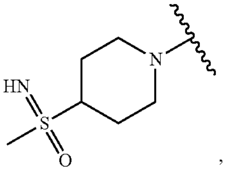 , 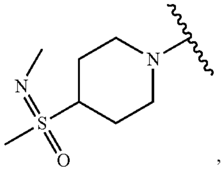 ,

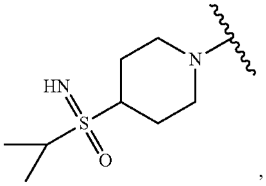 , 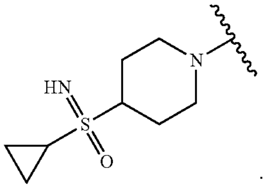 .

In some aspects, $R^4$ is

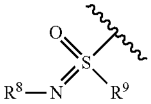 , with the following moieties being particularly preferred:

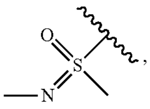 , 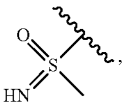 , 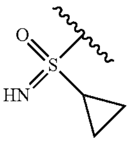 ,

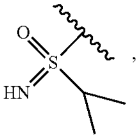 ,

In some aspects, $R^4$ is

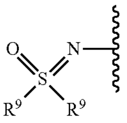

with the following moieties being particularly preferred:

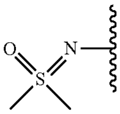
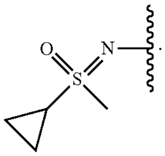

In some aspects, $R^4$ is

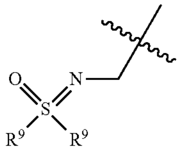

with the following moieties being particularly preferred:

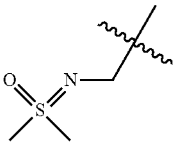
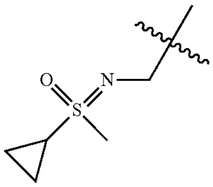

In some aspects, $R^4$ is

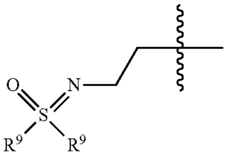

with the following moieties being particularly preferred:

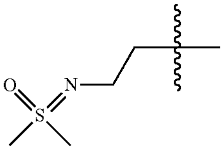
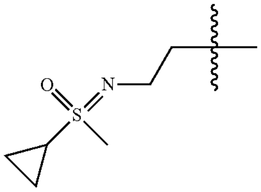

In some aspects, $R^4$ is

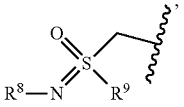

with the following moieties being particularly preferred:

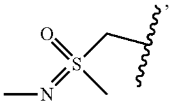
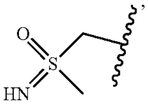
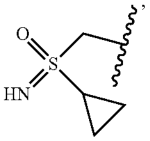
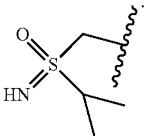

In some aspects, $R^4$ is

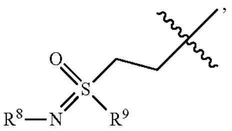

with the following moieties being particularly preferred:

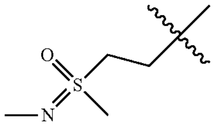
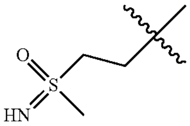

or

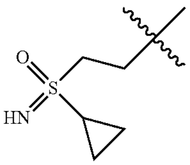
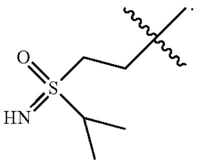

In some aspects, $R^4$ is

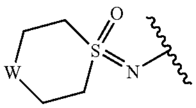

with the following moieties being particularly preferred:

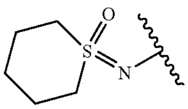
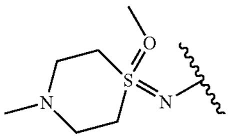
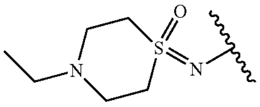
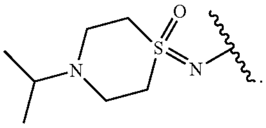

In some aspects, $R^4$ is
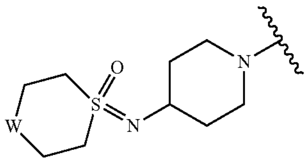
with the following moieties being particularly preferred:
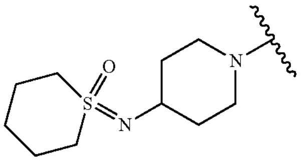
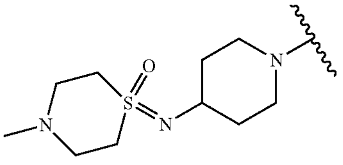
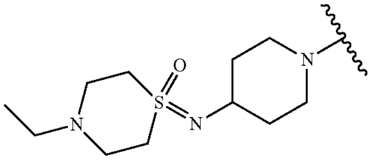
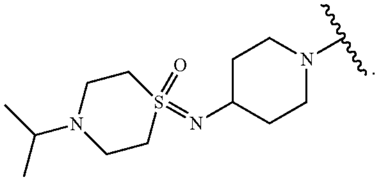
In some embodiments, $R^4$ is
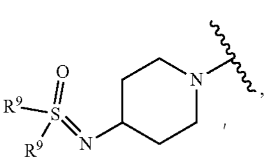
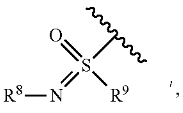
or
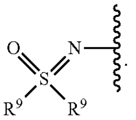
In yet other aspects, $R^4$ is
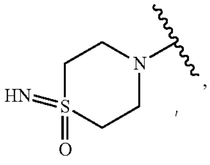
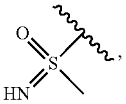
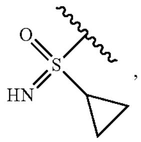
-continued
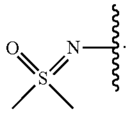
In several embodiments, as shown below, $R^1$ is —Cl, $R^2$ is indole, $R^3$ is —OMe, X is CH, $R^4$ is as defined elsewhere herein, and the structure of Formula (I) is represented by any one of the following:
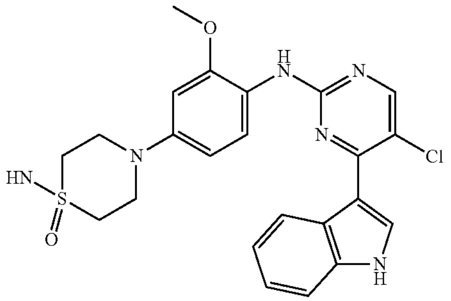
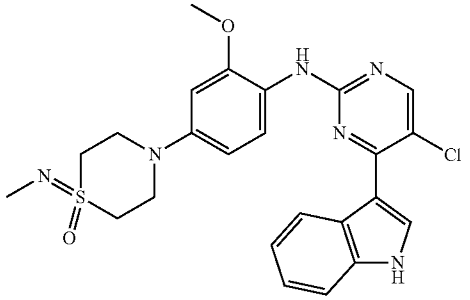
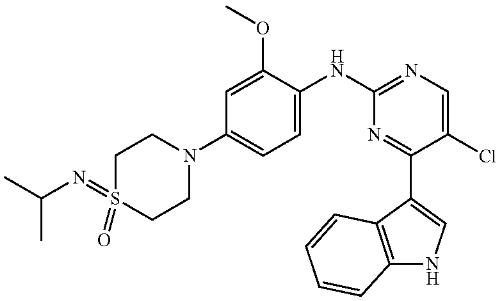
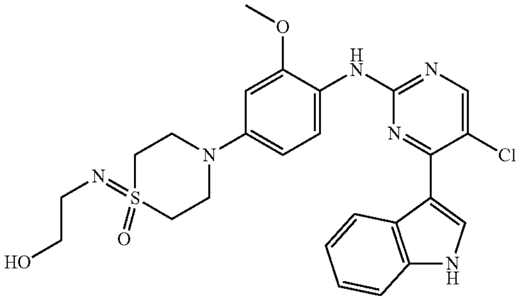

-continued
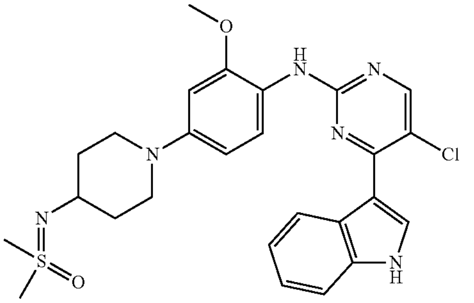
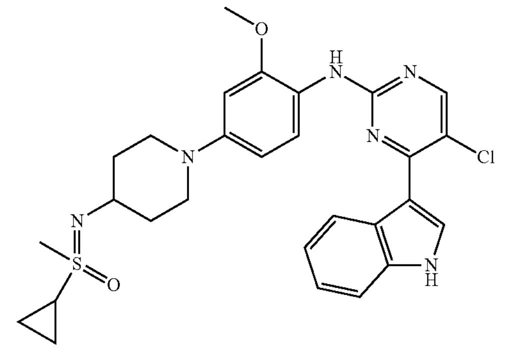
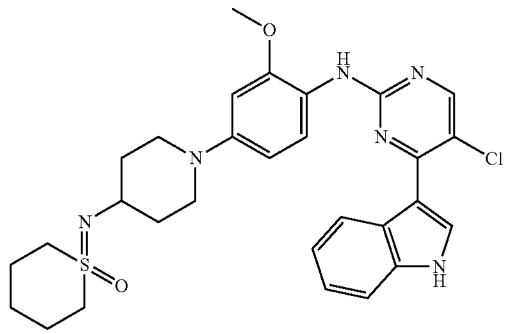
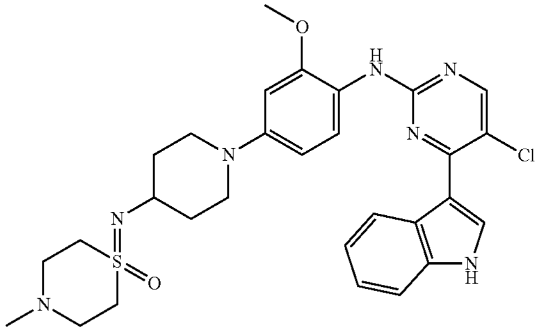
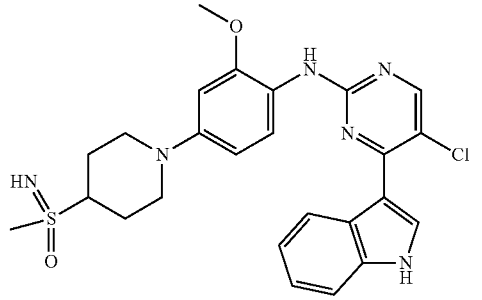
-continued
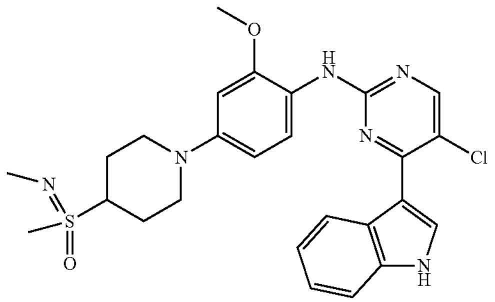
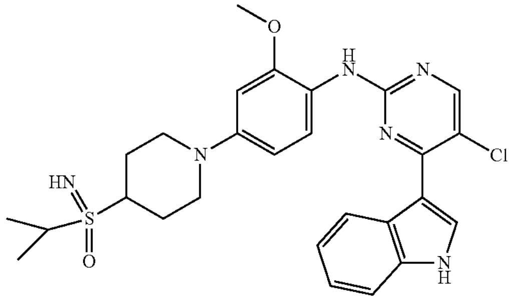
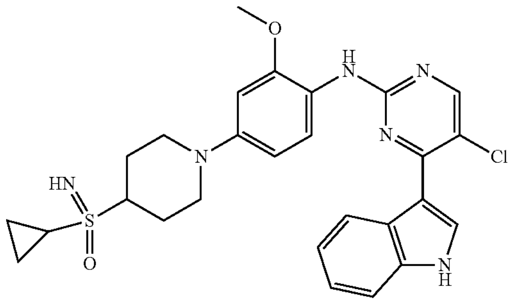
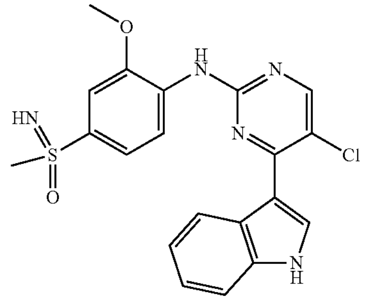
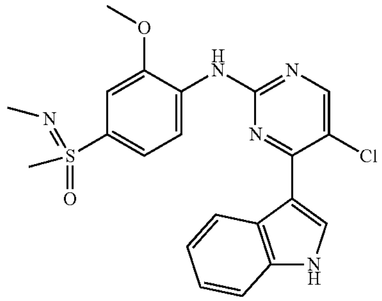

-continued
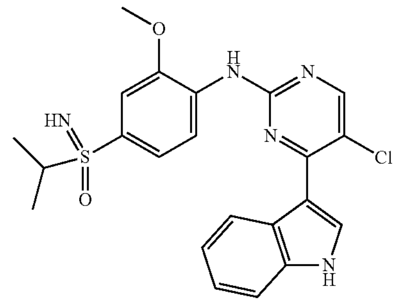
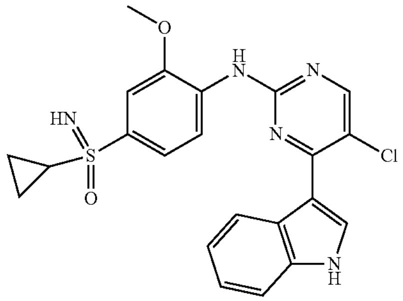
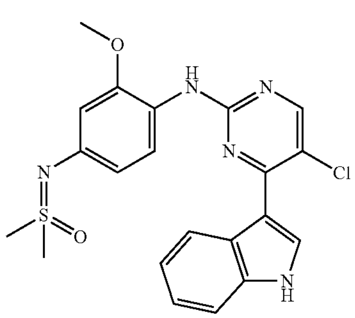
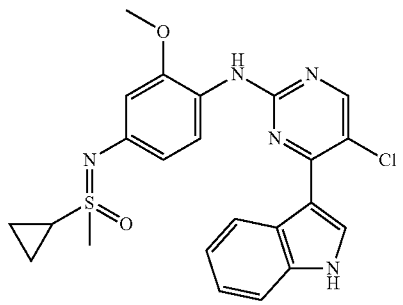
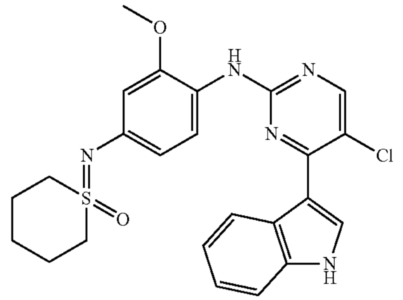
-continued
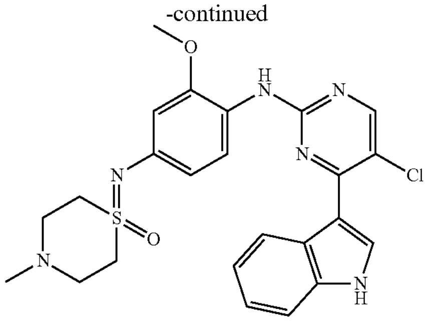
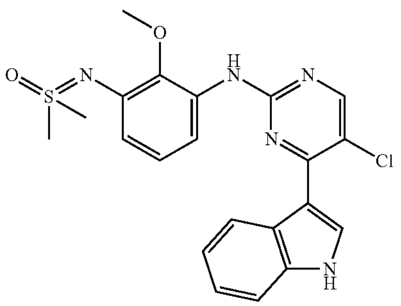
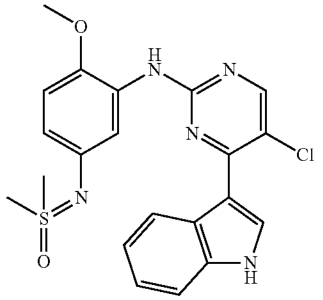
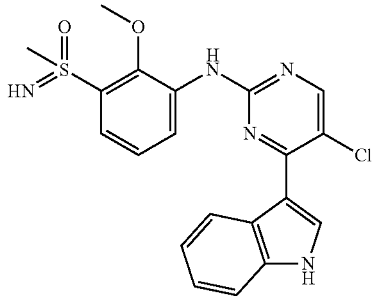
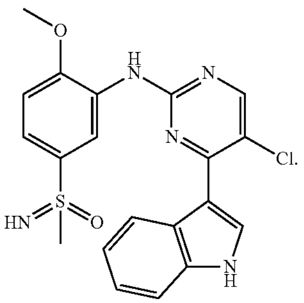
In several embodiments, $R^1$ is —Cl, $R^2$ is indole, $R^3$ is —H, X is CH, $R^4$ is as defined elsewhere herein, and the structure of Formula (I) is represented by the following:

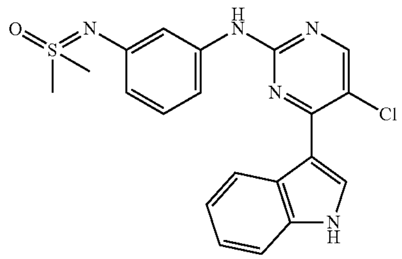

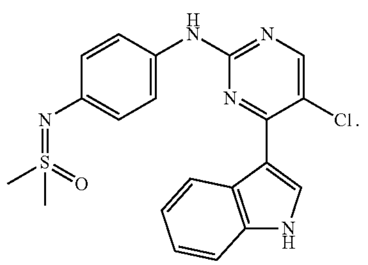

In several embodiments, $R^1$ is —Cl, $R^2$ is indole, $R^3$ is —H or —$OR^6$, $R^6$ is $C_1$-$C_6$-alkyl having 1 carbon (e.g., —$CH_3$), X is N, $R^4$ is as defined elsewhere herein, and the structure of Formula (I) is represented by any one of the following:

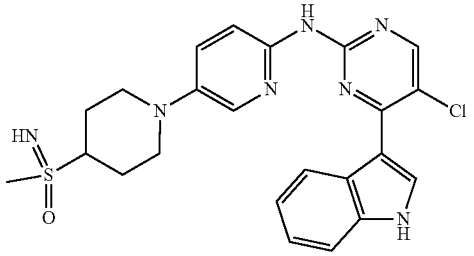

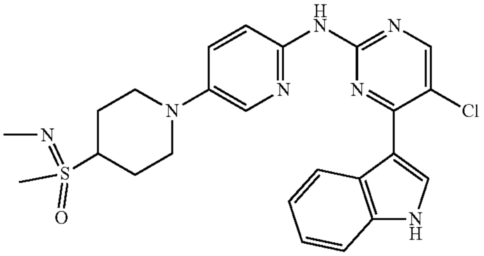

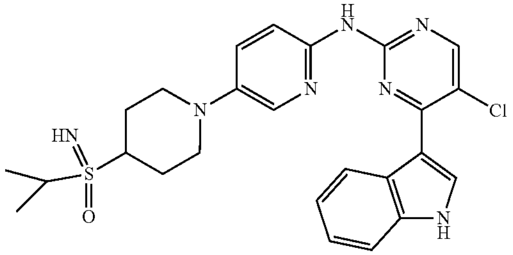

-continued

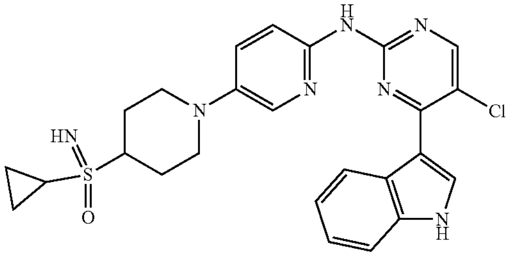

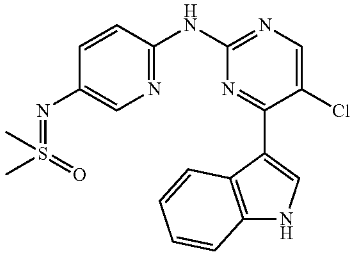

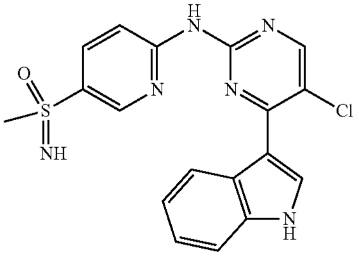

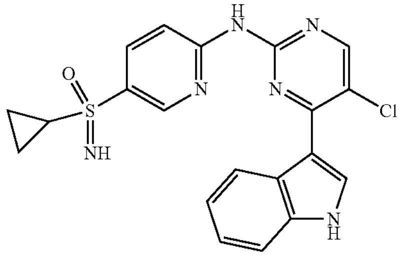

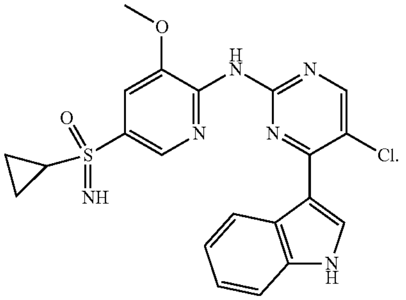

As shown above and elsewhere herein (including in Formula (IA)), $R^3$ of Formula (I) may be —H.

In several embodiments, $R^1$ is —Cl, $R^2$ is indole, $R^3$ is —$OR^6$, $R^6$ is $C_1$-$C_6$-alkyl having 1 carbon (e.g., —$CH_3$), X is CH, $R^4$ is as defined elsewhere herein, and the structure of Formula (I) is represented by any one of the following:

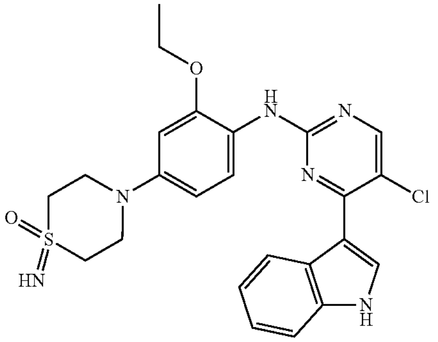

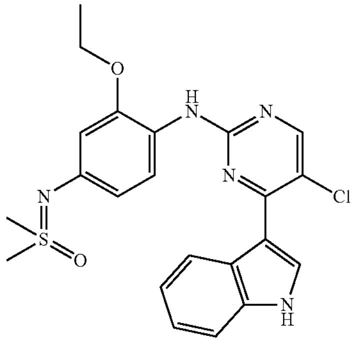

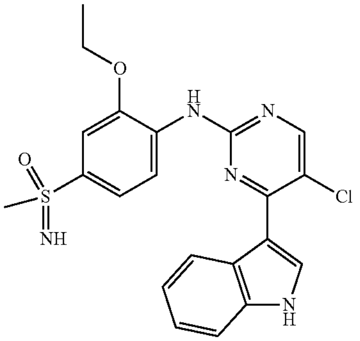

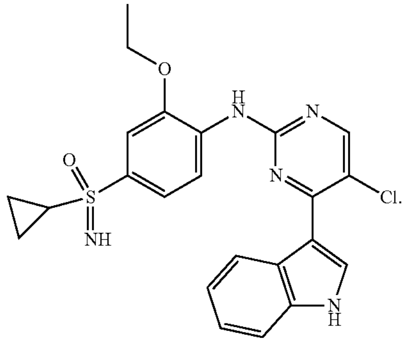

In several embodiments, $R^1$ is —Cl, $R^2$ is indole, $R^3$ is —$OR^6$, $R^6$ is $C_1$-$C_6$-alkyl having 3 carbons (e.g., —CH$(CH_3)_2$), X is CH, $R^4$ is as defined elsewhere herein, and the structure of Formula (I) is represented by any one of the following:

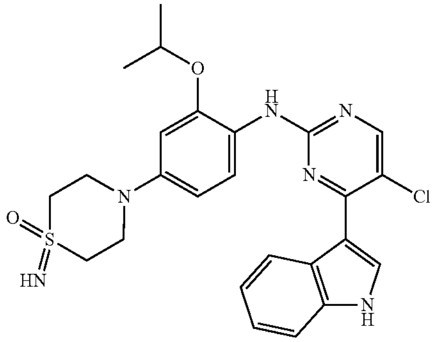

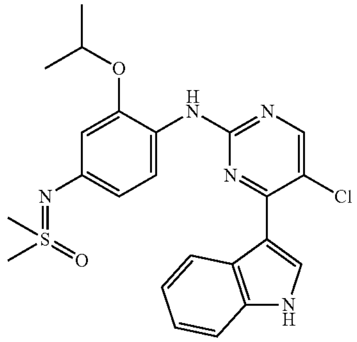

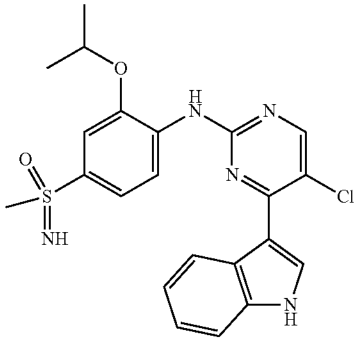

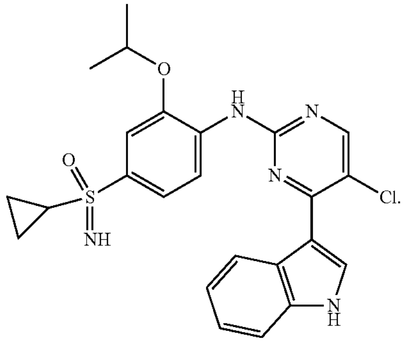

In several embodiments, $R^1$ is —Cl, $R^2$ is indole, $R^3$ is —$OR^6$, $R^6$ is —$(CH_2)_n$—$C_3$-$C_6$-cycloalkyl where n is 0 and the cycloalkyl has 3 carbons (e.g., cyclopropyl), X is CH, $R^4$ is as defined elsewhere herein, and the structure of Formula (I) is represented by any one of the following:

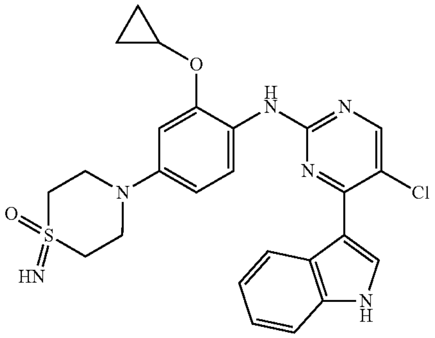
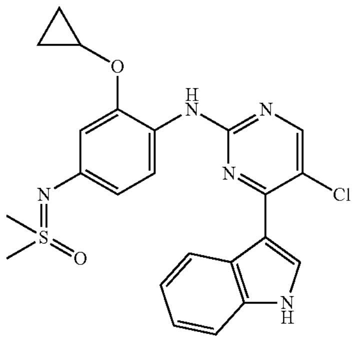
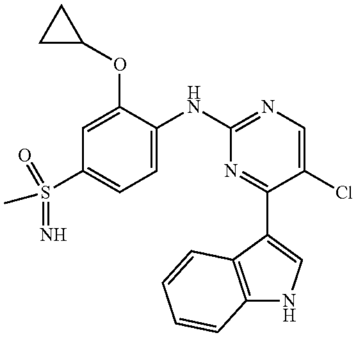
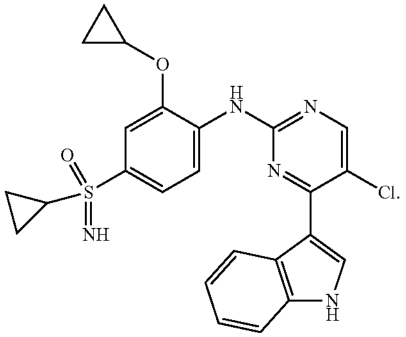
In several embodiments, $R^1$ is —Cl, $R^2$ is indole, $R^3$ is —$OR^6$, $R^6$ is —$(CH_2)_n$—$C_3$-$C_6$-cycloalkyl where n is 1 and the cycloalkyl has 3 carbons (e.g., —$(CH_2)$-cyclopropyl), X is CH, $R^4$ is as defined elsewhere herein, and the structure of Formula (I) is represented by any one of the following:
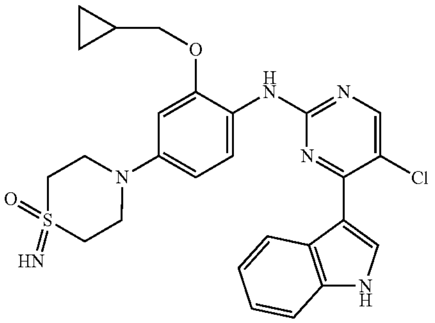
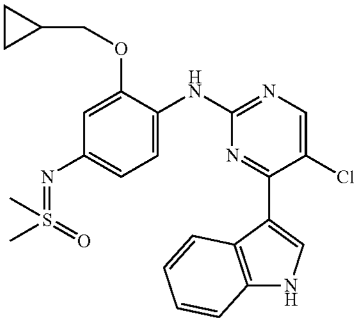
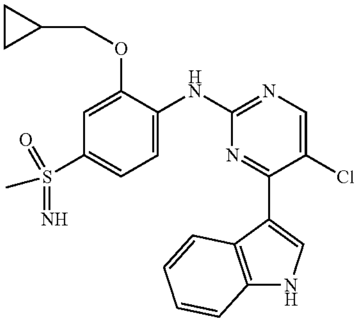
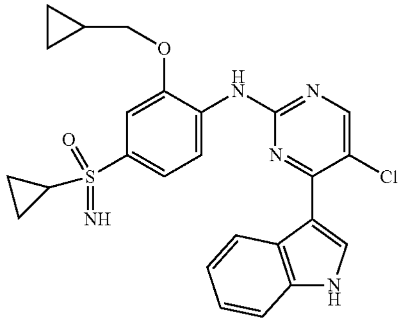

-continued

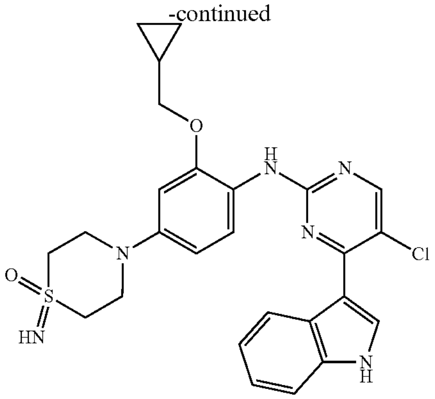

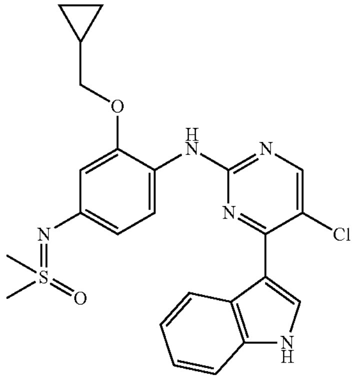

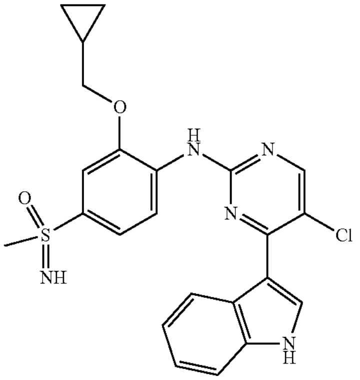

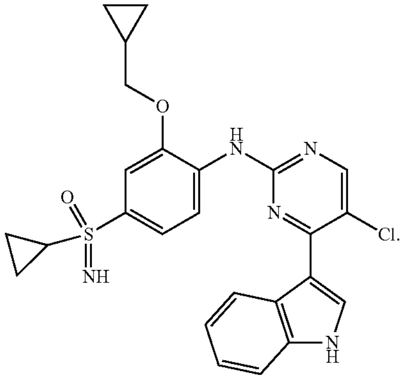

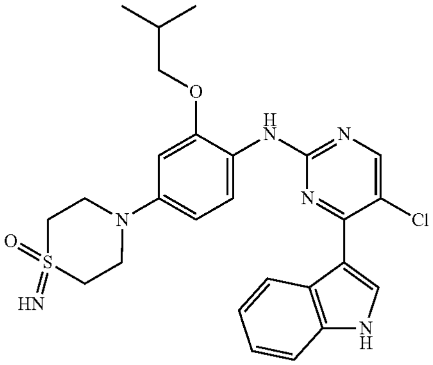

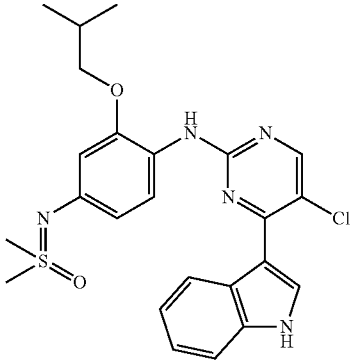

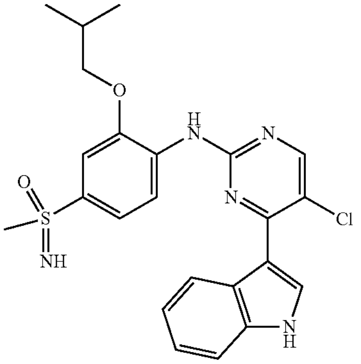

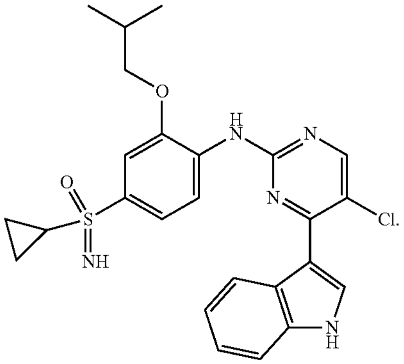

In several embodiments, $R^1$ is —Cl, $R^2$ is indole, $R^3$ is —$OR^6$, $R^6$ is $C_1$-$C_6$-alkyl having 4 carbons (e.g., —$CH_2CH(CH_3)_2$), X is CH, $R^4$ is as defined elsewhere herein, and the structure of Formula (I) is represented by any one of the following:

In several embodiments, $R^1$ is —Cl, $R^2$ is indole, $R^3$ is —$OR^6$, $R^6$ is —$(CH_2)_n$heteroaryl where n is 0, X is CH, $R^4$ is as defined elsewhere herein, and the structure of Formula (I) is represented by any one of the following:

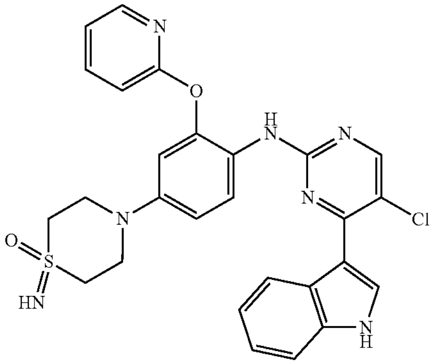

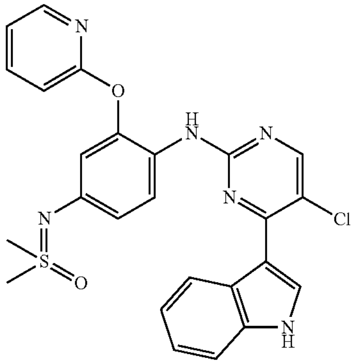

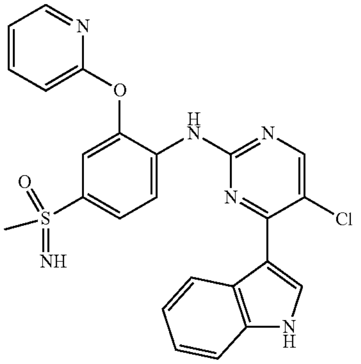

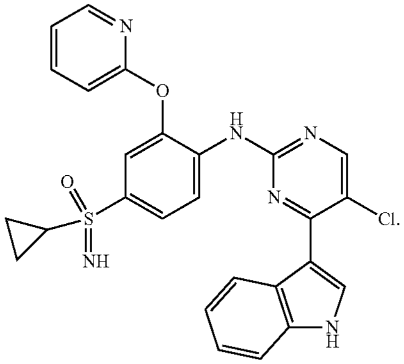

In several embodiments, $R^1$ is —Cl, $R^2$ is indole, $R^3$ is —$N(R^7)_2$, an instance of $R^7$ is —H and the other instance of $R^7$ is —$(CH_2)_n$heteroaryl where n is 0, X is CH, $R^4$ is as defined elsewhere herein, and the structure of Formula (I) is represented by any one of the following:

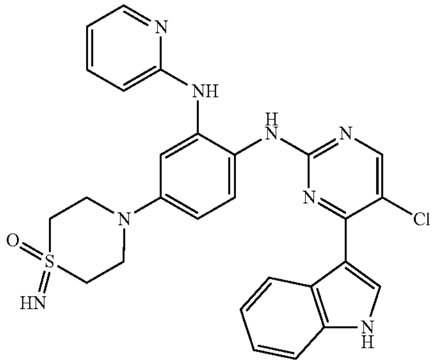

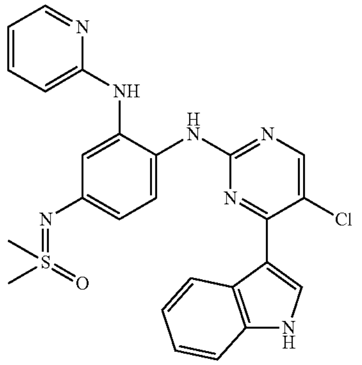

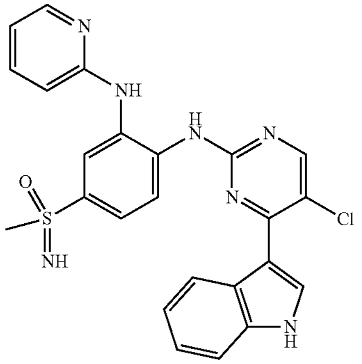

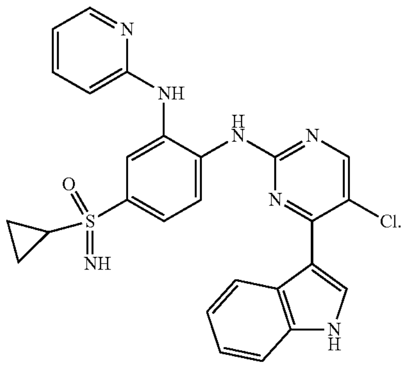

In several embodiments, $R^1$ is —Cl, $R^2$ is indole, $R^3$ is —NHCOCH=$CH_2$, X is CH, $R^4$ is as defined elsewhere herein, and the structure of Formula (I) is represented by any one of the following:

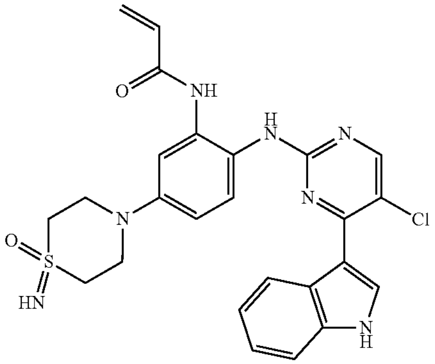
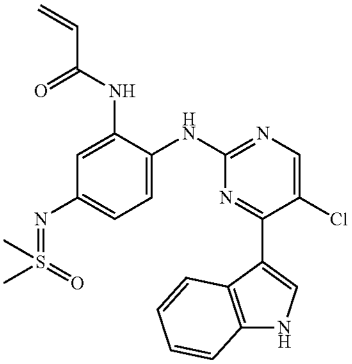
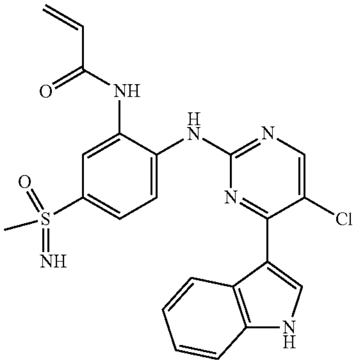
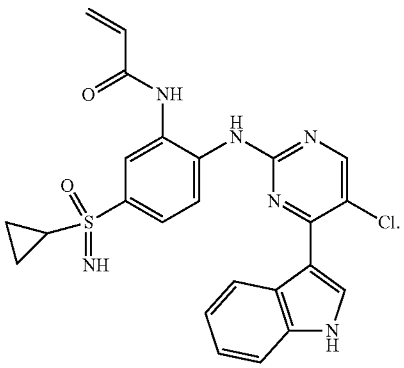
In several embodiments, $R^1$ is —Cl, $R^2$ is indole, $R^3$ is —NHCOCH═CHCH$_2$N(Me)$_2$, X is CH, $R^4$ is as defined elsewhere herein, and the structure of Formula (I) is represented by any one of the following:
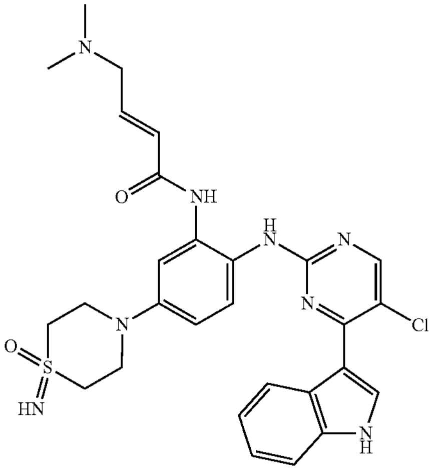
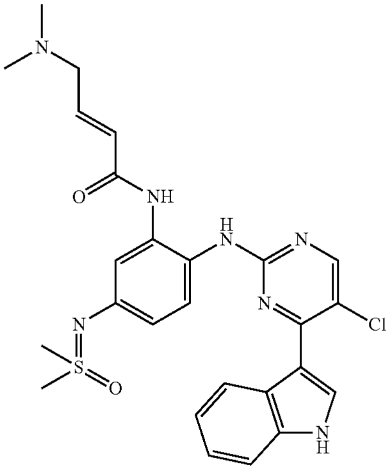
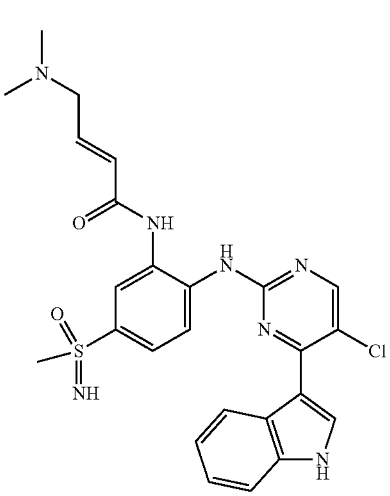

-continued

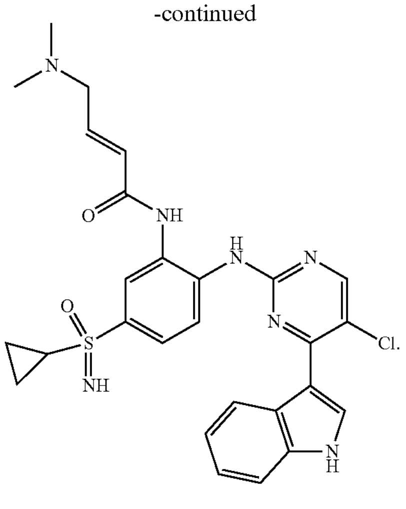

In several embodiments, as shown below, $R^1$ is —Cl, $R^2$ $R^2$ is heteroaryl comprising 9 atoms (e.g., pyrrolopyridine), $R^3$ is —OMe, X is CH, $R^4$ is as defined elsewhere herein, and the structure of Formula (I) is represented by any one of the following:

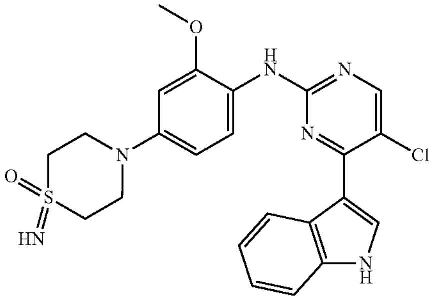

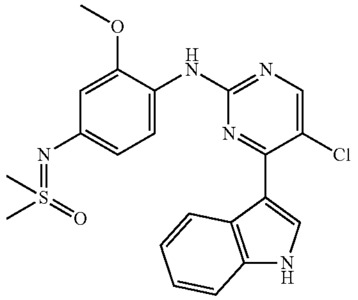

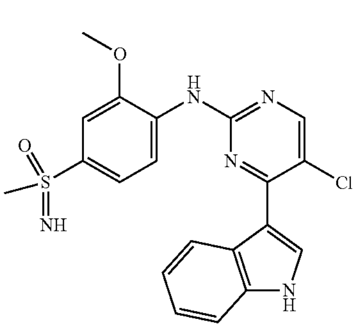

-continued

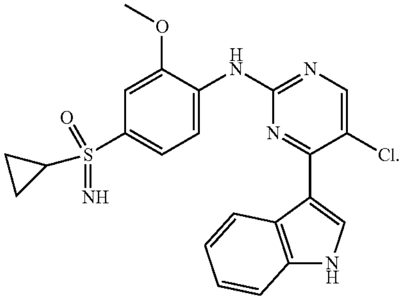

In several embodiments, as shown below, $R^1$ is —Cl, $R^2$ is indazole, $R^3$ is —OMe, X is CH, $R^4$ is as defined elsewhere herein, and the structure of Formula (I) is represented by any one of the following:

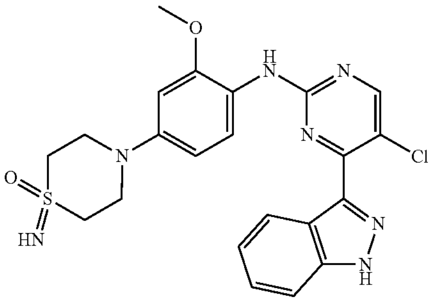

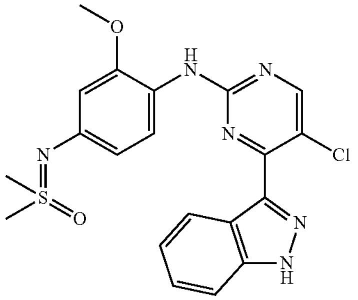

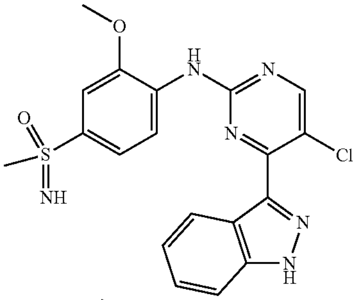

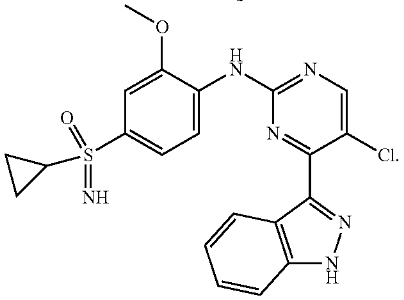

In several embodiments, as shown below, $R^1$ is —Cl, $R^2$ is heteroaryl comprising 9 atoms, $R^3$ is —OMe, X is CH, $R^4$ is as defined elsewhere herein, and the structure of Formula (I) is represented by any one of the following:

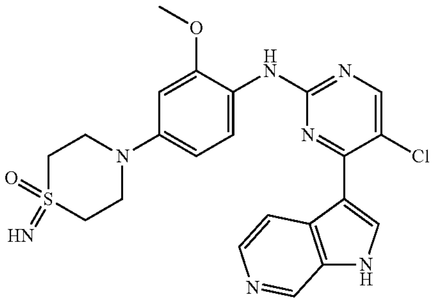

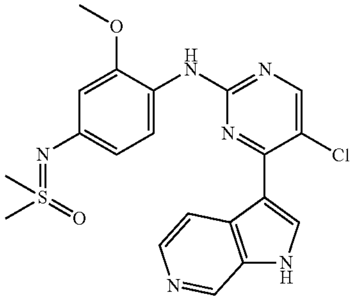 [SMILES: COc1cc(N=S(C)(C)=O)ccc1Nc1ncc(Cl)c(-c2c[nH]c3ccccc23)n1]

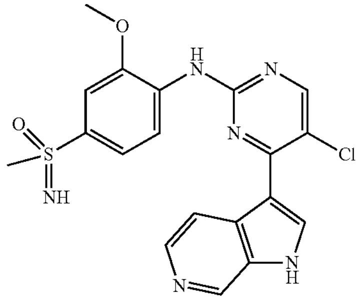

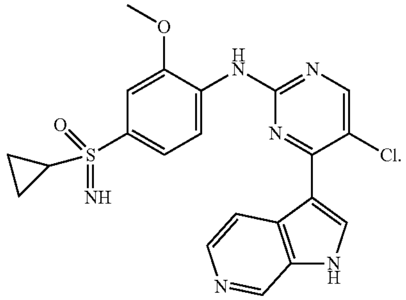

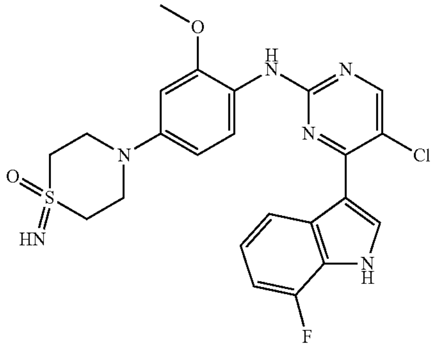

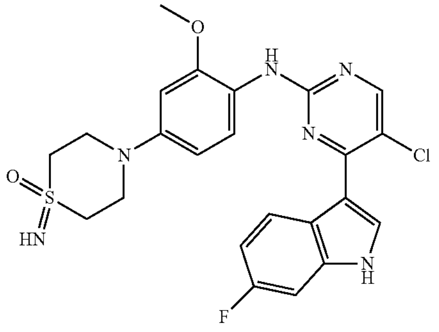

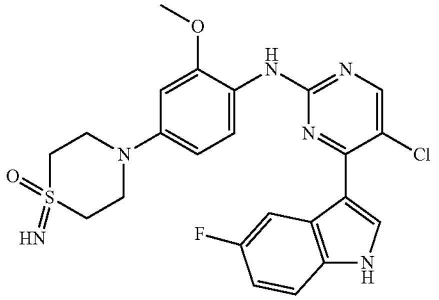

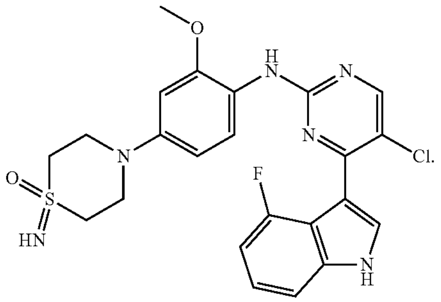

In several embodiments, as shown below, $R^1$ is —Cl, $R^2$ is heteroaryl comprising 9 atoms and is substituted with $R^5$, $R^5$ is —F, $R^3$ is —OMe, X is CH, $R^4$ is as defined elsewhere herein, and the structure of Formula (I) is represented by any one of the following:

In several embodiments, as shown below, $R^1$ is —Cl, $R^2$ is heteroaryl comprising 9 atoms and is substituted with $R^5$, $R^5$ is —$OR^6$, $R^6$ is -Me, $R^3$ is —OMe, X is CH, $R^4$ is as defined elsewhere herein, and the structure of Formula (I) is represented by any one of the following:

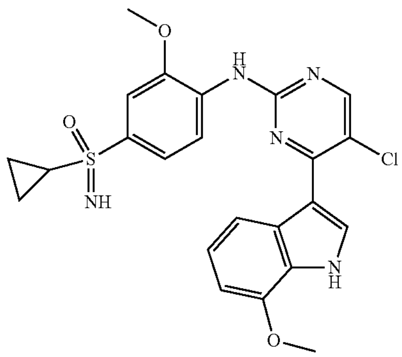
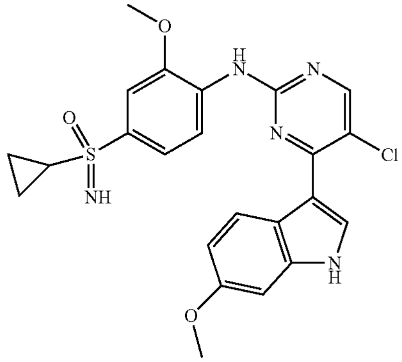
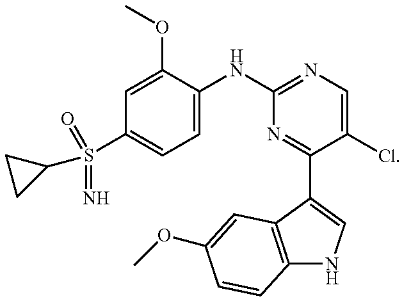
Cl.
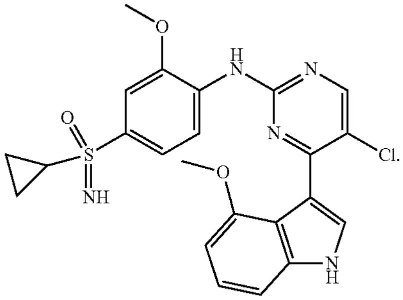
Cl.
In several embodiments, as shown below, $R^1$ is —Cl, $R^2$ is heteroaryl comprising 9 atoms and is substituted with $R^5$, $R^5$ is —NHCOCH=$CH_2$, $R^3$ is —OMe, X is CH, $R^4$ is as defined elsewhere herein, and the structure of Formula (I) is represented by any one of the following:
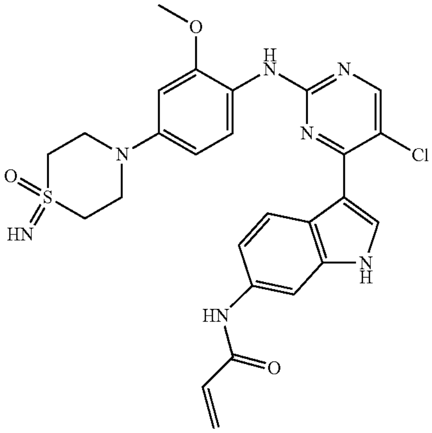
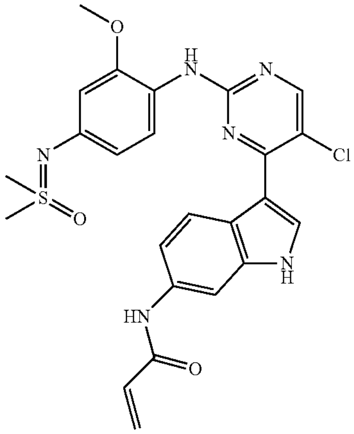
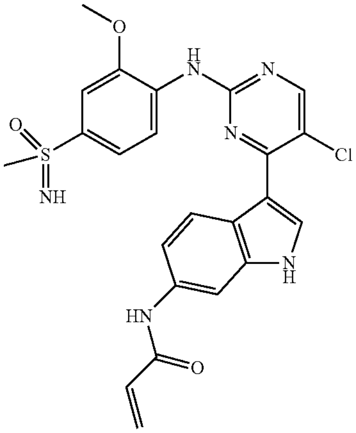

-continued

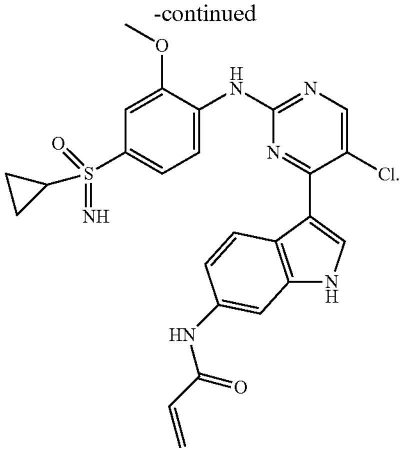

In several embodiments, as shown below, $R^1$ is —Cl, $R^2$ is heteroaryl comprising 9 atoms and is substituted with $R^5$, $R^5$ is $—CH_2NHCOCH{=}CH_2$, $R^3$ is —OMe, X is CH, $R^4$ is as defined elsewhere herein, and the structure of Formula (I) is represented by any one of the following:

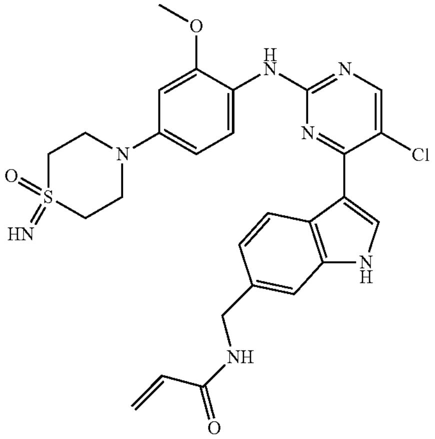

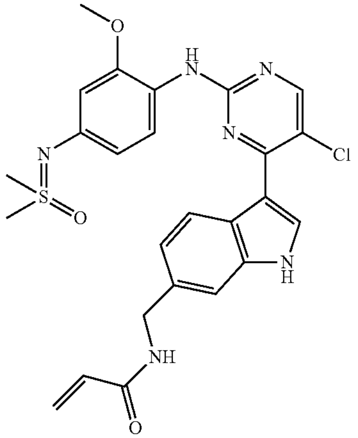

-continued

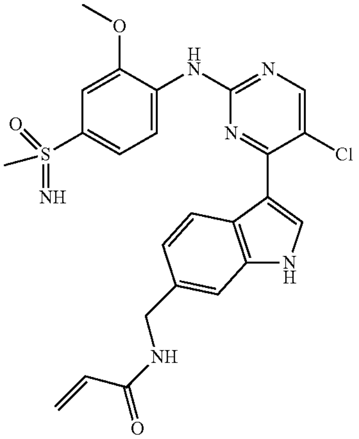

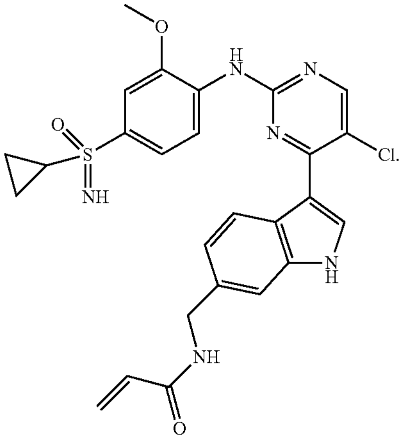

In several embodiments, as shown below, $R^1$ is —Cl, $R^2$ is heteroaryl comprising 9 atoms and is substituted with $R^5$, $R^5$ is -Me, $R^3$ is —OMe, X is CH, $R^4$ is as defined elsewhere herein, and the structure of Formula (I) is represented by any one of the following:

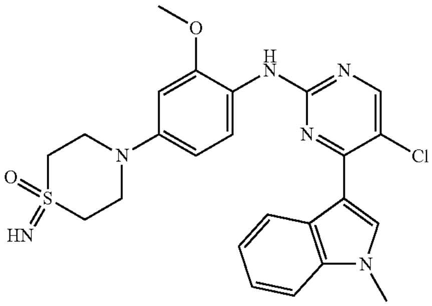

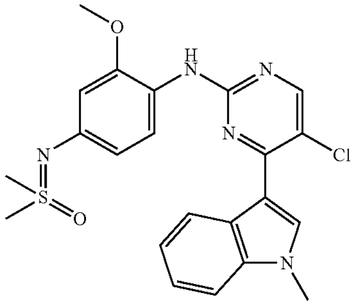

-continued

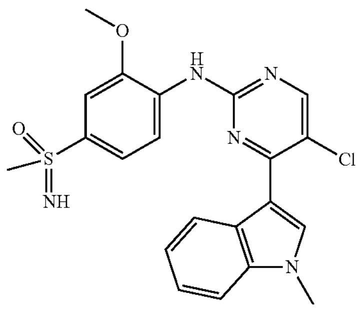

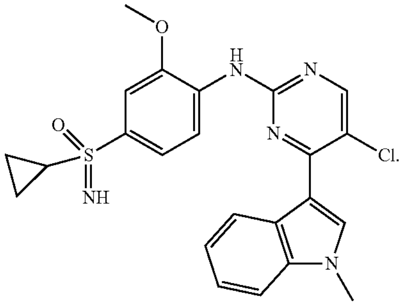

In several embodiments, as shown below, $R^1$ is —Cl, $R^2$ is quinoline, $R^3$ is —OMe, X is CH, $R^4$ is as defined elsewhere herein, and the structure of Formula (I) is represented by any one of the following:

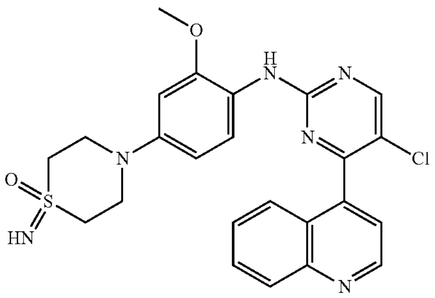

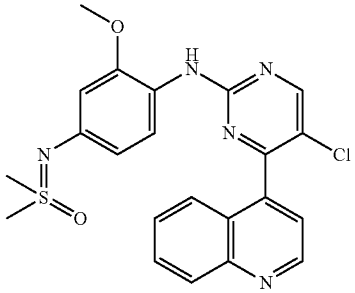

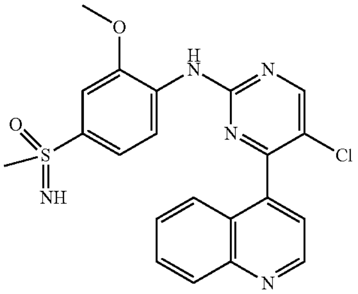

-continued

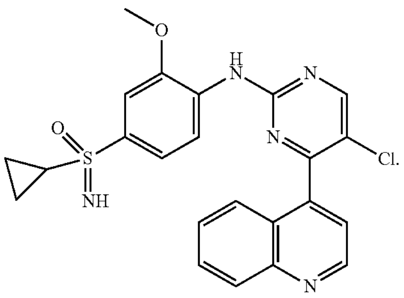

In several embodiments, as shown below, $R^1$ is —Cl, $R^2$ is quinazoline, $R^3$ is —OMe, X is CH, $R^4$ is as defined elsewhere herein, and the structure of Formula (I) is represented by any one of the following:

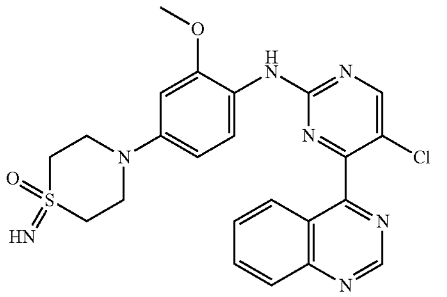

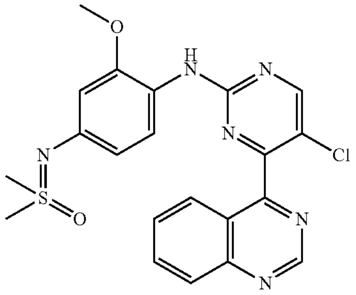

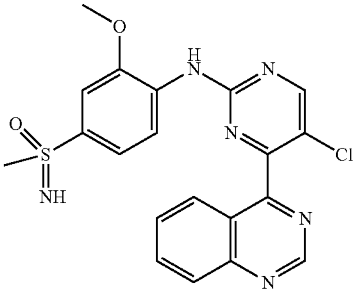

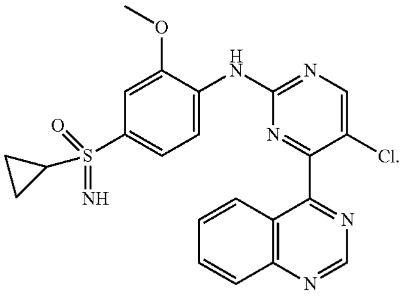

In several embodiments, as shown below, $R^1$ is —Cl, $R^2$ is indole, $R^3$ is —OMe, X is CH, $R^4$ is as defined elsewhere herein, and the structure of Formula (I) is represented by any one of the following:

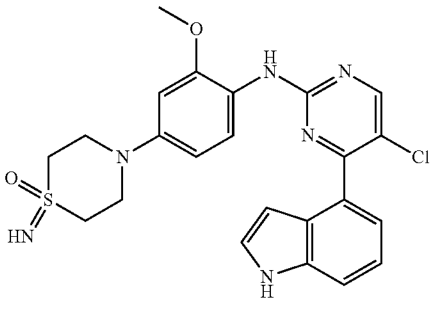

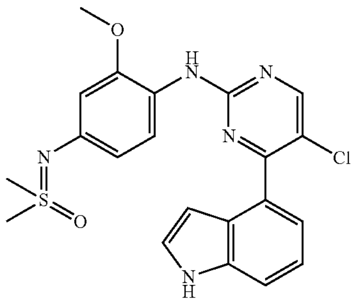

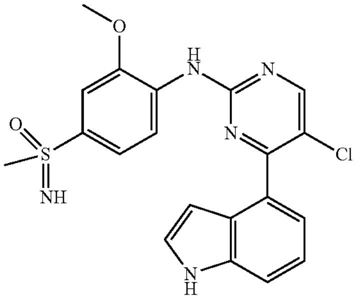

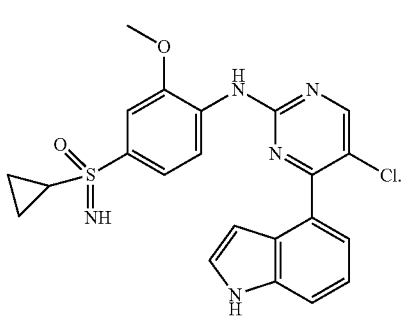

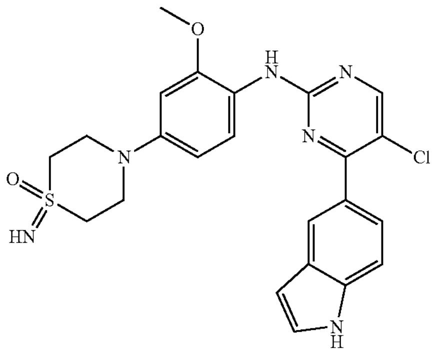

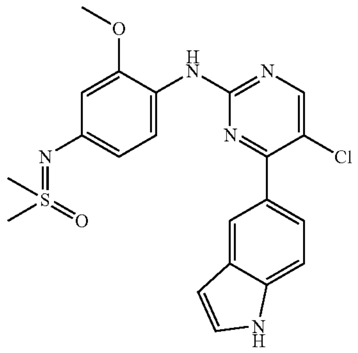

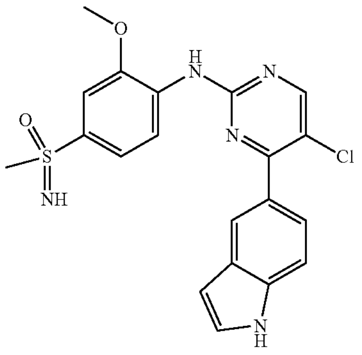

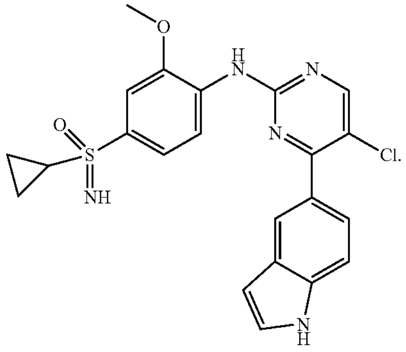

In several embodiments, as shown below, $R^1$ is —Cl, $R^2$ is indole, $R^3$ is —OMe, X is CH, $R^4$ is as defined elsewhere herein, and the structure of Formula (I) is represented by any one of the following:

In several embodiments, as shown below, $R^1$ is —F, $R^2$ is indole, $R^3$ is —OMe, X is CH, $R^4$ is as defined elsewhere herein, and the structure of Formula (I) is represented by any one of the following:

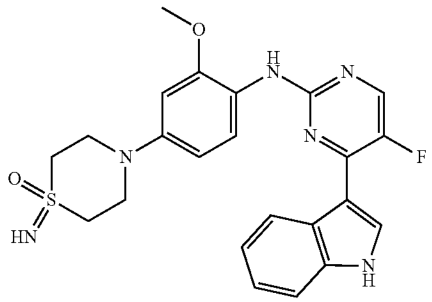

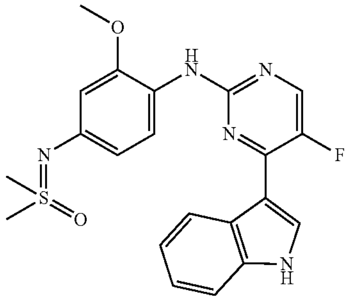

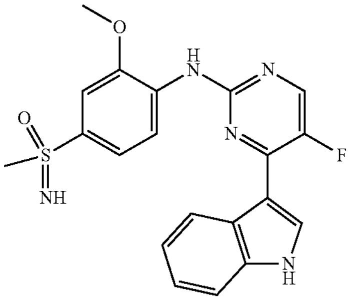

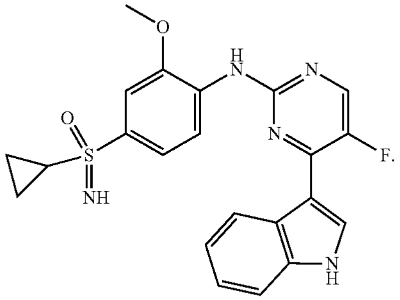

In several embodiments, as shown below, $R^1$ is —Br, $R^2$ is indole, $R^3$ is —OMe, X is CH, $R^4$ is as defined elsewhere herein, and the structure of Formula (I) is represented by any one of the following:

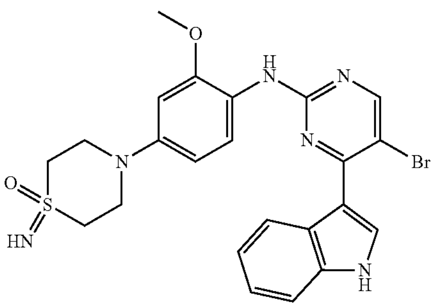

-continued

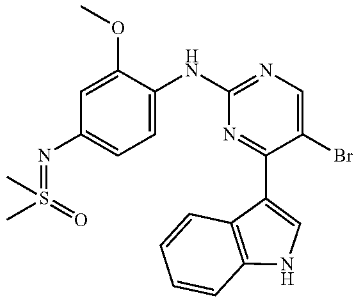

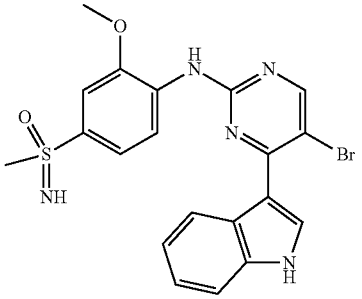

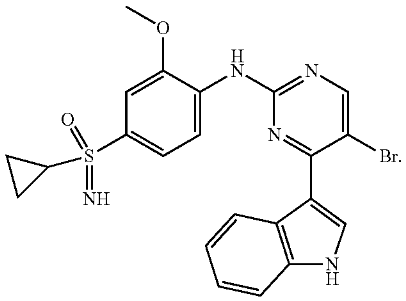

In several embodiments, as shown below, $R^1$ is —CN, $R^2$ is indole, $R^3$ is —OMe, X is CH, $R^4$ is as defined elsewhere herein, and the structure of Formula (I) is represented by any one of the following:

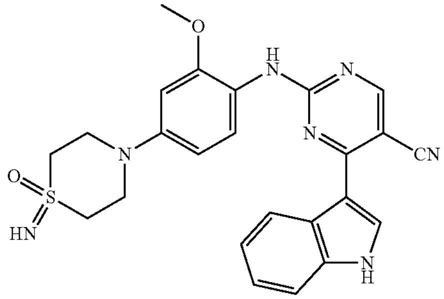

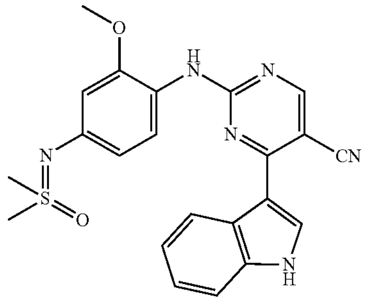

-continued
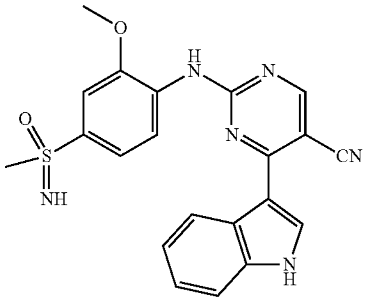
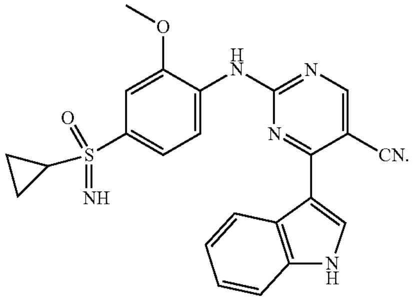
In several embodiments, as shown below, $R^1$ is -Me, $R^2$ is indole, $R^3$ is —OMe, X is CH, $R^4$ is as defined elsewhere herein, and the structure of Formula (I) is represented by any one of the following:
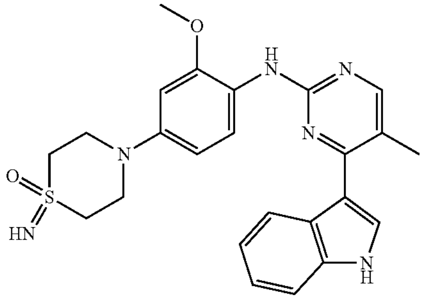
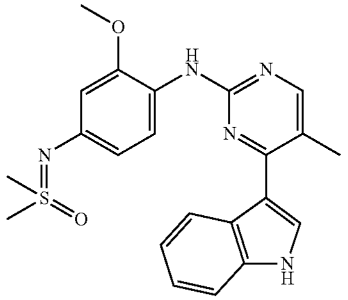
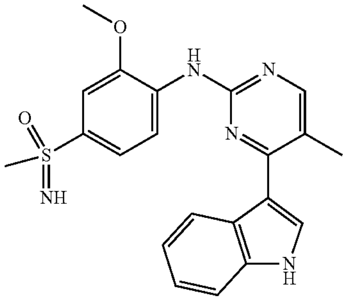
-continued
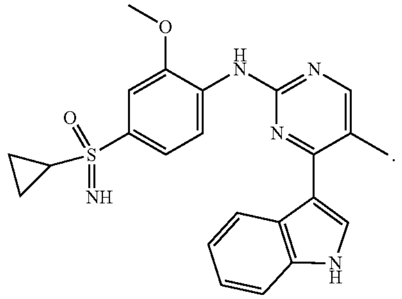
In some aspects, the compounds of are of the formula:
(i)
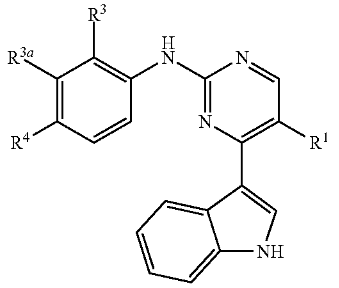
(ii)
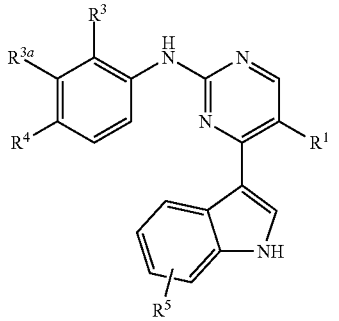
(iii)
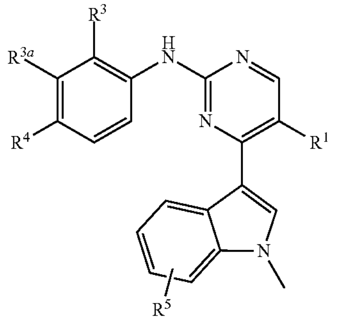
(iv)
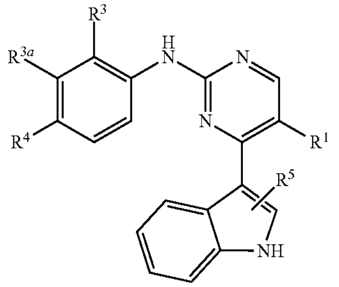

-continued (v)

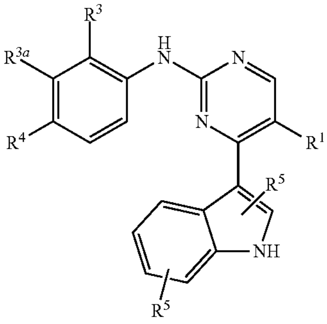

(vi)

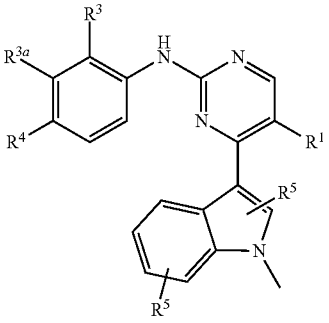

In these aspects, $R^4$ is as described elsewhere herein. In some aspects, $R^4$ is

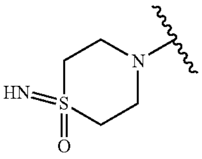
,
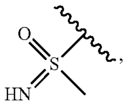
,
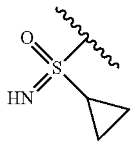
, or

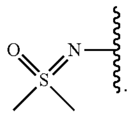
.

Also in these aspects, $R^1$ is preferably H, F, Cl, $C_{1-6}$alkyl (e.g., methyl). In some aspects, $R^1$ is H. In some aspects, $R^1$ is F. In some aspects, $R^1$ is Cl. In some aspects, $R^1$ is $C_{1-6}$alkyl (e.g., methyl).

Also in these aspects, $R^3$ is preferably H, F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl. Also in these aspects, $R^{3a}$ is preferably H, F, Cl, $OC_{1-6}$alkyl (e.g., $OCH_3$, OEt, OiPr, OiBu), $C_{1-6}$alkyl (e.g., methyl, ethyl, ipropyl), $NO_2$, $NH_2$, NHC(O)CH═$CH_2$, or O($C_{1-6}$alk)heterocycloalkyl. In some of these aspects, $R^3$ and $R^{3a}$ are each H. In some aspects, $R^{3a}$ is H and $R^3$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$ alk)heterocycloalkyl. In some aspects, $R^3$ is H and $R^{3a}$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl.

In those aspects including one or more $R^5$, each $R^5$ is preferably F, Cl, $C_{1-6}$alkyl (e.g., methyl, ethyl, ipropyl), $OC_{1-6}$alkyl (e.g., $OCH_3$, OEt, OiPr, OiBu), C(O)$C_{1-6}$alkyl, hydroxy$C_{1-6}$alkyl, $NH_2$, NHC(O)CH═$CH_2$, NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), $C_{1-6}$alk-NHC(O)CH═$CH_2$, NHC(O)CH═CH—$C_{1-6}$alk-$NH_2$, NHC(O)CH═CH—$C_{1-6}$alk-$NHC_{1-6}$alkyl, NHC(O)CH═CH—$C_{1-6}$alk-N($C_{1-6}$alkyl$)_2$, or NHC(O)$C_{1-6}$alkyl, NHC(O)$C_{3-6}$cycloalkyl.

In some aspects, the compounds are of the formula:

(vii)

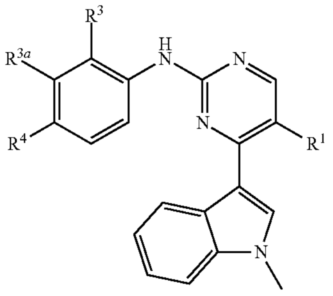

(viii)

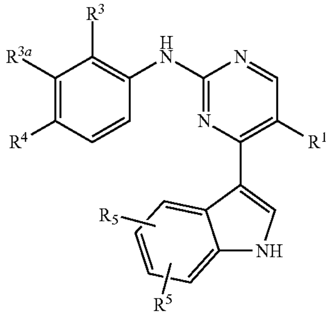

(ix)

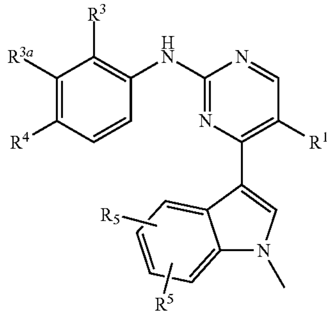

(x)

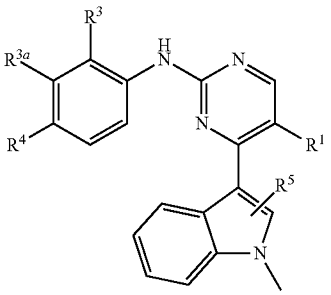

-continued (xi)

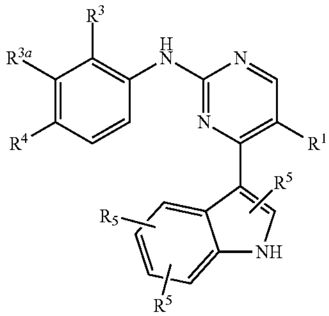

(xii)

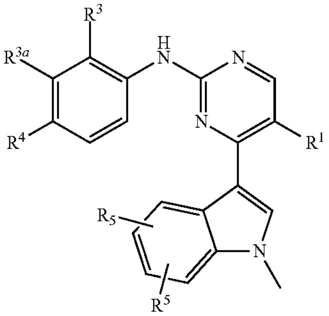

In these aspects, $R^4$ is as described elsewhere herein. In some aspects, $R^4$ is

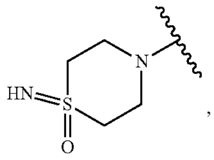
,
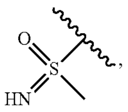
,
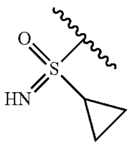
, or

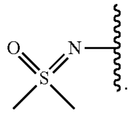
.

Also in these aspects, $R^1$ is preferably H, F, Cl, $C_{1-6}$alkyl (e.g., methyl). In some aspects, $R^1$ is H. In some aspects, $R^1$ is F. In some aspects, $R^1$ is Cl. In some aspects, $R^1$ is $C_{1-6}$alkyl (e.g., methyl).

Also in these aspects, $R^3$ is preferably H, F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl. Also in these aspects, $R^{3a}$ is preferably H, F, Cl, $OC_{1-6}$alkyl (e.g., $OCH_3$, OEt, OiPr, OiBu), $C_{1-6}$alkyl (e.g., methyl, ethyl, ipropyl), $NO_2$, $NH_2$, NHC(O)CH═$CH_2$, or O($C_{1-6}$alk)heterocycloalkyl. In some of these aspects, $R^3$ and $R^{3a}$ are each H. In some aspects, $R^{3a}$ is H and $R^3$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl. In some aspects, $R^3$ is H and $R^{3a}$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl.

In those aspects including one or more $R^5$, each $R^5$ is preferably F, Cl, $C_{1-6}$alkyl (e.g., methyl, ethyl, ipropyl), $OC_{1-6}$alkyl (e.g., $OCH_3$, OEt, OiPr, OiBu), C(O)$C_{1-6}$alkyl, hydroxy$C_{1-6}$alkyl, $NH_2$, NHC(O)CH═$CH_2$, NHC(O)$CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), $C_{1-6}$alk-NHC(O)CH═$CH_2$, NHC(O)CH═CH—$C_{1-6}$alk-$NH_2$, NHC(O)CH═CH—$C_{1-6}$alk-NH$C_{1-6}$alkyl, NHC(O)CH═CH—$C_{1-6}$alk-N($C_{1-6}$alkyl)$_2$, or NHC(O)$C_{1-6}$alkyl, NHC(O)$C_{3-6}$cycloalkyl.

In some aspects, the compounds of are of the formula (xiii)

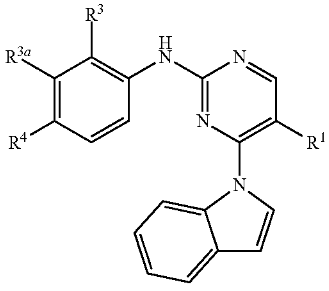

(xiv)

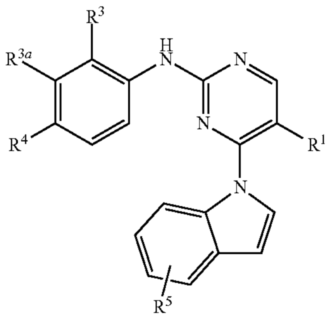

(xv)

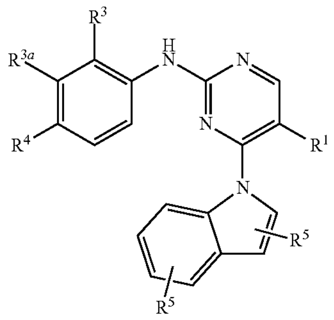

(xvi)

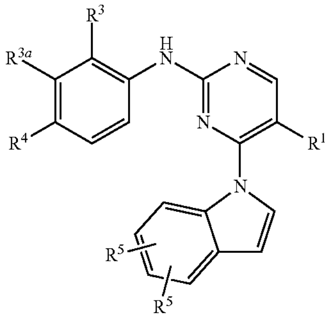

-continued (xvii)

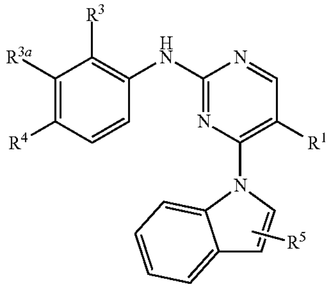

(xviii)

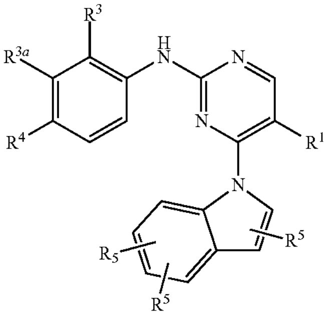

In these aspects, $R^4$ is as described elsewhere herein. In some aspects, $R^4$ is

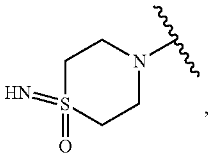
,
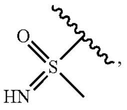
,
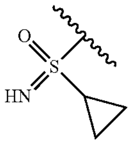
, or

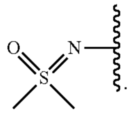

Also in these aspects, $R^1$ is preferably H, F, Cl, $C_{1-6}$alkyl (e.g., methyl). In some aspects, $R^1$ is H. In some aspects, $R^1$ is F. In some aspects, $R^1$ is Cl. In some aspects, $R^1$ is $C_{1-6}$alkyl (e.g., methyl).

Also in these aspects, $R^3$ is preferably H, F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl. Also in these aspects, $R^{3a}$ is preferably H, F, Cl, $OC_{1-6}$alkyl (e.g., $OCH_3$, OEt, OiPr, OiBu), $C_{1-6}$alkyl (e.g., methyl, ethyl, ipropyl), $NO_2$, $NH_2$, NHC(O)CH═$CH_2$, or O($C_{1-6}$alk)heterocycloalkyl. In some of these aspects, $R^3$ and $R^{3a}$ are each H. In some aspects, $R^{3a}$ is H and $R^3$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk)heterocycloalkyl. In some aspects, $R^3$ is H and $R^{3a}$ is F, Cl, $OC_{1-6}$alkyl (e.g., $OCH_3$, OEt, OiPr, OiBu), $C_{1-6}$alkyl, $NO_2$, $NH_2$, NHC(O)CH═$CH_2$, or O($C_{1-6}$alk) heterocycloalkyl.

In those aspects including one or more $R^5$, each $R^5$ is preferably F, Cl, $C_{1-6}$alkyl (e.g., methyl, ethyl, ipropyl), $OC_{1-6}$alkyl (e.g., $OCH_3$, OEt, OiPr, OiBu), C(O)$C_{1-6}$alkyl, hydroxy$C_{1-6}$alkyl, $NH_2$, NHC(O)CH═$CH_2$, NHC(O) $CR^{10}$═$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), $C_{1-6}$alk-NHC(O)CH═$CH_2$, NHC(O)CH═CH—$C_{1-6}$alk-$NH_2$, NHC(O)CH═CH—$C_{1-6}$alk-NH$C_{1-6}$alkyl, NHC(O)CH═CH—$C_{1-6}$alk-N($C_{1-6}$alkyl)$_2$, or NHC(O)$C_{1-6}$alkyl, NHC(O)$C_{3-6}$cycloalkyl.

In some aspects, the compounds are of the formula:

(xix)

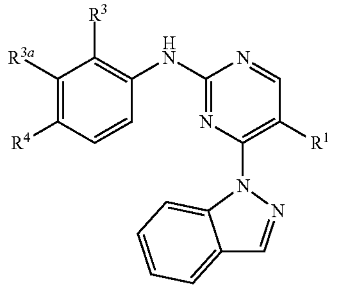

(xx)

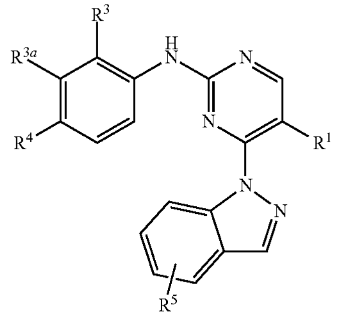

(xxi)

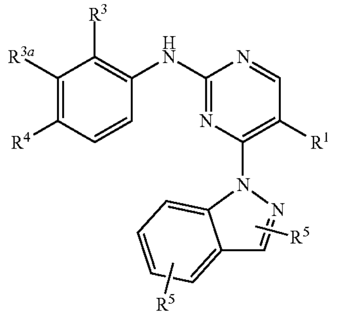

(xxii)

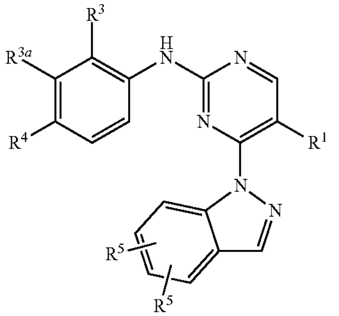

-continued (xviii)

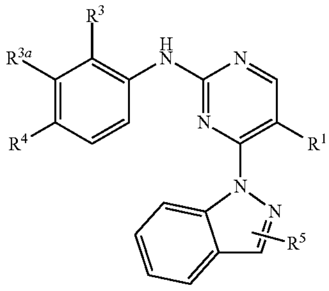

(xxiv)

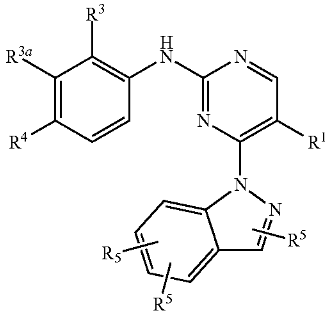

In these aspects, $R^4$ is as described elsewhere herein. In some aspects, $R^4$ is

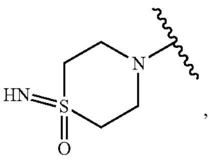, 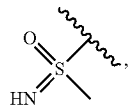, 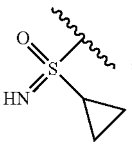, or

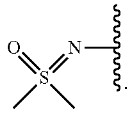.

Also in these aspects, $R^1$ is preferably H, F, Cl, $C_{1-6}$alkyl (e.g., methyl). In some aspects, $R^1$ is H. In some aspects, $R^1$ is F. In some aspects, $R^1$ is Cl. In some aspects, $R^1$ is $C_{1-6}$alkyl (e.g., methyl).

Also in these aspects, $R^3$ is preferably H, F, Cl, $OC_{1-6}$alkyl (e.g., $OCH_3$, OEt, OiPr, OiBu), $C_{1-6}$alkyl, $NO_2$, $NH_2$, NHC(O)CH=CH$_2$, or O($C_{1-6}$alk)heterocycloalkyl. Also in these aspects, $R^{3a}$ is preferably H, F, Cl, $OC_{1-6}$alkyl (e.g., $OCH_3$, OEt, OiPr, OiBu), $C_{1-6}$alkyl (e.g., methyl, ethyl, ipropyl), $NO_2$, $NH_2$, NHC(O)CH=CH$_2$, or O($C_{1-6}$alk)heterocycloalkyl. In some of these aspects, $R^3$ and $R^{3a}$ are each H. In some aspects, $R^{3a}$ is H and $R^3$ is F, Cl, $OC_{1-6}$alkyl (e.g., $OCH_3$, OEt, OiPr, OiBu), $C_{1-6}$alkyl, $NO_2$, $NH_2$, NHC(O)CH=CH$_2$, or O($C_{1-6}$alk)heterocycloalkyl. In some aspects, $R^3$ is H and $R^{3a}$ is F, Cl, $OC_{1-6}$alkyl (e.g., $OCH_3$, OEt, OiPr, OiBu), $C_{1-6}$alkyl, $NO_2$, $NH_2$, NHC(O)CH=CH$_2$, or O($C_{1-6}$alk) heterocycloalkyl.

In those aspects including one or more $R^5$, each $R^5$ is preferably F, Cl, $C_{1-6}$alkyl (e.g., methyl, ethyl, ipropyl), $OC_{1-6}$alkyl (e.g., $OCH_3$, OEt, OiPr, OiBu), C(O)$C_{1-6}$alkyl, hydroxy$C_{1-6}$alkyl, $NH_2$, NHC(O)CH=CH$_2$, NHC(O)$CR^{10}$=$CHR^{10}$ (wherein each $R^{10}$ is independently H, F, Cl, $C_{1-6}$alkyl, $C_{1-6}$haloalkyl, $C_{1-6}$alkoxy, or $C_{1-6}$hydroxyalkyl), $C_{1-6}$alk-NHC(O)CH=CH$_2$, NHC(O)CH=CH—$C_{1-6}$alk-$NH_2$, NHC(O)CH=CH—$C_{1-6}$alk-NH$C_{1-6}$alkyl, NHC(O)CH=CH—$C_1$-6alk-N($C_{1-6}$alkyl)$_2$, or NHC(O)$C_{1-6}$alkyl, NHC(O)$C_{3-6}$cycloalkyl.

The FGFR receptors (FGFR1, FGFR2, FGFR3, and FGFR4) share several structural features in common, including three extracellular immunoglobulin-like (Ig) domains, a hydrophobic transmembrane domain, and an intracellular tyrosine kinase domain split by a kinase insert domain, followed by a cytoplasmic c-terminal tail (Johnson et al., Adv. Cancer Res. 60:1-40, 1993; and Wilkie et al., Curr. Biol. 5:500-507, 1995). In FGFR1, the kinase insert domain spans positions 582 to 595 of the alpha Al isoform of FGFR1. In FGFR2, the kinase insert domain spans positions 585 to 598 of the FGFR2 Ille isoform. In FGFR3, the kinase insert domain spans positions 576 to 589 of the FGFR3 Ille isoform. In FGFR4, the kinase insert domain spans positions 571 to 584 of FGFR4 isoform 1. The c-terminal tail of FGFRs begins following the end of the tyrosine kinase domain and extends to the c-terminus of the protein. Several isoforms of each FGFR have been identified and are the result of alternative splicing of their mRNAs (Johnson et al., Mol. Cell. Biol. 11:4627-4634, 1995; and Chellaiah et al., J. Biol. Chem. 269:11620-11627, 1994).

A few of the receptor variants that result from this alternative splicing have different ligand binding specificities and affinities (Zimmer et al., J. Biol. Chem. 268:7899-7903, 1993; Cheon et al., Proc. Natl. Acad. Sci. U.S.A. 91:989-993, 1994; and Miki et al., Proc. Natl. Acad. Sci. U.S.A. 89:246-250, 1992). Protein sequences for FGFR proteins and nucleic acids encoding FGFR proteins are known in the art. Signaling by FGFRs regulates key biological processes including cell proliferation, survival, migration, and differentiation. Dysregulation of a FGFR gene, a FGFR protein, or expression or activity, or level of the same, has been associated with many types of cancer. For example, dysregulation of FGFRs can occur by multiple mechanisms, such as FGFR gene overexpression, FGFR gene amplification, activating mutations (e.g., point mutations or truncations), and chromosomal rearrangements that lead to FGFR fusion proteins. Dysregulation of a FGFR gene, a FGFR protein, or expression or activity, or level of the same, can result in (or cause in part) the development of a variety of different FGFR-associated cancers.

FGFR fusion proteins are known in the art. See, e.g., Baroy et al., *PloS One;* 11(9):e0163859. doi: 10.1371/journal.pone.0163859, 2016; Ren et al., *Int. J. Cancer,* 139(4):836-40, 2016; Marchwicka et al., *Cell Biosci.,* 6:7. doi: 10.1186/s13578-016-0075-9, 2016; PCT Patent Application Publication No. WO 2014/071419A2; U.S. Patent Application Publication No. 2015/0366866A1; PCT Patent Application Publication No. WO 2016/084883A1; PCT Patent Application Publication No. WO 2016/030509A1; PCT Patent Application Publication No. WO 2015/150900A2; PCT Patent Application Publication No. WO 2015/120094A2; Kasaian et al., *BMC Cancer.,* 15:984, 2015; Vakil et al., *Neuro-Oncology,* 18:Supp. Supplement 3, pp. iii93. Abstract Number: LG-64, 17th International Symposium on Pediatric Neuro-Oncology, Liverpool, United Kingdom, 2016; Astsaturov et al., *Journal of Clinical Oncology,* 34:Supp. Supplement 15, Abstract Number: 11504, 2016 Annual Meeting of the American Society of Clinical Oncology, Chicago, IL; Heinrich et al., *Journal of Clinical Oncology,* 34:Supp. Supplement 15, Abstract Number: 11012, 2016 Annual Meeting of the American Society of Clinical Oncology, Chicago, IL; Hall et al., *Molecular Cancer Therapeutics*, Vol. 14, No. 12, Supp. 2, Abstract Number: B151, AACR-NCI-EORTC International Conference: Molecular Targets and Cancer Therapeutics, 2015; Reuther et al., *Journal of Molecular Diagnostics*, Vol. 17, No. 6, pp. 813, Abstract Number: ST02, 2015 Annual Meeting of the Association for Molecular Pathology, Austin, TX; Moeini et al., *Clin. Cancer. Res.*, 22(2):291-300, 2016; Schrock et al, *J Thorac. Oneal*. pii 51556-0864(18)30674-9, 2018. doi: 10.1016/j.jtho.2018.05.027; Pekmezci et al, *Acta Nurotapho/. Commun.* 6(1):47. doi: 10.1186/s40478-018-0551-z; Lowery et al. *Clin Cancer Res*. pii: clincanres.0078.2018. doi: 10.1158/1078-0432.CCR-18-0078; Ryland et al. *J Clin Patho/*pii: jclinpath-2018-205195, 2018. doi: 10.1136/jclinpath-2018-205195; Ferguson et al. *J Neuropatho/ Exp Neural* 77(6):437-442, 2018. doi: 10.1093/jnen/nly022; Wu et al, *BMC Cancer* 18(1):343, 2018. doi: 10.1186/s12885-018-4236-6; Shibata et al, *Cancer Sci* 109 (5):1282-1291, 2018. doi: 10.1111/cas.13582; Papdopoulos et al, *Br J Cancer,* 1117(11):1592-1599, 2017. doi: 10.1038/bjc.2017.330; Hall et al, *PLoS One,* 11(9):e1062594, 2016. doi: 10.1371/journal.pone.0162594; Johnson et al, *Oncologist,* 22(12):1478-1490, 2017. doi: 10.1634/theoncologist.2017-0242; Yang et al, *Am J Hum Genet,* 98(5):843-856, 2016. doi: 10.1016/j.ajhg.2016.03.017; U.S. Patent Application Publication No. 2013/009621; Babina and Turner, *Nat Rev Cancer* 17(5):318-332, 2017. doi: 10.1038/nrc.2017.8; Ryland et al, *J Chn Patho/,* 2018 May 14. pii: jclinpath-2018-205195. doi: 10.1136/jclinpath-2018-205195; Kumar et al, *Am J Clin Patho/.* 143(5):738-748, 2015. doi: 10.1309/AJCPUD6W1JLQQMNA; Grand et al, *Genes Chromosomes Cancer* 40(1):78-83, 2004. doi: 10.1002/gcc.20023; Reeser, et al, *J Mo/ Diagn,* 19(5):682-696, 2017. doi: 10.1016/j.jmoldx.2017.05.006; Basturk, et al, *Mod Patho/,* 30(12):1760-1772, 2017. doi: 10.1038/modpathol.2017.60; Wang, et al, *Cancer* 123(20):3916-3924, 2017. doi: 10.1002/cncr.30837; Kim, et al, *Oncotarget,* 8(9):15014-15022, 2017. doi: 10.18632/oncotarget.14788; Busse, et al, *Genes Chromosomes Cancer,* 56(10):730-749, 2017. doi: 10.1002/gcc.22477; Shi, et al, *J Transl Med.,* 14(1):339, 2016. doi: 10.1186/s12967-016-1075-6, each of which is incorporated by reference herein.

FGFR point mutations are known in the art. See, e.g., UniParc entry UPI00000534B8; UniParc entry UPI0000001COF; UniParc entry UPI000002A99A; UniParc entry UPI000012A72A; UniParc entry UPI000059D1C2; UniParc entry UPI000002A9AC; Uniparc entry UPI000012A72C; Uniparc entry UPI000012A72D; Uniparc entry UPI000013EOB8; Uniparc entry UPI00010E06A3; Gen bank entry BAD92868.1; Ang et al., *Diagn. Mo/. Patho/*. Feb. 24, 2014; U.S. Patent Application Publication No. 2011/0008347; Gallo et al., *Cytokine Growth Factor Rev.* 26:425-449, 2015; Davies et al., *J. Cancer Res.* 65:7591, 2005; Kelleher et al., *Carcinogenesis* 34:2198, 2013; Cazier et al., *Nat. Commun.* 5:3756, 2014; Liu et al., *Genet. Mo/. Res.* 13:1109, 2014; Trudel et al., *Blood* 107:4039, 2006; Gallo et al., *Cytokine Growth Factor Rev.* 26:425, 2015; Liao et al., *Cancer Res.* 73:5195-5205, 2013; Martincorena et al., *Science* 348:880 (2015); U.S. Patent Application Publication No. US2016/0235744A1; U.S. Pat. No. 9,254,288B2; U.S. Pat. No. 9,267,176B2; U.S. Patent Application Publication No. S2016/0215350A1; European Patent Application Publication No. EP3023101A1; PCT Patent Application Publication No. WO2016105503A1; Rivera et al., *Acta. Neuropatho/.,* 131(6):847-63, 2016; Lo Iacono et al., *Oncotarget.,* 7(12):14394-404, 2016; Deeken et al., *Journal of Clinical Oncology,* 34:Supp. Supplement 15, pp. iii93. Abstract Number: el 7520, 2016 Annual Meeting of the American Society of Clinical Oncology, Chicago, IL; Sullivan et al., *Journal of Clinical Oncology,* 34:Supp. Supplement 15, pp. iii93. Abstract Number: 11596, 2016 Annual Meeting of the American Society of Clinical Oncology, Chicago, IL; Nguyen et al., *Molecular Cancer Therapeutics*, Vol. 14, No. 12, Supp. 2, Abstract Number: C199, AACR-NCI-EORTC International Conference: Molecular Targets and Cancer Therapeutics, 2015; Li et al., *Hum. Patho/.,* 55:143-50, 2016; European Patent No. EP2203449B1; Yoza et al., *Genes Cells,* (10):1049-1058, 2016; U.S. Pat. No. 9,254,288B2; European Patent Application Publication No. 3023101A1; PCT Application Publication No. WO 2015/099127A1; European Patent No. EP2203449B1; Yoza et al., *Genes Cells,* (10):1049-1058, 2016; Bunney et al., *EbioMedicine,* 2(3):194-204, 2015; Byron et al., *Neop/asia,* 15(8):975-88, 2013; European Patent Application Publication No. EP3023101A1; PCT Application Publication No. WO 2015/099127A1; Thussbas et al., *J. Clin. Oneal.,* 24(23):3747-55, 2006; Chell et al., *Oncogene,* 32(25):3059-70, 2013; Tanizaki et al, *Cancer Res.* 75(15):3149-3146 doi: 10.1158/0008-5472.CAN-14-3771; Yang et al, *EBioMedicine* pii S2352-3964(18)30218-4. doi: 10.1016/j.ebiom.2018.06.011; Jakobsen, et al *Oncotarget* 9(40): 26195-26208, 2018. doi: 10.18632/oncotarget.25490; Stone, et al *Acta Neuropatho/* 135(1):115-129, 2017. doi: 10.1007/s00401-017-1773-z; Pekmezci et al, *Acta Nurotaphol. Commun.* 6(1):47. doi: 10.1186/s40478-018-0551-z; De Mattos-Arruda et al, *Oncotarget* 9(29):20617-20630, 2018. doi: 10.18632/oncotarget.25041; Oliveira et al, *J Exp Clin Cancer Res* 37(1):84, 2018. doi: 10.1186/513046-018-0746-y; Cha et al, *Mo/ Oneal* 12(7):993-1003, 2018. doi: 10.1002/1878-0261.12194; Ikeda et al, *Oncologist,* 23(5):586-593, 2018. doi: 10.1634/theoncologist.2017-0479; Pelaez-Garda et al, *PLoS One,* 8(5):e63695, 2013. doi: 10.1371/journal-.pone.0063695; Shimada et al, *Oncotarget,* 8(55):93567-93579, 2017. doi: 10.18632/oncotarget.20510; Welander et al, *World J Surg,* 42(2):482-489, 2018. doi: 10.1007/s00268-01 7-4320-0; Chandrani et al, *Ann Oneal,* 28(3):597-603, 2017. doi: 10.1093/annonc/mdw636; Dalin et al, *Nat Commun,* 8(1):1197, 2017. doi: 10.1038/s41467-017-01178-z; Taurin et al, *Intl Gyneco/ Cancer,* 28(1):152-160, 2018. doi: 10.1097/IGC.0000000000001129; Haugh et al, *J Invest Dermatol* 138(2):384-393, 2018. doi: 10.1016/j.jid.2017.08.022; Babina and Turner, *Nat Rev Cancer* 17(5): 318-332, 2017. doi: 10.1038/nrc.2017.8; Greenman et al, *Nature* 446(7132):153-158, 2007. doi: 10.1038/nature05610; Helsten et al, *Clin Cancer Res,* 22(1):259-267, 2016. doi: 10.1158/1078-0432.CCR-14-3212; Kim et al, *BMC Urol,* 18:68, 2018. doi: 10.1186/s12894-018-0380-1; Goyal et al, *Cancer Discov,* 7(3):252-263, 2017. doi: 10.1158/2159-8290.CD-16-1000; Premov et al, *Oncogene,* 36(22):3168-3177, 2017. doi: 10.1038/onc.2016.464; Geelvink et al, *Int J Mo/ Sci.* 19(9): pii:E2548, 2018. doi: 10.3390/ijms19092548; Lee et al, *Exp Ther Med.* 16(2): 1343-1349, 2018. doi: 10.3892/etm.2018.6323; Kas et al, *Cancer Res,* 78(19):5668-5679, 2018. doi: 10.1158/0008-5472.CAN-18-0757; Chesi et al, *Blood,* 97(3):729-736, 2001. PMID: 11157491. Note that the deletion of FGFR3 isoform IIIe residues 795-808 also deletes the stop codon, elongating the protein by 99 amino acids (ATGPQQCEGSLAAHPAAGAQPLPGMRLSADGETATQSFGLCVCVCVCVCVCTSACACV RAHLASRCRGTLGVPAA VQRSPDWCCSTEGPLFWGDPVQNVSGPTRWDPVGQGAGPDMARPLPLHHGTSQGALG PSHTQS); Ge, et al, *Am J Cancer Res.* 7(7):1540-1553, 2017. PMID: 28744403; Jiao et al, *Nat Genet,* 45(12):1470-1473, 2013. doi: 10.1038/ng.2813; Jusakul et al, *Cancer Discov.* 7(10):1116-1135, 2017. doi: 10.1158/2159-8290.CD-17-0368; Guyard et al, *Respir Res.,* 18(1):120, 2018. doi: 10.1186/s12931-017-0605-y; Paik et al, *Clin Cancer Res.,* 23(18):5366-5373, 2017. doi: 10.1158/1078-0432.CCR-17-0645; Roy et al, *Mod Patho/,* 30(8):1133-1143, 2017. doi: 10.1038/modpathol.2017.33; Chakrabarty et al, *Br J Cancer,* 117(1):136-143, 2017. doi: 10.1038/bjc.2017.148; Hoang et al, *Sci Trans/Med.,* 5(197): 197ra102. doi: 10.1126/scitranslmed.3006200; Kim et al, *Ann Oneal.,* 28(6):1250-1259. doi: 10.1093/annonc/mdx098, each of which is incorporated by reference herein.

Compounds of the disclosure have been found to inhibit FGFR1, FGFR2 and/or FGFR3, and are therefore believed to be useful for treating diseases and disorders which can be treated with an inhibitor of FGFR1, FGFR2, FGFR3 and/or FGFR4. For example, compounds of the disclosure can be useful in treating FGFR-associated diseases and disorders, e.g., proliferative disorders such as cancers, including hematological cancers and solid tumor, and angiogenesis-related disorders. Compounds of the disclosure may also be useful in treating disorders arising from autosomal dominant mutations in FGFR, e.g., FGFR3, including, for example, developmental disorders. Developmental disorders to be treated with compounds of the disclosure include Achondroplasia (Ach) and related chondrodysplasia syndromes, including Hypochondroplasia (Hch), Severe Achondroplasia with Developmental Delay and Acanthosis Nigricans (SADDAN), and Thanatophoric dysplasia (TD).

Non-limiting examples of FGFR-associated diseases and disorders include Acanthosis nigricans, Achondroplasia, Apert syndrome, Beare-Stevenson syndrome (BSS), Camptodactyly, tall stature, and hearing loss syndrome (CATSHL) syndrome, cleft lip and palate, congenital heart disease (e.g., associated with ambiguous genitalia), craniosynostosis, Crouzon syndrome, ectrodactyly, encephalocraniocutaneous lipomatosis, Hartsfield syndrome, hypochondroplasia, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, lethal pulmonary acinar dysplasia, microphthalmia, Muenke coronal craniosynostosis, osteoglophonic dysplasia, Pfeiffer syndrome, seborrheic keratosis, syndactyly, thanatophoric dysplasia (e.g., type I or type II), trigonocephaly 1 (also called metopic craniosynostosis), and tumor-induced osteomalacia. Non-limiting examples of FGFR1 associated diseases and disorders include congenital heart disease (e.g., associated with ambiguous genitalia), craniosynostosis, encephalocraniocutaneous lipomatosis, Hartsfield syndrome, hypogonadotropic hypogonadism (e.g., hypogonadotropic hypogonadism 2 with or without anosmia, Kallman syndrome), ichthyosis vulgaris and/or atopic dermatitis, Jackson-Weiss syndrome, osteoglophonic dysplasia, Pfeiffer syndrome, trigonocephaly 1 (also called metopic craniosynostosis), and tumor-induced osteomalacia.

Non-limiting examples of FGFR2-associated diseases and disorders include Apert syndrome, Beare-Stevenson syndrome (BSS), Crouzon syndrome, ectrodactyly, Jackson-Weiss syndrome, lethal pulmonary acinar dysplasia, Pfeiffer syndrome, and syndactyly. Non-limiting examples of FGFR3-associated diseases and disorders include acanthosis nigricans, achondroplasia, Camptodactyly, tall stature, and hearing loss syndrome (CATSHL) syndrome, cleft lip and palate, craniosynostosis, hypochondroplasia, microphthalmia, Muenke coronal craniosynostosis, seborrheic keratosis, and thanatophoric dysplasia (e.g., type I or type II).

See also, See UniParc entry UPI00000534B8; UniParc entry UPI0000001COF; Uni Pare entry UPI000002A99A; UniParc entry UPI000012A72A; Yong-Xing et al., *Hum. Mol. Genet.* 9(13):2001-2008, 2000; Eeva-Maria Laitinen et al., *PLoS One* 7(6):e39450, 2012; Hart et al., *Oncogene* 19(29):3309-3320, 2000; Shiang et al., *Cell* 76:335-342, 1994; Rosseau et al., *Nature* 371:252-254, 1994; Tavormina et al., *Nature Genet.* 9:321-328, 1995; Bellus et al., *Nature Genet.* 10:357-359, 1995; Muenke et al., *Nature Genet.* 8:269-274, 1994; Rutland et al., *Nature Genet.* 9:173-176, 1995; Reardon et al., *Nature Genet.* 8:98-103, 1994; Wilkie et al., *Nature Genet.* 9:165-172, 1995; Jabs et al., *Nature Genet.* 8:275-279, 1994; Japanese Patent No. JP05868992B2; Ye et al., *Plast. Reconstr. Surg.,* 137(3):952-61, 2016; U.S. Pat. No. 9,447,098B2; Bellus et al., *Am. J. Med. Genet.* 85(1):53-65, 1999; PCT Patent Application Publication No. WO2016139227A1; Australian Patent Application Publication No. AU2014362227A1; Chinese Patent No. CN102741256B; Ohishi et al., *Am. J. Med. Genet. A.*, doi: 10.1002/ajmg.a.37992, 2016; Nagahara et al., *Clin. Pediatr. Endocrinol.,* 25(3): 103-106, 2016; Hibberd et al., *Am. J. Med. Genet. A.*, doi: 10.1002/ajmg.a.37862, 2016; Dias et al., *Exp. Mol. Pathol.,* 101(1):116-23, 2016; Lin et al., *Mol. Med. Rep.,* 14(3):1941-6, 2016; Barnett et al., *Hum. Mutat.,* 37(9):955-63, 2016; Krstevska-Konstantinova et al., *Med. Arch.,* 70(2):148-50, 2016; Kuentz et al., *Br. J. Dermatol.*, doi: 10.1111/bjd.14681, 2016; Ron et al., Am. J. Case Rep., 15; 17:254-8, 2016; Fernandes et al., *Am. J. Med. Genet. A.,* 170(6):1532-7, 2016; Lindy et al., *Am. J. Med. Genet. A.,* 170(6):1573-9, 2016; Bennett et al., *Am. J. Hum. Genet.,* 98(3):579-87, 2016; lchiyama et al., *J. Eur. Acad. Dermatol. Venereal.,* 30(3):442-5, 2016; Zhao et al., *Int. J. Clin. Exp. Med.,* 8(10):19241-9, 2015; Hasegawa et al., *Am. J. Med. Genet.* A., 170A(5):1370-2, 2016; Legeai-Mallet, *Endocr. Dev.,* 30:98-105, 2016; Takagi, *Am. J. Med. Genet.* A., 167A(ll):2851-4, 2015; Goncalves, *Fertil. Steril.,* 104 (5):1261-7.el, 2015; Miller et al., *Journal of Clinical Oncology,* 34:Supp. Supplement 15, pp. iii93. AbstractNumber: e22500, 2016 Annual Meeting of the American Society of Clinical Oncology, Chicago, IL; Sarabipour et al., *J. Mol. Biol.,* 428(20):3903-3910, 2016; Escobar et al., *Am. J. Med. Genet. A.,* 170(7):1908-11, 2016; Mazen et al., *Sex Dev.,* 10(1):16-22, 2016; Taylan et al., *J Allergy Clin Immunol,* 136(2):507-9, 2015. doi: 10.1016/j.jaci.2015.02.010; Kant et al, *Euro Journ Endocrinol,* 172(6):763-770, 2015. doi: 10.1530/EJE-14-0945; Gonzalez-Del Angel et al, *Am J med Genet A,* 176(1):161-166, 2018. doi: 10.1002/ajmg.a.38526; Lei and Deng, *Int J Blot Sci* 13(9):1163:1171, 2017. doi: 10.7150/ijbs.20792; Lajeunie et al, *Eur J Hum Genet,* 14(3): 289-298, 2006. doi: 10.1038/sj.ejhg.5201558; Karadimas et al, *Prenat Diagn,* 26(3):258-261, 2006. doi: 10.1002/pd.1392; lbrahimi et al, *Hum Mo/ Genet* 13(19):2313-2324, 2004. doi: 10.1093/hmg/ddh235; Trarbach et al, *J Clin Endocrinol Metab.,* 91(10):4006-4012, 2006. doi: 10.1210/jc.2005-2793; Dode et al, *Nat Genet,* 33(4):463-465, 2003. doi: 10.1038/ng1122, each of which is incorporated by reference herein.

The term "angiogenesis-related disorder" means a disease characterized in part by an increased number or size of blood vessels in a tissue in a subject or patient, as compared to a similar tissue from a subject not having the disease. Non-limiting examples of angiogenesis-related disorders include: cancer (e.g., any of the exemplary cancers described herein, such as prostate cancer, lung cancer, breast cancer, bladder cancer, renal cancer, colon cancer, gastric cancer, pancreatic cancer, ovarian cancer, melanoma, hepatoma, sarcoma, and lymphoma), exudative macular degeneration, proliferative diabetic retinopathy, ischemic retinopathy, retinopathy of prematurity, neovascular glaucoma, iritis rubeosis, corneal neovascularization, cyclitis, sickle cell retinopathy, and pterygium.

Compounds of the disclosure inhibit wild-type FGFR1, FGFR2, FGFR3, and/or FGFR4. In other aspects, compounds of the disclosure inhibit a mutated FGFR1, FGFR2, FGFR3, and/or FGFR4. In other aspects, compounds of the disclosure inhibit FGFR1, FGFR2, FGFR3, and/or FGFR4 that includes an FGFR kinase inhibitor mutation.

In some embodiments of any of the methods or uses described herein, the cancer (e.g., FGFR-associated cancer) is a hematological cancer. In some embodiments of any of the methods or uses described herein, the cancer (e.g., FGFR-associated cancer) is a solid tumor. In some embodiments of any of the methods or uses described herein, the cancer (e.g., FGFR-associated cancer) is a lung cancer (e.g., small cell lung carcinoma, non-small cell lung carcinoma, squamous cell carcinoma, lung adenocarcinoma, large cell carcinoma, mesothelioma, lung neuroendocrine carcinoma, smoking-associated lung cancer), prostate cancer, colorectal cancer (e.g., rectal adenocarcinoma), endometrial cancer (e.g., endometrioid endometrial cancer, endometrial adenocarcinoma), breast cancer (e.g., hormone-receptor-positive breast cancer, triple-negative breast cancer, neuroendocrine carcinoma of the breast), skin cancer (e.g., melanoma, cutaneous squamous cell carcinoma, basal cell carcinoma, large squamous cell carcinoma), gallbladder cancer, liposarcoma (e.g., dedifferentiated liposarcoma, myxoid liposarcoma), pheochromocytoma, myoepithelial carcinoma, urothelial carcinoma, spermatocytic seminoma, stomach cancer, head and neck cancer (e.g., head and neck (squamous) carcinoma, head and neck adenoid cystic adenocarcinoma), brain cancer (e.g., glialneural tumors, glioma, neuroblastoma, glioblastoma, pilocytic astrocytoma, Rosette forming glioneural tumor, dysembryoplastic neuroepithelial tumor, anaplastic astrocytoma, medulloblastoma, ganglioglioma, oligodendroglioma), malignant peripheral nerve sheath tumor, sarcoma (e.g., soft tissue sarcoma (e.g., leiomyosarcoma), osteosarcoma), esophageal cancer (e.g., esophageal adenocarcinoma), lymphoma, bladder cancer (e.g., bladder urothelial (transition cell) carcinoma), cervical cancer (e.g., cervical squamous cell carcinoma, cervical adenocarcinoma), fallopian tube cancer (e.g., fallopian tube carcinoma), ovarian cancer (e.g., ovarian serous cancer, ovarian mucinous carcinoma), cholangiocarcinoma, adenoid cystic carcinoma, pancreatic cancer (e.g., pancreatic exocrine carcinoma, pancreatic ductal adenocarcinoma, pancreatic cancer intraepithelial neoplasia), salivary gland cancer (e.g., pleomorphic salivary gland adenocarcinoma, salivary adenoid cystic cancer), oral cancer (e.g., oral squamous cell carcinoma), uterine cancer, gastric or stomach cancer (e.g., gastric adenocarcinoma), gastrointestinal stromal tumors, myeloma (e.g., multiple myeloma), lymphoepithelioma, anal cancer (e.g., anal squamous cell carcinoma), prostate cancer (e.g., prostate adenocarcinoma), renal cell carcinoma, thymic cancer, gastroesophogeal junction adenocarcinoma, testicular cancer, rhabdomyosarcoma (e.g., alveolar rhabdomyosarcoma, embryonic rhabdomyosarcoma), renal papillary carcinoma, liver cancer (e.g., hepatocellular carcinoma, intrahepatic cholangiocarcinoma), carcinoid, myeloid proliferative disorders (also called myeloid proliferative neoplasms (MPN); e.g., 8pll myeloproliferative syndrome (EMS, also called stem cell leukemia/lymphoma), acute myeloid leukemia (AML), chronic myeloid leukemia (CML), lymphoma (e.g., T-cell lymphoma, T-lymphoblastic lymphoma, acute lymphoblastic leukemia (ALL), B-cell lymphoma), myeloid and lymphoid neoplasms, chronic neutrophilic leukemia, phosphaturic mesenchymal tumor, thyroid cancer (e.g. anaplastic thyroid carcinoma), or biliary duct cancer.

In some embodiments of any of the methods or uses described herein, the cancer (e.g., FGFR-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and para nasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, para nasal sinus and nasal cavity cancer, parathyroid cancer, penile cancer, pharyngeal cancer, pheochromocytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are FGFR associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult Tcell ALL, AML with trilineage myelodysplasia (AML/TMDS), mixed lineage leukemia (MLL), myelodysplastic syndromes (MDSs), myeloproliferative disorders (MPD), and multiple myeloma (MM).

Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a FGFR-associated cancer) is AML or CMML.

In some embodiments, the cancer (e.g., the FGFR-associated cancer) is a solid tumor. Examples of solid tumors (e.g., solid tumors that are FGFR-associated cancers) include, for example, lung cancer (e.g., lung adenocarcinoma, non-small-cell lung carcinoma, squamous cell lung cancer), bladder cancer, colorectal cancer, brain cancer, testicular cancer, bile duct cancer cervical cancer, prostate cancer, and sparmatocytic seminomas. See, for example, Turner and Grose, *Nat. Rev. Cancer,* 10(2):116-129, 2010.

In some embodiments, the cancer is selected from the group consisting of bladder cancer, brain cancer, breast cancer, cholangiocarcinoma, head and neck cancer, lung cancer, multiple myeloma, rhabdomyosarcoma, urethral cancer, and uterine cancer. In some embodiments, the cancer is selected from the group consisting of lung cancer, breast cancer, and brain cancer. In some embodiments, a FGFR1-associated cancer is selected from the group consisting of lung cancer, breast cancer, and brain cancer. In some embodiments, the cancer is selected from the group consisting of breast cancer, uterine cancer, cholangiocarcinoma, and lung cancer. In some embodiments, a FGFR2-associated cancer is selected from the group consisting of breast cancer, uterine cancer, cholangiocarcinoma, and lung cancer. In some embodiments, the cancer is selected from the group consisting of lung cancer, bladder cancer, urethral cancer, multiple myeloma, and head and neck cancer. In some embodiments, a FGFR3-associated cancer is selected from the group consisting of lung cancer, bladder cancer, urethral cancer, multiple myeloma, and head and neck cancer. In some embodiments, the cancer is selected from lung cancer, rhabdomyosarcoma, and breast cancer. In some embodiments, a FGFR4-associated cancer is selected from lung cancer, rhabdomyosarcoma, and breast cancer.

In some aspects, the compounds of the disclosure are useful in treating cancers associated with amplification or overexpression of FGFR1, for example, Breast cancer or carcinoma (e.g., hormone receptor-positive breast cancer, ductal carcinoma in situ (breast)), pancreatic ductal adenocarcinoma, pancreatic exocrine carcinoma, smoking-associated lung cancer, small cell lung cancer, lung adenocarcinoma, non-small cell lung cancer, squamous cell lung cancer or carcinoma, prostate cancer or carcinoma, ovarian cancer, fallopian tube carcinoma, bladder cancer, rhabdomyosarcoma, head and neck carcinoma (e.g., head and neck squamous cell carcinoma), esophageal cancer (e.g., esophageal squamous cell carcinoma), sarcoma (e.g., osteosarcoma), hepatocellular carcinoma, renal cell carcinoma, colorectal cancer (e.g., colorectal adenocarcinoma), prostate cancer, salivary gland tumors, glioblastoma multiforme, urinary bladder cancer, urothelial carcinoma, carcinoma of unknown primary, squamous non-lung tumors, gastric cancer, gastroesophageal junction carcinoma, adenoid cystic carcinoma, anal squamous cell carcinoma, oral squamous cell carcinoma, cholangiocarcinoma, hemangioendothelioma, leiomyosarcoma, melanoma, neuroendocrine carcinoma, squamous cell carcinoma, uterine carcinosarcoma.

In some aspects, the compounds of the disclosure are useful in treating cancers associated with amplification of FGFR2, for example, Gastric cancer, gastroesophageal junction adenocarcinoma, breast cancer (e.g., triple negative breast cancer), colon cancer, colorectal cancer (e.g., colorectal adenocarcinoma), urothelial cancer, bladder adenocarcinoma, carcinoma of unknown primary, cholangiocarcinoma, endometrial adenocarcinoma, esophageal adenocarcinoma, gallbladder carcinoma, ovarian cancer, fallopian tube carcinoma, pancreatic exocrine carcinoma, sarcoma, squamous cell carcinoma. In some aspects, the compounds of the disclosure are useful in treating cancers associated with overexpression of FGFR2, for example, Myxoid lipocarcinoma, rectal cancer, renal cell carcinoma, breast cancer.

In some aspects, the compounds of the disclosure are useful in treating cancers associated with upregulation of activity of FGFR3, for example, Colorectal cancer, hepatocellular carcinoma, pancreatic exocrine carcinoma. In some aspects, the compounds of the disclosure are useful in treating cancers associated with overexpression of activity of FGFR3, for example, Multiple myeloma, thyroid carcinoma. In some aspects, the compounds of the disclosure are useful in treating cancers associated with amplification of activity of FGFR3, for example, Bladder cancer and salivary adenoid cystic cancer, urothelial cancer, breast cancer, carcinoid, carcinoma of unknown primary, colorectal cancer (e.g., colorectal adenocarcinoma), gallbladder carcinoma, gastric cancer, gastroesophageal junction adenocarcinoma, glioma, mesothelioma, non-small cell lung carcinoma, small cell lung cancer, ovarian cancer, fallopian tube carcinoma, pancreatic exocrine carcinoma.

In some aspects, the compounds of the disclosure are useful in treating cancers associated with amplification of FGFR4, for example, Rhabdomyosarcoma, prostate cancer or carcinoma, breast cancer, urothelial cancer, carcinoid, carcinoma of unknown primary, esophageal adenocarcinoma, head and neck carcinoma, hepatocellular carcinoma, non-small cell lung carcinoma, ovarian cancer, fallopian tube carcinoma, peritoneal carcinoma, renal cell carcinoma.

In some aspects, the compounds of the disclosure are useful in treating cancers associated with upregulation of activity of FGFR4, for example, Colorectal cancer, hepatocellular carcinoma, adrenal carcinoma, breast cancer.

In some aspects, the compounds of the disclosure are useful in treating cancers associated with overexpression of activity of FGFR4, for example, Pancreatic intraepithelial neoplasia, and pancreatic ductal adenocarcinoma.

In some aspects, the compounds of the disclosure are more selective for an FGFR kinase over another kinase that is not an FGFR kinase. For example, the compounds of the disclosure are at least 3-fold more selective for an FGFR kinase over another kinase that is not an FGFR kinase. In some aspects, the compounds of the disclosure are at least 10, 20, 30, 40, 50, 60, 70, 80, 90, 200, 300, 400, 500, 600, 700, 800, 900, or at least 1000 fold more selective for an FGFR kinase over another kinase that is not an FGFR kinase. Kinases that are not FGFR kinases include, for example, KDR kinase and Aurora B kinase.

In some embodiments, the compounds of the disclosure exhibit brain and/or central nervous system (CNS) penetrance. Such compounds are capable of crossing the blood brain barrier and inhibiting a FGFR kinase in the brain and/or other CNS structures. In some embodiments, the compounds provided herein are capable of crossing the blood brain barrier in a therapeutically effective amount. For example, treatment of a subject with cancer (e.g., a FGFR-associated cancer such as a FGFR-associated brain or CNS cancer) can include administration (e.g., oral administration) of the compound to the subject. In some such embodiments, the compounds provided herein are useful for treating a primary brain tumor or metastatic brain tumor. For example, a FGFR-associated primary brain tumor or metastatic brain tumor.

In some embodiments, the compounds of the disclosure, exhibit one or more of high GI absorption, low clearance, and low potential for drug-drug interactions.

In some aspects, compounds of the disclosure can be used for treating a subject diagnosed with (or identified as having) a FGFR-associated disease or disorder (e.g., a FGFR-associated cancer) that include administering to the subject a therapeutically effective amount of a compound of the disclosure. Also provided herein are methods for treating a subject identified or diagnosed as having a FGFR-associated disease or disorder (e.g., a FGFR-associated cancer) that include administering to the subject a therapeutically effective amount of a compound of the disclosure. In some embodiments, the subject that has been identified or diagnosed as having a FGFR-associated disease or disorder (e.g., a FGFR-associated cancer) through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the FGFR-associated disease or disorder is a FGFR-associated cancer. For example, the FGFR-associated cancer can be a cancer that includes one or more FGFR inhibitor resistance mutations.

Also provided are methods for treating a disease or disorder in a subject in need thereof, the method comprising: (a) detecting a FGFR-associated disease or disorder in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy. In some embodiments, the subject was previously treated with a first FGFR inhibitor or previously treated with another treatment. In some embodiments, the subject is determined to have a FGFR-associated disease or disorder through the use of a regulatory agency-approved, e.g., FDA approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a FGFR-associated cancer in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy). In some embodiments, the subject was previously treated with a first FGFR inhibitor or previously treated with another anticancer treatment, e.g., at least partial resection of the tumor or radiation therapy. In some embodiments, the subject is determined to have a FGFR-associated cancer through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the cancer is a FGFR associated cancer. For example, the FGFR-associated cancer can be a cancer that includes one or more FGFR inhibitor resistance mutations. In some embodiments, the cancer is a FGFR associated cancer. For example, the FGFR-associated cancer can be a cancer that includes one or more FGFR activating mutations.

Also provided are methods of treating a subject that include performing an assay on a sample obtained from the subject to determine whether the subject has a dysregulation of a FGFR gene, a FGFR kinase, or expression or activity or level of any of the same, and administering (e.g., specifically or selectively administering) a therapeutically effective amount of a compound of the disclosure or pharmaceutically acceptable salt or solvate thereof to the subject determined to have a dysregulation of a FGFR gene, a FGFR kinase, or expression or activity or level of any of the same. Some embodiments of these methods further include administering to the subject an additional therapy or therapeutic agent (e.g., a second FGFR inhibitor, a second compound of the disclosure, or immunotherapy). In some embodiments of these methods, the subject was previously treated with a first FGFR inhibitor or previously treated with another anticancer treatment, e.g., at least partial resection of a tumor or radiation therapy. In some embodiments, the subject is a subject suspected of having a FGFR-associated disease or disorder (e.g., a FGFR-associated cancer), a subject presenting with one or more symptoms of a FGFR-associated disease or disorder (e.g., a FGFR-associated cancer), or a subject having an elevated risk of developing a FGFR-associated disease or disorder (e.g., a FGFR-associated cancer). In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a FGFR gene, a FGFR kinase, or expression or activity or level of any of the same includes one or more FGFR inhibitor resistance mutations.

Also provided herein are methods of selecting a treatment for a subject, wherein the methods include a step of performing an assay on a sample obtained from the subject to determine whether the subject has a dysregulation of a FGFR gene, a FGFR kinase, or expression or activity or level of any of the same (e.g., one or more FGFR inhibitor resistance mutations), and identifying or diagnosing a subject determined to have a dysregulation of a FGFR gene, a FGFR kinase, or expression or activity or level of any of the same, as having a FGFR-associated cancer. Some embodiments further include administering the selected treatment to the subject identified or diagnosed as having a FGFR-associated cancer. For example, in some embodiments, the selected treatment can include administration of a therapeutically effective amount of a compound of the disclosure to the subject identified or diagnosed as having a FGFR-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of treating a FGFR-associated cancer in a subject that include (a) administering one or more (e.g., two or more, three or more, four or more, five or more, or ten or more) doses of a first FGFR kinase inhibitor to a subject identified or diagnosed as having a FGFR associated cancer (e.g., any of the types of FGFR-associated cancers described herein) (e.g., identified or diagnosed as having a FGFR-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second FGFR inhibitor or a compound of the disclosure as a monotherapy or in conjunction with an additional therapy or therapeutic agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some examples of these methods, the first FGFR inhibitor is: ARQ-087, ASP5878, AZD4547, B-701, BAY1179470, BAY1187982, BGJ398, brivanib, Debio-1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, TAS-120 or RLY-4008.

Compounds of the disclosure can also be administered with additional therapy or therapeutic agents. In some aspects, the additional therapy or therapeutic agent includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Compounds of the disclosure may also be useful as adjuvants to cancer treatment, that is, they can be used in combination with one or more additional therapies or therapeutic agents, for example a chemotherapeutic agent that works by the same or by a different mechanism of action. In some embodiments, a compound of the disclosure can be used prior to administration of an additional therapeutic agent or additional therapy. For example, a subject in need thereof can be administered one or more doses of a compound of the disclosure for a period of time and then under go at least partial resection of the tumor. In some embodiments, the treatment with one or more doses of a compound of the disclosure reduces the size of the tumor (e.g., the tumor burden) prior to the at least partial resection of the tumor. In some embodiments, a subject has a cancer (e.g., a locally advanced or metastatic tumor) that is refractory or intolerant to standard therapy (e.g., administration of a chemotherapeutic agent, such as a first FGFR inhibitor or a multikinase inhibitor, immunotherapy, radiation, or a platinum-based agent (e.g., cisplatin)). In some embodiments, a subject has a cancer (e.g., a locally advanced or metastatic tumor) that is refractory or intolerant to prior therapy (e.g., administration of a chemotherapeutic agent, such as a first FGFR inhibitor or a multikinase inhibitor, immunotherapy, radiation, or a platinum-based agent (e.g., cisplatin)).

In some embodiments of any the methods described herein, the compound of the disclosure is administered in combination with a therapeutically effective amount of at least one additional therapeutic agent selected from one or more additional therapies or therapeutic (e.g., chemotherapeutic) agents.

Non-limiting examples of additional therapeutic agents include: other FGFR-targeted therapeutic agents (i.e. a first or second FGFR kinase inhibitor), other kinase inhibitors (e.g., receptor tyrosine kinase targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

Also provided herein are methods of treating a disease or disorder, comprising administering to a subject in need thereof a pharmaceutical combination for treating the disease or disorder which comprises (a) a compound of the disclosure, (b) an additional therapeutic agent, and (c) optionally at least one pharmaceutically acceptable carrier for simultaneous, separate or sequential use for the treatment of the disease or disorder, wherein the amounts of the compound of the disclosure and the additional therapeutic agent are together effective in treating the disease or disorder. In some embodiments, the compound of the disclosure, and the additional therapeutic agent are administered simultaneously as separate dosages. In some embodiments, the compound of the disclosure, and the additional therapeutic agent are administered as separate dosages sequentially in any order, in jointly therapeutically effective amounts, e.g. in daily or intermittently dosages. In some embodiments, the compound of the disclosure, and the additional therapeutic agent are administered simultaneously as a combined dosage. In some embodiments, the disease or disorder is a FGFR-associated disease or disorder. In some embodiments, the subject has been administered one or more doses of a compound of the disclosure, prior to administration of the pharmaceutical composition.

In some embodiments, the treatment period is at least 7 days (e.g., at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, or at least or about 30 days).

In some embodiments, the treatment period is at least 21 days (e.g., at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 32 days, at least or about 33 days, at least or about 34 days, at least or about 35 days, at least or about 36 days, at least or about 37 days, at least or about 38 days, at least or about 39 days, or at least or about 40 days).

Also provided herein are pharmaceutical compositions that contain, as the active ingredient, a compound of the disclosure, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

The compositions comprising a compound of the disclosure can be formulated in a unit dosage form, each dosage containing from about 5 to about 1,000 mg (1 g), more usually about 100 mg to about 500 mg, of the active ingredient. The term "unit dosage form" refers to physically discrete units for human subjects and other subjects, each unit containing a predetermined quantity of active material (i.e., a compound of the disclosure) to produce the desired therapeutic effect, with a suitable pharmaceutical excipient.

In some embodiments, the compositions provided herein contain from about 5 mg to about 50 mg of the active ingredient, i.e., the compound of the disclosure. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient. In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like. In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

In several embodiments, not only can the compounds of the disclosure be used for therapy in patients with FGFR mutations (either point mutations or various fusions) to provide superior benefits, but in situations in which these mutations are likely to arise (such as in erdafitinib and/or infigratinib (BGJ398), pemigatinib, or TAS-120 therapy), where numerous activating and resistance mutations recur in patients, it may be especially advantageous. In several embodiments, the compounds of the disclosure can be used as a therapeutic intervention in patients bearing these mutations, either in combination with a pan-FGFR inhibitor or as a monotherapy where genomic testing supports mutations for which the compounds of the disclosure are active.

In several embodiments, a method of treating a cancer is provided. In several embodiments, the method of treating cancer includes administering one or more compounds of the disclosure. In several embodiments, the method comprises, in response to a determination of the presence of a FGFR mutant polypeptide or a FGFR mutant polynucleotide in a sample from the subject, administering to the subject an effective amount of compounds of the disclosure. This can thereby treat the cancer in the subject. In several embodiments, the FGFR mutant is one of the ones disclosed herein and/or an activating mutant (including a point mutation or FGFR fusion).

In several embodiments, the method of treating cancer includes administering one or more compounds of the disclosure to a patient who is suspected of having a cancer or being at risk of having a cancer. In several embodiments, the method comprises administering to the subject an effective amount of a compound of the disclosure, this can be done with or without a diagnosis or analysis of the subject's kinases (including whether or not the kinases are wild-type or mutant).

In several embodiments, the FGFR mutants are fusions that can be caused by chromosomal translocations in cancers. These translocations can lead to fusion proteins that exert their oncogenic effects through overexpression or growth factor independent activation of an otherwise normal gene or creation of a chimeric gene in which parts of two genes are fused together. Fusions of FGFR genes with other genes or parts of genes have been found most commonly in FGFR2 and FGFR3. The most common fusion partner reported for FGFR3 is TACC3 (Transforming Acidic Coiled-Coil Containing Protein).

Table 0.1 summarizes the frequency of FGFR specific fusions:

TABLE 0.1

| Specific Fusion (N) | Tumor types (N) |
|---|---|
| FGFR3-TACC3 (11) | CUP (1), cervical carcinoma (1), Endometrial adeno-carcinoma (1), gallbladder carcinoma (1), glioma (1), NSCLC (1), renal cell carcinoma (1), urothelial carcinoma (4). |
| FGFR2-TACC3 (1) | Cholangiocarcinoma (1) |
| FGFR2-NPM1 (3) | Colorectal carcinoma (2), large cell lung carcinoma (1) |
| FGFR2-TACC2 (2) | CUP (1), Gastric/GE Junction adeno-carcinoma (1) |
| FGFR2-BICC1 (2) | CUP (1), Cholangiocarcinoma (1) |
| FGFR2-C10orf68 (1) | Gastric/GE Junction adeno-carcinoma (1) |
| FGFR3-JAKMIP1 (1) | Bladder urothelial (transition cell) carcinoma (1) |
| FGFR2-KIAA1598 (1) | Cholangiocarcinoma (1) |
| FGFR2-NCALD (1) | Breast carcinoma (1) |
| FGFR2-NOL4 (1) | Cholangiocarcinoma (1) |
| FGFR1-NTM (1) | Bladder urothelial (transition cell) carcinoma (1) |
| FGFR2-PPAPDC1A (1) | Prostate carcinoma (1) |
| FGFR3-TNIP2 (1) | Bladder urothelial (transition cell) carcinoma (1) |
| FGFR3-WHSC1 (1) | Breast carcinoma (1) |

An analysis of FGFR fusions identified in The Cancer Genome Atlas (TCGA) found a number of translocations which illustrate both the recurrence and lack of (absolute) tumor type specificity for FGFR1, 2, and 3 fusions (Table 0.2).

TABLE 0.2

| Cancer | Fusion | Samples in Cancer Type |
|---|---|---|
| Acute Myeloid Leukemia | FGFR3--TACC3 | 1 |
| Bladder Urothelial Carcinoma | FGFR3--TACC3 | 7 |
| Brain Lower Grade Glioma | FGFR3--ELAVL3 | 1 |
| Brain Lower Grade Glioma | FGFR3--TACC3 | 2 |
| Brain Lower Grade Glioma | FGFR3--FBXO28 | 1 |
| Breast invasive carcinoma | ERLIN2--FGFR1 | 1 |
| Breast invasive carcinoma | FGFR2--CASP7 | 1 |
| Breast invasive carcinoma | FGFR2--CCDC6 | 1 |
| Cervical squamous cell carcinoma and endocervical adenocarcinoma | FGFR3--TACC3 | 5 |
| Cholangiocarcinoma | FGFR2--BICC1 | 2 |
| Cholangiocarcinoma | FGFR2--CCDC186 | 1 |
| Cholangiocarcinoma | FGFR2--FRK | 1 |
| Cholangiocarcinoma | FGFR2--SHTN1 | 1 |
| Esophageal carcinoma | FGFR3--TACC3 | 2 |
| Glioblastoma multiforme | FGFR3--AMBRA1 | 1 |
| Glioblastoma multiforme | FGFR3--TACC3 | 1 |

TABLE 0.2-continued

| Cancer | Fusion | Samples in Cancer Type |
|---|---|---|
| Head and Neck squamous cell carcinoma | FGFR3--TACC3 | 2 |
| Kidney renal papillary cell carcinoma | FGFR3--TACC3 | 2 |
| Liver hepatocellular carcinoma | FGFR2--BICC1 | 1 |
| Liver hepatocellular carcinoma | FGFR2--SMN1 | 1 |
| Lung squamous cell carcinoma | BAG4--FGFR1 | 1 |
| Lung squamous cell carcinoma | FGFR3--TACC3 | 6 |
| Lung squamous cell carcinoma | FGFR2--CCAR2 | 1 |
| Lung squamous cell carcinoma | FGFR2--EIF4A2 | 1 |
| Ovarian serous cystadenocarcinoma | FGFR3--MLLT10 | 1 |
| Prostate adenocarcinoma | FGFR3--AES | 1 |
| Stomach adenocarcinoma | FGFR3--TACC3 | 1 |
| Stomach adenocarcinoma | FGFR2--TACC2 | 1 |
| Thyroid carcinoma | FGFR2--OFD1 | 1 |
| Uterine Corpus Endometrial Carcinoma | FGFR2--SHTN1 | 1 |

In several embodiments, mutations in FGFR are polyclonal. Thus, when the FGFR or FGFR-fusion driven cancer metastasizes, the individual metastases can have distinct mutational patterns in the FGFR kinase domain. For example, a patient with distinct liver metastases can have a gatekeeper mutation in a subset of the metastases but not necessarily in all of them at the time of treatment or biopsy. The presence of the founding mutation from the primary tumor i.e. a FGFR fusion would likely remain in all patients. In several embodiments, it is that founding mutation that is targeted by any one or more of the methods provided herein. In several embodiments, both the founding mutation and other mutations are targeted by any one or more of the methods provided herein. In several embodiments, only the later mutations are targeted by one or more of the methods provided herein. In several embodiments, the method of any of the methods provided herein can be one where a compound of the disclosure is administered in an amount adequate to treat a tumor in a subject who has metastasized, and wherein the tumor that is being treated is the primary tumor. In several embodiments, any of the methods provided herein can use an adequate amount of a compound of the disclosure to treat a subset of the tumors in a subject. For example, the subset can include or focus on the tumors with a founding mutation (the primary tumor(s)). Thus, in several embodiments, the therapy need not be directed to, or include an amount of the disclosure to treat every tumor, but just a subset of the tumors (for example the primary tumors with the founding mutation). In several embodiments, the treated tumor is not the primary tumor, but may be a metastases with a detectable resistance or activating mutation not found in the primary tumor. In several embodiments, the method comprises administering the disclosure in an amount adequate to treat a tumor in a subject who has metastasized, and wherein the treated tumor is not the primary tumor, and wherein the treated tumor is a metastases with a detectable resistance or activating mutation not found in the primary tumor.

In several embodiments, a subject with any of the fusion arrangements in Tables 0.1 or 0.2 can obtain an enhanced benefit from a compound of the disclosure therapy. In several embodiments, any of the methods provided herein with respect to various point mutations can be applied to tumors or subjects that have any one or more of the above noted fusions. For example, a method of treating a subject having a cancer can comprise acquiring knowledge of a presence of an FGFR mutation (e.g., fusion) in a FGFR polynucleotide or FGFR polypeptide in said subject. The method can further comprise administering to the subject an effective amount of a compound of the disclosure. The FGFR mutation is at least one of the following fusions: BAG4-FGFR1, BCR-FGFR1, CEP110-FGFR1, CUX1-FGFR1, CNTRL-FGFR1, CFS1-FGFR1, ERLIN2-FGFR1, ETV6-FGFR1, FGFR1-NTM, FGFR1OP-FGFR1, FGFR1OP2-FGFR1, HERVK-FGFR1, LRRFIP-FGFR1, TRIM24-FGFR1, MYO18A-FGFR1, LRRFIP1-FGFR1, ZNF198-FGFR1, ZMYM2-FGFR1, MYO18A-FGFR1, RANBP2-FGFR1, TPR-FGFR1, FGFR2-BICC1, FGFR2-CIT, FGFR2-CASP7, FGFR2-CCAR2, FGFR2-CCDC186, FGFR2-CCDC6, FGFR2-EIF4A2, FGFR2-KIAA1967, SLC45A3-FGFR2, FGFR2-FRK, FGFR2-AFF3, FGFR2-OFD1, FGFR2-ZMYM4, FGFR2-OPTN, FGFR2-SHTN1, FGFR2-LZTFL1, FGFR2-SMN1, FGFR2-TACC1, FGFR2-C10orf68, FGFR2-KIAA1598, FGFR2-NCALD, FGFR2-NOL4, FGFR2-NPM1, FGFR2-PPAPDC1A, FGFR2-TACC2, FGFR2-TACC3, FGFR3-AES, FGFR3-AMBRA1, FGFR3-ELAVL3, FGFR3-FBXO28, FGFR3-MLLT10, FGFR3-TACC3, FGFR3-JAKMIP1, FGFR3-BAIAP2L1, FGFR3-TNIP2, FGFR3-WHSC1, FGFR3-PPHLN1.

In several embodiments, the compound can be used to treat subjects with other types of mutations in FGFR, including allosteric mutations, such as FGFR3 S249C.

In several embodiments, the tumor type to be treated is that designated as corresponding to the denoted particular fusion in one of Tables 0.1 or 0.2.

In several embodiments, a method of treating a subject having a cancer is provided. The method comprises acquiring knowledge of a presence of an FGFR mutation in a FGFR polynucleotide or FGFR polypeptide in said subject. The method can further comprise administering to the subject an effective amount of a compound of the disclosure. The FGFR mutant polypeptide or nucleic acid includes one or more of the following fusions: BAG4-FGFR1, BCR-FGFR1, CEP110-FGFR1, CUX1-FGFR1, CNTRL-FGFR1, CFS1-FGFR1, ERLIN2-FGFR1, ETV6-FGFR1, FGFR1-NTM, FGFR10P-FGFR1, FGFR10P2-FGFR1, HERVK-FGFR1, LRRFIP-FGFR1, TRIM24-FGFR1, MYO18A-FGFR1, LRRFIP1-FGFR1, ZNF198-FGFR1, ZMYM2-FGFR1, MYO18A-FGFR1, RANBP2-FGFR1, TPR-FGFR1, FGFR2-BICC1, FGFR2-CIT, FGFR2-CASP7, FGFR2-CCAR2, FGFR2-CCDC186, FGFR2-CCDC6, FGFR2-EIF4A2, FGFR2-KIAA1967, SLC45A3-FGFR2, FGFR2-FRK, FGFR2-AFF3, FGFR2-OFD1, FGFR2-ZMYM4, FGFR2-OPTN, FGFR2-SHTN1, FGFR2-LZTFL1, FGFR2-SMN1, FGFR2-TACC1, FGFR2-C10orf68, FGFR2-KIAA1598, FGFR2-NCALD, FGFR2-NOL4, FGFR2-NPM1, FGFR2-PPAPDC1A, FGFR2-TACC2, FGFR2-TACC3, FGFR3-AES, FGFR3-AMBRA1, FGFR3-ELAVL3, FGFR3-FBXO28, FGFR3-MLLT10, FGFR3-TACC3, FGFR3-JAKMIP1, FGFR3-BAIAP2L1, FGFR3-TNIP2, FGFR3-WHSC1, FGFR3-PPHLN1.

In several embodiments, a method of treating a cancer is provided. The method comprises, in response to a determination of the presence of a FGFR2 fusion polypeptide or a FGFR2 fusion polynucleotide in a sample from the subject, administering to the subject an effective amount of a compound of the disclosure. This treats the cancer in the subject. The administration of a compound of the disclosure is at least as effective on the fusion polypeptide as it is on the respective wild-type kinase of FGFR2. In several embodiments, a compound of the disclosure is at least 5, 10, 20, 30, 40, 50, 60, 70, 80, 90, 100, 110, 120, 130, 140, 150, 200, 300, 400, 500, 1000% more potent on the mutant FGFR as on the wild-type FGFR on inhibiting FGFR kinase activity.

In several embodiments, the method and/or percent is determined by the method as provided in the present examples.

In several embodiments, a method of treating a subject having a cancer is provided. The method comprises acquiring knowledge of a presence of an FGFR mutation in a FGFR polynucleotide or FGFR polypeptide in said subject. The method can further comprise administering to the subject an effective amount of a compound of the disclosure. The FGFR mutant polypeptide includes at least one of: A) for FGFR1: V561M of FGFR1, B) for FGFR2: E565G, K526E, K641R, K659N, N549H, R612T, and V564F, C) for FGFR 3: G697C, K650E, K650M, K650Q, and/or V555M of FGFR3, or D) For FGFR4: N535K, V550E, V550L, and/or V550M of FGFR4.

In several embodiments, a method of treating a subject having a cancer is provided. The method comprises administering a compound of the disclosure to a subject. The subject has at least two FGFR point mutations. The at least two point mutations occur at two positions selected from at least two within any one of the following groupings: a) for FGFR2: 565, 526, 641, 659, 549, 612, and 564, b) for FGFR1: 561 of FGFR1, c) for FGFR 3: 697, 650, and/or 555 of FGFR3, or d) for FGFR4: 535 or 550 of FGFR4.

In several embodiments, one, two, three, four, or five or more mutations at these positions are present. In several embodiments at least two point mutations are selected from: a) for FGFR2: E565G, K526E, K641R, K659N, N549H, R612T, and V564F, b) for FGFR1: V561M of FGFR1, c) for FGFR 3: G697C, K650E, K650M, K650Q, and/or V555M of FGFR3, or d) For FGFR4: N535K, V550E, V550L, and/or V550M for FGFR4. In several embodiments, one, two, three, four, or five or more of these particular mutations are present.

In several embodiments, a method of treating a cancer is provided, the method comprises, in response to a determination of the presence of a FGFR activating mutation in a subject, administering to the subject an effective amount of a compound of the disclosure thereby treating the cancer in the subject, wherein the FGFR activating mutation is a driver in a non-fused cancer. In several embodiments, an effective amount of a compound of the disclosure is an amount that reduces the activity of the FGFR mutant to a level that is adequate to provide some treatment to the subject, for example, by reducing one or more symptoms. In several embodiments, the activity of the mutant FGFR is reduced by a compound of the disclosure to near, or lower than, wild-type activity. In several embodiments, the activity for the FGFR mutant, when a compound of the disclosure is administered, is reduced to 500, 400, 300, 200, 190, 180, 170, 160, 150, 140, 130, 120, 110, 105, 104, 103, 102, 101, 100, 95, 90, or lower percent of the activity of wild-type FGFR.

In several embodiments, a method of treating cancer in a subject in need thereof is provided. The method comprises administering an inhibitor of FGFR kinase activity to a subject determined to have a genetic fusion of FGFR and a second gene, wherein the inhibitor of FGFR is at least as effective against the genetic fusion of FGFR, as it is against a wild-type FGFR kinase. In several embodiments, the inhibitor can be a compound of the disclosure. In several embodiments, the inhibitor of FGFR kinase activity is at least 5, 10, 20, 30, 40, 50, 60, 70, 80, 90, 100, 110, 120, 130, 140, 150, 200, 300, 400, 500, 1000, 5000, or 10,000% more potent on the fused FGFR as on the wild-type FGFR. In several embodiments, a compound of the disclosure is at least 1.1, 2, 5, 10, 20, 30, 40, 50, 60, 70, 80, 90, or 100 fold as potent for the mutant as it is for wild-type. In several embodiments, the IC50 for a compound of the disclosure is 0.5, 0.1, 0.05, or 0.01% as large for the mutant FGFR as it is for wild type (that is, the numerical value for the IC50 is lower for the mutant).

In several embodiments, the $IC_{50}$ of a compound of the disclosure to the FGFR mutant or mutation is no higher than about 100 nM (e.g., it is at least as good in potency as 100 nM). In several embodiments, the $IC_{50}$ of a compound of the disclosure to the FGFR mutant or mutation is no higher than about 10 nM (e.g., it is at least as good in potency as 10 nM). In several embodiments, the $IC_{50}$ of a compound of the disclosure to the FGFR mutant or mutation is no higher than single digit nM (e.g., it is at least as good in potency as single digit nM). In several embodiments, the $IC_{50}$ of a compound of the disclosure to the FGFR mutant or mutation is at least as effective for the FGFR mutant or mutation as it is for a wild type FGFR.

In several embodiments of the method, the subject has been (or is still) on a multi-targeted kinase inhibitor ("MKI") or a targeted FGFR inhibitor. While on the MKI or the targeted FGFR inhibitor, the subjects tumor become 564F) resistant to the prior MKI or the targeted FGFR inhibitor. At this point, one can either simply administer a compound of the disclosure. In the alternative, one can determine if the subject now has a tumor that has a FGFR mutation in it (such as amino acid changes that result in resistance to the prior therapy). If the subject does have a tumor with the noted mutation, one can then dose the subject with a compound of the disclosure.

In several embodiments, the FGFR is a FGFR2 mutant. In several embodiments, the FGFR2 mutant includes at least one mutation as follows: E565G, K526E, K641R, K659N, N549H, R612T, and/or V564F of FGFR2.

In several embodiments, the FGFR is a FGFR1 mutant. In several embodiments, the FGFR1 mutant includes a mutation as follows: V561M and/or FGFR1OP-FGFR1 of FGFR1.

In several embodiments, the FGFR mutant is a FGFR3 mutant. In several embodiments, the FGFR3 includes a mutation as follows: G697C, K650E, K650M, K650Q, and/or V555M of FGFR3.

In several embodiments, the FGFR is an FGFR4. In several embodiments, the FGFR4 includes a mutation as follows: N535K, V550E, V550L, and/or V550M of FGFR4.

In several embodiments, the method of using a compound of the disclosure can be directed to treating a variety of cancers or cancer generically. In several embodiments, the cancer is one or more of: urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas. In several embodiments, the subject has an intrahepatic cholangiocarcinoma. This list denotes some, but not all of the FGFR mutant related cancers. In several embodiments, the cancer can include any of the previous options and/or any of the following: urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas. In several embodiments, the subject has an intrahepatic cholangiocarcinoma.

EXAMPLES

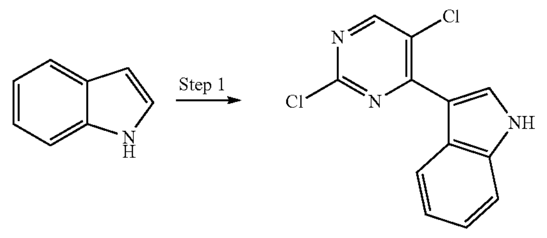

3-(2,5-dichloropyrimidin-4-yl)-1H-indole

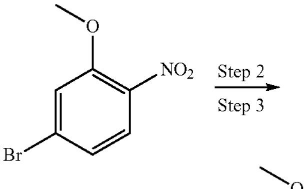

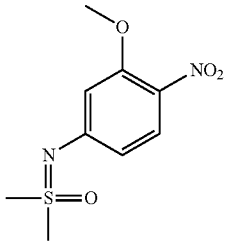

4-[[dimethyl(oxo)-$\lambda^6$-sulfanylidene]amino]-2-methoxy-aniline

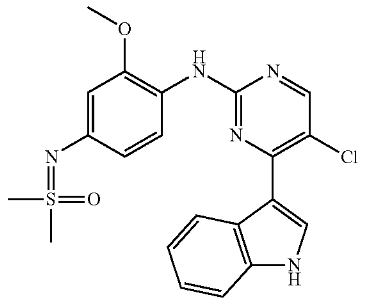

Example 1

Example 1. 5-chloro-N-[4-[[dimethyl(oxo)-$\lambda^6$-sulfanylidene]amino]-2-methoxy-phenyl]-4-(1H-indol-3-yl)pyrimidin-2-amine

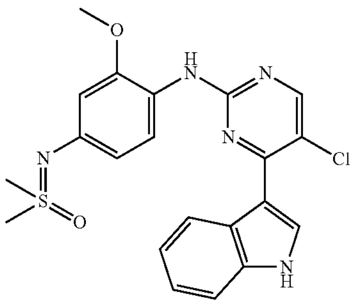

Step 1. 3-(2,5-Dichloropyrimidin-4-yl)-1H-indole. 3.4 M Methyl magnesium bromide in 2-methyltetrahydrofuran (3.17 mL, 10.8 mmol, 2 equiv) was added dropwise over 10 minutes to a solution of indole (1.28 g, 10.8 mmol, 2 equiv) in THF (6 mL) at 0° C. After stirring at 0-2° C. for 30 minutes, 2,4,5-trichloropyrimidine (1.0 g, 5.4 mmol, 1 equiv) was added dropwise, resulting in a yellow solution. The ice bath was removed, and the solution was stirred at room temperature for 1 hour, resulting in a red solution. After heating at 60° C. for 1.5 hours, the mixture was cooled to room temperature and acetic acid (634 μL, 11.06 mmol, 2.05 equiv) was added dropwise. Water (10 mL) and THF (2 mL) were added, and the mixture was stirred for 20 minutes at 60° C. The layers were separated and heptanes (11 mL) was added to the organic solution resulting in the precipitation of a solid. The solid was collected by filtration, washed with heptanes (2 mL) and dried under vacuum at 4° C. overnight to give a yellow solid (1.01 g, 66% yield). Analysis: LCMS: m/z=264.0 (M+H)

Step 2. (3-Methoxy-4-nitro-phenyl)imino-dimethyl-oxo-$\lambda^6$-sulfane. A 40 mL vial was charged with 5-bromo-2-nitroanisole (0.99 g, 4.26 mmol, 1.0 equiv), sodium tert-butoxide (0.61 g, 6.35 mmol, 1.5 equiv), 2-(di-tert-butylphosphino))-1,1'-biphenyl (0.27 g, 0.91 mmol, 0.21 equiv) and tris(dibenzylideneacetone)dipalladium(0) (0.31 g, 0.34 mmol, 0.08 equiv). A solution of S,S-dimethylsulfoximine (0.62 g, 6.66 mmol, 1.5 equiv) in 1,4-dioxane (12 mL) was prepared, added to the reaction vial and followed by a rinse of the weigh vial with additional 1,4-dioxane (12 mL). The mixture was sparged with nitrogen then heated at 80° C. for 4 hours. After cooling to room temperature, the mixture was diluted with water (50 mL) and methyl tert-butyl ether (100 mL). The layers were separated and the aqueous phase was extracted with methyl tert-butyl ether (50 mL) and dichloromethane (2×50 mL). The combined organics were dried over sodium sulfate, filtered and concentrated under reduced pressure onto silica gel (6 g). Purification on an Interchim automated chromatography system (40 g Sorbtech silica gel column), eluting with a gradient of 0 to 5% methanol in dichloromethane gave crude product. The mixture was repurified on an Interchim automated chromatography system (25 g Sorbtech silica gel column), eluting with a gradient of 0 to 100% methyl tert-butyl ether (containing 5% methanol) in heptanes to give an orange solid (0.55 g, 53% yield). Analysis: LCMS: m/z=245 (M+H).

Step 3. 4-[[Dimethyl(oxo)-$\lambda^6$-sulfanylidene]amino]-2-methoxy-aniline. A Parr flask was charged with 10% palladium on carbon (0.26 g, 50% wet), product step 2 (0.55 g, 2.25 mmol, 1.0 equiv) and ethanol (50 mL). The mixture was hydrogenated at 40 psi for 4 hours, filtered through Celite, and the filter cake washed with ethanol (100 mL). The filtrate was concentrated under reduced pressure to give a purple wax (0.46 g, 95% yield). Analysis: LCMS: m/z=215 (M+H).

Step 4. 5-chloro-N-[4-[[dimethyl(oxo)-$\lambda^6$-sulfanylidene]amino]-2-methoxy-phenyl]-4-(1H-indol-3-yl)pyrimidin-2-amine. A mixture of product step 3 (110 mg, 0.51 mmol, 1.3 equiv), product step 1 (101 mg, 0.38 mmol, 1.0 equiv) and N,N-diisopropylethylamine (0.25 mL, 1.43 mmol, 3.7 equiv) in 1-methoxy-2-propanol (1 mL) was heated in a CEM microwave at 150° C. for 4 hours. The mixture was concentrated under reduced pressure and purified on an Interchim automated chromatography system (25 g Sorbtech column), eluting with a gradient of 0 to 100% methyl tert-butyl ether (containing 5% methanol) in heptanes, followed by methyl tert-butyl ether (containing 10% methanol), then 10% methanol in dichloromethane to give a red foam (23 mg, 13% yield). Analysis: LCMS: m/z=442 (M+H); $^1$H NMR (400 MHz, DMSO-d6) δ=11.82 (br s, 1H), 8.47 (d, J=3.1 Hz, 1H), 8.33 (s, 2H), 8.25 (s, 1H), 7.47 (t, J=7.9 Hz, 2H), 7.17 (ddd, J=1.1, 7.1, 8.1 Hz, 1H), 7.01 (t, J=7.4 Hz, 1H), 6.62 (d, J=2.3 Hz, 1H), 6.57 (dd, J=2.2, 8.3 Hz, 1H), 3.73 (s, 3H), 3.23 (s, 6H).

Example 2. 5-Chloro-N-[4-[[dimethyl(oxo)-$\lambda^6$-sulfanylidene]amino]-2-ethoxy-phenyl]-4-(1H-indol-3-yl)pyrimidin-2-amine

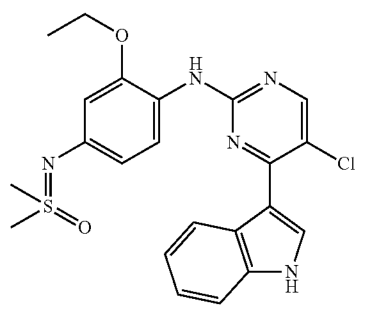 [SMILES: CCOc1cc(N=S(C)(C)=O)ccc1Nc1ncc(Cl)c(-c2c[nH]c3ccccc23)n1]

Step 1. 1-(Benzenesulfonyl)-3-(2,5-dichloropyrimidin-4-yl)indole. 3-(2,5-Dichloropyrimidin-4-yl)-1H-indole (2.64 g, 10 mmol, 1.0 equiv) and sodium tert-butoxide (1.12 g, 11.6 mmol, 1.16 equiv) were sequentially added to a solution of benzenesulfonyl chloride (2.10 g, 11.9 mmol. 1.2 equiv) in N,N-dimethylformamide (30 mL). After 3 hours, the mixture was diluted with additional N,N-dimethylformamide (20 mL) and additional benzenesulfonyl chloride (1.5 g, 8.5 mmol. 0.85 equiv) and sodium tert-butoxide (0.85 g, 8.8 mmol, 0.88 equiv) were added. After stirring overnight, the mixture was diluted with water (100 mL), the resulting solid was filtered and washed with water (200 mL). The crude solids were purified using an Interchim automated chromatography system (80 g Sorbtech silica gel column), eluting with a gradient of 0 to 15% ethyl acetate in hexanes then 15 to 100% dichloromethane in hexanes to give a yellow solid compound 2-1 (1.31 g, 32% yield). Analysis: LCMS: m/z=404 (M+H).

Step 2. N-(4-Bromo-2-ethoxyphenyl)-5-chloro-4-(1-(phenylsulfonyl)-1H-indol-3-yl)pyrimidin-2-amine (2-2): 4-Bromo-2-ethoxyaniline (Combi-blocks, 0.20 g, 0.92 mmol, 1.2 equiv), compound 2-1 (0.30 g, 0.74 mmol, 1.0 equiv) and methanesulfonic acid (0.10 mL, 1.5 mmol, 2.1 equiv) in 1-methoxy-2-propanol (10 mL) were heated at 120° C. overnight. The mixture was cooled to room temperature, diluted with ethyl acetate (30 mL) and washed with half-saturated sodium bicarbonate (10 mL). The aqueous layer was extracted with additional ethyl acetate (10 mL). The combined organic extracts were concentrated onto silica gel (12 g) and purified on an Interchim automated chromatography system (Sorbtech 40 g silica gel column), eluting with a gradient of 0 to 100% ethyl acetate in heptanes, followed by 100% dichloromethane to give impure product. This material was re-purified on an Interchim automated chromatography system (Sorbtech 40 g silica gel column), eluting with a gradient of 0 to 100% acetone in hexanes to give a white solid (0.35 g, 81% yield). Analysis: LCMS: m/z=583 (M+H); $^1$H NMR (400 MHz, acetone-d6) δ=8.66 (s, 1H), 8.60 (d, J=0.9 Hz, 1H), 8.30-8.25 (m, 2H), 8.18-8.09 (m, 3H), 8.04 (s, 1H), 7.76-7.69 (m, 1H), 7.67-7.62 (m, 2H), 7.50-7.42 (m, 1H), 7.39-7.29 (m, 1H), 7.19 (d, J=2.2 Hz, 1H), 7.07 (dd, J=2.2, 8.7 Hz, 1H), 4.26-4.17 (m, 2H), 1.44 (dt, J=1.2, 7.0 Hz, 3H).

Step 3. 5-Chloro-N-[4-[[dimethyl(oxo)-$\lambda^6$-sulfanylidene]amino]-2-ethoxy-phenyl]-4-(1H-indol-3-yl)pyrimidin-2-amine. A mixture of product step 2 (0.35 g, 0.59 mmol, 1.0 equiv), 2-(di-tert-butylphosphino))-1,1'-biphenyl (26 mg, 0.087 mmol, 0.15 equiv), tris(dibenzylideneacetone)-dipalladium(0) (27 mg, 0.029 mmol, 0.05 equiv), sodium tert-butoxide (114 mg, 1.18 mmol, 2.0 equiv) and S,S-dimethylsulfoximine (111 mg, 1.19 mmol, 2.0 equiv) in 1,4-dioxane (11 mL) was heated at 85° C. for 3 hours. The mixture was cooled to room temperature, diluted with methanol (1 mL) and saturated sodium bicarbonate solution (1 mL) and stirred overnight at 80° C. The mixture was then treated with 5M sodium hydroxide solution (0.2 mL, 1 mmol, 1.6 equiv) and stirred at 80° C. for 12 h. The mixture was cooled to rt and diluted with water (5 mL) and dichloromethane (10 mL). The aqueous phase was extracted with dichloromethane (2×10 mL). The combined organics were concentrated onto silica gel (7 g) and purified using an Interchim automated chromatography system (Biotage Sfär 25 g silica gel column), eluting with a gradient of 5 to 90% acetone in heptanes to give a crude solid (90 mg, 85% purity). Further purification by reverse phase chromatography (Teledyne ACCQPrep 125, Waters Atlantis T3 Prep OBD column, 5 μm, 19×250 mm, 20 to 70% acetonitrile in water with 0.1% formic acid) gave a yellow solid (50 mg, 19% yield) as. Analysis: LCMS: m/z=456 (M+H); $^1$H NMR (400 MHz, acetone-d6) δ=8.59-8.51 (m, 2H), 8.40-8.33 (m, 1H), 8.14 (d, J=8.6 Hz, 1H), 7.74-7.62 (m, 1H), 7.57-7.47 (m, 1H), 7.23 (ddd, J=1.2, 7.0, 8.1 Hz, 1H), 7.15 (ddd, J=1.1, 7.1, 8.1 Hz, 1H), 6.69 (d, J=2.2 Hz, 1H), 6.63 (dd, J=2.3, 8.5 Hz, 1H), 4.12 (q, J=7.0 Hz, 2H), 3.19 (s, 6H), 1.47-1.40 (m, 3H).

Example 3-8 were Synthesized Using Methods Analogous for Example 1 and Example 2

Example 3
5-chloro-N-[4-[[dimethyl(oxo)-$\lambda^6$-sulfanylidene]amino]-2-isopropoxy-phenyl]-4-(1H-indol-3-yl)pyrimidin-2-amine

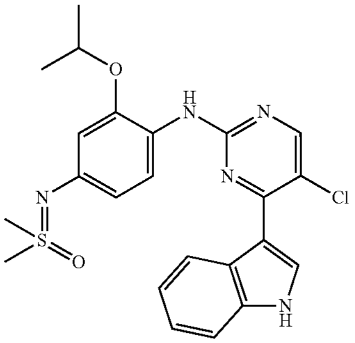 [SMILES: CC(C)Oc1cc(N=S(C)(C)=O)ccc1Nc1ncc(Cl)c(-c2c[nH]c3ccccc23)n1]

LCMS: m/z = 470 (M + H); $^1$H NMR (400 MHz, acetone-d6) δ = 8.57 (d, J = 7.9 Hz, 1H), 8.55-8.51 (m, 1H), 8.37 (s, 1H), 8.22-8.17 (m, 1H), 7.70 (s, 1H), 7.53 (td, J = 0.9, 8.1 Hz, 1H), 7.23 (ddd, J = 1.2, 6.9, 8.2 Hz, 1H), 7.16 (ddd, J = 1.1, 7.1, 8.1 Hz, 1H), 6.72 (d, J = 2.3 Hz, 1H), 6.63 (dd, J = 2.3, 8.6 Hz, 1H), 4.63 (spt, J = 6.1 Hz, 1H), 3.19 (s, 6H), 1.38 (d, J = 6.0 Hz, 6H).

Example 4
5-chloro-N-[4-[[dimethyl(oxo)-$\lambda^6$-sulfanylidene]amino]-2-isobutoxy-phenyl]-4-(1H-indol-3-yl)pyrimidin-2-amine

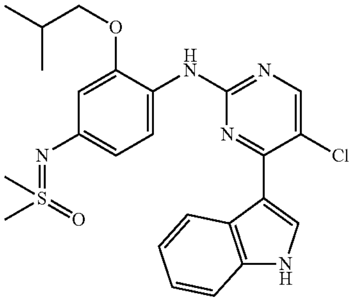 [SMILES: CC(C)COc1cc(N=S(C)(C)=O)ccc1Nc1ncc(Cl)c(-c2c[nH]c3ccccc23)n1]

LCMS: m/z = 484 (M + H); 1H NMR (400 MHz, acetone-d6) δ = 8.63-8.52 (m, 2H), 8.37 (d, J = 0.9 Hz, 1H), 8.12 (dd, J = 5.3, 8.4 Hz, 1H), 7.80-7.65 (m, 1H), 7.53 (d, J = 8.1 Hz, 1H), 7.26-7.19 (m, 1H), 7.19-7.12 (m, 1H), 6.69 (d, J = 2.2 Hz, 1H), 6.64 (dd, J = 2.3, 8.5 Hz, 1H), 2.81 (s, 8H), 2.79-2.77 (m, 4H), 2.21-2.11 (m, 1H), 1.08 (dd, J = 1.8, 6.7 Hz, 6H).

Example 5
5-chloro-N-[3-[[dimethyl(oxo)-$\lambda^6$-sulfanylidene]amino]-2-methoxy-phenyl]-4-(1H-indol-3-yl)pyrimidin-2-amine

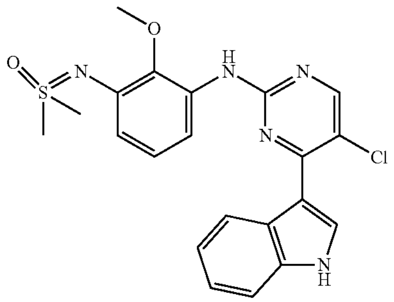 [SMILES: COc1c(N=S(C)(C)=O)cccc1Nc1ncc(Cl)c(-c2c[nH]c3ccccc23)n1]

HCl salt, LCMS: m/z = 442.1 (M + H); 1H NMR (400 MHz, CD3OD) δ = 9.00 (s, 1H), 8.33 (s, 1H), 8.19 (br d, J = 7.3 Hz, 1H), 7.80-7.61 (m, 1H), 7.51 (td, J = 0.9, 8.2 Hz, 1H), 7.42-7.34 (m, 3H), 7.28 (ddd, J = 1.1, 7.2, 8.1 Hz, 1H), 7.25-7.20 (m, 1H), 7.11 (t, J = 7.6 Hz, 1H), 3.84 (s, 3H), 3.36 (s, 6H).

-continued

| | | |
|---|---|---|
| Example 6<br>5-chloro-N-[5-[[dimethyl(oxo)-$\lambda^6$-sulfanylidene]amino]-2-methoxy-phenyl]-4-(1H-indol-3-yl)pyrimidin-2-amine | 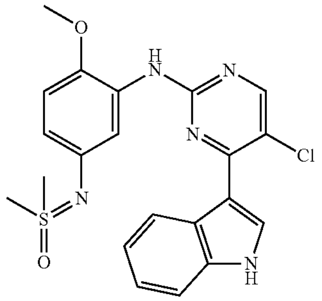 [SMILES: COc1ccc(N=S(C)(C)=O)cc1Nc1ncc(Cl)c(-c2c[nH]c3ccccc23)n1] | LCMS: m/z = 442.1 (M + H); 1H NMR (400 MHz, THF) δ = 10.86 (br s, 1H), 10.80 (s, 2H), 8.58-8.51 (m, 1H), 8.43-8.38 (m, 1H), 8.34 (d, J = 0.7 Hz, 1H), 8.13 (dd, J = 2.6, 4.0 Hz, 1H), 7.82 (s, 1H), 7.42-7.36 (m, 1H), 7.19-7.14 (m, 2H), 6.78 (d, J = 8.6 Hz, 1H), 6.67 (ddd, J = 0.5, 2.6, 8.6 Hz, 1H), 3.86 (s, 3H), 3.00 (s, 6H). |
| Example 7<br>5-chloro-N-[3-[[dimethyl(oxo)-$\lambda^6$-sulfanylidene]amino]phenyl]-4-(1H-indol-3-yl)pyrimidin-2-amine | 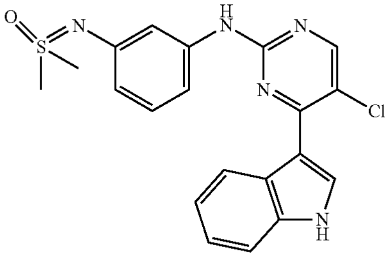 [SMILES: CS(C)(=O)=Nc1cccc(Nc2ncc(Cl)c(-c3c[nH]c4ccccc34)n2)c1] | LCMS: m/z = 412.1 (M + H)+; 1H NMR (400 MHz, CD3OD) δ = 8.96 (s, 1H), 8.32 (s, 1H), 8.21 (br d, J = 8.1 Hz, 1H), 7.58-7.53 (m, 1H), 7.51 (td, J = 0.8, 8.2 Hz, 1H), 7.49-7.43 (m, 2H), 7.32-7.25 (m, 2H), 7.12-7.06 (m, 1H), 3.75-3.72 (m, 1H), 3.69-3.64 (m, 3H), 3.59-3.57 (m, 7H). |
| Example 8<br>5-chloro-N-[4-[[dimethyl(oxo)-$\lambda^6$-sulfanylidene]amino]phenyl]-4-(1H-indol-3-yl)pyrimidin-2-amine | 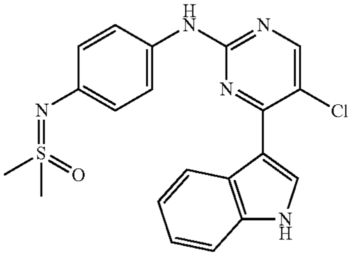 [SMILES: CS(C)(=O)=Nc1ccc(Nc2ncc(Cl)c(-c3c[nH]c4ccccc34)n2)cc1] | LCMS: m/z = 412 (M + H)+; 1H NMR (400 MHz, DMSO-d6) δ = 11.87 (br s, 1H), 9.38 (s, 1H), 8.56 (br d, J = 8.4 Hz, 1H), 8.48 (s, 1H), 8.40 (s, 1H), 7.57-7.53 (m, 2H), 7.49 (td, J = 0.9, 7.9 Hz, 1H), 7.21 (ddd, J = 1.2, 7.2, 8.2 Hz, 1H), 7.13-7.07 (m, 1H), 6.88 (d, J = 7.9 Hz, 2H), 3.18 (s, 6H). |
| Example 9<br>N-[4-[[dimethyl(oxo)-$\lambda^6$-sulfanylidene]amino]-2-ethoxy-phenyl]-5-methyl-4-(7-methyl-1H-indol-3-yl)pyrimidin-2-amine | 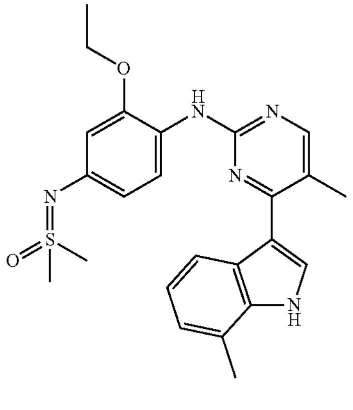 [SMILES: CCOc1cc(N=S(C)(C)=O)ccc1Nc1ncc(C)c(-c2c[nH]c3c(C)cccc23)n1] | LCMS (ESI) m/z = 450.2 (M + H)+; 1H NMR (400 MHz, CD3OD) δ = 8.22 (d, J = 8.6 Hz, 1H), 8.17 (s, 1H), 8.15-8.11 (m, 1H), 7.80 (s, 1H), 7.04-6.98 (m, 2H), 6.72 (d, J = 2.2 Hz, 1H), 6.64 (dd, J = 2.3, 8.5 Hz, 1H), 4.11 (q, J = 7.0 Hz, 2H), 3.19 (s, 6H), 2.54 (s, 3H), 2.39 (d, J = 0.5 Hz, 3H), 1.44 (t, J = 7.0 Hz, 3H). |
| Example 10<br>N-[4-[[dimethyl(oxo)-$\lambda^6$-sulfanylidene]amino]phenyl]-4-(1H-indol-3-yl)pyrimidin-2-amine | 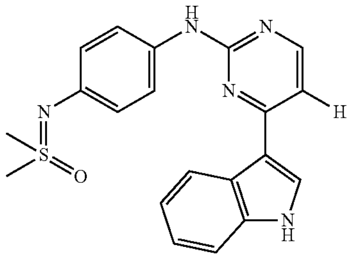 [SMILES: CS(C)(=O)=Nc1ccc(Nc2nccc(-c3c[nH]c4ccccc34)n2)cc1] | LCMS: m/z = 378.1 (M + H)+; 1H NMR (400 MHz, DMSO-d6) δ = 11.73 (br s, 1H), 9.13 (s, 1H), 8.58 (d, J = 7.9 Hz, 1H), 8.27 (t, J = 2.7 Hz, 2H), 7.65-7.59 (m, 2H), 7.46 (d, J = 7.9 Hz, 1H), 7.22-7.17 (m, 2H), 7.12 (ddd, J = 1.1, 7.1, 7.9 Hz, 1H), 6.93-6.88 (m, 2H), 3.19 (s, 6H). |

-continued

| | | |
|---|---|---|
| Example 11<br>N-[4-[[dimethyl(oxo)-λ$^6$-sulfanylidene]amino]phenyl]-4-(1H-indol-3-yl)-5-methyl-pyrimidin-2-amine | 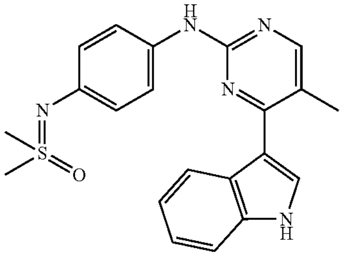 | LCMS: m/z = 392.2 (M + H)+; 1H NMR (400 MHz, DMSO-d6) δ = 11.70 (br s, 1H), 9.03 (s, 1H), 8.54 (d, J = 7.9 Hz, 1H), 8.22 (s, 1H), 7.97 (s, 1H), 7.65-7.59 (m, 2H), 7.47 (d, J = 7.9 Hz, 1H), 7.19 (dt, J = 1.2, 7.5 Hz, 1H), 7.09 (ddd, J = 1.0, 7.1, 8.0 Hz, 1H), 6.87-6.82 (m, 2H), 3.17 (s, 6H), 2.36 (s, 3H). |
| Example 12<br>N-[4-[[dimethyl(oxo)-λ$^6$-sulfanylidene]amino]phenyl]-6-(1H-indol-3-yl)pyrimidin-4-amine | 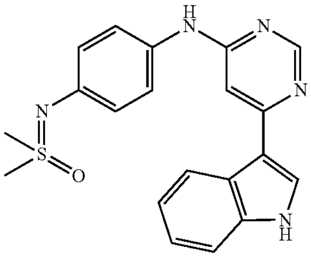 [SMILES: CS(C)(=O)=Nc1ccc(Nc2cc(-c3c[nH]c4ccccc34)ncn2)cc1] | LCMS: m/z = 378.1 (M + H)+; 1H NMR (400 MHz, DMSO-d6) δ = 11.65 (br s, 1H), 9.23 (s, 1H), 8.54 (d, J = 0.9 Hz, 1H), 8.24-8.18 (m, 1H), 8.08 (s, 1H), 7.52-7.46 (m, 3H), 7.22-7.14 (m, 2H), 7.12 (d, J = 1.0 Hz, 1H), 6.95-6.89 (m, 2H), 3.19 (s, 6H). |
| Example 13<br>N-[4-[[dimethyl(oxo)-λ$^6$-sulfanylidene]amino]phenyl]-4-indol-1-yl-pyrimidin-2-amine | 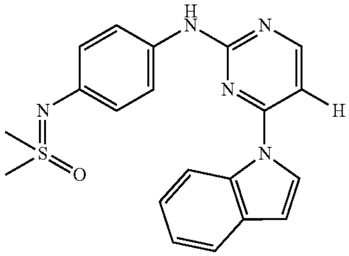 [SMILES: CS(C)(=O)=Nc1ccc(Nc2nccc(-n3ccc4ccccc43)n2)cc1] | LCMS: m/z = 378 (M + H)+; 1H NMR (400 MHz, acetone-d6) δ = 8.58-8.47 (m, 2H), 8.30 (dd, J = 0.6, 5.6 Hz, 1H), 7.85 (d, J = 3.7 Hz, 1H), 7.52-7.46 (m, 3H), 7.14-7.03 (m, 2H), 6.93 (d, J = 5.6 Hz, 1H), 6.90-6.85 (m, 2H), 6.64 (dd, J = 0.6, 3.7 Hz, 1H), 3.05 (s, 6H). |
| Example 14<br>N-[4-[[dimethyl(oxo)-λ$^6$-sulfanylidene]amino]phenyl]-4-indol-1-yl-5-methyl-pyrimidin-2-amine | 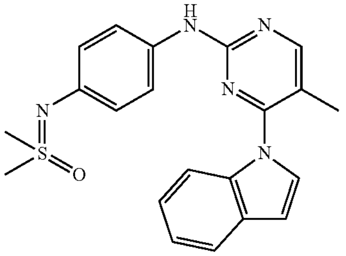 | LCMS: m/z = 392.2 (M + H)+; 1H NMR (400 MHz, DMSO-d6) δ = 9.46 (s, 1H), 8.49 (d, J = 0.5 Hz, 1H), 7.75-7.71 (m, 2H), 7.68-7.63 (m, 1H), 7.57-7.52 (m, 2H), 7.24-7.15 (m, 2H), 6.85-6.80 (m, 2H), 6.74 (dd, J = 0.6, 3.4 Hz, 1H), 3.15 (s, 6H), 2.16 (s, 3H). |
| Example 15<br>N-[4-[[dimethyl(oxo)-λ$^6$-sulfanylidene]amino]phenyl]-6-indol-1-yl-pyrimidin-4-amine | 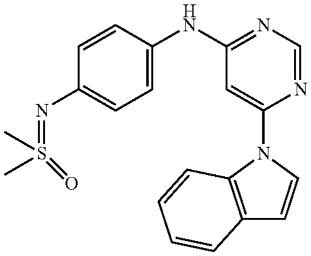 [SMILES: CS(C)(=O)=Nc1ccc(Nc2cc(-n3ccc4ccccc43)ncn2)cc1] | LCMS: m/z = 378.1 (M + H)+; 1H NMR (400 MHz, Acetonitrile-d3) δ = 9.75 (br s, 1H), 8.56 (d, J = 1.0 Hz, 1H), 8.29-8.22 (m, 2H), 7.98 (d, J = 2.9 Hz, 1H), 7.56 (s, 1H), 7.52-7.49 (m, 1H), 7.44-7.40 (m, 2H), 7.25-7.18 (m, 2H), 7.04 (d, J = 1.2 Hz, 1H), 7.02-6.98 (m, 2H), 3.11 (s, 6H). |

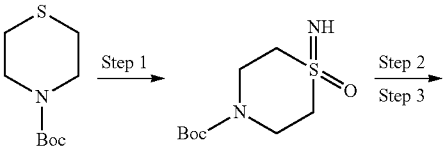

-continued

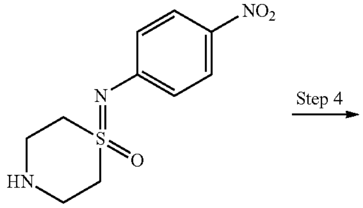

-continued

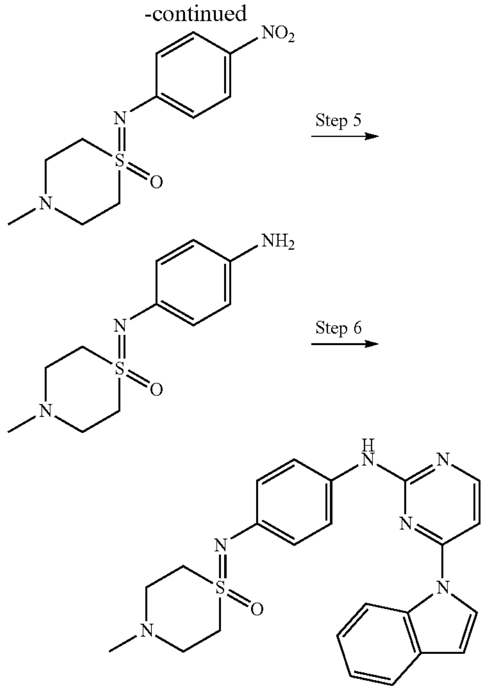

Example 16

Example 16. 4-Indol-1-yl-N-[4-[(4-methyl-1-oxo-1,4-thiazinan-1-ylidene)amino]phenyl]-pyrimidin-2-amine

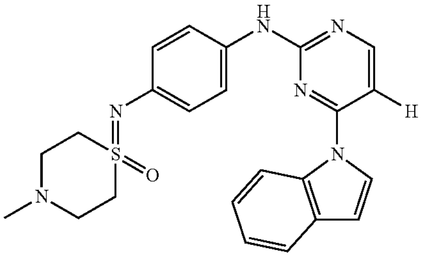 [SMILES: CN1CCS(=O)(=Nc2ccc(Nc3nccc(-n4ccc5ccccc54)n3)cc2)CC1]

Step 1. tert-Butyl 1-imino-1-oxo-1,4-thiazinane-4-carboxylate. A solution of BOC-thiomorpholine (4.91 g, 24.1 mmol, 1.0 equiv) in methanol (50 mL) was treated with (diacetoxyiodo)benzene (16.3 g, 50.6 mmol, 2.1 equiv) and ammonium acetate (3.0 g, 38.9 mmol, 1.6 equiv). After 2 hours the mixture was diluted with water (100 mL) and saturated sodium bicarbonate (50 mL). The pH was adjusted slowly to 6 with 5M sodium hydroxide. The mixture was extracted with dichloromethane (3×50 mL). The combined organic layers were washed with saturated brine (50 mL), dried over sodium sulfate, filtered and concentrated under reduced pressure. The residue was diluted with hexanes (20 mL) and triturated. The solids were collected and dried at 40° C. overnight to give an off-white solid (3.9 g, 69% yield). Analysis: LCMS: m/z=235 (M+H).

Step 2. tert-Butyl 1-(4-nitrophenyl)imino-1-oxo-1,4-thiazinane-4-carboxylate. A mixture of product step 1 (752 mg, 1.07 equiv), 4-bromonitrobenzene (607 mg, 3.0 mmol, 1.0 equiv), tris(dibenzylideneacetone)dipalladium(0) (160 mg, 0.17 mmol, 0.06 equiv), 2-(di-tert-butylphosphino)biphenyl (135 mg, 0.45 mmol, 0.15 equiv) and sodium tert-butoxide (346 mg, 3.6 mmol, 1.2 equiv) in 1,4-dioxane (30 mL) was heated at 80° C. overnight. The mixture was cooled to room temperature then concentrated onto silica gel (10 g). The crude product was purified on a Büchi automated chromatography system (Sorbtech 40 g column), eluting with a gradient of 5 to 100% ethyl acetate in heptanes to give a white solid (775 mg, 72% yield). Analysis: LCMS: m/z=356 (M+H).

Step 3. 1-(4-Nitrophenyl)imino-1,4-thiazinane 1-oxide. A solution of product step 2 (0.77 g, 2.16 mmol, 1 equiv) in dichloromethane (20 mL) was treated with trifluoroacetic acid (5 mL, 30 equiv) for 90 minutes. The volatiles were removed under reduced pressure to give a solid as the trifluoroacetic acid salt. Analysis: LCMS: m/z=256 (M+H).

Step 4. 4-Methyl-1-(4-nitrophenyl)imino-1,4-thiazinane 1-oxide. The product from step 3 was combined with 1,2-dichloroethane (20 mL), 37% aqueous formaldehyde (1 mL, 13.4 mmol, 6.2 equiv) and sodium triacetoxyborohydride (1.21 g, 5.7 mmol, 2.6 equiv). After stirring at room temperature overnight, acetic acid (2 mL) was added, followed by additional 37% aqueous formaldehyde (1 mL, 6.2 equiv) and sodium triacetoxyborohydride (1.2 g, 2.6 equiv). After stirring overnight additional sodium triacetoxyborohydride (0.8 g, 1.7 equiv) and 37% aqueous formaldehyde (1 mL, 6.2 equiv) were added and the mixture was stirred for 4 hours. The mixture was diluted with saturated sodium bicarbonate (50 mL) and extracted with dichloromethane (2×50 mL). The combined organic layers were washed with saturated sodium bicarbonate (40 mL) then concentrated onto silica gel (5 g). The crude product was purified on a Büchi automated chromatography system (Biotage Sfär 25 g column), eluting with a gradient of 0 to 10% methanol in dichloromethane to give a yellow solid (0.48 g, 83% yield). Analysis: LCMS: m/z=270 (M+H).

Step 5. 4-[(4-Methyl-1-oxo-1,4-thiazinan-1-ylidene)amino]aniline A mixture of product step 4 (0.48 g, 1.78 mmol, 1 equiv) and 10% platinum on carbon (0.18 g, 0.046 mmol, 0.026 equiv, 50% wet) in ethanol (40 mL) was hydrogenated at 40 psi for 30 minutes, then filtered through Celite. The filter pad was washed with ethanol (40 mL) and the filtrate was concentrated under reduced pressure to give a brown wax (0.48 g, 100% yield). Analysis: LCMS: m/z=240 (M+H).

Step 6. 4-Indol-1-yl-N-[4-[(4-methyl-1-oxo-1,4-thiazinan-1-ylidene)amino]phenyl]-pyrimidin-2-amine. A mixture of product step 5 (76 mg, 0.33 mmol, 1.0 equiv), cesium carbonate (365 mg, 1.12 mmol, 3.4 equiv), 4,5-bis(diphenylphosphino)-9,9-dimethylxanthene (43 mg, 0.074 mmol, 0.22 equiv), tris(dibenzylideneacetone)-dipalladium(0) (31 mg, 0.033 mmol, 0.10 equiv) and compound 25-6 (109 mg, 0.45 mmol, 1.3 equiv) in 1,4-dioxane (8 mL) was heated at 85° C. for 6 hours. After cooling to room temperature, the mixture was filtered through Celite, which was washed with methanol (30 mL). The filtrate was concentrated under reduced pressure. The crude product was purified on a Teledyne ACCQPrep automated chromatography system (Waters Atlantis T3 Prep OBD column, 5 μm, 19×250 mm), eluting with a gradient of 25 to 33% acetonitrile in water with 0.1% formic acid. The product fractions were basified with 5M sodium hydroxide then extracted with dichloromethane and concentrated under reduced pressure to give a grey solid (91 mg, 64% yield). Analysis: LCMS: m/z=433 (M+H)+; 1H NMR (400 MHz, CD2Cl2) δ=8.41 (d, J=8.4 Hz, 1H), 8.39 (d, J=5.7 Hz, 1H), 7.76 (d, J=3.7 Hz, 1H), 7.66-7.59 (m, 1H), 7.53-7.46 (m, 2H), 7.29-7.25 (m, 1H), 7.24-7.20 (m, 1H), 7.18 (s, 1H), 7.11-7.07 (m, 2H), 6.86 (d, J=5.6 Hz, 1H), 6.74 (dd, J=0.7, 3.6 Hz, 1H), 3.37-3.30 (m, 2H), 3.23 (ddd, J=4.0, 9.1, 13.3 Hz, 2H), 2.97-2.85 (m, 4H), 2.40 (s, 3H).

Example 17. N-[4-[[dimethyl(oxo)-$\lambda^6$-sulfanylidene]amino]-2-nitro-phenyl]-4-indol-1-yl-pyrimidin-2-amine

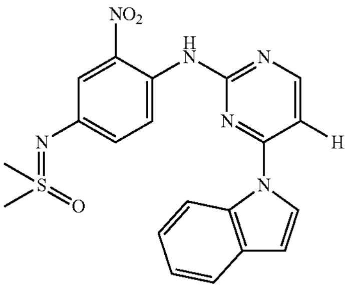

Step 1. N-(4-Bromo-2-nitrophenyl)-4-(1H-indol-1-yl)pyrimidin-2-amine (29-3): A 60% dispersion of sodium hydride in mineral oil (0.11 g, 2.62 mmol, 1.5 equiv) was added to a mixture of 1-(2-chloropyrimidin-4-yl)-1H-indole (0.41 g, 1.79 mmol, 1.0 equiv) and 4 -bromo-2-nitroaniline (0.43 g, 198 mmol, 1.1 equiv) in 1-methyl-2-pyrrolidone (8 mL). The mixture was heated to 110° C. under nitrogen for 90 minutes then diluted with water (16 mL). The mixture was cooled to room temperature, the resulting solids were filtered, washed with water (32 mL) and dried under vacuum at 40° C. overnight to give an orange solid (0.60 g, 82% yield). Analysis: LCMS: m/z=410 (M+H); $^1$H NMR (400 MHz, DMSO-d6) δ=10.14 (s, 1H), 8.56-8.52 (m, 1H), 8.46 (d, J=5.7 Hz, 1H), 8.24 (d, J=2.2 Hz, 1H), 8.12 (d, J=3.8 Hz, 1H), 8.02-7.98 (m, 1H), 7.97-7.93 (m, 1H), 7.67-7.63 (m, 1H), 7.35 (d, J=5.9 Hz, 1H), 7.28-7.21 (m, 2H), 6.86-6.81 (m, 1H).

Step 2. N-[4-[[dimethyl(oxo)-$\lambda^6$-sulfanylidene]amino]-2-nitro-phenyl]-4-indol-1-yl-pyrimidin-2-amine. A mixture of S,S-dimethylsulfoximine (105 mg, 1.1 mmol, 2.2 equiv), product step 1 (206 mg, 0.50 mmol, 1.0 equiv), tris(dibenzylideneacetone) dipalladium(0) (23 mg, 0.025 mmol, 0.05 equiv), 2-(di-tert-butylphosphino)biphenyl (15 mg, 0.05 mmol, 0.10 equiv) and sodium tert-butoxide (104 mg, 1.12 mmol, 2.2 equiv) in 1,4-dioxane (9 mL) was heated at 85° C. overnight. The mixture was cooled to room temperature and concentrated onto silica gel (8 g). The crude product was purified on a Büchi automated chromatography system (Sorbtech 40 g column), eluting with a gradient of 5 to 70% acetone in heptanes to give a solid (40 mg, 19% yield) Analysis: LCMS: m/z=423 (M+H).

Example 18. 4-[[dimethyl(oxo)-$\lambda^6$-sulfanylidene]amino]-N1-(4-indol-1-ylpyrimidin-2-yl)benzene-1,2-diamine

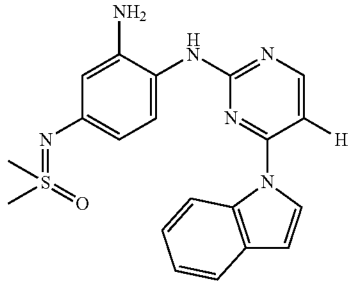 [SMILES: CS(C)(=O)=Nc1ccc(Nc2nccc(-n3ccc4ccccc43)n2)c([N+](=O)[O-])c1]

4-[[dimethyl(oxo)-$\lambda^6$-sulfanylidene]amino]-N1-(4-indol-1-ylpyrimidin-2-yl)benzene-1,2-diamine. Example 17 (40 mg, 0.095 mmol, 1 equiv) in a 2 to 1 mixture of ethanol and THF (15 mL) was treated with tin(II) chloride dihydrate (144 mg, 0.64 mmol, 6.7 equiv). After 24 hours, additional tin(II) chloride dihydrate (85 mg, 4 equiv) was added and the reaction was stirred overnight. The mixture was diluted with water (8 mL), 5M sodium hydroxide (2 mL) and methyl tert-butyl ether (20 mL). The layers were separated and the aqueous layer was extracted with additional methyl tert-butyl ether (10 mL). The combined organic extracts were washed with saturated brine (10 mL), dried over sodium sulfate, filtered and concentrated to give a solid (40 mg 100% yield). Analysis: LCMS: m/z=393 (M+H).

Example 19. N-[5-[[dimethyl(oxo)-$\lambda^6$-sulfanylidene]amino]-2-[(4-indol-1-ylpyrimidin-2-yl)amino]phenyl]prop-2-enamide

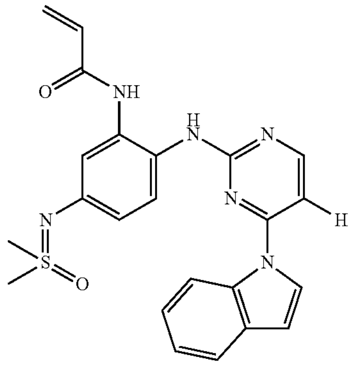 [SMILES: C=CC(=O)Nc1cc(N=S(C)(C)=O)ccc1Nc1nccc(-n2ccc3ccccc32)n1]

N-[5-[[dimethyl(oxo)-$\lambda^6$-sulfanylidene]amino]-2-[(4-indol-1-ylpyrimidin-2-yl)amino]phenyl]prop-2-enamide. A solution of acryloyl chloride (16 mg, 0.18 mmol, 1.8 equiv) in dichloromethane (0.7 mL) was added at 0° C. to a solution of example 18 (40 mg, 0.095 mmol, 1 equiv) and triethylamine (0.05 mL, 0.36 mmol, 3.8 equiv) in dichloromethane (5 mL). Additional acryloyl chloride (16 mg, 0.18 mmol, 1.8 equiv) in dichloromethane (0.7 mL) and triethylamine (0.05 mL, 0.36 mmol, 3.8 equiv) were added after 4 hours. After stirring overnight, the reaction mixture was concentrated under reduced pressure. The crude product was purified on a Teledyne ACCQPrep automated chromatography system (Waters Atlantis T3 Prep OBD column, 5 μm, 19×250 mm), eluting with a gradient of 10 to 55% acetonitrile in water with 0.1% formic acid. The product fractions were basified with saturated sodium bicarbonate then extracted with dichloromethane (2×25 mL) and concentrated under reduced pressure to give a grey solid (21 mg, 50% yield). Analysis: LCMS: m/z=433 (M+H)+; 1H NMR (400 MHz, acetone) δ=9.23 (br s, 1H), 8.48 (br s, 1H), 8.37 (d, J=5.6 Hz, 1H), 8.32-8.23 (m, 1H), 7.95 (d, J=3.7 Hz, 1H), 7.61-7.56 (m, 1H), 7.55-7.49 (m, 2H), 7.20-7.14 (m, 2H), 7.06 (d, J=5.7 Hz, 1H), 6.93 (dd, J=2.4, 8.6 Hz, 1H), 6.75 (dd, J=0.6, 3.7 Hz, 1H), 6.54-6.46 (m, 1H), 6.38-6.32 (m, 1H), 5.69 (dd, J=2.1, 10.0 Hz, 1H), 3.25 (s, 6H).

Example 20. N-[5-[[Dimethyl(oxo)-$\lambda^6$-sulfanylidene]amino]-2-[[4-(1H-indol-3-yl)-5-methyl-pyrimidin-2-yl]amino]phenyl]prop-2-enamide

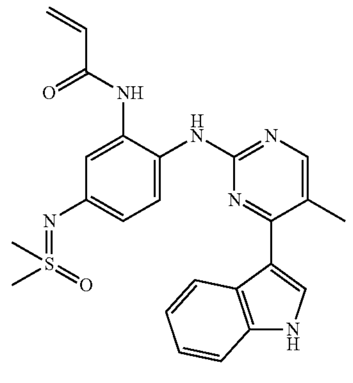

This example was synthesized using 3-(2-chloro-5-methyl-pyrimidin-4-yl)-1-methyl-indole and 4-[[dimethyl(oxo)-$\lambda^6$-sulfanylidene]amino]-2-nitro-aniline by the procedure for example 19. Analysis: LCMS: m/z=461 (M+H)+; $^1$H NMR (400 MHz, DMSO-d6) δ=11.71 (br d, J=1.3 Hz, 1H), 9.83 (s, 1H), 8.36 (d, J=8.3 Hz, 1H), 8.18-8.10 (m, 2H), 7.97 (d, J=2.9 Hz, 1H), 7.58-7.54 (m, 1H), 7.44 (d, J=8.1 Hz, 1H), 7.25 (br d, J=1.6 Hz, 1H), 7.15 (ddd, J=1.1, 7.1, 8.1 Hz, 1H), 7.02-6.92 (m, 1H), 6.78 (dd, J=2.4, 8.6 Hz, 1H), 6.45 (dd, J=10.1, 17.0 Hz, 1H), 6.24 (dd, J=2.0, 17.0 Hz, 1H), 5.73 (dd, J=1.8, 10.1 Hz, 1H), 3.23 (s, 6H), 2.35 (s, 3H).

Example 21. 1-[1-[2-[4-[[Dimethyl(oxo)-$\lambda^6$-sulfanylidene]amino]anilino]-5-methyl-pyrimidin-4-yl]indol-3-yl]ethanone

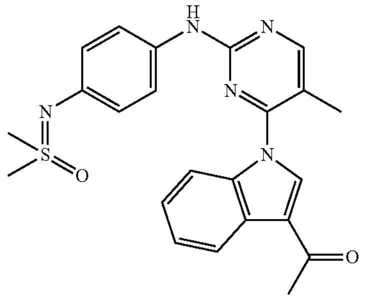 [SMILES: CC(=O)c1cn(-c2nc(Nc3ccc(N=S(C)(C)=O)cc3)ncc2C)c2ccccc12]

Step 1. 1-(1-(2-Chloro-5-methylpyrimidin-4-yl)-1H-indol-3-yl)ethan-1-one. A mixture of 3-acetylindole (1.5 g, 9.4 mmol, 1.0 equiv), potassium carbonate (1.81 g, 13.2 mmol, 1.4 equiv), 2,4-dichloro-5-methyl-pyrimidine (3.06 g, 18.8 mmol, 2.0 equiv) and 1-hydroxybenzotriazole (0.13 g, 0.9 mmol, 0.1 equiv) in anhydrous N,N-dimethylacetamide (12 mL) was heated at 60° C. for 72 hours. After cooling to room temperature, the solid which formed was filtered off and washed with ethyl acetate (15 mL). The filtrate was diluted with additional ethyl acetate (20 mL), and water (30 mL). The layers were separated and the organic layer was washed with saturated brine (2×20 mL), dried over sodium sulfate, filtered and concentrated under reduced pressure. The residue was purified on an Interchim automated chromatography system (Sorbtech 25 g column), eluting with a gradient of 0 to 90% ethyl acetate in heptanes to give a white solid (0.25 g, 9% yield). Analysis: LCMS: m/z=286.1 (M+H); $^1$H NMR (400 MHz, $CDCl_3$) δ=8.85 (s, 1H), 8.74 (d, J=6.4 Hz, 1H), 8.52 (s, 1H), 8.44 (d, J=6.4 Hz, 1H), 7.55-7.45 (m, 2H), 2.63 (s, 3H), 2.40 (s, 3H).

Step 2. 1-[1-[2-[4-[[Dimethyl(oxo)-$\lambda^6$-sulfanylidene]amino]anilino]-5-methyl-pyrimidin-4-yl]indol-3-yl]ethenone. A mixture of product step 1 (140 mg, 0.5 mmol, 1 equiv), cesium carbonate (0.49 g, 1.5 mmol, 3 equiv), 4,5-bis(diphenylphosphino)-9,9-dimethylxanthene (30 mg, 0.05 mmol, 0.1 equiv), tris(dibenzylideneacetone)dipalladium(0) (23 mg, 0.025 mmol, 0.05 equiv) and 4-[[dimethyl(oxo)-$\lambda^6$-sulfanylidene]amino]aniline (184 mg, 1.0 mmol, 2 equiv) in 1,4-dioxane (6 mL) was heated at 80° C. for 5.5 hours. After cooling to room temperature, the solids which formed were filtered off and washed with ethyl acetate (15 mL). The filtrate was diluted with additional ethyl acetate (10 mL) and water (15 mL). The layers were separated and the aqueous layer was extracted with ethyl acetate (2×10 mL). The combined organic layers were dried over sodium sulfate, filtered and concentrated under reduced pressure. The residue was purified on an Interchim automated chromatography system (RediSep Gold 15 g C18 column), eluting with a gradient of 0 to 100% acetonitrile in water to give an off-white solid (42 mg, 19% yield). Analysis: LCMS: m/z=434.2 (M+H)+; $^1$H NMR (400 MHz, DMSO-d6) δ=8.91 (s, 1H), 8.84 (s, 1H), 8.49 (d, J=8.4 Hz, 1H), 8.22 (d, J=7.3 Hz, 1H), 8.18 (d, J=0.9 Hz, 1H), 7.45-7.41 (m, 2H), 7.28-7.24 (m, 1H), 7.17 (ddd, J=1.2, 7.2, 8.3 Hz, 1H), 7.05-7.00 (m, 2H), 3.25 (s, 6H), 2.54-2.52 (m, 3H), 2.23 (s, 3H).

Example 22. 1-[1-[2-[4-[[dimethyl(oxo)-$\lambda^6$-sulfanylidene]amino]anilino]-5-methyl-pyrimidin-4-yl]indol-3-yl]ethanol

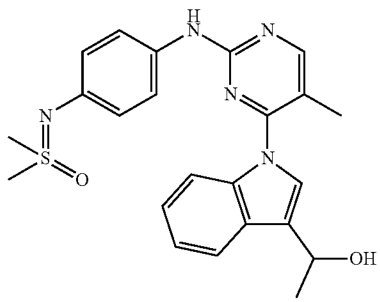 [SMILES: Cc1cnc(Nc2ccc(N=S(C)(C)=O)cc2)nc1-n1cc(C(C)O)c2ccccc21]

1-[1-[2-[4-[[dimethyl(oxo)-$\lambda^6$-sulfanylidene]amino]anilino]-5-methyl-pyrimidin-4-yl]indol-3-yl]ethanol. Sodium borohydride (17.5 mg, 0.4 mmol, 7.0 equiv) was added to a solution of example 21 (25 mg, 58 μmol, 1.0 equiv) in anhydrous THF (3 mL) and the resulting mixture was stirred at room temperature overnight. The reaction was quenched with 1M HCl (0.1 mL). THF was removed under reduced pressure and the product was extracted with ethyl acetate (3×5 mL). The combined organic layers were dried over sodium sulfate, filtered and concentrated under reduced pressure. The residue was purified on a Biotage automated chromatography system (RediSep Gold 5.5 g C18 column), eluting with a gradient of 0 to 70% acetonitrile in water to give a colorless viscous oil (12 mg, 48% yield). Analysis: LCMS: m/z=436.2 (M+H)+; $^1$H NMR (400 MHz, CD3OD) δ=8.49-8.40 (m, 1H), 8.06 (d, J=0.9 Hz, 1H), 8.02 (d, J=0.9 Hz, 1H), 7.69-7.63 (m, 1H), 7.50-7.43 (m, 2H), 7.15-7.11 (m, 2H), 7.11-7.06 (m, 2H), 5.13 (dq, J=0.7, 6.5 Hz, 1H), 3.24 (s, 6H), 2.20 (d, J=0.9 Hz, 3H), 1.63 (d, J=6.5 Hz, 3H).

Example 23-33 were Synthesized Using Methods Analogous for Examples 1-15

| | | |
|---|---|---|
| Example 23<br>N-[6-[[dimethyl(oxo)-$\lambda^6$-sulfanylidene]amino]-3-pyridyl]-4-(1H-indol-3-yl)-5-methyl-pyrimidin-2-amine | 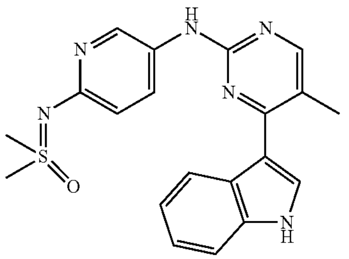 | LCMS: m/z = 393.2 (M + H)+; $^1$H NMR (400 MHz, Methanol-d4) δ = 8.44 (dd, J = 0.6, 2.8 Hz, 1H), 8.37 (td, J = 1.0, 8.0 Hz, 1H), 8.17 (d, J = 0.6 Hz, 1H), 7.99 (dd, J = 2.8, 8.7 Hz, 1H), 7.87 (s, 1H), 7.44 (td, J = 0.9, 8.1 Hz, 1H), 7.19 (ddd, J = 1.2, 7.0, 8.1 Hz, 1H), 7.09 (ddd, J = 1.1, 7.1, 8.1 Hz, 1H), 6.79 (dd, J = 0.7, 8.7 Hz, 1H), 3.38 (s, 6H), 2.41 (d, J = 0.6 Hz, 3H) |
| Example 24<br>N-[4-[[dimethyl(oxo)-$\lambda^6$-sulfanylidene]amino]-3-methyl-phenyl]-4-(1H-indol-3-yl)-5-methyl-pyrimidin-2-amine | 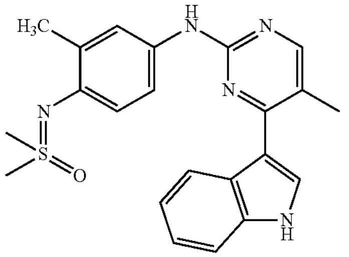 | LCMS: 406.2 m/z (M + H)+; $^1$H NMR (400 MHz, Methanol-d4) δ = 8.46 (d, J = 8.1 Hz, 1H), 8.14 (s, 1H), 7.83 (s, 1H), 7.57 (d, J = 2.3 Hz, 1H), 7.43 (d, J = 8.2 Hz, 1H), 7.33 (dd, J = 2.5, 8.5 Hz, 1H), 7.19 (t, J = 7.5 Hz, 1H), 7.12-7.07 (m, 1H), 7.06 (d, J = 8.4 Hz, 1H), 3.16(s, 6H), 2.38 (s, 3H), 2.23 (s, 3H) |
| Example 25<br>N-[3-chloro-4-[[dimethyl(oxo)-$\lambda^6$-sulfanylidene]amino]phenyl]-4-(1H-indol-3-yl)-5-methyl-pyrimidin-2-amine | 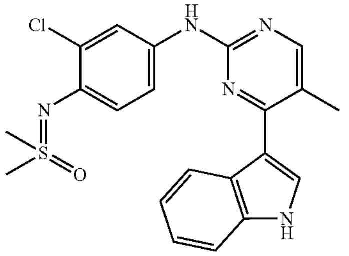 | LCMS: m/z = 426.1 (M + H)+; 1H NMR (400 MHz, Methanol-d4) δ = 8.46 (ddd, J = 0.7, 1.2, 8.1 Hz, 1H), 8.17 (s, 1H), 7.95 (d, J = 2.4 Hz, 1H), 7.82 (s, 1H), 7.46-7.38 (m, 2H), 7.19 (ddd, J = 1.2, 7.0, 8.1 Hz, 1H), 7.17-7.10 (m, 2H), 3.18 (s, 6H), 2.37 (d, J = 0.5 Hz, 3H) |
| Example 26<br>N-[4-[[dimethyl(oxo)-$\lambda^6$-sulfanylidene]amino]-3-methoxy-phenyl]-4-(1H-indol-3-yl)-5-methyl-pyrimidin-2-amine | 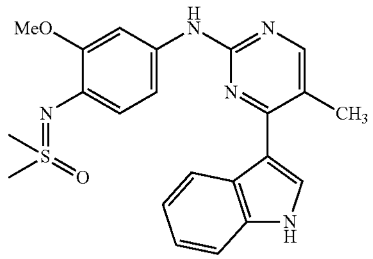 | LCMS: m/z = 409.1 (M + H)+; $^1$H NMR (400 MHz, CDCl3) δ = 8.51 (br s, 1H), 8.38 (d, J = 8.0 Hz, 1H), 8.29 (s, 1H), 7.71 (d, J = 2.4 Hz, 1H), 7.68 (d, J = 2.8 Hz, 1H), 7.48-7.43 (m, 1H), 7.41 (d, J = 8.0 Hz, 1H), 7.32-7.20 (m, 2H), 7.11 (br s, 1H), 6.98 (dd, J = 2.4, 8.8 Hz, 1H), 3.74 (s, 3H), 2.40 (s, 3H). |
| Example 27<br>N-[4-[[dimethyl(oxo)-$\lambda^6$-sulfanylidene]amino]-3-(2-morpholinoethoxy)phenyl]-4-(1H-indol-3-yl)-5-methyl-pyrimidin-2-amine | 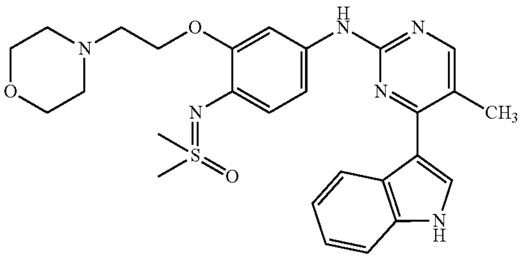 | LCMS: m/z = 508.1 (M + H)+; $^1$H NMR (400 MHz, CDCl3) δ = 8.36 (d, J = 8.0 Hz, 1H), 8.28 (s, 1H), 7.80 (d, J = 2.4 Hz, 1H), 7.67 (d, J = 2.8 Hz, 1H), 7.45 (d, J = 8.0 Hz, 1H), 7.40 (d, J = 8.8 Hz, 1H), 7.29-7.21 (m, 1H), 7.08 (s, 1H), 6.90 (dd, J = 2.4, 8.8 Hz, 1H), 4.00 (t, J = 6.0 Hz, 2H), 3.66 (t, J = 4.8 Hz, 4H), 2.71 (t, J = 6.0 Hz, 2H), 2.49 (t, J = 4.8 Hz, 2H), 2.39 (s, 3H) |

-continued

Example 28
N-[4-[[dimethyl(oxo)-$\lambda^6$-sulfanylidene]amino]phenyl]-5-methyl-4-(6-methyl-1H-indol-3-yl)pyrimidin-2-amine

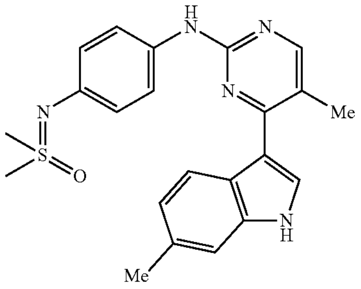 [SMILES: Cc1ccc2c(-c3nc(Nc4ccc(N=S(C)(C)=O)cc4)ncc3C)c[nH]c2c1]

LCMS: m/z = 406 (M + H)+; $^1$H NMR (400 MHz, DMSO-d6) δ = 11.55 (br s, 1H), 9.01 (br s, 1H), 8.42 (br d, J = 7.2 Hz, 1H), 8.20 (br s, 1H), 7.89 (br s, 1H), 7.62 (br d, J = 7.7 Hz, 2H), 7.25 (br s, 1H), 6.92 (br d, J = 7.8 Hz, 1H), 6.85 (br d, J = 7.6 Hz, 2H), 3.24-3.10 (m, 6H), 2.42 (br s, 3H), 2.35 (br s, 3H)

Example 29
N-[4-[[dimethyl(oxo)-$\lambda^6$-sulfanylidene]amino]phenyl]-4-(6-fluoro-1H-indol-3-yl)-5-methyl-pyrimidin-2-amine

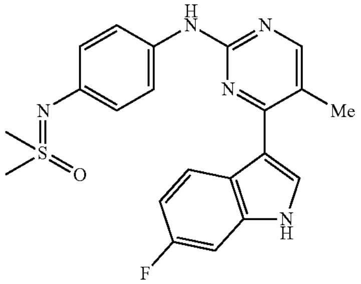 [SMILES: Cc1cnc(Nc2ccc(N=S(C)(C)=O)cc2)nc1-c1c[nH]c2cc(F)ccc12]

LCMS: m/z = 410.1 (M + H)+; $^1$H NMR (400 MHz, DMSO-d6) δ = 11.75 (br d, J = 1.0 Hz, 1H), 9.05 (s, 1H), 8.57 (dd, J = 5.9, 8.9 Hz, 1H), 8.23 (d, J = 0.6 Hz, 1H), 7.99 (d, J = 2.8 Hz, 1H), 7.61-7.56 (m, 2H), 7.24 (dd, J = 2.3, 9.8 Hz, 1H), 6.92 (dt, J = 2.5, 9.3 Hz, 1H), 6.88-6.84 (m, 2H), 3.17 (s, 6H), 2.35 (s, 3H)

Example 30
N-[4-[[dimethyl(oxo)-$\lambda^6$-sulfanylidene]amino]phenyl]-4-(6-methoxy-1H-indol-3-yl)-5-methyl-pyrimidin-2-amine

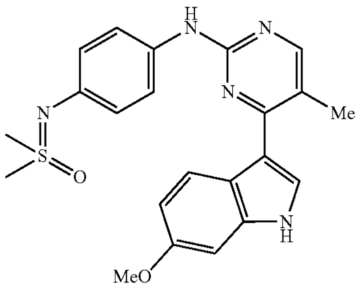 [SMILES: COc1ccc2c(-c3nc(Nc4ccc(N=S(C)(C)=O)cc4)ncc3C)c[nH]c2c1]

LCMS: m/z = 422.2 (M + H)+; $^1$H NMR (400 MHz, DMSO-d6) δ = 11.51 (br s, 1H), 9.00 (s, 1H), 8.45 (d, J = 8.8 Hz, 1H), 8.20 (s, 1H), 7.85 (d, J = 2.8 Hz, 1H), 7.63-7.57 (m, 2H), 6.95 (d, J = 2.2 Hz, 1H), 6.87-6.83 (m, 2H), 6.71 (dd, J = 2.4, 8.9 Hz, 1H), 3.80 (s, 3H), 3.17 (s, 6H), 2.34 (s, 3H)

Example 31
N-[4-[[dimethyl(oxo)-$\lambda^6$-sulfanylidene]amino]-3-methoxy-phenyl]-5-methyl-4-(7-methyl-1H-indol-3-yl)pyrimidin-2-amine

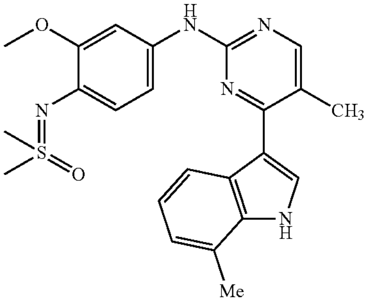

LCMS: m/z = 436.2 (M + H)+; $^1$H NMR (400 MHz, DMSO-d6) δ = 11.66 (br s, 1H), 9.04 (s, 1H), 8.38-8.30 (m, 1H), 8.25 (s, 1H), 7.92 (d, J = 2.3 Hz, 1H), 7.49 (t, J = 2.3 Hz, 1H), 7.25 (td, J = 2.4, 8.5 Hz, 1H), 7.01-6.97 (m, 2H), 6.84 (d, J = 8.4 Hz, 1H), 3.60 (s, 3H), 3.11 (s, 6H), 2.52 (s, 3H), 2.36 (s, 3H)

Example 32
N-[4-[[dimethyl(oxo)-$\lambda^6$-sulfanylidene]amino]-3-methoxy-phenyl]-4-(7-fluoro-1H-indol-3-yl)-5-methyl-pyrimidin-2-amine

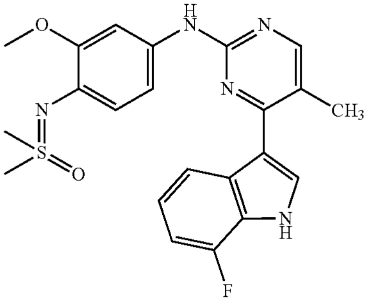

LCMS: m/z = 440.2 (M + H)+; 1H NMR (400 MHz, DMSO-d6) δ 12.22 (br s, 1H), 9.09 (s, 1H), 8.34-8.29 (m, 1H), 8.28 (s, 1H), 8.00 (s, 1H), 7.46 (d, J = 2.3 Hz, 1H), 7.23 (dd, J = 2.4, 8.5 Hz, 1H), 7.08-7.00 (m, 2H), 6.85 (d, J = 8.4 Hz, 1H), 3.60 (s, 3H), 3.12 (s, 6H), 2.36 (s, 3H)

-continued

| | | |
|---|---|---|
| Example 33 N-[4-[[dimethyl(oxo)-λ$^6$-sulfanylidene]amino]-3-methoxy-phenyl]-4-(7-methoxy-1H-indol-3-yl)-5-methyl-pyrimidin-2-amine | 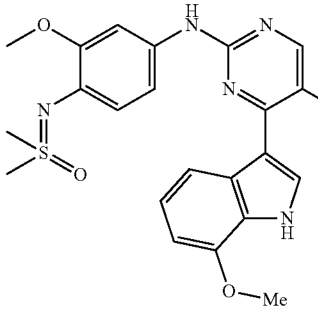 | LCMS: m/z = 452.2 (M + H)+; 1H NMR (400 MHz, DMSO-d6) δ = 11.84 (br s, 1H), 9.04 (s, 1H), 8.24 (s, 1H), 8.09 (d, J = 8.1 Hz, 1H), 7.82 (s, 1H), 7.48 (d, J = 2.3 Hz, 1H), 7.25 (dd, J = 2.4, 8.5 Hz, 1H), 7.00 (t, J = 7.9 Hz, 1H), 6.84 (d, J = 8.4 Hz, 1H), 6.76 (d, J = 7.6 Hz, 1H), 3.95 (s, 3H), 3.61 (s, 3H), 3.12 (s, 6H), 2.34 (s, 3H) |

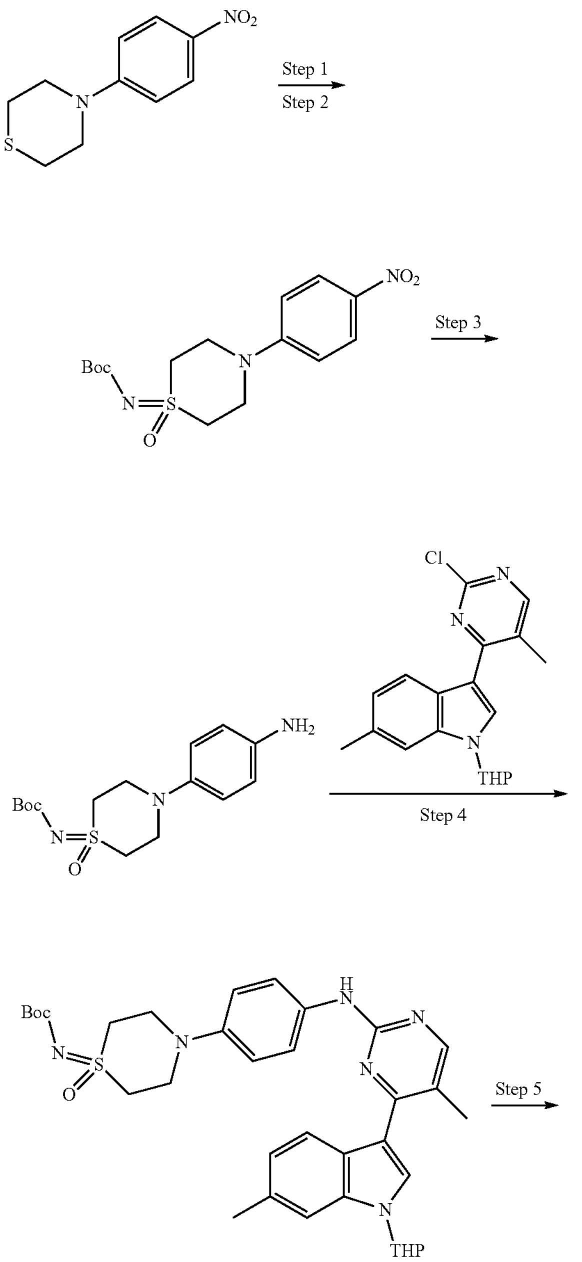

Example 34

Example 34. N-[4-(1-imino-1-oxo-1,4-thiazinan-4-yl)phenyl]-5-methyl-4-(6-methyl-1H-indol-3-yl) pyrimidin-2-amine

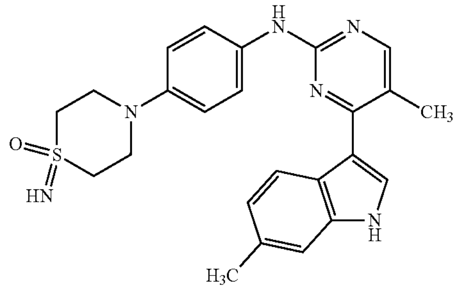 [SMILES: Cc1ccc2c(-c3nc(Nc4ccc(N5CCS(=N)(=O)CC5)cc4)ncc3C)c[nH]c2c1]

Step 1. 4-(4-Nitrophenyl)thiomorpholine 1-oxide (83-2): A suspension of 4-(4-nitrophenyl)thiomorpholine (5 g, 22.32 mmol, 1 equiv) and iron(III) chloride (0.102 g, 0.62 mmol, 0.028 equiv) in acetonitrile (130 mL) was stirred at room temperature for 10 minutes. Periodic acid (5.55 g, 24.44 mmol, 1.096 equiv) was added slowly at 10° C. during 10 minutes. After stirring at room temperature for 4 hours, the reaction was quenched with saturated sodium thiosulfate (30 mL). The reaction mixture was stirred at room temperature for 14 hours. The reaction was extracted with ethyl acetate (3x75 mL). The combined organic layers were washed with saturated brine (100 mL), dried over sodium sulfate, filtered and concentrated under reduced pressure. The crude product was triturated with a 1 to 2 mixture of dichloromethane and heptane (50 mL) to give a yellow solid (4.89 g, 91% yield). Analysis: LCMS: m/z=241.1 (M+H)+.

Step 2. tert-Butyl N-[4-(4-nitrophenyl)-1-oxo-1,4-thiazinan-1-ylidene]carbamate. A suspension of product step 1 (1 g, 4.16 mmol, 1 equiv), tert-butyl carbamate (0.97 g, 8.33 mmol, 2 equiv), magnesium oxide (0.66 g, 16.65 mmol, 4 equiv), rhodium(II) acetate dimer (0.042 g, 0.095 mmol, 0.023 equiv) and (diacetoxyiodo)benzene (2 g, 6.21 mmol, 1.5 equiv) in dichloromethane (35 mL) was stirred at room temperature for 20 hours. The reaction mixture was filtered through a plug of silica gel, and was washed with dichloromethane (100 mL). The filtrate was concentrated under reduced pressure. The residue was purified on a Büchi automated chromatography system (Sorbtech 25 g silica gel column), eluting with a gradient of 0 to 10% methanol in dichloromethane to give a light-yellow solid (0.4 g, 27% yield). Analysis: LCMS: m/z=356.1 (M+H)+.

Step 3. tert-Butyl N-[4-(4-aminophenyl)-1-oxo-1,4-thiazinan-1-ylidene]carbamate. A Parr flask was charged with 10% palladium on carbon (0.060 g, 0.56 mmol, 0.50 equiv, 50% water wet), step 2 product (0.4 g, 1.13 mmol, 1.0 equiv), dichloromethane (90 mL), ethanol (75 mL), and trimethylamine (0.7 mL). The mixture was hydrogenated at 10 psi for 2 hours at room temperature. The reaction mixture was filtered through a plug of Celite, which was washed with a 1 to 1 mixture of dichloromethane and methanol (100 mL). The filtrate was concentrated under reduced pressure, re-dissolved in dichloromethane and then washed with saturated sodium bicarbonate, saturated brine, dried over sodium sulfate, filtered and concentrated under reduced pressure to give a light pink solid (0.29 g, 79% yield). Analysis: LCMS: m/z=226.1=((M-Boc)+H)+.

Step 4. tert-butyl N-[4-[4-[[5-methyl-4-(6-methyl-1-tetrahydropyran-2-yl-indol-3-yl)pyrimidin-2-yl]amino]phenyl]-1-oxo-1,4-thiazinan-1-ylidene]carbamate. A solution of product step 4 (0.15 g, 0.46 mmol, 1 equiv) and 3-(2-chloro-5-methyl-pyrimidin-4-yl)-6-methyl-1-tetrahydropyran-2-yl-indole (0.157 g, 0.46 mmol, 1.1 equiv) in an anhydrous 1,4-dioxane (15 mL) was sparged with nitrogen for 20 minutes. XantPhos Pd(allyl)Cl (0.028 g, 0.4 mmol, 0.08 equiv) and cesium carbonate (0.3 g, 0.92 mmol, 2 equiv) were added to the stirred reaction mixture at 40° C. After heating at 85-95° C. for 18 hours, additional XantPhos Pd(allyl)Cl (0.028 g, 0.4 mmol, 0.08 equiv) and cesium carbonate (0.3 g, 0.92 mmol, 2 equiv) were added. After heating at 85-95° C. for an additional 6 hours, the reaction was cooled to room temperature and diluted with water (20 mL) and ethyl acetate (20 mL) was added. The reaction mixture was filtered through a plug of Celite and washed with ethyl acetate (50 mL). The layers were separated, and the aqueous layer was extracted with ethyl acetate (2×10 mL). The combined organic layers were washed with saturated brine (100 mL), dried over sodium sulfate, filtered and concentrated under reduced pressure. The crude product was purified on a Büchi automated chromatography system (Sorbtech 80 g silica gel column), eluting with a gradient of 0 to 80% ethyl acetate in heptanes to give an off-white solid (0.085 g, 29% yield). Analysis: LCMS: m/z=631.3 (M+H)+; $^1$H NMR (300 MHz, CDCl3) δ=8.26-8.18 (m, 2H), 7.68 (s, 1H), 7.62 (d, J=8.8 Hz, 2H), 7.29 (s, 1H), 7.19 (s, 1H), 7.06-7.00 (m, 1H), 6.90 (d, J=8.8 Hz, 2H), 5.54 (dd, J=2.9, 8.8 Hz, 1H), 4.22-4.14 (m, 1H), 3.88-3.74 (m, 3H), 3.73-3.61 (m, 4H), 3.47-3.33 (m, 2H), 2.52 (s, 3H), 2.37 (s, 3H), 2.11 (br d, J=3.5 Hz, 3H), 1.85-1.64 (m, 3H), 1.50 (s, 9H).

Step 5. N-[4-(1-imino-1-oxo-1,4-thiazinan-4-yl)phenyl]-5-methyl-4-(6-methyl-1H-indol-3-yl)pyrimidin-2-amine. A solution of product step 4 (0.075 g, 0.119 mmol, 1 equiv)) in acetonitrile (5 mL), water (1 mL) and 4N HCl in 1,4-dioxane (3 mL, 12 mmol, 100 equiv) was heated at 110° C. in a CEM microwave for 1 hour. The reaction mixture was diluted with water (20 mL) and washed with dichloromethane (10 mL). The aqueous layer was neutralized with solid sodium carbonate to pH=9 and extracted with ethyl acetate (3×20 mL). The combined organic layers were washed with saturated brine (50 mL), dried over sodium sulfate, filtered and concentrated under reduced pressure. The crude product was triturated with a 1 to 3 mixture of dichloromethane and heptane (5 ml) and the isolated solid was dried under vacuum at 50° C. for 14 hours to give a tan solid (0.015 g, 25% yield). Analysis: LCMS: m/z=447.2 (M+H)+; $^1$H NMR (400 MHz, $CDCl_3$) δ=11.55 (br s, 1H), 9.01 (s, 1H), 8.40 (d, J=8.2 Hz, 1H), 8.20 (s, 1H), 7.89 (d, J=2.4 Hz, 1H), 7.67 (d, J=8.9 Hz, 2H), 7.25 (s, 1H), 7.00-6.85 (m, 3H), 3.80-3.67 (m, 3H), 3.61-3.50 (m, 2H), 3.02 (br t, J=4.9 Hz, 4H), 2.42 (s, 3H), 2.34 (s, 3H).

Example 35. 5-Chloro-N-[4-(1-imino-1-oxo-1,4-thiazinan-4-yl)-2-methoxy-phenyl]-4-(1H-indol-3-yl)pyrimidin-2-amine

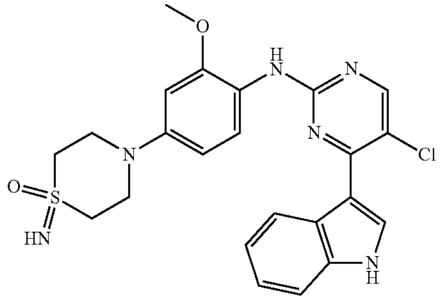 [SMILES: COc1cc(N2CCS(=N)(=O)CC2)ccc1Nc1ncc(Cl)c(-c2c[nH]c3ccccc23)n1]

This example was synthesized from 3-(2,5-dichloropyrimidin-4-yl)-1H-indole and 4-(1-imino-1-oxo-1,4-thiazinan-4-yl)-2-methoxy-aniline by the procedure for example 19. Analysis: LCMS m/z=481 (M+1, 1 Cl isotopic distribution); $^1$H NMR (500 MHz, DMSO-d6) δ 11.83 (s, 1H), 8.48-8.46 (m, 1H), 8.32 (s, 1H), 8.29 (s, 1H), 8.27 (br s, 1H), 7.47 (d, J= 8.65 Hz, 1H), 7.45 (d, J=8.28 Hz, 1H), 7.16 (t, J=7.45 Hz, 1H), 6.99 (t, J=7.45 Hz, 1H), 6.74-6.72 (m, 1H), 6.60-6.57 (m, 1H), 3.91-3.85 (m, 2H), 3.80 (s, 1H), 3.78 (s, 3H), 3.68-3.62 (m, 2H), 3.07-3.03 (m, 4H).

Example 36. 5-Chloro-4-(1H-indol-3-yl)-N-[2-methoxy-4-(methylsulfonimidoyl)-phenyl]pyrimidin-2-amine

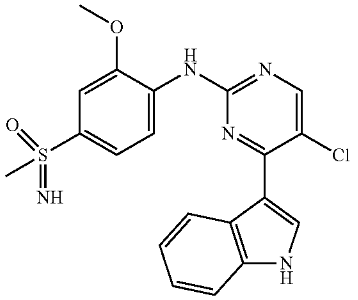 [SMILES: COc1cc(S(C)(=N)=O)ccc1Nc1ncc(Cl)c(-c2c[nH]c3ccccc23)n1]

This example was synthesized from 3-(2,5-dichloropyrimidin-4-yl)-1H-indole and tert-butyl N-[(4-amino-3-methoxy-phenyl)-methyl-oxo-$\lambda^6$-sulfanylidene]carbamate. LCMS m/z=428 (M+1, 1 Cl isotopic distribution); $^1$H NMR (500 MHz, DMSO-d6) δ 11.97 (br s, 1H), 8.54 (s, 1H), 8.52 (s, 2H), 8.42 (d, J=8.10 Hz, 1H), 8.32 (d, J=8.41 Hz, 1H), 7.55 (d, J=1.97 Hz, 1H), 7.53-7.49 (m, 2H), 7.25-7.21 (m, 1H), 7.15-7.12 (m, 1H), 4.12 (s, 1H), 3.96 (s, 3H), 3.10 (d, J=0.95 Hz, 3H).

Example 37. 5-Chloro-N-[4-(N,S-dimethylsulfonimidoyl)-2-methoxy-phenyl]-4-(1H-indol-3-yl) pyrimidin-2-amine

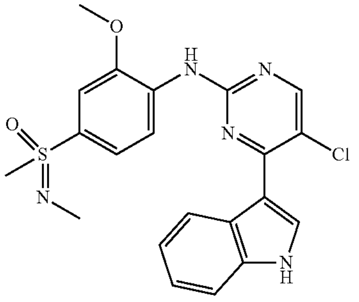 [SMILES: CN=S(C)(=O)c1ccc(Nc2ncc(Cl)c(-c3c[nH]c4ccccc34)n2)c(OC)c1]

This example was synthesized from 3-(2,5-dichloropyrimidin-4-yl)-1H-indole and 4-(N,S-dimethylsulfonimidoyl)-2-methoxy-aniline. LCMS m/z=442 (M+1, 1 Cl isotopic distribution); $^1$H NMR (500 MHz, DMSO-d6) δ 11.97 (br s, 1H), 8.57 (s, 1H), 8.54-8.51 (m, 2H), 8.41 (d, J=8.12 Hz, 1H), 8.34 (d, J=8.27 Hz, 1H), 7.51 (d, J=8.04 Hz, 1H), 7.43-7.38 (m, 2H), 7.23 (t, J=7.65 Hz, 1H), 7.11 (t, J=7.65 Hz, 1H), 3.96 (s, 3H), 3.14 (s, 3H), 2.54 (s, 3H).

Examples 38-59 were Synthesized Using Methods Analogous for Examples 1, 2, 16 and 34

| | | |
|---|---|---|
| Example 38<br>5-Chloro-4-(1H-indol-3-yl)-N-[2-methoxy-4-[(4-methyl-1-oxo-1,4-thiazinan-1-ylidene)-amino]phenyl]pyrimidin-2-amine | 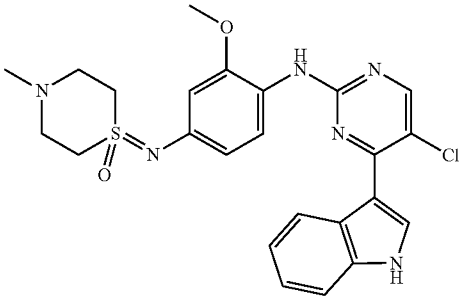 [SMILES: COc1cc(N=S2(=O)CCN(C)CC2)ccc1Nc1ncc(Cl)c(-c2c[nH]c3ccccc23)n1] | LCMS m/z = 497 (M + 1, 1 Cl isotopic distribution); 1H NMR (500 MHz, DMSO-d6) δ 11.89 (br.s, 1H), 8.46 (s, 1H), 8.32 (s, 1H), 8.26 (s, 1H), 8.27-8.35 (m, 1H), 7.43-7.50 (m, 2H), 7.16 (t, J = 7.5 Hz, 1H), 7.01 (t, J = 7.3 Hz, 1H), 6.66 (d, J = 2.1 Hz, 1H), 6.58 (dd, J = 8.3, 2.1 Hz, 1H), 3.74 (s, 3H), 3.33-3.41 (m, 2H), 3.24-3.30 (m, 2H), 2.84-2.92 (m, 2H), 2.77-2.84 (m, 2H), 2.31 (s, 3H) |
| Example 39<br>5-Chloro-4-(1H-indol-3-yl)-N-[2-methoxy-4-[(4-ethyl-1-oxo-1,4-thiazinan-1-ylidene)-amino]phenyl]pyrimidin-2-amine | 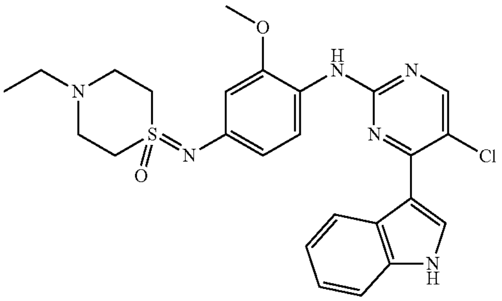 [SMILES: CCN1CCS(=O)(=Nc2ccc(Nc3ncc(Cl)c(-c4c[nH]c5ccccc45)n3)c(OC)c2)CC1] | LCMS m/z = 512 (M + 1, 1 Cl isotopic distribution); $^1$H NMR (500 MHz, DMSO-d6) δ 11.85 (br.s, 1H), 8.46 (s, 1H), 8.32 (s, 1H), 8.26 (s, 1H), 8.27-8.34 (m, 1H), 7.43-7.49 (m, 2H), 7.16 (t, J = 7.0 Hz, 1H), 7.01 (t, J = 7.3 Hz, 1H), 6.66 (d, J = 2.1 Hz, 1H), 6.58 (dd, J = 8.2, 2.1 Hz, 1H), 3.74 (s, 3H), 3.35-3.39 (m, 2H), 3.23-3.30 (m, 2H), 2.92-3.00 (m, 2H), 3.79-3.89 (m, 2H), 2.51-2.56 (m, 2H), 1.1 (t, J = 7.1 Hz, 3H) |
| Example 40<br>5-Chloro-4-(1H-indol-3-yl)-N-[4-[(4-isopropyl-1-oxo-1,4-thiazinan-1-ylidene)amino]-2-methoxy-phenyl]pyrimidin-2-amine | 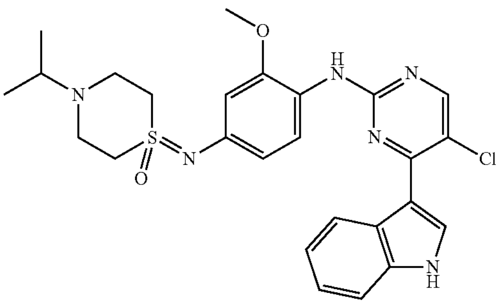 [SMILES: COc1cc(N=S2(=O)CCN(C(C)C)CC2)ccc1Nc1ncc(Cl)c(-c2c[nH]c3ccccc23)n1] | LCMS m/z = 525 (M + 1, 1 Cl isotopic distribution); $^1$H NMR (500 MHz, DMSO-d6) δ 11.83 (br.s, 1H), 8.46 (d, 1H, J = 2.8 Hz), 8.32 (s, 1H), 8.27 (s, 1H), 8.26-8.34 (m, 1H), 7.45 (d, 2H, J = 8.2 Hz), 7.16 (t, 1H, J = 7.3 Hz), 7.01 (t, 1H, J = 7.3 Hz), 3.34-3.43 (m, 2H), 3.18-3.26 (m, 2H), 2.82-2.99 (m, 5H), 1.80 (d, 3H, J = 6.6 Hz) |

-continued

Example 41
5-chloro-4-indol-1-yl-N-[2-methoxy-4-(methylsulfonimidoyl)phenyl]pyrimidin-2-amine

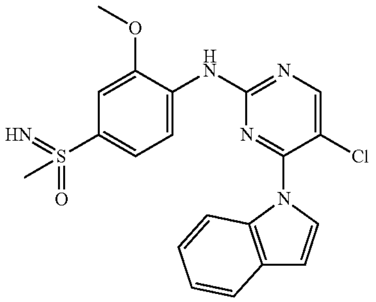 [SMILES: COc1cc(S(C)(=N)=O)ccc1Nc1ncc(Cl)c(-n2ccc3ccccc32)n1]

LCMS m/z = 428 (M + 1, 1 Cl isotopic distribution); $^1$H NMR (500 MHz, DMSO-d6) δ 8.95 (s, 1H), 8.78 (s, 1H), 8.18 (d, 1H, J = 8.2 Hz), 7.86 (d, 1H, J = 3.4 Hz), 7.82 (d, 1H, J = 8.2 Hz), 7.66 (d, 1H, J = 7.3 Hz), 7.54 (d, 1H, J = 2.1 Hz), 7.47 (dd, 1H, J = 1.8, 8.5 Hz), 7.2-7.3 (m, 2H), 6.80 (d, 1H, J = 3.4 Hz), 4.12 (s, 1H), 3.95 (s, 3H), 3.07 (s, 3H)

Example 42
4-Indol-1-yl-N-[2-methoxy-4-(methylsulfonimidoyl)phenyl]-5-methyl-pyrimidin-2-amine

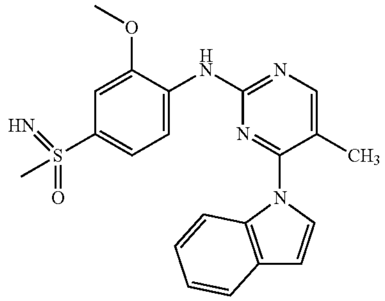

LCMS m/z = 408 (M + 1); $^1$H NMR (500 MHz, DMSO-d6) δ 8.63 (s, 1H), 8.45-8.39 (m, 2H), 7.78 (d, J = 3.7 Hz, 1H), 7.76 (d, J = 8.2 Hz, 1H), 7.67 (d, J = 7.6 Hz, 1H), 7.51 (d, J = 1.8 Hz, 1H), 7.45 (dd, J = 2.0, 8.4 Hz, 1H), 7.27-7.17 (m, 2H), 6.77 (d, J = 3.4 Hz, 1H), 4.07 (s, 1H), 3.97 (s, 3H), 3.05 (s, 3H), 2.24 (s, 3H)

Example 43
4-Indol-1-yl-N-[2-methoxy-4-(methylsulfonimidoyl)phenyl]-pyrimidin-2-amine

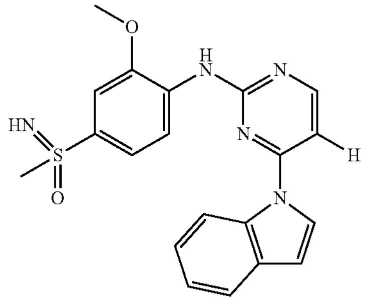 [SMILES: COc1cc(S(C)(=N)=O)ccc1Nc1nccc(-n2ccc3ccccc32)n1]

LCMS m/z = 394 (M + 1); $^1$H NMR (500 MHz, DMSO-d6) δ 8.76 (s, 1H), 8.61 (d, J = 8.2 Hz, 1H), 8.52 (d, J = 5.8 Hz, 1H), 8.27 (d, J = 8.9 Hz, 1H), 8.15 (d, J = 3.4 Hz, 1H), 7.64 (d, J = 7.3 Hz, 1H), 7.57 (s, 1H), 7.56 (d, J = 7.1 Hz, 1H), 7.31 (d, J = 5.5 Hz, 1H), 7.29-7.19 (m, 2H), 6.83 (d, J = 3.7 Hz, 1H),4.14(s, 1H), 3.96 (s, 3H), 3.11 (s, 3H)

Example 44
5-Chloro-N-[4-(1-imino-1-oxo-1,4-thiazinan-4-yl)-2-methoxy-phenyl]-4-indol-1-yl-pyrimidin-2-amine

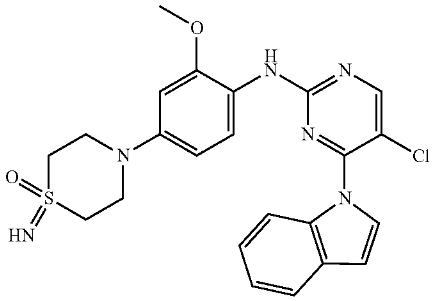 [SMILES: COc1cc(N2CCS(=N)(=O)CC2)ccc1Nc1ncc(Cl)c(-n2ccc3ccccc32)n1]

LCMS m/z = 483 (M + 1, 1 Cl isotopic distribution); $^1$H NMR (500 MHz, DMSO-d6) δ 8.77 (s, 1H), 8.58 (s, 1H), 7.83 (d, 1H, J = 3.4 Hz), 7.74 (brd, 1H, J = 7.3 Hz), 7.61 (br d, 1H, J = 7.6 Hz), 7.38 (d, 1H, J = 8.5 Hz), 7.1-7.2 (m, 2H), 6.74 (d, 1H, J = 3.4 Hz), 6.70 (s, 1H), 6.53 (br d, 1H, J = 8.5 Hz), 3.8-3.9 (m, 2H), 3.82 (s, 3H), 3.77 (s, 1H), 3.6-3.7 (m, 2H), 2.94-3.04 (m, 4H)

Example 45
N-[4-(1-Imino-1-oxo-1,4-thiazinan-4-yl)-2-methoxy-phenyl]-4-indol-1-yl-pyrimidin-2-amine

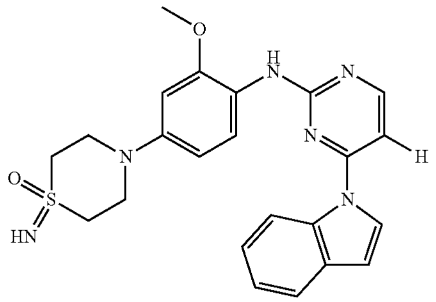 [SMILES: COc1cc(N2CCS(=N)(=O)CC2)ccc1Nc1nccc(-n2ccc3ccccc32)n1]

LCMS m/z = 449 (M + 1); $^1$H NMR (500 MHz, DMSO-d6) δ 8.48 (s, 1H), 8.42 (br s, 1H), 8.35 (d, 1H, J = 5.8 Hz), 8.07 (d, 1H, J = 3.7 Hz), 7.58 (d, 1H, J = 7.6 Hz), 7.44 (br d, 1H, J = 8.5 Hz), 7.14-7.20 (m, 1H), 7.08-7.14 (m, 1H), 7.06 (d, 1H, J = 5.8 Hz), 6.77 (d, 1H, J = 3.4 Hz), 6.74 (br d, 1H, J = 2.4 Hz), 6.62 (dd, 1H, J = 2.6, 8.7 Hz), 3.86-3.94 (m, 2H), 3.81 (s, 1H), 3.78 (s, 3H), 3.63-3.70 (m, 2H), 3.06 (t, 4H, J = 4.9 Hz)

-continued

| | | |
|---|---|---|
| Example 46 N-[4-(1-imino-1-oxo-1,4-thiazinan-4-yl)-2-methoxy-phenyl]-4-indol-1-yl-5-methyl-pyrimidin-2-amine | 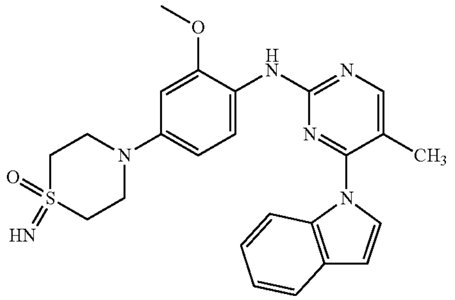 [SMILES: COc1cc(N2CCS(=N)(=O)CC2)ccc1Nc1ncc(C)c(-n2ccc3ccccc32)n1] | LCMS m/z = 463 (M + 1); $^1$H NMR (600 MHz, DMSO-d6) δ 8.43 (s, 1H), 8.16 (s, 1H), 7.71 (d, 1H, J = 3.5 Hz), 7.69 (d, 1H, J = 8.2 Hz), 7.60-7.63 (m, 2H), 7.12-7.20 (m, 2H), 6.71 (dd, 1H, J = 0.6, 3.4 Hz), 6.69 (d, 1H, J = 2.8 Hz), 6.50 (dd, 1H, J = 2.7, 8.7 Hz), 3.83 (s, 3H), 3.79-3.83 (m, 2H), 3.76 (s, 1H), 3.55-3.62 (m, 2H), 3.00 (t, 4H, J = 4.8 Hz), 2.16 (s, 3H) |
| Example 47 5-Chloro-N-[4-(cyclopropyl-sulfonimidoyl)phenyl]-4-(1H-indol-3-yl)pyrimidin-2-amine | 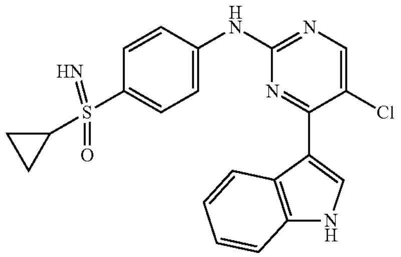 [SMILES: N=S(=O)(c1ccc(Nc2ncc(Cl)c(-c3c[nH]c4ccccc34)n2)cc1)C1CC1] | LCMS m/z = 424 (M + 1, 1 Cl isotopic distribution); $^1$H NMR (500 MHz, DMSO-d6) δ 11.99 (br s, 1H), 10.09 (s, 1H), 8.62 (d, J = 7.9 Hz, 1H), 8.55 (s, 1H), 8.54 (s, 1H), 8.02-7.98 (m, 2H), 7.80-7.76 (m, 2H), 7.53 (d, J = 8.2 Hz, 1H), 7.25 (t, J = 7.5 Hz, 1H), 7.18 (t, J = 7.5 Hz, 1H), 4.00 (s, 1H), 2.64-2.59 (m, 1H), 1.12-1.06 (m, 1H), 0.98-0.84 (m, 3H) |
| Example 48 4-(1H-Indol-3-yl)-5-methyl-N-[4-(methylsulfonimidoyl)-phenyl]pyrimidin-2-amine | 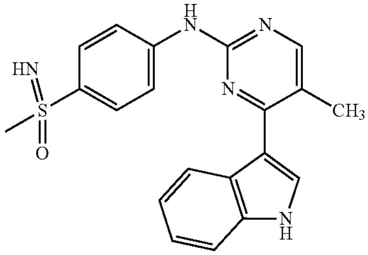 | LCMS m/z = 378 (M + 1); $^1$H NMR (500 MHz, DMSO-d6) δ 11.80 (br. s. 1H), 9.82 (s, 1H), 8.57 (d, J = 8.23 Hz, 1H), 8.36 (s, 1H), 8.00-8.08 (m, 3H), 7.78 (d, J = 8.59 Hz, 2H), 7.50 (d, J = 8.23 Hz, 1H), 7.22 (t, J = 7.70 Hz, 1H), 7.15 (t, J = 7.34 Hz, 1H), 3.97 (s, 1H), 3.03 (s, 3H), 2.41 (s, 3H) |
| Example 49 4-(1H-Indol-3-yl)-5-methyl-N-[4-[(4-methyl-1-oxo-1,4-thiazinan-1-ylidene)amino]-phenyl]pyrimidin-2-amine | 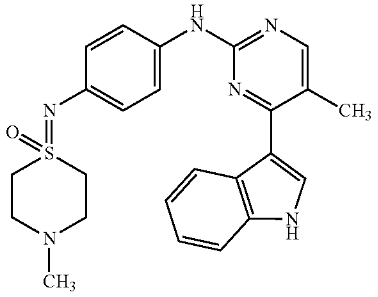 [SMILES: Cc1cnc(Nc2ccc(N=S3(=O)CCN(C)CC3)cc2)nc1-c1c[nH]c2ccccc12] | LCMS m/z = 447 (M + 1); $^1$H NMR (500 MHz, DMSO-d6) δ 11.70 (br.s, 1H), 9.05 (s, 1H), 8.54 (d, J = 7.8 Hz, 1H), 8.22 (s, 1H), 7.97 (d, J = 2.9 Hz, 1H), 7.62 (d, J = 8.8 Hz, 2H), 7.46 (d, J = 8.1 Hz, 1H), 7.19 (td, J = 7.6 Hz, J = 1.0 Hz, 1H), 7.08 (t, J = 7.3 Hz, 1H), 6.87 (d, J = 8.8 Hz, 2H), 3.20-3.35 (m, 4H), 2.82-2.89 (m, 2H), 2.72-2.80 (m, 2H), 2.35 (s, 3H), 2.30 (s, 3H) |
| Example 50 5-Chloro-N-[4-(cyclopropyl-sulfonimidoyl)phenyl]-4-(1-methylindol-3-yl)pyrimidin-2-amine | 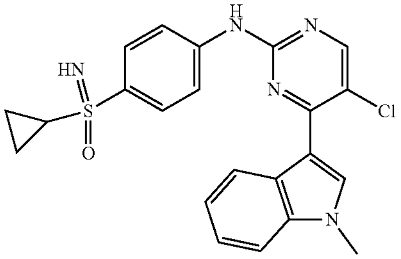 [SMILES: Cn1cc(-c2nc(Nc3ccc(S(=N)(=O)C4CC4)cc3)ncc2Cl)c2ccccc21] | LCMS m/z = 438 (M + 1, 1 Cl isotopic distribution); $^1$H NMR (600 MHz, DMSO-d6) δ 10.10 (s, 1 H), 8.67 (d, J = 8.3 Hz, 1 H), 8.60 (s, 1 H), 8.55 (s, 1 H), 7.98-8.00 (m, 2 H), 7.77-7.79 (m, 2 H), 7.58 (d, J = 8.3 Hz, 1 H), 7.33 (ddd, J = 8.1, 7.0, 1.2 Hz, 1 H), 7.23 (ddd, J = 8.1, 7.1, 1.0 Hz, 1 H), 4.01 (s, 1 H), 3.95 (s, 3 H), 2.60-2.64 (m, 1 H), 1.07-1.11 (m, 1 H), 0.84-0.98 (m, 3 H) |

-continued

| | | |
|---|---|---|
| Example 51 N-[4-(Cyclopropyl-sulfonimidoyl)-phenyl]-4-(1H-indol-3-yl)-5-methyl-pyrimidin-2-amine | 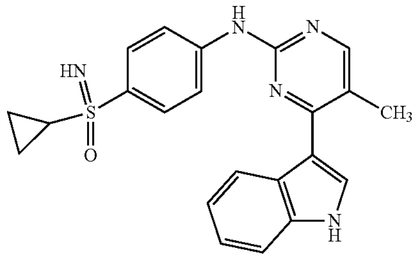 [SMILES: Cc1cnc(Nc2ccc(S(=N)(=O)C3CC3)cc2)nc1-c1c[nH]c2ccccc12] | LCMS m/z = 404 (M + 1); 1H NMR (500 MHz, DMSO-d6) δ 11.80 (s, 1 H), 9.81 (s, 1 H), 8.57 (d, J = 7.93 Hz, 1 H), 8.36 (s, 1 H), 8.03-8.06 (m, 3 H), 7.73 (d, J = 8.60 Hz, 2 H), 7.50 (d, J = 7.93 Hz, 1 H), 7.23 (t, J = 7.51 Hz, 1 H), 7.15 (t, J = 7.46 Hz, 1 H), 3.94 (s, 1 H), 2.57-2.64 (m, 1 H), 2.41 (s, 3 H), 1.04-1.12 (m, 1 H), 0.82-0.98 (m, 3 H) |
| Example 52 5-Chloro-4-(1H-indol-3-yl)-N-[4-(methylsulfonimidoyl)-phenyl]pyrimidin-2-amine | 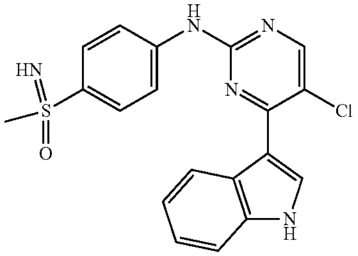 [SMILES: CS(=N)(=O)c1ccc(Nc2ncc(Cl)c(-c3c[nH]c4ccccc34)n2)cc1] | LCMS m/z = 398 (M + 1, 1 Cl isotopic distribution); $^1$H NMR (500 MHz, DMSO-d6) δ 11.98 (s, 1 H) 10.11 (s, 1 H) 8.62 (d, J = 7.93 Hz, 1 H) 8.56 (s, 1 H) 8.54 (d, J = 2.75 Hz, 1 H) 8.01 (d, J = 8.85 Hz, 2 H) 7.82 (d, J = 8.85 Hz, 2 H) 7.53 (d, J = 8.24 Hz, 1 H) 7.22-7.28 (m, 1H) 7.16-7.22 (m, 1 H) 4.03 (s, 1 H) 3.04 (s, 3 H) |
| Example 53 5-Chloro-N-[4-(1-imino-1-oxo-1,4-thiazinan-4-yl)phenyl]-4-(1H-indol-3-yl)pyrimidin-2-amine | 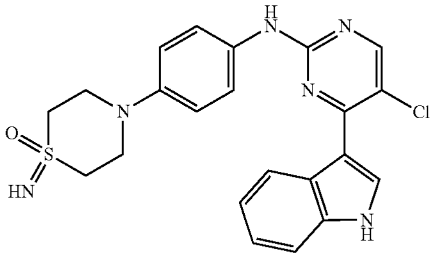 [SMILES: N=S1(=O)CCN(c2ccc(Nc3ncc(Cl)c(-c4c[nH]c5ccccc45)n3)cc2)CC1] | LCMS m/z = 453 (M + 1, 1 Cl isotopic distribution); $^1$H NMR (500 MHz, DMSO-d6) δ 11.88 (br.s, 1H), 9.39 (s, 1H), 8.50-8.59 (m, 1H), 8.48 (s, 1H), 8.39 (s, 1H), 7.60 (d, J = 8.7 Hz, 2H,), 7.49 (d, J = 8.2 Hz 1H), 7.21 (t, J = 7.8 Hz, 1H), 7.10 (t, J = 7.5 Hz, 1H), 6.98 (d, J = 8.7 Hz, 2H), 3.71-3.82 (m, 3H), 3.52-3.63 (m, 2H), 2.98-3.07 (m, 4H) |
| Example 54 N-[4-(1-Imino-1-oxo-1,4-thiazinan-4-yl)phenyl]-4-(1H-indol-3-yl)-5-methyl-pyrimidin-2-amine | 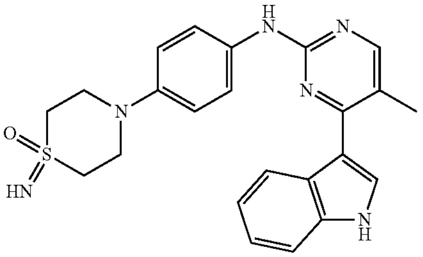 [SMILES: Cc1cnc(Nc2ccc(N3CCS(=N)(=O)CC3)cc2)nc1-c1c[nH]c2ccccc12] | LCMS m/z = 433 (M + 1); 1H NMR (500 MHz, DMSO-d6) δ 11.70 (br s, 1 H), 9.05 (s, 1 H), 8.53 (br d, J = 7.93 Hz, 1 H), 8.22 (s, 1 H), 7.98 (d, J = 2.75 Hz, 1 H), 7.68 (m, J = 9.16 Hz, 2 H), 7.47 (d, J = 7.93 Hz, 1 H), 7.19 (t, J = 7.61 Hz, 1 H), 7.09 (t, J = 7.48 Hz, 1 H), 6.95 (m, J = 9.16 Hz, 2 H), 3.83 (s, 1H), 3.66-3.82 (m, 2 H), 3.46-3.60 (m, 2 H), 3.02 (br t, J = 4.88 Hz, 4 H), 2.36 (s, 3 H) |
| Example 55 5-Chloro-4-(1H-indol-3-yl)-N-[4-[(4-methyl-1-oxo-1,4-thiazinan-l-ylidene)amino]-phenyl]pyrimidin-2-amine | 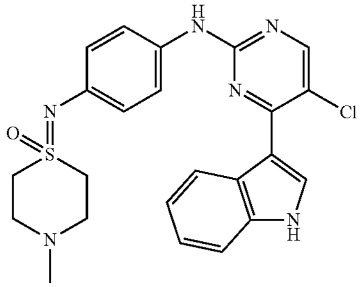 [SMILES: CN1CCS(=O)(=Nc2ccc(Nc3ncc(Cl)c(-c4c[nH]c5ccccc45)n3)cc2)CC1] | LCMS m/z = 467 (M + 1, 1 Cl isotopic distribution); $^1$H NMR (500 MHz, DMSO-d6) δ 11.88 (br.s, 1H), 9.40 (s, 1H), 8.53-8.60 (m, 1H), 8.48 (d, J = 3.0 Hz, 1H), 8.39 (br.s, 1H), 7.53-7.57 (m, 2H), 7.49 (dt, J = 8.0 Hz, J = 0.8 Hz, 1H), 7.21 (td, J = 7.5 Hz, J = 1.0 Hz, 1H), 7.10 (t, J = 7.6 Hz, 1H), 6.91 (d, J = 8.8 Hz, 2H), 3.22-3.35 (m, 4H), 2.83-2.90 (m, 2H), 2.74-2.80 (m, 2H), 2.30 (s, 3H) |

-continued

| | | |
|---|---|---|
| Example 56<br>5-Chloro-4-(2-methyl-1H-indol-3-yl)-N-[4-(methylsulfonimidoyl)phenyl]-pyrimidin-2-amine | 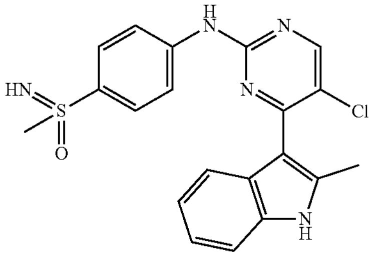 [SMILES: Cc1[nH]c2ccccc2c1-c1nc(Nc2ccc(S(C)(=N)=O)cc2)ncc1Cl] | LCMS m/z = 412 (M + 1, 1 Cl isotopic distribution); $^1$H NMR (500 MHz, DMSO-d6) δ 11.62 (s, 1 H), 10.24 (s, 1 H), 8.66 (s, 1 H), 7.97-8.00 (m, 2 H), 7.77-7.80 (m, 2 H), 7.48 (d, J = 7.93 Hz, 1 H), 7.39 (d, J = 8.24 Hz, 1 H), 7.09-7.13 (m, 1 H), 7.03-7.07 (m, 1H), 3.99 (s, 1 H), 3.01 (d, J = 1.1 Hz, 3 H), 2.50 (s, 3 H) |
| Example 57<br>5-Methyl-4-(2-methyl-1H-indol-3-yl)-N-[4-(methylsulfonimidoyl)phenyl]-pyrimidin-2-amine | 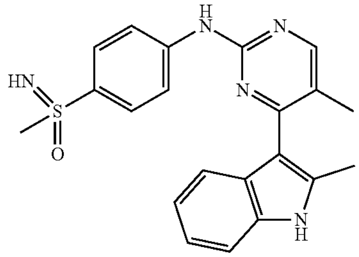 | LCMS m/z = 412 (M + 1, 1 Cl isotopic distribution); $^1$H NMR (500 MHz, DMSO-d6) δ 11.62 (s, 1 H), 10.24 (s, 1 H), 8.66 (s, 1 H), 7.97-8.00 (m, 2 H), 7.77-7.80 (m, 2 H), 7.48 (d, J = 7.93 Hz, 1 H), 7.39 (d, J = 8.24 Hz, 1 H), 7.09-7.13 (m, 1 H), 7.03-7.07 (m, 1H), 3.99 (s, 1 H), 3.01 (d, J = 1.1 Hz, 3 H), 2.50 (s, 3 H) |
| Example 58<br>5-Fluoro-N-[4-(1-imino-1-oxo-1,4-thiazinan-4-yl)phenyl]-4-(1H-indol-3-yl)pyrimidin-2-amine | 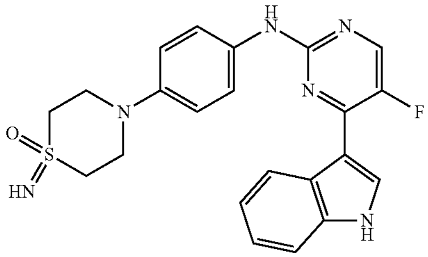 [SMILES: N=S1(=O)CCN(c2ccc(Nc3ncc(F)c(-c4c[nH]c5ccccc45)n3)cc2)CC1] | LCMS m/z = 437 (M + 1); 1H NMR (500 MHz, DMSO-d6) δ 11.92 (br.s, 1H), 9.25 (s, 1H), 8.69 (br d, J = 7.9 Hz, 1 H) 8.36 (d, J = 3.9 Hz, 1H) 8.16 (t, J = 3.0 Hz, 1H) 7.60-7.63 (m, 2H) 7.50 (d, J = 8.1 Hz, 1H) 7.23 (ddd, J = 8.1, 7.0,1.2 Hz, 1H) 7.13 (t, J = 7.5 Hz, 1 H) 6.99-7.02 (m, 2 H) 3.72-3.82 (m, 3H) 3.55-3.62 (m, 2H) 3.04 (t, J = 4.8 Hz, 4H) |
| Example 59<br>N-[4-[[Dimethyl(oxo)-λ$^6$-sulfanylidene]amino]phenyl]-5-fluoro-4-(1H-indol-3-yl)pyrimidin-2-amine | 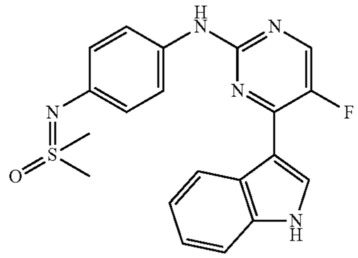 [SMILES: CS(C)(=O)=Nc1ccc(Nc2ncc(F)c(-c3c[nH]c4ccccc34)n2)cc1] | LCMS m/z = 396 (M + 1); $^1$H NMR (500 MHz, DMSO-d6) δ 11.92 (br s, 1 H) 9.24 (s, 1 H) 8.70 (d, J = 7.8 Hz, 1 H) 8.35 (d, J = 4.0 Hz, 1 H) 8.15 (t, J = 2.9 Hz, 1 H) 7.54 (d, J = 8.9 Hz, 2 H) 7.49 (d, J = 8.0 Hz, 1 H)7.21 (dt, J = 8.0, 1.3 Hz, 1 H) 7.08-7.17 (m, 1 H) 6.89 (d, J = 8.9 Hz, 2 H) 3.18 (s, 6 H) |

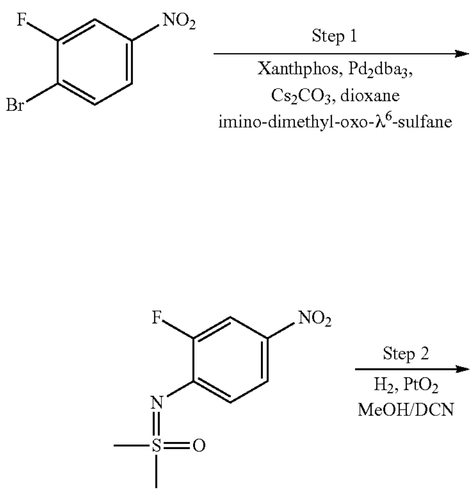

-continued

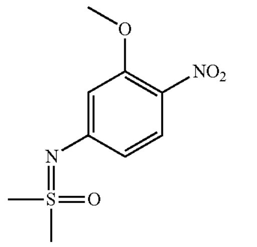

4-[[dimethyl(oxo)-λ$^6$-sulfanylidene]-amino]-3-fluoro-aniline

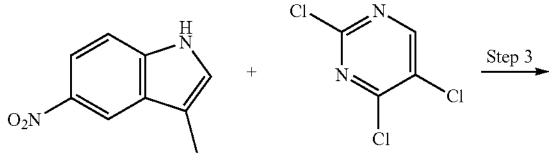

-continued

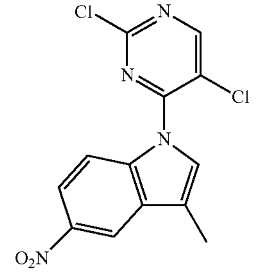

1-(2,5-dichloropyrimidin-4-yl)-3-methyl-5-nitro-indole

-continued

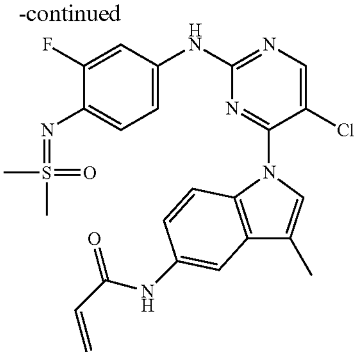

Example 60

Example 60. N-[1-[5-Chloro-2-[4-[[dimethyl(oxo)-λ$^6$-sulfanylidene]amino]-3-fluoro-anilino]pyrimidin-4-yl]-3-methyl-indol-5-yl]prop-2-enamide

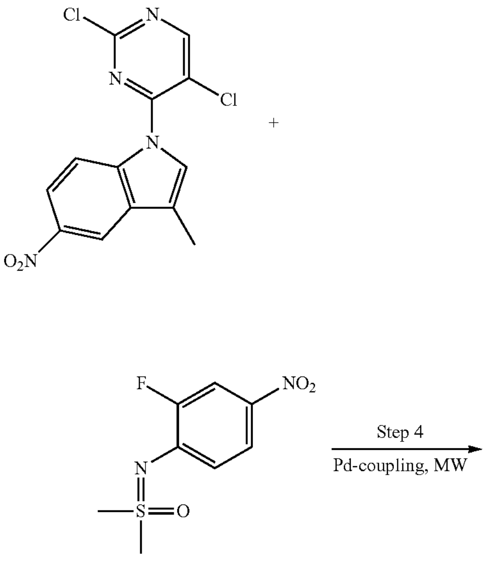

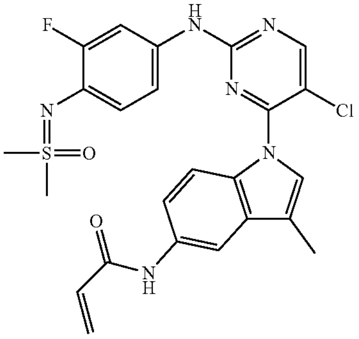 [SMILES: C=CC(=O)Nc1ccc2c(c1)c(C)cn2-c1nc(Nc2ccc(N=S(C)(C)=O)c(F)c2)ncc1Cl]

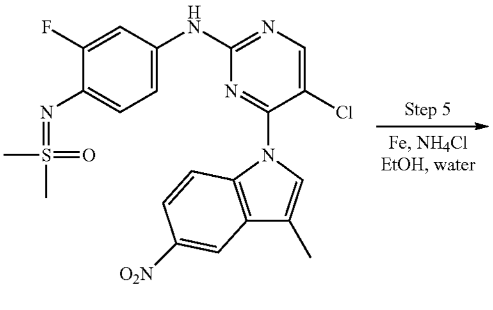

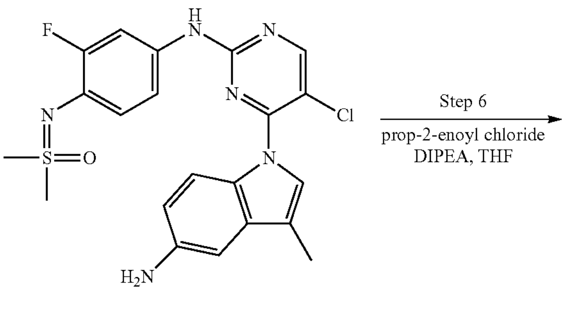

Step 1. (2-Fluoro-4-nitro-phenyl)imino-dimethyl-oxo-λ$^6$-sulfane. A suspension of 1-bromo-2-fluoro-4-nitro-benzene (3.3 g, 15 mmol), imino-dimethyl-oxo-λ$^6$-sulfane (1.4 g, 15 mmol) and cesium carbonate (7.3 g, 22.5 mmol) in dry dioxane (40 mL) was degassed with Argon for 10 min. Xantphos (868 mg, 1.5 mmol) and tris(dibenzylideneacetone)dipalladium (0) (687 mg, 0.75 mmol) were then added and the mixture was irradiated in MW reactor at 100° C. for 30 min. After cooling to RT and filtration over pad of Celite, the solvent was removed in vacuo. The residue was triturated with acetone and the product was collected by filtration and dried to give a yellow solid (2.8 g, 81%). LCMS m/z=233 (M+1).

Step 2. 4-[[Dimethyl(oxo)-λ$^6$-sulfanylidene]amino]-3-fluoro-aniline. To a suspension of (2-fluoro-4-nitro-phenyl)imino-dimethyl-oxo-λ$^6$-sulfane (2.8 g, 12.3 mmol) in MeOH/DCM (5:3, 200 mL) was added $PtO_2$ (559 mg, 2.46 mmol). The reaction mixture was then shaken in a Parr apparatus under 2.0 bar of H2 at 25° C. for 20 min. Upon completion, reaction mixture was filtrated over Celite pad and rinsed with DCM. The dark green filtrate was evaporated in vacuo to dryness to give a dark brown solid (2.36 g, 95%). LCMS m/z=203 (M+1); $^1$H NMR (500 MHz, DMSO-d6) δ 6.74 (t, J=9.7, 1H), 6.31 (dd, J=13.1, 2.4 Hz, 1H), 6.22 (dd, J=8.4, 2.4 Hz, 1H), 4.90 (s, 2H), 3.08 (s, 6H).

Step 3. 1-(2,5-Dichloropyrimidin-4-yl)-3-methyl-5-nitro-indole. A solution of 3-methyl-5-nitro-1H-indole (467 mg, 2.7 mmol.) in DMF (5 mL) at 0° C. (ice bath), was added NaH (60% dispersion in mineral oil, 127 mg, 1.2 eq.) cautiously portion-wise. The suspension was stirred at ice bath temperature for 30 min. The resulting slurry was then transferred to a cold (0° C.) solution 2,4,5-trichloropyrimidine (583 mg, 3.2 mmol., 1.20 eq.) in DMF (5 mL) and stirred for 30 min. Upon completion, water (10 mL) was added cautiously with stirring. The precipitate was collected, washed with EtOAc (3 mL) and dried in vacuo to afford a yellow powder (725 mg, 83%). LCMS m/z=323, 325 (M+1, 1 Cl).

Step 4. 5-Chloro-N-[4-[[dimethyl(oxo)-$\lambda^6$-sulfanylidene]amino]-3-fluoro-phenyl]-4-(3-methyl-5-nitro-indol-1-yl)pyrimidin-2-amine. A suspension of 1-(2,5-dichloropyrimidin-4-yl)-3-methyl-5-nitro-indole (500 mg, 1.55 mmol), 4-[[dimethyl(oxo)-$\lambda^6$-sulfanylidene]amino]-3-fluoro-aniline (344 mg, 1.79 mmol, 1.1 eq) cesium carbonate (1 g, 3.09 mmol, 2 eq) and 4,5-bis(diphenylphosphino)-9,9-dimethylxanthene (89.5 mg, 0.16 mmol, 0.1 eq) in dry dioxane (16 mL) was degassed with Argon for 5 min. Palladium (II) acetate (27.8 mg, 0.124 mmol, 0.08 eq) was added and the reaction mixture was heated in MW at 80° C. for 30 min. After cooling to RT, the reaction mixture was filtered through Celite and washed thoroughly with DCM. The solution was concentrated in vacuo and the remaining residue was purified by column chromatography (silica gel; eluent DCM:MeOH=100:4) to afford a brown solid (595 mg, 79%). LCMS m/z=489, 491 (M+1, 1 Cl isotopic distribution).

Step 5. 1-[5-Chloro-2-[4-[[dimethyl(oxo)-$\lambda^6$-sulfanylidene]amino]-3-fluoro-anilino]pyrimidin-4-yl]-3-methyl-indol-5-amine. A suspension of product step 4 (595 mg, 1.22 mmol), iron (816 mg, 14.6 mmol) and ammonium chloride (130 mg, 2.43 mmol) in EtOH (27 mL) and water (9 mL) was stirred at reflux for 1 hour. Additional iron (406 mg, 14.6 mmol) and ammonium chloride (106 mg) were added and stirring was continued at 90° C. for 30 min. Upon completion the reaction mixture was diluted with DCM (30 mL) and the mixture stirred at RT for 5 min, filtrated through celite and concentrated in vacuo to dryness to afford a yellow solid (515 mg, 68%). LCMS m/z=458, 460 (M+1, 1 Cl isotopic distribution).

Step 6. N-[1-[5-Chloro-2-[4-[[dimethyl(oxo)-$\lambda^6$-sulfanylidene]amino]-3-fluoro-anilino]pyrimidin-4-yl]-3-methyl-indol-5-yl]prop-2-enamide. To a solution of product step 5 (510 mg, 1.11 mmol) in dry THF (15 ml) was added N,N-diisopropylethylamine (287 mg, 2.22 mmol) followed by acryloyl chloride (0.0898 mL, 1.11 mmol). The resulting mixture was stirred at RT for 30 min. Water (0.1 mL) was added with stirring, then the reaction mixture was evaporated to dryness giving the crude product. Purification by prep HPLC afforded a yellow solid (75 mg; 13%). LCMS m/z=513, 515 (M+1, 1 Cl isotopic distribution); $^1$H NMR (DMSO-d6, 500 MHz) δ: 10.19 (br s, 1H), 9.94 (br s, 1H), 8.66 (s, 1H), 8.07 (s, 1H), 7.88 (d, 1H, J=8.2 Hz), 7.70 (s, 1H), 7.6-7.7 (m, 1H), 7.43 (d, 1H, J=8.9 Hz), 7.27 (d, 1H, J=8.5 Hz), 7.03 (t, 1H, J=9.0 Hz), 6.48 (dd, 1H, J=10.1, 17.1 Hz), 6.2-6.3 (m, 1H), 5.75 (dd, 1H, J=1.8, 10.1 Hz), 3.20 (s, 6H), 2.29 (d, 3H, J=0.9 Hz).

Example 61. N-[1-[5-Chloro-2-[4-[[dimethyl(oxo)-$\lambda^6$-sulfanylidene]amino]anilino]pyrimidin-4-yl]-3-methyl-indol-5-yl]prop-2-enamide

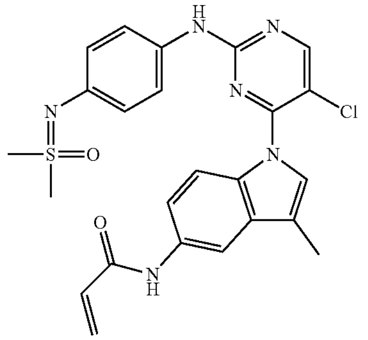 [SMILES: C=CC(=O)Nc1ccc2c(c1)c(C)cn2-c1nc(Nc2ccc(N=S(C)(C)=O)cc2)ncc1Cl]

This example was synthesized using 4-[[methyl(oxo)-$\lambda^6$-sulfanylidene]amino]aniline and 1-(2,5-dichloropyrimidin-4-yl)-3-methyl-5-nitro-indole by the procedure for example 1. LCMS m/z=495, 497 (M+1, 1 Cl isotopic distribution); $^1$H NMR (500 MHz, DMSO-d6) δ: 10.18 (s, 1H), 9.75 (s, 1H), 8.60 (s, 1H), 8.05 (d, J=1.8 Hz, 1H), 7.82-7.89 (m, 1H), 7.70 (s, 1H), 7.51 (d, J=8.9 Hz, 2H), 7.42 (d, J=8.5 Hz, 1H), 6.85 (d, J=8.5 Hz, 2H), 6.47 (dd, J=17.1, 10.1 Hz, 1H), 6.27 (dd, J=16.9, 2.0 Hz, 1H), 5.75 (dd, J=10.2, 2.0 Hz, 1H), 3.17 (s, 6H), 2.28 (s, 3H).

Example 62. N-[1-[5-Cyano-2-[4-[[dimethyl(oxo)-$\lambda^6$-sulfanylidene]amino]-3-fluoro-anilino]pyrimidin-4-yl]-3-methyl-indol-5-yl]prop-2-enamide

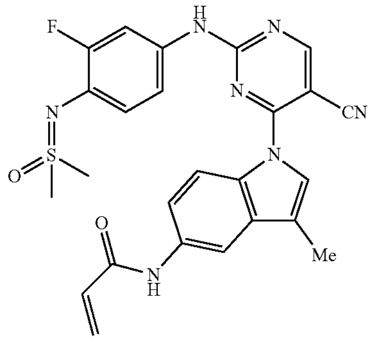 [SMILES: C=CC(=O)Nc1ccc2c(c1)c(C)cn2-c1nc(Nc2ccc(N=S(C)(C)=O)c(F)c2)ncc1C#N]

Step 1: 4-Chloro-2-[4-[[dimethyl(oxo)-$\lambda^6$-sulfanylidene]amino]-3-fluoro-anilino]pyrimidine-5-carbonitrile. To a solution of 2,4-dichloropyrimidine-5-carbonitrile (200 mg, 1.15 mmol) in DCE/t-BuOH (1:1, 2 mL) was added zinc-chloride (0.700 mol/L solution in THF, 1.81 mL, 1.26 mmol, 1.1 eq) at 0° C. and the resulting mixture was stirred for 30 min. Then 4-[[dimethyl(oxo)-$\lambda^6$-sulfanylidene]amino]-3-fluoro-aniline (232 mg, 1.15 mmol, 1 eq) was added followed by dropwise addition of triethylamine (0.176 mL, 1.26 mmol, 1.1 eq) in 0.5 mL of DCE/t-BuOH. The reaction mixture was stirred at RT for 30 min. Upon complete conversion the mixture was evaporated to dryness and the residue was triturated with MeOH/water, collected and dried to afford a brown solid (148 mg). LCMS m/z=340, 342 (M+1, 1 Cl isotopic distribution).

Step 2: 2-[4-[[Dimethyl(oxo)-$\lambda^6$-sulfanylidene]amino]-3-fluoro-anilino]-4-(3-methyl-5-nitro-indol-1-yl)pyrimidine-5-carbonitrile. To a solution of 3-methyl-5-nitro-1H-indole (76.7 mg, 0.436 mmol, 1 eq) in DMF (1 mL), cooled to 0° C. (ice bath), NaH (60% dispersion in mineral oil, 20.9 mg, 0.523 mmol, 1.2 eq.) was added cautiously portion-wise. The suspension was stirred in an ice bath for 30 min. The resulting slurry was then transferred to a cold (0° C.) solution of 4-chloro-2-[4-[[dimethyl(oxo)-lambda6-sulfanylidene]amino]-3-fluoro-anilino]pyrimidine-5-carbonitrile (148 mg, 0.436 mmol, 1 eq) in DMF (2 mL) and stirred at RT overnight. Upon completion, water (10 mL) was added cautiously and in portions with stirring. The precipitate was collected, washed with water and dried in vacuo to give a yellow solid (185 mg, 89%). LCMS m/z=480 (M+1).

Step 3: 4-(5-amino-3-methyl-indol-1-yl)-2-[4-[[dimethyl(oxo)-$\lambda^6$-sulfanylidene]amino]-3-fluoro-anilino]pyrimidine-5-carbonitrile. The product from step 2 (185 mg, 0.386 mmol) was reduced using conditions for example 60 step 5 (185 mg, 0.386 mmol) to give a brown solid (107 mg, 62%). LCMS m/z=450 (M+1).

Step 4: N-[1-[5-Cyano-2-[4-[[dimethyl(oxo)-$\lambda^6$-sulfanylidene]amino]-3-fluoro-anilino]pyrimidin-4-yl]-3-methyl-indol-5-yl]prop-2-enamide. The title compound was prepared using the procedure for Example 60 step 6 starting with product step 3 (107 mg, 0.238 mmol) to give a beige solid (15 mg, 13%). LCMS m/z=504 (M+1); $^1$H NMR (500 MHz, DMSO-d6) δ: 10.36-10.56 (m, 1H), 10.25 (s, 1H), 8.91 (s, 1H), 8.51 (br s, 1H), 8.07 (d, J=1.5 Hz, 1H), 7.82-7.95 (m, 1H), 7.66 (br s, 1H), 7.37-7.62 (m, 1H), 7.20-7.35 (m, 1H), 7.08-7.15 (m, 1H), 6.47 (dd, J=17.1, 10.1 Hz, 1H), 6.28 (dd, J=16.9, 1.7 Hz, 1H), 5.76 (dd, J=10.2, 1.7 Hz, 1H), 3.24 (s, 6H), 2.29 (s, 3H).

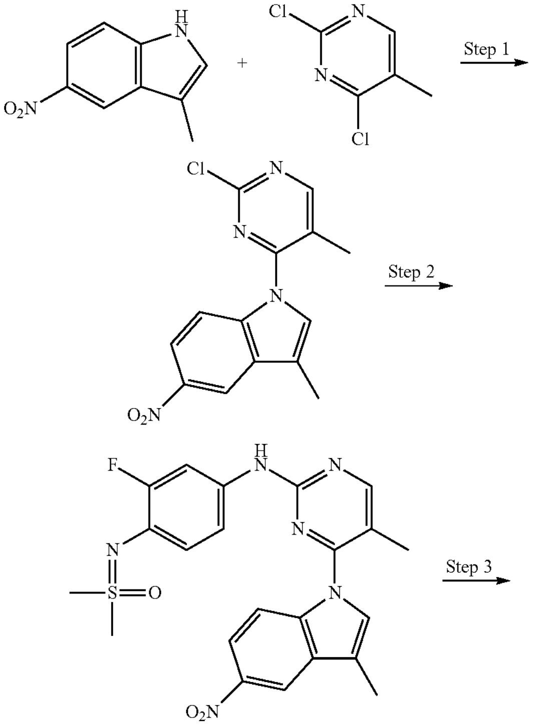

-continued

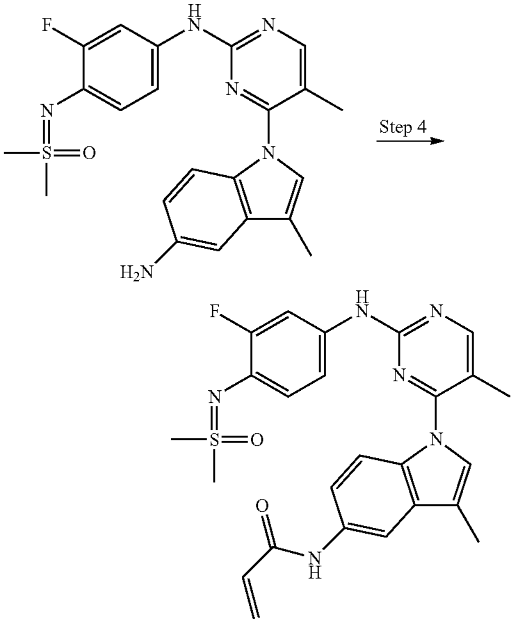

Example 63

Example 63. N-[1-[2-[4-[[dimethyl(oxo)-$\lambda^6$-sulfanylidene]amino]-3-fluoro-anilino]-5-methyl-pyrimidin-4-yl]-3-methyl-indol-5-yl]prop-2-enamide

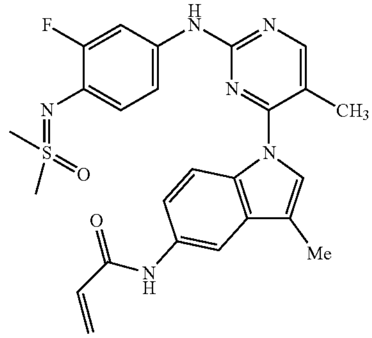

Step 1. 1-(2-Chloro-5-methyl-pyrimidin-4-yl)-3-methyl-5-nitro-indole. To a solution of 3-methyl-5-nitro-1H-indole (2.0 g, 11.4 mmol) in dry DMF (14 mL), cooled to 0° C. (ice bath), was added NaH (60.0%, 0.681 g, 17.0 mmol) portion wise. Resulting dark red suspension was stirred at 0° C. for 30 min and then slowly transferred to a solution of 2,4-dichloro-5-methyl-pyrimidine (2.22 g, 13.6 mmol) in dry DMF (6 ml). The reaction mixture was stirred at RT for 2 h. Water was added (20 ml) and the resulting precipitate was collected by filtration, washed with water, MeOH and dried in vacuo to afford a yellow solid (3.0 g, Yield 75%). LCMS m/z=303.1 (M+H).

Step 2. A suspension of 1-(2-chloro-5-methyl-pyrimidin-4-yl)-3-methyl-5-nitro-indole (300.0 mg, 0.99 mmol), 4-[[dimethyl(oxo)-$\lambda^6$-sulfanylidene]amino]-3-fluoro-aniline (220.5 mg, 1.09 mmol, 1.1 eq), cesium carbonate (645.7 mg, 1.98 mmol, 2 eq) and 4,5-bis(diphenylphosphino)-9,9-dimethylxanthene (58.5 mg, 0.10 mmol, 0.1 eq) in dry dioxane (10 mL) was degassed with Argon for 5 min. Palladium (II) acetate (17.8 mg, 0.08 mmol, 0.08 eq) was then added and the reaction mixture heated in MW at 80° C. for 45 min. After cooling to RT, the solvent was removed in vacuo and the remaining residue was dissolved in EtOAc, and washed with saturated $NaHCO_3$ solution, water and brine. The organic layer was concentrated in vacuo and the remaining residue was triturated with DCM to afford a crude solid used in the next step. LCMS m/z=469.00 (M+H).

Step 3. 1-[2-[4-[[Dimethyl(oxo)-$\lambda^6$-sulfanylidene]amino]-3-fluoro-anilino]-5-methyl-pyrimidin-4-yl]-3-methyl-indol-5-amine. A suspension of product step 3 (560 mg, 1.20 mmol), iron (801.0 mg, 14.34 mmol, 12 eq) and ammonium chloride (255.7 mg, 4.78 mmol, 4 eq) in EtOH (5 mL) and water (1.5 mL) was stirred at reflux for 4.5 h. Upon complete conversion, the reaction mixture was filtrated through celite and concentrated in vacuo to dryness. The remaining residue was suspended in DCM and washed with saturated $NaHCO_3$ solution, water and brine. The organic layer was separated, dried over $MgSO_4$ and evaporated to dryness to afford a crude product used in the next step. LCMS m/z=438.99 (M+H).

Step 4. N-[1-[2-[4-[[dimethyl(oxo)-$\lambda^6$-sulfanylidene]amino]-3-fluoro-anilino]-5-methyl-pyrimidin-4-yl]-3-methyl-indol-5-yl]prop-2-enamide. To a solution of product step 3 (200 mg, 0.456 mmol) in dry THF (1 ml) was added diisopropylethylamine (155 μl, 1.140 mmol, 2.5 eq) followed by prop-2-enoyl chloride (37 μl, 0.456 mmol, 1 eq). The resulting mixture was stirred at RT for 1 h. The reaction mixture was diluted with saturated $NaHCO_3$ solution (10 ml) and the product was extracted with DCM (3×10 ml). Combined organic layers were evaporated in vacuo to give crude product, which was purified by prep HPLC to give a yellow solid (27 mg). LCMS m/z=493.15 (M+H). $^1$H NMR (500 MHz, DMSO-d6): δ 10.15 (s, 1H) 9.62 (s, 1H) 8.48 (s, 1H) 8.07 (s, 1H) 7.80 (d, J=8.8 Hz, 1H) 7.70 (d, J=2.4 Hz, 1H) 7.57 (s, 1H) 7.39 (d, J=8.5 Hz, 1H) 7.28 (d, J=8.3 Hz, 1H) 6.99 (t, J=9.1 Hz, 1H) 6.47 (dd, J=17.0, 10.0 Hz, 1H) 6.26 (dd, J=16.9, 1.6 Hz, 1H) 5.71-5.76 (m, 1H) 3.18 (s, 6H) 2.29 (s, 3H) 2.24 (s, 3H).

Examples 64-88 were Synthesized Using Methods for Examples 60-63 and Analogous Intermediates Described Previously Example 64
N-[1-[5-Chloro-2-[4-[[dimethyl(oxo)-$\lambda^6$-sulfanylidene]amino]-3-methoxy-anilino]pyrimidin-4-yl]-3-methyl-indol-5-yl]prop-2-enamide

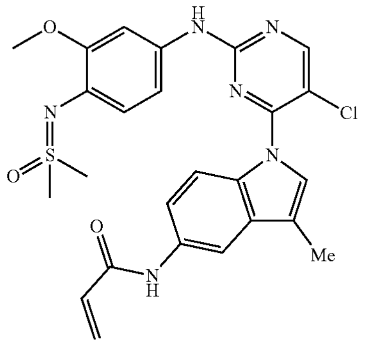 [SMILES: C=CC(=O)Nc1ccc2c(c1)c(C)cn2-c1nc(Nc2ccc(N=S(C)(C)=O)c(OC)c2)ncc1Cl]

LCMS m/z = 525.14 (M + 1, 1 Cl isotopic distribution); $^1$H NMR (500 MHz, DMSO-d6) δ 10.18 (s, 1H), 9.77 (s, 1H), 8.63 (s, 1H), 8.06 (d, J = 1.84 Hz, 1H), 7.85 (br s, 1H), 7.71 (s, 1H), 7.43-7.38 (m, 2H), 7.11 (d, J = 8.16 Hz, 1H), 6.87 (d, J = 8.51 Hz, 1H), 6.47 (dd, J = 10.10, 16.96 Hz, 1H), 6.26 (dd, J = 2.00, 16.96 Hz, 1H), 5.75 (dd, J = 1.94, 10.05 Hz, 1H), 3.59 (s, 3H), 3.12 (s, 6H), 2.28 (s, 3H)

Example 65
N-[1-[5-Chloro-2-[4-[[dimethyl(oxo)-$\lambda^6$-sulfanylidene]amino]-2-ethoxy-anilino]pyrimidin-4-yl]-3-methyl-indol-5-yl]prop-2-enamide

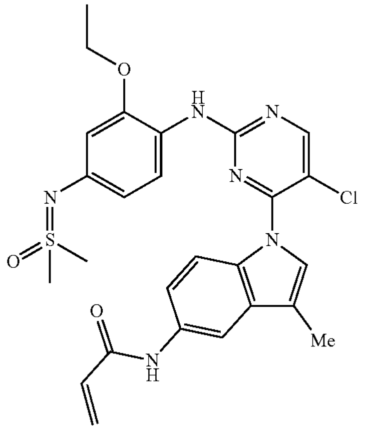 [SMILES: C=CC(=O)Nc1ccc2c(c1)c(C)cn2-c1nc(Nc2ccc(N=S(C)(C)=O)cc2OCC)ncc1Cl]

LCMS m/z = 539, 541 (M + 1, 1 Cl isotopic distribution); $^1$H NMR (500 MHz, DMSO-d6) δ 10.16 (s, 1H), 8.58 (s, 1H), 8.53 (s, 1H), 7.77 (d, J = 8.5 Hz, 1H), 7.70 (s, 1H), 7.34-7.42 (m, 3H), 6.58 (d, J = 2.1 Hz, 1H), 6.43-6.53 (m, 2H), 6.26 (dd, J = 17.1, 1.8 Hz, 1H), 5.74 (dd, J = 10.2, 1.7 Hz, 1H), 4.00 (q, J = 6.8 Hz, 2H), 3.19 (s, 6H), 2.26 (s, 3H), 1.26 (t, J = 7.0 Hz, 3H)

-continued

| | | |
|---|---|---|
| Example 66<br>N-[1-[5-chloro-2-[4-[[dimethyl(oxo)-$\lambda^6$-sulfanylidene]amino]anilino]-pyrimidin-4-yl]indol-5-yl]prop-2-enamide | 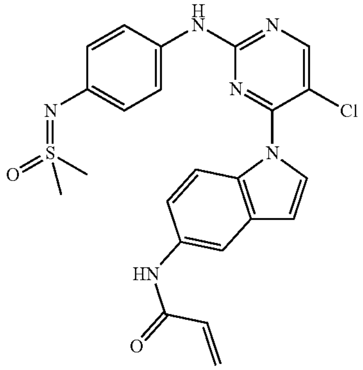 [SMILES: C=CC(=O)Nc1ccc2c(ccn2-c2nc(Nc3ccc(N=S(C)(C)=O)cc3)ncc2Cl)c1] | LCMS m/z = 481, 483 (M + 1, 1 Cl isotopic distribution); $^{1}$H NMR (500 MHz, DMSO-d6) δ 10.16 (s, 1H), 9.81 (s, 1H), 8.65 (s, 1H), 8.12 (d, J = 1.8 Hz, 1H), 7.86 (d, J = 3.4 Hz, 1H), 7.82 (br d, J = 8.5 Hz, 1H), 7.53-7.49 (m, 2H), 7.41 (dd, J = 1.5, 8.9 Hz, 1H), 6.88-6.83 (m, J = 8.9 Hz, 2H), 6.77 (d, J = 3.7 Hz, 1H), 6.47 (dd, J = 10.2, 16.9 Hz, 1H), 6.26 (dd, J = 2.0, 16.9 Hz, 1H), 5.76-5.73 (m, 1H), 3.17 (s, 6H) |
| Example 67<br>(E)-N-[1-[5-Chloro-2-[4-[[dimethyl(oxo)-$\lambda^6$-sulfanylidene]amino]anilino]-pyrimidin-4-yl]indol-5-yl]-4-(dimethylamino)but-2-enamide | 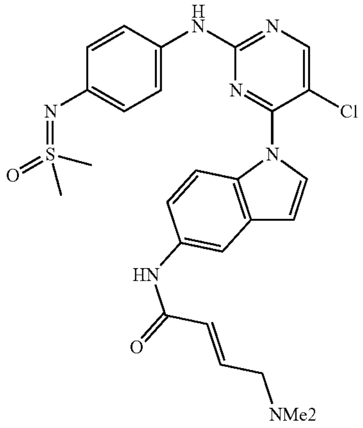 [SMILES: CN(C)C/C=C/C(=O)Nc1ccc2c(ccn2-c2nc(Nc3ccc(N=S(C)(C)=O)cc3)ncc2Cl)c1] | LCMS m/z = 538, 540 (M + 1, 1 Cl isotopic distribution); $^{1}$H NMR (500 MHz, DMSO-d6) δ 10.06 (s, 1H), 9.80 (s, 1H), 8.64 (s, 1H), 8.10 (d, J = 1.8 Hz, 1H), 7.86 (d, J = 3.4 Hz, 1H), 7.81 (br d, J = 8.2 Hz, 1H), 7.54-7.48 (m, 2H), 7.41 (d, J = 8.4 Hz, 1H), 6.89-6.82 (m, J = 8.9 Hz, 2H), 6.79-6.70 (m, 2H), 6.30 (d, J = 15.6 Hz, 1H), 3.17 (s, 6H), 3.10-3.03 (m, 2H), 2.19 (s, 6H) |
| Example 68<br>N-[1-[5-Chloro-2-[4-[[dimethyl(oxo)-$\lambda^6$-sulfanylidene]amino]anilino]-pyrimidin-4-yl]indol-5-yl]propanamide | 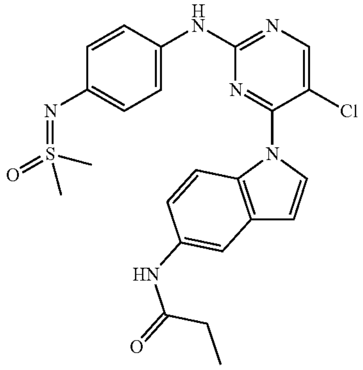 [SMILES: CCC(=O)Nc1ccc2c(ccn2-c2nc(Nc3ccc(N=S(C)(C)=O)cc3)ncc2Cl)c1] | LCMS m/z = 483, 485 (M + 1, 1 Cl isotopic distribution); $^{1}$H NMR (500 MHz, DMSO-d6) δ 9.85 (s, 1H), 9.80 (s, 1H), 8.64 (s, 1H), 8.02 (d, J = 2.1 Hz, 1H), 7.84 (d, J = 3.4 Hz, 1H), 7.79 (br d, J = 9.2 Hz, 1H), 7.51 (d, J = 7.8 Hz, 2H), 7.34 (dd, J = 1.7, 9.0 Hz, 1H), 6.85 (d, J = 8.9 Hz, 2H), 6.74 (d, J = 3.4 Hz, 1H), 3.17 (s, 6H), 2.34 (q, J = 7.6 Hz, 2H), 1.11 (t, J = 7.6 Hz, 3H) |
| Example 69<br>N-[1-[5-Chloro-2-[4-[(4-methyl-1-oxo-1,4-thiazinan-1-ylidene)amino]anilino]pyrimidin-4-yl]indol-5-yl]prop-2-enamide | 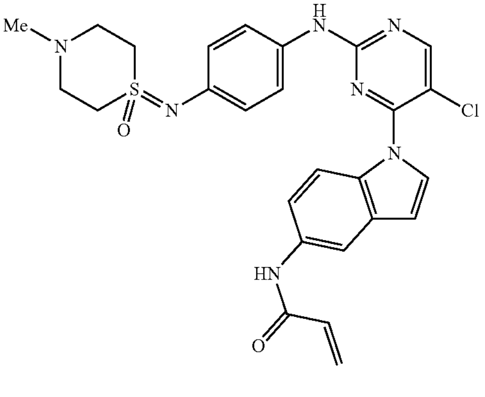 [SMILES: C=CC(=O)Nc1ccc2c(ccn2-c2nc(Nc3ccc(N=S4(=O)CCN(C)CC4)cc3)ncc2Cl)c1] | LCMS m/ z = 536.53 (M + 1); $^{1}$H NMR (500 MHz, DMSO-d6) δ 10.15 (s, 1H), 9.81 (s, 1H), 8.65 (s, 1H), 8.11 (s, 1H), 7.86 (d, J = 3.22 Hz, 1H), 7.81 (d, J = 8.50 Hz, 1H), 7.51 (d, J = 8.50 Hz, 2H), 7.41 (d, J = 8.72 Hz, 1H), 6.89 (d, J = 8.72 Hz, 2H), 6.77 (d, J = 3.14 Hz, 1H), 6.47 (dd, J = 17.09, 10.29 Hz, 1H), 6.26 (dd, J = 17.09, 1.05 Hz, 1H), 5.75 (d, J = 10.11 Hz, 1H), 3.21-3.30 (m, 4H), 2.80-2.88 (m, 2H), 2.70-2.78 (m, 2H), 2.28 (s, 3H) |

-continued

Example 70
N-[1-[5-Chloro-2-[4-(methylsulfonimidoyl)anilino]-pyrimidin-4-yl]indol-5-yl]prop-2-enamide

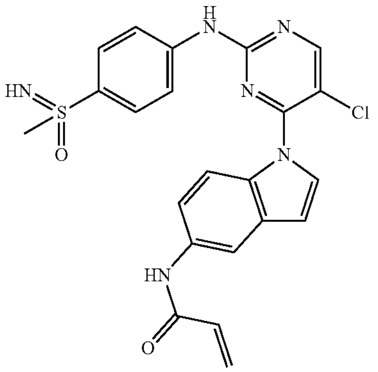 [SMILES: C=CC(=O)Nc1ccc2c(ccn2-c2nc(Nc3ccc(S(C)(=N)=O)cc3)ncc2Cl)c1]

LCMS m/z = 467, 469 (M + 1, 1 Cl isotopic distribution); $^1$H NMR (500 MHz, DMSO-d6) δ 10.47 (s, 1H), 10.19 (s, 1H), 8.81 (s, 1H), 8.16 (s, 1H), 7.95 (br d, J = 8.9 Hz, 2H), 7.91-7.85 (m, 2H), 7.82 (br d, J = 8.9 Hz, 2H), 7.44 (d, J = 8.9 Hz, 1H), 6.81 (d, J = 3.4 Hz, 1H), 6.48 (dd, J = 10.2, 16.9 Hz, 1H), 6.27 (dd, J = 1.8, 16.8 Hz, 1H), 5.75 (dd, J = 2.4, 9.5 Hz, 1H), 4.04 (s, 1H), 3.02 (s, 3H)

Example 71
N-[1-[5-chloro-2-[2-methoxy-4-(methylsulfonimidoyl)-anilino]pyrimidin-4-yl]indol-5-yl]prop-2-enamide

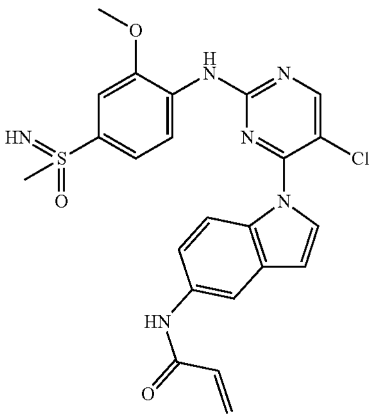 [SMILES: C=CC(=O)Nc1ccc2c(ccn2-c2nc(Nc3ccc(S(C)(=N)=O)cc3OC)ncc2Cl)c1]

LCMS m/z = 497, 499 (M + 1, 1 Cl isotopic distribution); $^1$H NMR (600 MHz, DMSO-d6) δ 10.17 (s, 1H), 8.94 (s, 1H), 8.76 (s, 1H), 8.19 (d, J = 8.3 Hz, 1H), 8.13 (d, J = 1.7 Hz, 1H), 7.89 (d, J = 3.5 Hz, 1H), 7.82 (d, J = 8.8 Hz, 1H), 7.54 (d, J = 1.8 Hz, 1H), 7.48 (dd, J = 1.9, 8.3 Hz, 1H), 7.41 (dd, J = 1.7, 8.9 Hz, 1H), 6.79 (d, J = 3.5 Hz, 1H), 6.47 (dd, J = 10.2, 16.8 Hz, 1H), 6.27 (dd, J = 1.8, 17.1 Hz, 1H), 5.75 (dd, J = 1.7, 10.2 Hz, 1H), 4.12 (s, 1H), 3.95 (s, 3H), 3.07 (s, 3H)

Example 72
N-1-[5-Chloro-2-[4-(1-imino-1-oxo-1,4-thiazinan-4-yl)anilino]pyrimidin-4-yl]indol-5-yl]prop-2-enamide

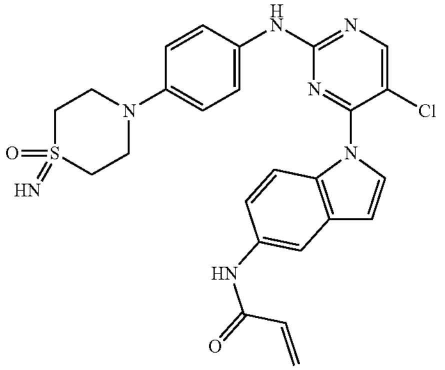 [SMILES: C=CC(=O)Nc1ccc2c(ccn2-c2nc(Nc3ccc(N4CCS(=N)(=O)CC4)cc3)ncc2Cl)c1]

LCMS m/z = 522.63 (M + 1); $^1$H NMR (500 MHz, DMSO-d6) δ 10.14 (s, 1H), 9.82 (s, 1H), 8.65 (s, 1H), 8.14 (d, J = 1.81 Hz, 1H), 7.87 (d, J = 3.51 Hz, 1H), 7.76-7.82 (m, 1H), 7.55-7.59 (m, 2H), 7.38 (d, J = 8.51 Hz, 1H), 6.96 (d, J = 8.95 Hz, 2H), 6.77 (d, J = 3.47 Hz, 1H), 6.47 (dd, J = 10.16 Hz, 17.04 Hz, 1H), 6.27 (dd, J = 1.90 Hz, 17.01 Hz, 1H), 5.75 (dd, J = 1.90 Hz, 10.16 Hz, 1H), 3.72-3.79 (m, 3H), 3.53-3.60 (m, 2H), 2.95-3.02 (m, 4H)

Example 73
N-[1-[5-chloro-2-[4-(1-imino-1-oxo-1,4-thiazinan-4-yl)anilino]pyrimidin-4-yl]indol-5-yl]propanamide

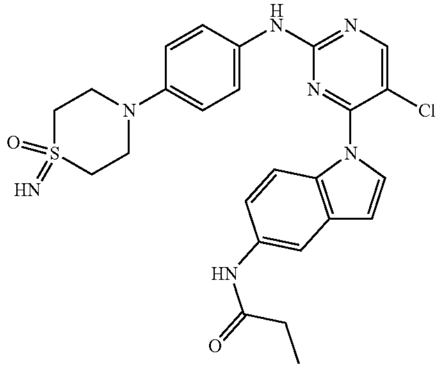 [SMILES: CCC(=O)Nc1ccc2c(ccn2-c2nc(Nc3ccc(N4CCS(=N)(=O)CC4)cc3)ncc2Cl)c1]

LCMS m/z = 524.59 (M + 1); $^1$H NMR (500 MHz, DMSO-d6) δ 9.84 (s, 1H), 9.80 (s, 1H), 8.64 (s, 1H), 8.04 (d, J = 1.93 Hz, 1H), 7.85 (d, J = 3.48 Hz, 1H), 7.71-7.79 (m, 1H), 7.55-7.58 (m, 2H), 7.31 (d, J = 8.17 Hz, 1H), 6.96 (d, J = 9.14 Hz, 2H), 6.74 (dd, J = 0.57, 3.51Hz, 1H), 3.83 (br.s., 1H), 3.73-3.78 (m, 2H), 3.54-3.59 (m, 2H), 2.96-3.03 (m, 4H), 2.34 (q, J = 7.52 Hz, 2H), 1.11 (t, J = 7.63 Hz, 3H)

-continued

Example 74
N-[1-[5-Methyl-2-[4-(methylsulfonimidoyl)anilino]-pyrimidin-4-yl]indol-5-yl]prop-2-enamide

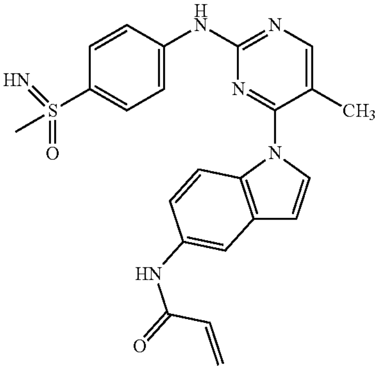

LCMS m/z = 447 (M + 1); $^1$H NMR (500 MHz, DMSO-d6) δ: 10.21 (s, 1H), 10.15 (s, 1H), 8.62 (s, 1H), 8.16 (s, 1H), 7.98 (br d, J = 8.9 Hz, 2H), 7.85-7.74 (m, 4H), 7.41 (br d, J = 8.9 Hz, 1H), 6.76 (d, J = 3.1 Hz, 1H), 6.48 (dd, J = 10.2, 16.9 Hz, 1H), 6.27 (br d, J = 17.1 Hz, 1H), 5.74 (br d, J = 10.7 Hz, 1H), 4.50-4.95 (br s, 1H), 3.07 (s, 3H), 2.26 (s, 3H)

Example 75
N-[1-[2-[2-methoxy-4-(methylsulfonimidoyl)anilino]-5-methyl-pyrimidin-4-yl]indol-5-yl]prop-2-enamide

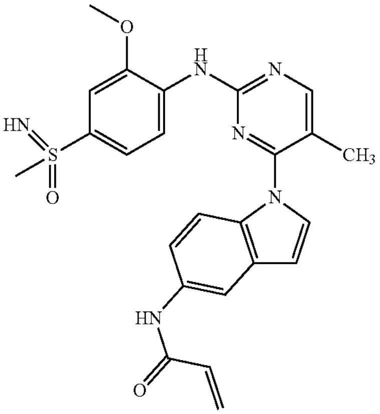

LCMS m/z = 477 (M + 1); $^1$H NMR (500 MHz, DMSO-d6) δ: 10.15 (s, 1 H), 8.61 (s, 1 H), 8.43 (d, J = 8.54 Hz, 1 H), 8.41 (s, 1 H), 8.15 (d, J = 1.83 Hz, 1 H), 7.78 (d, J = 3.36 Hz, 1 H), 7.76 (d, J = 8.85 Hz, 1 H), 7.51 (d, J = 1.83 Hz, 1 H), 7.46 (dd, J = 8.54, 1.83 Hz, 1 H), 7.40 (dd, J = 9.00, 1.98 Hz, 1H), 6.76 (d, J = 3.36 Hz, 1 H), 6.48 (dd, J = 16.94, 10.22 Hz, 1 H), 6.26 (dd, J = 16.94, 1.98 Hz, 1 H), 5.74 (dd, J = 10.07, 1.83 Hz, 1 H), 4.06 (s, 1H), 3.97 (s, 3 H), 3.06 (s, 3 H), 2.26 (s, 3 H)

Example 76
N-[1-[5-Chloro-2-[4-[[dimethyl(oxo)-λ$^6$-sulfanylidene]amino]anilino]-pyrimidin-4-yl]indol-4-yl]prop-2-enamide

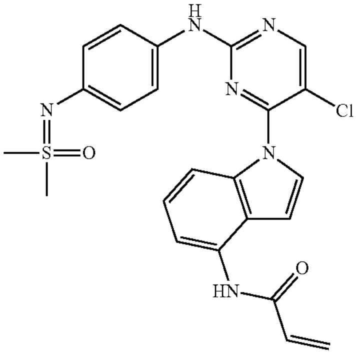 [SMILES: C=CC(=O)Nc1cccc2c1ccn2-c1nc(Nc2ccc(N=S(C)(C)=O)cc2)ncc1Cl]

LCMS m/z = 481, 483 (M + 1, 1 Cl isotopic distribution); $^1$H NMR (600 MHz, DMSO-d6) δ: 9.95 (s, 1 H), 9.85 (s, 1 H), 7.86 (br d, J = 7.70 Hz, 1 H), 7.81 (d, J = 3.67 Hz, 1 H), 7.56 (br d, J = 8.25 Hz, 1 H), 7.48-7.53 (m, 2H), 7.21 (t, J = 8.07 Hz, 1 H), 7.06 (d, J = 3.48 Hz, 1 H), 6.85 (br d, J = 8.80 Hz, 2 H), 6.70 (br d, J = 10.09 Hz, 1 H), 6.31 (dd, J = 17.06, 1.83 Hz, 1 H), 5.79-5.80 (m, 1 H), 5.78-5.81 (m, 1 H), 3.17 (s, 6H)

Example 77
N-[1-[5-Chloro-2-[4-[[dimethyl(oxo)-λ$^6$-sulfanylidene]amino]anilino]-pyrimidin-4-yl]indol-4-yl]propanamide

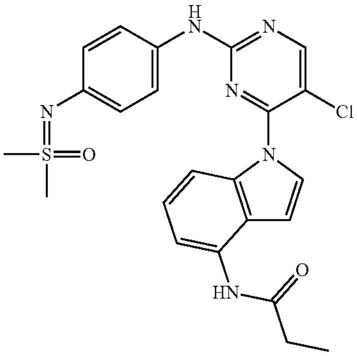 [SMILES: CCC(=O)Nc1cccc2c1ccn2-c1nc(Nc2ccc(N=S(C)(C)=O)cc2)ncc1Cl]

LCMS m/z = 483, 485 (M + 1, 1 Cl isotopic distribution); $^1$H NMR (600 MHz, DMSO-d6) δ: 9.83 (s, 1 H), 9.69 (s, 1 H), 8.67 (s, 1 H), 7.78 (d, J = 3.48 Hz, 1 H), 7.74 (br d, J = 7.70 Hz, 1 H), 7.48-7.55 (m, 3 H), 7.17 (t, J = 8.07 Hz, 1 H), 7.03 (d, J = 3.30 Hz, 1 H), 6.85 (d, J = 8.80 Hz, 2 H), 3.16 (s, 6 H), 2.44-2.49 (m, 2H), 1.14 (t, J = 7.61 Hz, 3 H)

-continued

Example 78
N-[1-[5-Chloro-2-[4-[[dimethyl(oxo)-λ$^6$-sulfanylidene]amino]anilino]-pyrimidin-4-yl]indol-4-yl]cyclopropanecarboxamide

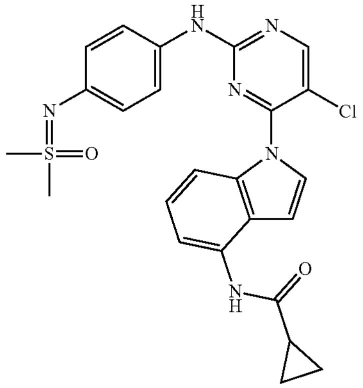 [SMILES: CS(C)(=O)=Nc1ccc(Nc2ncc(Cl)c(-n3ccc4c(NC(=O)C5CC5)cccc43)n2)cc1]

LCMS m/z = 495 (M + 1, 1 Cl isotopic distribution); $^1$H NMR (600 MHz, DMSO-d6) δ 10.00 (s, 1 H), 9.84 (s, 1 H), 8.67 (s, 1 H), 7.79 (d, J = 3.67 Hz, 1 H), 7.75 (br d, J = 7.15 Hz, 1 H), 7.48-7.55(m, 3H), 7.16 (t, J = 8.07 Hz, 1 H), 7.07 (d, J = 3.48 Hz, 1 H), 6.85 (br d, J = 8.62 Hz, 2 H), 3.16 (s, 6H), 2.02-2.11 (m, 1 H), 0.82-0.88

Example 79
1-[5-Chloro-2-[4-[[dimethyl(oxo)-λ$^6$-sulfanylidene]amino]anilino]-pyrimidin-4-yl]indol-4-amine

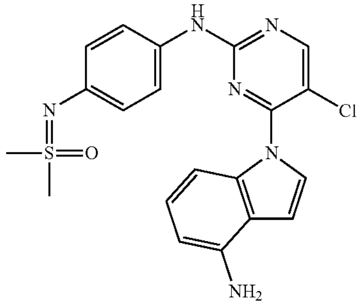 [SMILES: CS(C)(=O)=Nc1ccc(Nc2ncc(Cl)c(-n3ccc4c(N)cccc43)n2)cc1]

LCMS m/z = 427 (M + 1, 1 Cl isotopic distribution); $^1$H NMR (300 MHz, DMSO-d6) δ 9.77 (s, 1 H), 8.61 (s, 1 H), 7.46-7.58 (m, 3 H), 6.78-7.02 (m, 5 H), 6.32 (d, J = 7.32 Hz, 1 H), 5.41 (s, 2H), 3.15 (s, 6H)

Example 80
N-[1-[5-Chloro-2-[4-[[dimethyl(oxo)-λ$^6$-sulfanylidene]amino]anilino]-pyrimidin-4-yl]indol-5-yl]cyclopropanecarboxamide

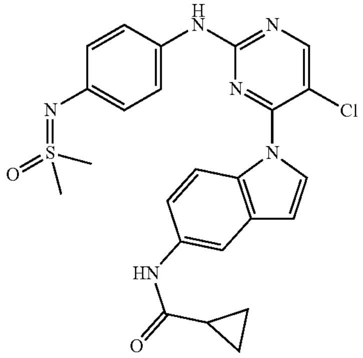 [SMILES: CS(C)(=O)=Nc1ccc(Nc2ncc(Cl)c(-n3ccc4cc(NC(=O)C5CC5)ccc43)n2)cc1]

LCMS m/z = 495 (M + 1, 1 Cl isotopic distribution); $^1$H NMR (500 MHz, DMSO-d6) δ 10.17 (s, 1H), 9.80 (s, 1H), 8.64 (s, 1H), 8.00 (d, J = 1.8 Hz, 1H), 7.85 (d, J = 3.7 Hz, 1H), 7.79 (br d, J = 8.5 Hz, 1H), 7.54-7.48 (m, 2H), 7.35 (dd, J = 1.7, 9.0 Hz, 1H), 6.85 (d, J = 8.9 Hz, 2H), 6.73 (d, J = 3.7 Hz, 1H), 3.17 (s, 6H), 1.80 (s, 1H), 0.84-0.75 (m, 4H)

Example 81
N-1-[5-Chloro-2-[4-(1-imino-1-oxo-1,4-thiazinan-4-yl)anilino]pyrimidin-4-yl]indol-4-yl]prop-2-enamide

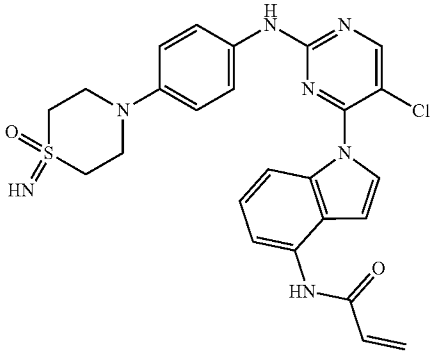 [SMILES: C=CC(=O)Nc1cccc2c1ccn2-c1nc(Nc2ccc(N3CCS(=N)(=O)CC3)cc2)ncc1Cl]

LCMS m/z = 522.58 (M + 1); $^1$H NMR (500 MHz, DMSO-d6) δ 9.95 (s, 1H), 9.85 (br.s., 1H), 8.68 (s, 1H), 7.84 (d, J = 7.82 Hz, 1H), 7.81 (d, J = 3.59 Hz, 1H), 7.53-7.59 (m, 3H), 7.21 (t, J = 8.11 Hz, 1H), 7.05 (d, J = 3.66 Hz, 1H), 6.95 (d, J = 8.90 Hz, 2H), 6.71 (dd, J = 9.89, 16.82 Hz, 1H), 6.31 (dd, J = 1.95, 17.08 Hz, 1H), 5.80 (dd, J = 1.93, 10.10 Hz, 1H), 3.87 (br.s., 1H), 3.72-3.79 (m, 2H), 3.52-3.59 (m, 2H), 2.95-3.03 (m, 4H)

-continued

| | | |
|---|---|---|
| Example 82<br>1-[5-Chloro-2-[4-(1-imino-1-oxo-1,4-thiazinan-4-yl)anilino]pyrimidin-4-yl]indol-4-amine | 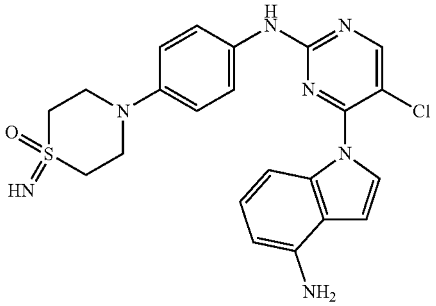 [SMILES: N=S1(=O)CCN(c2ccc(Nc3ncc(Cl)c(-n4ccc5c(N)cccc54)n3)cc2)CC1] | LCMS m/z = 468 (M + 1, 1 Cl isotopic distribution); $^1$H NMR (600 MHz, DMSO-d6) δ 9.79 (br.s., 1H), 8.63 (s, 1H), 7.56-7.60 (m, 3H), 6.90-6.99 (m, 4H), 6.88 (d, J = 3.62 Hz, 1H), 6.34 (d, J = 7.54 Hz, 1H), 5.42 (br.s., 2H), 3.72-3.79 (m, 3H), 3.52-3.59 (m, 2H), 2.96-3.00 (m, 4H) |
| Example 83<br>N-[1-[5-Chloro-2-[4-(1-imino-1-oxo-1,4-thiazinan-4-yl)anilino]pyrimidin-4-yl]indol-4-yl]propanamide | 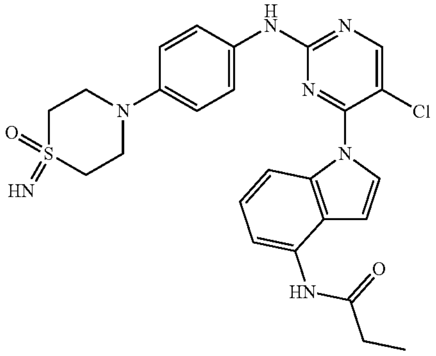 [SMILES: CCC(=O)Nc1cccc2c1ccn2-c1nc(Nc2ccc(N3CCS(=N)(=O)CC3)cc2)ncc1Cl] | LCMS m/z = 525 (M + 1, 1 Cl isotopic distribution); $^1$H NMR (500 MHz, DMSO-d6) δ 9.84 (br.s., 1H), 9.69 (br.s., 1H), 8.67 (s, 1H), 7.78 (d, J = 3.58 Hz, 1H), 7.73 (d, J = 7.70 Hz, 1H), 7.55-7.58 (m, 2H), 7.52 (d, J = 8.21 Hz, 1H), 7.17 (t, J = 7.95 Hz, 1H), 7.02 (d, J = 3.42 Hz, 1H), 6.95 (d, J = 8.94 Hz, 2H), 3.72-3.79 (m, 3H), 3.52-3.59 (m, 2H), 2.96-3.00 (m, 4H), 2.47 (q, J = 2.45 Hz, 2H), 1.14 (t, J = 7.58 Hz, 3H) |
| Example 84<br>N-[1-[5-Chloro-2-[4-[[dimethyl(oxo)-λ$^6$-sulfanylidene]amino]-3-fluoro-anilino]pyrimidin-4-yl]-4-methyl-indol-5-yl]prop-2-enamide | 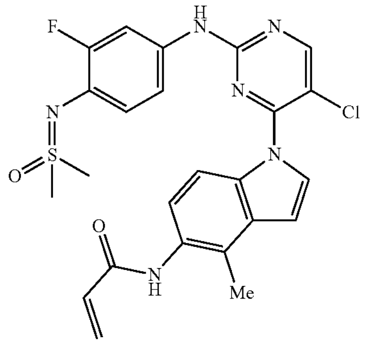 [SMILES: C=CC(=O)Nc1ccc2c(ccn2-c2nc(Nc3ccc(N=S(C)(C)=O)c(F)c3)ncc2Cl)c1C] | LCMS m/z = 513 (M + 1); $^1$H NMR (300 MHz, DMSO-d6) δ 2.37 (s, 3H)3.18(s, 6H) 5.70-5.76 (m, 1H) 6.23 (dd, J = 17.07, 1.92 Hz, 1H) 6.52 (dd, J = 16.90, 10.10 Hz, 1H) 6.86 (d, J = 2.96 Hz, 1H) 7.01 (t, J = 9.03 Hz, 1H) 7.21 (d, J = 8.71 Hz, 1H) 7.23-7.34 (m, 1H) 7.62 (d, J = 2.61 Hz, 1H) 7.66 (d, J = 7.48 Hz, 1H) 7.84 (d, J = 3.48 Hz, 1H) 8.71 (s, 1H) 9.65 (s, 1H) 10.02 (s, 1H) |
| Example 85<br>N-[1-[5-chloro-2-[4-[[dimethyl(oxo)-λ$^6$-sulfanylidene]amino]anilino]-pyrimidin-4-yl]-6-methyl-indol-5-yl]prop-2-enamide | 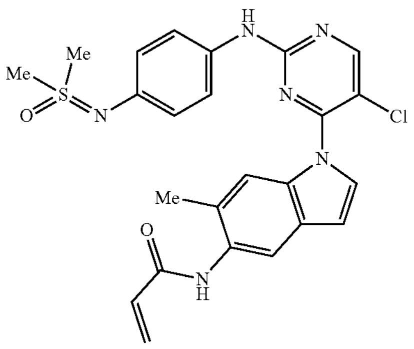 [SMILES: C=CC(=O)Nc1cc2ccn(-c3nc(Nc4ccc(N=S(C)(C)=O)cc4)ncc3Cl)c2cc1C] | LCMS m/z = 495, 497 (M + 1, 1 Cl isotopic distribution); $^1$H NMR (600 MHz, DMSO-d6) δ 9.83 (s, 1 H), 9.52 (s, 1 H), 8.66 (s, 1H), 7.80 (d, J = 3.5 Hz, 1 H), 7.68 (s, 1 H), 7.74 (s, 1 H), 7.50-7.54 (m, 2H), 6.82-6.88 (m, 2H), 6.72 (d, J = 3.5 Hz, 1 H), 6.50-6.58 (m, 1 H), 6.22-6.27 (m, 1 H), 5.73-5.76 (m, 1 H), 3.16 (s, 6 H), 2.27 (s, 3 H) |

-continued

Example 86
N-[1-[5-Chloro-2-[4-[[dimethyl(oxo)-$\lambda^6$-sulfanylidene]amino]anilino]-pyrimidin-4-yl]indazol-5-yl]prop-2-enamide

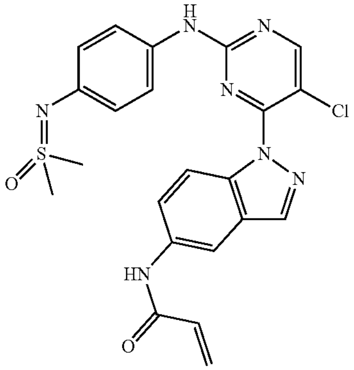 [SMILES: C=CC(=O)Nc1ccc2c(cnn2-c2nc(Nc3ccc(N=S(C)(C)=O)cc3)ncc2Cl)c1]

LCMS m/z = 482, 484 (M + 1, 1 Cl isotopic distribution); $^1$H NMR (600 MHz, DMSO-d6) δ: 10.39 (s, 1H), 9.80 (s, 1H), 8.63 (s, 1H), 8.51 (s, 1H), 8.40 (d, J = 1.8 Hz, 1H), 8.35-8.20 (m, 1H), 7.68-7.61 (m, 1H), 7.52-7.47 (m, J = 8.6 Hz, 2H), 6.91-6.88 (m, 2H), 6.48 (dd, J = 10.2, 17.0 Hz, 1H), 6.31 (dd, J = 1.8, 17.1 Hz, 1H), 5.81-5.78 (m, 1H), 3.19 (s, 6H)

Example 87
1-[5-Chloro-2-[4-[[dimethyl(oxo)-$\lambda^6$-sulfanylidene]amino]anilino]-pyrimidin-4-yl]indazol-5-amine

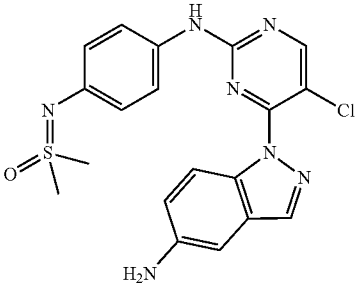 [SMILES: CS(C)(=O)=Nc1ccc(Nc2ncc(Cl)c(-n3ncc4cc(N)ccc43)n2)cc1]

LCMS m/z = 428 (M + 1, 1 Cl isotopic distribution); $^1$H NMR (600 MHz, DMSO-d6) δ 9.69 (s, 1H), 8.54 (s, 1H), 8.22 (s, 1H), 8.22-8.21 (m, 1H), 7.49 (br d, J = 8.8 Hz, 2H), 6.89 (d, J = 8.4 Hz, 2H), 6.86 (d, J = 2.0 Hz, 1H), 6.87 (br s, 1H), 5.41-5.03 (m, 2H), 3.19 (s, 6H)

Example 88
N-[1-[5-Chloro-2-[2-methoxy-4-(methylsulfonimidoyl)-anilino]-pyrimidin-4-yl]indol-5-yl]prop-2-enamide

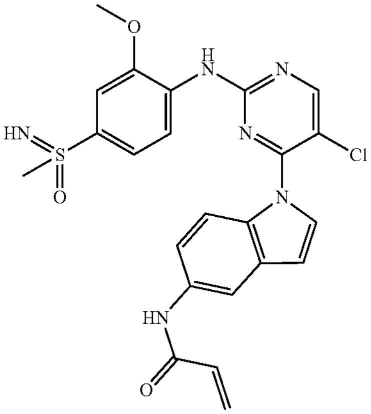 [SMILES: C=CC(=O)Nc1ccc2c(ccn2-c2nc(Nc3ccc(S(C)(=N)=O)cc3OC)ncc2Cl)c1]

LCMS m/z = 511 (M + 1); $^1$H NMR (500 MHz, DMSO-d6) δ 8.94 (br.s, 1H), 8.76 (s, 1H), 8.59-8.65 (m,1H), 8.16 (d, J = 8.5 Hz, 1H), 7.85 (d, J = 3.3 Hz, 1H), 7.75 (d, J = 8.5 Hz, 1H), 7.52-.7.55 (m, 2H), 7.47 (dd, J = 8.5 Hz, J = 2.0 Hz, 1H), 7.17 (dd, J = 8.5 Hz, J = 1.5 Hz, 1H), 6.77 (d, J = 3.5 Hz, 1H), 6.29 (dd, J = 17.0 Hz, J = 10.2 Hz, 1H), 6.14 (dd, J = 17.0 Hz, J = 2.1 Hz 1H), 5.62 (dd, J = 10.0 Hz, J = 2.2 Hz, 1H), 4.44 (d, J = 5.9 Hz, 2H), 4.12 (br.s, 1H), 3.94 (s, 3H), 3.06 (s, 3H).

Example 89. N-[3-[5-chloro-2-[4-(methylsulfonimidoyl)anilino]pyrimidin-4-yl]-1H-indol-6-yl]prop-2-enamide

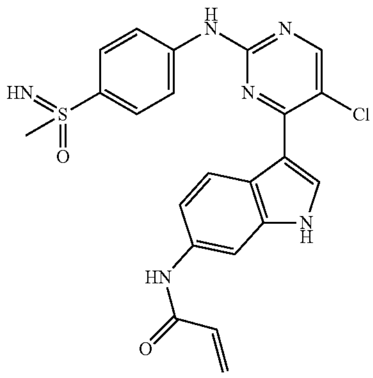 [SMILES: C=CC(=O)Nc1ccc2c(-c3nc(Nc4ccc(S(C)(=N)=O)cc4)ncc3Cl)c[nH]c2c1]

Step 1. 3-Bromo-6-nitro-1-(p-tolylsulfonyl)indole. To a solution of 6-nitro-1-(p-tolylsulfonyl)indole (4.35 g, 13.8 mmol) in dry $CCl_4$ (90 mL) stirred at 80° C. was added bromine (7.08 ml, 137.5 mmol, 10 eq) dropwise. The resulting mixture was stirred at 80° C. for 60 minutes and quenched with 10% $Na_2S_2O_3$ (500 ml). The mixture was extracted with EtOAc and concentrated. The residue was triturated with DCM and the precipitate was collected by filtration and dried in vacuum oven to a beige solid (4.51 g). LCMS m/z=315 (M−1).

Step 2. 6-Nitro-1-(p-tolylsulfonyl)-3-(4,4,5,5-tetramethyl-1,3,2-dioxaborolan-2-yl)indole. A mixture of 3-bromo-6-nitro-1-(p-tolylsulfonyl)indole (2.4 g, 6.0 mmol), bis(pinacolato)diboron (1.8 g, 7.2 mmol, 1.2 eq) and KOAc (1.2 g, 12.0 mmol, 2 eq) in dry dioxane (45 ml) was bubbled with argon for 10 min when [1,1'-bis(diphenylphosphino) ferrocene]dichloropalladium(II) dichloromethane adduct (150.0 mg, 0.18 mmol, 0.03 eq) was added. The resulting mixture was irradiated in MW reactor for 30 minutes at 140° C. The reaction mixture was diluted with water and product was extracted with EtOAc. Combined organic layers were washed with brine and evaporated in vacuo to dryness. The residue was purified by flash chromatography (isocratic at 100% of DCM) to afford 6-nitro-1-(p-tolylsulfonyl)-3-(4,4,5,5-tetramethyl-1,3,2-dioxaborolan-2-yl)indole as a yellow solid (1.17 g).

Step 3. 3-(2,5-Dichloropyrimidin-4-yl)-6-nitro-1-(p-tolylsulfonyl)indole. 6-Nitro-1-(p-tolylsulfonyl)-3-(4,4,5,5-tetramethyl-1,3,2-dioxaborolan-2-yl)indole (1.17 g, 2.65 mmol), 2,4,5-trichloropyrimidine (303 μL, 2.65 mmol, 1 eq) and sodium carbonate (0.56 g, 5.29 mmol, 2 eq) were suspended in acetonitrile (10 mL) and water (4 mL) and was bubbled with argon for 10 minutes. Tetrakis(triphenylphosphine)palladium(0) (153 mg, 0.13 mmol, 0.05 eq) was added and the resulting mixture was irradiated in MW reactor for 30 minutes at 80° C. The reaction mixture was diluted with water and product was extracted with EtOAc. Combined organic layers were washed with water and brine and then evaporated in vacuo to dryness. The residue was triturated with $Et_2O$ and the precipitate was collected by filtration and dried to give a solid (692 mg). LCMS m/z=461 (M−1). $^1H$ NMR (300 MHz, DMSO-d6) δ 1.31 (s, 3H) 7.41-7.50 (m, 2H) 8.07 (m, J=7.5 Hz, 2H) 8.31 (d, J=2.1 Hz, 1H) 8.41 (br d, J=9.4 Hz, 1H) 8.72 (d, J=2.1 Hz, 1H) 8.78 (d, J=2.1 Hz, 1H) 9.04 (d, J=5.2 Hz, 1H).

Step 4. N-[3-[5-chloro-2-[4-(methylsulfonimidoyl)anilino]pyrimidin-4-yl]-1H-indol-6-yl]prop-2-enamide. The title compound was synthesized using the procedure for Example 60, starting with 3-(2,5-dichloropyrimidin-4-yl)-6-nitro-1-(p-tolylsulfonyl)indole and tert-butyl N-[(4-aminophenyl)-methyl-oxo-$\lambda^6$-sulfanylidene]carbamate. BOC deprotection using TFA in DCM and deprotection of OTs group achieved using $Cs_2CO_3$ in THF/MeOH to give a yellow solid. LCMS m/z=467 (M+1, 1 Cl isotopic distribution). $^1H$ NMR (600 MHz, DMSO-d6) δ 11.97 (d, J=2.4 Hz, 1H) 10.23 (s, 1H) 10.14 (s, 1H) 8.57 (d, J=8.4 Hz, 1H) 8.56 (s, 1H) 8.52 (d, J=2.9 Hz, 1H) 8.26 (d, J=1.8 Hz, 1H) 8.04 (d, J=9.0 Hz, 2H) 7.86 (d, J=9.0 Hz, 2H) 7.26 (dd, J=8.6, 1.8 Hz, 1H) 6.49 (dd, J=17.0, 10.2 Hz, 1H) 6.28 (dd, J=16.9, 1.8 Hz, 1H) 5.76 (dd, J=10.1, 2.0 Hz, 1H) 3.15 (s, 3H).

Example 90. N-[3-[5-Chloro-2-[4-(cyclopropylsulfonimidoyl)anilino]pyrimidin-4-yl]-1H-indol-6-yl]prop-2-enamide

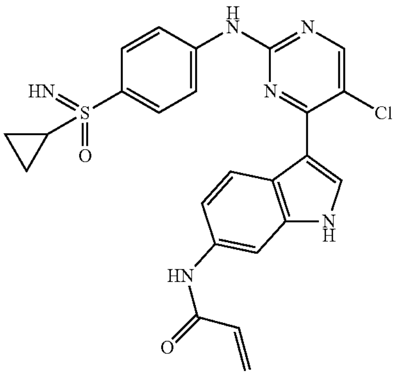 [SMILES: C=CC(=O)Nc1ccc2c(-c3nc(Nc4ccc(S(=N)(=O)C5CC5)cc4)ncc3Cl)c[nH]c2c1]

The title compound was synthesized using the procedure for Example 89, starting with 3-(2,5-dichloropyrimidin-4-yl)-6-nitro-1-(p-tolylsulfonyl)indole and tert-butyl N-[(4-aminophenyl)-cyclopropyl-oxo-$\lambda^6$-sulfanylidene]carbamate. LCMS m/z=493 (M+1, 1 Cl isotopic distribution). $^1H$ NMR (500 MHz, DMSO-d6) δ 11.95 (br.s, 1H), 10.21 (s, 1H), 10.07 (s, 1H), 8.56 (d, J=8.6 Hz, 1H), 8.54 (s, 1H), 8.51 (s, 1H), 8.24 (d, J=1.5 Hz, 1H), 7.99 (d, J=9.2 Hz, 2H), 7.78 (d, J=8.9 Hz, 2H) 7.25 (dd, J=8.6, 1.5 Hz, 1H), 6.48 (dd, J=16.7, 10.2 Hz, 1H), 6.27 (dd, J=16.9, 1.8 Hz, 1H), 5.75 (dd, J=10.0, 1.8 Hz, 1H), 4.00 (s, 1H), 2.59-2.65 (m, 1H), 1.05-1.13 (m, 1H), 0.92-0.99 (m, 1H), 0.83-0.92 (m, 2H).

Example 91. N-[3-[5-chloro-2-[4-(methylsulfonimidoyl)anilino]pyrimidin-4-yl]-1H-indol-7-yl]prop-2-enamide

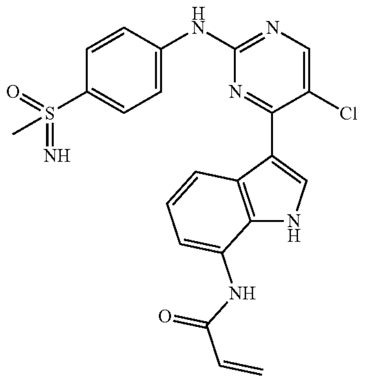 [SMILES: C=CC(=O)Nc1cccc2c(-c3nc(Nc4ccc(S(C)(=N)=O)cc4)ncc3Cl)c[nH]c12]

The title compound was synthesized using the procedure for Example 89 starting with 3-(2,5-dichloropyrimidin-4-yl)-1-methyl-7-nitro-indole and tert-butyl N-[(4-aminophenyl)-methyl-oxo-λ$^6$-sulfanylidene]carbamate. LCMS m/z=467 (M+1, 1 Cl isotopic distribution). $^1$H NMR (500 MHz, DMSO-d6) δ 11.65 (br s, 1H), 10.15 (br s, 1H), 10.13 (s, 1H), 8.58 (s, 1H), 8.53 (s, 1H), 8.43 (d, J=8.2 Hz, 1H), 8.04-7.98 (m, 2H), 7.85-7.80 (m, 2H), 7.53 (d, J=7.6 Hz, 1H), 7.17 (t, J=7.8 Hz, 1H), 6.57 (dd, J=10.2, 16.9 Hz, 1H), 6.34 (dd, J=1.8, 17.1 Hz, 1H), 5.84 (dd, J=1.5, 10.4 Hz, 1H), 4.02 (s, 1H), 3.04 (s, 3H).

Example 92. N-[3-[5-chloro-2-[4-[[dimethyl(oxo)-λ$^6$-sulfanylidene]amino]anilino]pyrimidin-4-yl]-1-methyl-indol-6-yl]prop-2-enamide

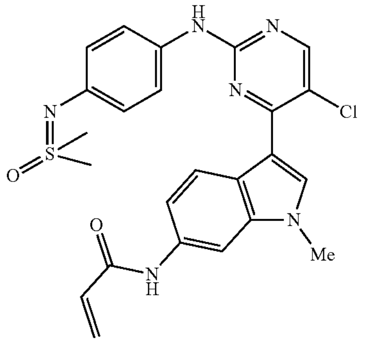 [SMILES: C=CC(=O)Nc1ccc2c(-c3nc(Nc4ccc(N=S(C)(C)=O)cc4)ncc3Cl)cn(C)c2c1]

Step 1. 1-Methyl-6-nitro-3-(4,4,5,5-tetramethyl-1,3,2-dioxaborolan-2-yl)indole. In a 100 ml tube were charged boron tribromide (1M in DCM, 45.4 mL), DCM (20 ml) and 2,6-lutidine (5.29, 45.4 mmol). The solution was cooled in an ice bath for 10 minutes and then solution of 1-methyl-6-nitro-indole (2.0 g, 11.4 mmol) in DCM (10 ml) was added dropwise during 10 minutes. The reaction mixture was allowed to warn to RT and stirred. After 1 h, the reaction mixture was cooled to 0° C. and a solution of pinacol (5.37 g, 45.4 mmol) in N, N-diisopropylethylamine (29.7 ml, 170.3 mmol) was added dropwise during 35 min. The resulting mixture was allowed to reach RT and stirred for 1 h. The reaction mixture was then diluted with DCM (700 ml) and washed with $NaHCO_3$ solution (3×500 ml), water (1×500 ml) and brine (1×500 ml). After evaporation of the organic layer the crude product was purified by flash chromatography (EtOAc/CyHex=1/3) to afford to give a green solid (1.65 g). LCMS m/z=303 (M+1)

Step 2. 3-(2,5-dichloropyrimidin-4-yl)-1-methyl-6-nitro-indole. A suspension of 1-methyl-6-nitro-3-(4,4,5,5-tetramethyl-1,3,2-dioxaborolan-2-yl)indole (530 mg, 1.75 mmol), 2,4,5-trichloropyrimidine (221 μL, 1.93 mmol, 1.1 eq) and sodium carbonate (0.37 g, 3.51 mmol, 2 eq) in acetonitrile (12 mL) and water (6 mL) was bubbled with argon for 10 minutes. Tetrakis(triphenylphosphine)palladium(0) (0.10 mg, 0.09 mmol, 0.05 eq) was added and the resulting mixture was irradiated in MW reactor for 60 minutes at 80° C. The reaction mixture was poured into water and resulting precipitate was collected by filtration and dried in vacuo to give a yellow solid (250 mg). LCMS m/z=323 (M+1); $^1$H NMR (500 MHz, DMSO-d6) δ 4.09 (s, 3H) 8.18 (dd, J=8.85, 2.14 Hz, 1H) 8.61 (d, J=1.83 Hz, 1H) 8.63 (d, J=9.16 Hz, 1H) 8.83 (s, 1H) 9.06 (s, 1H).

Step 3. N-[3-[5-chloro-2-[4-[[dimethyl(oxo)-λ$^6$-sulfanylidene]amino]anilino]pyrimidin-4-yl]-1-methyl-indol-6-yl]prop-2-enamide. The target example was synthesize using the procedure for example 60 with 3-(2,5-dichloropyrimidin-4-yl)-1-methyl-6-nitro-indole and 4-[[methyl(oxo)-λ$^6$-sulfanylidene]amino]aniline. LCMS m/z=493 (M+1, 1 Cl isotopic distribution); $^1$H NMR (500 MHz, DMSO-d6) δ: 10.26 (s, 1H) 9.38 (s, 1H) 8.56 (br s, 1H) 8.52 (s, 1H) 8.38 (s, 1H) 8.15 (s, 1H) 7.54 (d, J=8.85 Hz, 2H) 7.25 (br d, J=8.54 Hz, 1H) 6.89 (d, J=7.72 Hz, 2H) 6.49 (dd, J=16.78, 10.07 Hz, 1H) 6.28 (dd, J=16.94, 1.98 Hz, 1H) 5.74-5.79 (m, 1H) 3.87 (s, 3H) 3.19 (s, 6H).

Example 93. N-[3-[5-Chloro-2-[4-[[dimethyl(oxo)-λ$^6$-sulfanylidene]amino]-3-fluoro-anilino]pyrimidin-4-yl]-1-methyl-indol-6-yl]prop-2-enamide

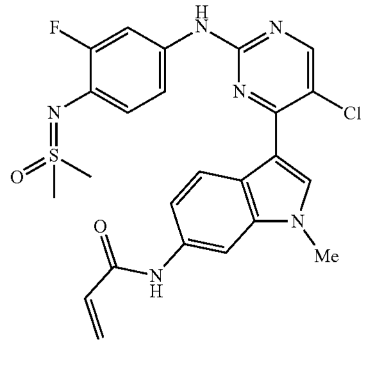 [SMILES: C=CC(=O)Nc1ccc2c(-c3nc(Nc4ccc(N=S(C)(C)=O)c(F)c4)ncc3Cl)cn(C)c2c1]

The target example was synthesize using the procedure for example 60 with 3-(2,5-dichloropyrimidin-4-yl)-1-methyl-6-nitro-indole and 4-[[dimethyl(oxo)-λ$^6$-sulfanylidene]amino]-3-fluoro-aniline. LCMS m/z=513 (M+1, 1 Cl isotopic distribution); $^1$H NMR (500 MHz, DMSO-d6) δ 10.28 (s, 1H), 9.60 (s, 1H), 8.5-8.6 (m, 1H), 8.53 (s, 1H), 8.44 (s, 1H), 8.17 (s, 1H), 7.73 (dd, 1H, J=2.4, 13.4 Hz), 7.27-7.31 (m, 2H), 7.06 (t, 1H, J=9.2 Hz), 6.50 (dd, 1H, J=10.2, 16.9 Hz), 6.28 (dd, 1H, J=1.8, 17.1 Hz), 5.77 (dd, 1H, J=1.8, 10.1 Hz), 3.88 (s, 3H), 3.22 (s, 6H).

Example 94. N-[3-[5-Chloro-2-[[6-[[dimethyl(oxo)-$\lambda^6$-sulfanylidene]amino]-3-pyridyl]amino]pyrimidin-4-yl]-1-methyl-indol-6-yl]prop-2-enamide

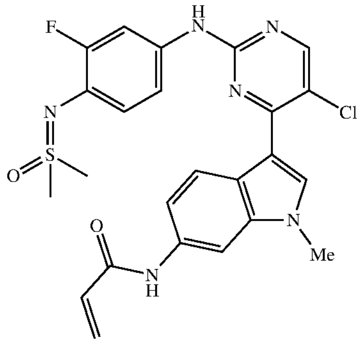 [SMILES: C=CC(=O)Nc1ccc2c(-c3nc(Nc4ccc(N=S(C)(C)=O)c(F)c4)ncc3Cl)cn(C)c2c1]

The target example was synthesize using the procedure for example 60 with 3-(2,5-dichloropyrimidin-4-yl)-1-methyl-6-nitro-indole and 6-[[dimethyl(oxo)-$\lambda^6$-sulfanylidene]amino]pyridin-3-amine. LCMS m/z=496 (M+1, 1 Cl isotopic distribution). $^1$H NMR (500 MHz, DMSO-d6) δ 10.25 (s, 1H) 9.40 (s, 1H) 8.52 (s, 1H) 8.48 (br s, 1H) 8.38 (s, 1H) 8.35 (d, J=2.6 Hz, 1H) 8.12 (d, J=1.5 Hz, 1H) 7.88 (dd, J=8.7, 2.8 Hz, 1H) 7.26 (br d, J=8.7 Hz, 1H) 6.63 (d, J=8.7 Hz, 1H) 6.48 (dd, J=16.9, 10.0 Hz, 1H) 6.27 (dd, J=16.9, 2.1 Hz, 1H) 5.71-5.81 (m, 1H) 3.86 (s, 3H) 3.31 (s, 6H).

Kinase Assays

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. Streptavidin-coated magnetic beads were treated with biotinylated small molecule ligands for 30 minutes at room temperature to generate affinity resins for kinase assays. The liganded beads were blocked with excess biotin and washed with blocking buffer SeaBlock (Pierce), 1% BSA, 0.05% Tween 20, 1 mM DTT to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT).

Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Binding Constants (Kds)

Binding constants were calculated with a standard dose-response curve using the Hill equation:

$$\text{Response} = \text{Background} + \frac{\text{Signal} - \text{Background}}{1 + \left(\frac{Kd^{\text{Hill Slope}}}{\text{Dose}^{\text{Hill Slope}}}\right)}$$

The Hill Slope was set to −1. Curves were fitted using a non-linear least square fit with the Levenberg-Marquardt algorithm.

Cell lines used for Cell Viability Assays

| Cell line | Mutation or Fusion | Source |
|---|---|---|
| Ba/F3 FGFR1 | FGFR1-BCR | Advanced Cellular Dynamics, (Seattle, WA) |
| Ba/F3 FGFR3 | FGFR3--BAIAP2L1 fusion | Advanced Cellular Dynamics, (Seattle, WA) |
| RT112/84 (Bladder Cancer) | FGFR3-TACC3 fusion | American Type Culture Collection (Manassas, VA) |
| UM-UC-14 (Bladder Cancer) | FGFR3(S249C) | Sigma, (St. Louis, MO) |
| SNU-16 (Gastric Carcinoma) | FGFR2 amplification | American Type Culture Collection (Manassas, VA) |
| KG-1 (Acute Myeloid Leukemia) | FGFR1OP2-FGFR1 fusion | American Type Culture Collection (Manassas, VA) |

Ba/F3 Cell Viability Assays

Experimental Purpose: Recombinant kinase fusions are transduced into parental Ba/F3, which becomes dependent upon this constitutive kinase activity for IL3-independent survival. Inhibition of kinase activity leads to cell death, which is monitored using CellTiter-Glo® 2.0 (Promega) which measures intracellular ATP concentration that in turn serves as a marker for viability. FGFR1-BCR Ba/F3 and FGFR3-BAIAP2L1 Ba/F3 were obtained from Advanced Cellular Dynamics (Seattle, WA)

Cell Viability Assay Procedure: Cell Titer-Glo® 2.0 Luminescent cell viability assay reagent was purchased from Promega (Madison, WI). FGFR1-BCR Ba/F3 and FGFR3-BAIAP2L1 Ba/F3 cells were cultured in RPMI1640 media supplemented with 10% fetal bovine serum. Cultures were maintained at 37° C. in a humidified atmosphere of 5% CO2 and 95% air.

Cells were plated in 96-well clear bottom/white plates (Corning #3903) at 10,000 cells/well in 100 μl of media, incubated overnight. The next day, test compound DMSO stock solutions were made at 10 mM and 2 μM final concentration. Compounds were then added to cells in a 9-dose, 10-fold dilution series starting at 30 μM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $CO_2$ for 48 hours. Then 50 μl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter).

RT112/84, UM-UC-14, SNU-16 and KG-1 Cancer Cell Line Cell Viability Assays

To detect the change of intracellular ATP by Cell Titer-Glo® and to evaluate the inhibitory effect of the compounds on cancer cell lines by determining the in vitro $IC_{50}$ value of the compounds.

Cell Titer-Glo® 2.0 Luminescent cell viability assay reagent was purchased from Promega (Madison, WI). RT112/84, SNU-16, and KG-1 cell lines were purchased from American Type Culture Collection (Manassas, VA). UM-UC-14 cell line was purchased from Sigma (St. Louis, MO). RT112/84, UM-UC-14, SNU-16, and KG-1 cells were cultured in RPMI1640 media supplemented with 10% fetal bovine serum. Cultures were maintained at 37° C. in a humidified atmosphere of 5% $CO_2$ and 95% air.

Cell Viability Assay Procedure: Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $CO_2$ for 72 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter).

The Kd values are shown in Table 1

TABLE 1

| Example | FGFR1 (Kd nM) | FGFR2 (Kd nM) | FGFR3 (Kd nM) | FGFR3 (V555M) (Kd nM) | FGFR4 (Kd, nM) |
|---|---|---|---|---|---|
| 1 | 140 | 370 | 170 | 15 | 130 |
| 2 | 480 | 1900 | 430 | 53 | 39 |
| 3 | 4500 | 11000 | 4700 | | 290 |
| 4 | 21000 | 30000 | 30000 | 4100 | 210 |
| 5 | 3300 | 14000 | 4300 | 420 | 6200 |
| 6 | 390 | 1700 | 1100 | 90 | 2000 |
| 7 | 21 | 140 | 40 | 4 | 280 |
| 8 | 19 | 24 | 29 | 4 | 180 |
| 9 | 350 | 3300 | 370 | 57 | 57 |
| 10 | 350 | 3300 | 370 | 57 | 57 |
| 11 | 350 | 3300 | 370 | 57 | 57 |
| 12 | 350 | 3300 | 370 | 57 | 57 |
| 13 | 350 | 3300 | 370 | 57 | 57 |
| 14 | 190 | 110 | 170 | 9 | 1500 |
| 15 | 29000 | 14000 | 18000 | 3700 | 30000 |
| 16 | 2200 | 600 | 570 | 140 | 9500 |
| 17 | 30000 | 30000 | 30000 | 30000 | 30000 |
| 18 | 30000 | 21000 | 20000 | 12000 | 30000 |
| 19 | 30000 | 30000 | 30000 | 3000 | 30000 |
| 20 | 37 | 51 | 27 | 4 | 120 |
| 21 | 30000 | 30000 | 27000 | 30000 | 30000 |
| 22 | 30000 | 30000 | 30000 | 30000 | 30000 |
| 23 | 8 | 6 | 12 | 1 | 130 |
| 24 | 4 | 7 | 10 | 1 | 87 |
| 25 | 7 | 9 | 13 | 2 | 89 |

TABLE 1-continued

| Example | FGFR1 (Kd nM) | FGFR2 (Kd nM) | FGFR3 (Kd nM) | FGFR3 (V555M) (Kd nM) | FGFR4 (Kd, nM) |
|---|---|---|---|---|---|
| 26 | 42 | 2 | 10 | 1 | 91 |
| 27 | 2 | 1 | 2 | 0 | 110 |
| 28 | 27 | 63 | 44 | 4 | 290 |
| 29 | 15 | 46 | 21 | 4 | 210 |
| 30 | 27 | 41 | 35 | 2 | 190 |
| 31 | 1 | 3 | 5 | 0.5 | 62 |
| 32 | 2 | 3 | 3 | 1 | 52 |
| 33 | 4 | 6 | 19 | 2 | 120 |
| 34 | 14 | 39 | 30 | 2 | 230 |
| 35 | 72 | 200 | 130 | 9 | 86 |
| 36 | 72 | 67 | 89 | 4 | 57 |
| 37 | 500 | 1200 | 290 | 28 | 120 |
| 38 | 25 | 92 | 34 | 3 | 26 |
| 39 | 58 | 170 | 57 | 6 | 66 |
| 40 | 80 | 860 | 110 | 10 | 100 |
| 41 | 9000 | 18000 | 6000 | 180 | 6300 |
| 42 | 3000 | 3300 | 1800 | 110 | 4200 |
| 43 | 5000 | 4000 | 3400 | 680 | 7500 |
| 44 | 2200 | 15000 | 2800 | 42 | 4100 |
| 45 | 7800 | 9000 | 4900 | 1100 | 5100 |
| 46 | 2700 | 4400 | 2200 | 160 | 5600 |
| 47 | 18 | 16 | 37 | 4 | 190 |
| 48 | 7 | 6 | 16 | 2 | 160 |
| 49 | 8 | 4 | 8 | 1 | 120 |
| 50 | 330 | 170 | 190 | 26 | 3000 |
| 51 | 10 | 6 | 18 | 3 | 130 |
| 52 | 27 | 9 | 24 | 6 | 390 |
| 53 | 5 | 3 | 11 | 1 | 74 |
| 54 | 10 | 7 | 13 | 2 | 100 |
| 55 | 13 | 6 | 23 | 2 | 110 |
| 56 | 64 | 34 | 49 | 3 | 740 |
| 57 | 50 | 43 | 53 | 6 | 680 |
| 58 | 11 | 19 | 15 | 7 | 120 |
| 59 | 18 | 50 | 22 | 11 | 130 |
| 60 | 14 | 3.2 | 3.5 | 1.7 | 42 |
| 61 | 21 | 6 | 6 | 2 | 100 |
| 62 | 79 | 16 | 20 | 11 | 170 |
| 63 | 10 | 3 | 3 | 1 | 39 |
| 64 | 5 | 4 | 4 | 1 | 59 |
| 65 | 4000 | 7900 | 1700 | 970 | 1300 |
| 66 | 61 | 37 | 21 | 5.3 | 680 |
| 67 | 130 | 120 | 62 | 9.8 | 510 |
| 68 | 630 | 340 | 320 | 24 | 2400 |
| 69 | 33 | 28 | 14 | 3.8 | 160 |
| 70 | 230 | 25 | 21 | 9.2 | 370 |
| 71 | 6000 | 3000 | 1500 | 140 | 3400 |
| 72 | 77 | 100 | 17 | 5.7 | 240 |
| 73 | 290 | 380 | 180 | 18 | 1300 |
| 74 | 140 | 77 | 41 | 20 | 560 |
| 75 | 5000 | 1600 | 1100 | 380 | 500 |
| 76 | 160 | 370 | 160 | 12 | 3000 |
| 77 | 170 | 260 | 130 | 7 | 2600 |
| 78 | 250 | 290 | 140 | 5 | 4600 |
| 79 | 140 | 140 | 87 | 7 | 1000 |
| 80 | 740 | 680 | 340 | 23 | 5300 |
| 81 | 51 | 62 | 23 | 2 | 1900 |
| 82 | 59 | 50 | 42 | 2 | 450 |
| 83 | 86 | 79 | 59 | 3 | 1100 |
| 84 | 390 | 330 | 150 | 11 | 2300 |
| 85 | 330 | 89 | 180 | 16 | 2300 |
| 86 | 90 | 63 | 46 | 7.1 | 240 |
| 87 | 160 | 130 | 130 | 16 | 2400 |
| 88 | 20000 | 26000 | 8800 | 840 | 30000 |
| 89 | 76 | 50 | 70 | 7.5 | 510 |
| 90 | 47 | 59 | 41 | 4 | 360 |
| 91 | 19 | 24 | 48 | 2 | 130 |
| 92 | 63 | 13 | 12 | 3 | 230 |
| 93 | | | | | |
| 94 | | | | | |

The IC50 values are shown in Table 2

TABLE 2

| | Ba/F3 Cells | | Cancer Cell Viability Assays | | | |
|---|---|---|---|---|---|---|
| | FGFR3 | FGFR1 | | | | |
| Example | (IC50 nM) | (IC50 nM) | KG1 | SNU-16 | RT112/84 (IC50 nM) | UM-UC-14 |
| 3 | | | | 73 | 100 | |
| 11 | 15 | 115 | | 108 | 153 | |
| 23 | | | | 132 | 118 | |
| 24 | | | | 60 | 33 | |
| 25 | | | | 117 | 63 | |
| 26 | 15 | 75 | | 173 | 111 | |
| 27 | | 11 | | 16 | 43 | |
| 31 | 40 | 2 | | 5 | 23 | |
| 38 | | | | 130 | 119 | |
| 49 | | | | 189 | 78 | |
| 51 | | | | 45 | 48 | |
| 52 | | | | 83 | 76 | |
| 53 | | | | 31 | 22 | |
| 54 | | | | 44 | 33 | |
| 55 | | | | 40 | 49 | |
| 56 | 273 | | | 857 | 377 | |
| 57 | 431 | | | 803 | 610 | |
| 60 | 10 | 2 | 4 | | 16 | 6 |
| 61 | 15 | 2 | 6 | | 23 | 12 |
| 62 | 46 | 9 | 17 | | 64 | 152 |
| 63 | 5 | 1 | 1 | | 8 | 3 |
| 64 | 12 | 3 | 1 | | 12 | 3 |
| 66 | 28 | 6 | 20 | 65 | 113 | 34 |
| 67 | | | | 1452 | 421 | |
| 69 | | | | 14 | 82 | |
| 70 | 34 | 8 | 9 | 12 | 159 | 34 |
| 74 | | | | 9 | 713 | |
| 85 | 459 | 171 | | | | |
| 90 | | | | 71 | 81 | |
| 91 | | | | 19 | 48 | |
| 92 | 15 | 1 | 5 | | 47 | 10 |
| 93 | 14 | 1 | | | | |
| 94 | 23 | 4 | | | | |

ASPECTS

Aspect 1. A compound of Formula (I) or a pharmaceutically acceptable salt thereof:

(I)

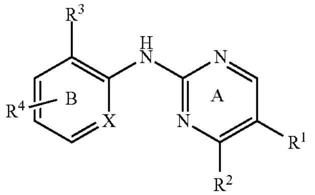

where $R^1$ is selected from the group consisting of —H, —F, —Cl, —Br, —CN, —$CF_3$, —$CH_3$, and —C(O)$NH_2$;

$R^2$ is a heteroaryl comprising 5-10 atoms optionally substituted with $R^5$;

X is selected from —CH— and N;

$R^3$ is selected from the group consisting of —H, —F, —Cl, —Br, —$CF_3$, $OCF_3$, optionally substituted $C_1$-$C_3$-alkyl, —$OR^6$, CN, —$N(R^7)_2$, —NHCO—($C_1$-$C_6$-alkyl), —NHCOCH═$CH_2$, and —NHCOCH═$CHCH_2N(Me)_2$;

$R^5$ is independently selected from the group consisting of —F, —Cl, —$OR^6$, —$N(R^7)_2$, —CN, —$CF_3$, —$OCF_3$, —NHCO—($C_1$-$C_3$-alkyl) where $C_1$-$C_3$-alkyl is optionally substituted, —NHCOCH═$CH_2$, —NHCOCH═$CHCH_2N(Me)_2$, $(CH_2)_n$NHCOCH═$CH_2$, and —$(CH_2)_n$NHCOCH═$CHCH_2N(Me)_2$;

each instance of $R^6$ is selected from the group consisting of —H, optionally substituted $C_1$-$C_6$-alkyl, optionally substituted $C_1$-$C_6$-alkenyl, —$(CH_2)_n$—$C_3$-$C_6$-cycloalkyl, and —$(CH_2)_n$heteroaryl;

each instance of $R^7$ is independently selected from the group consisting of —H, optionally substituted —$C_1$-$C_6$-alkyl, —$(CH_2)_n$—$C_3$-$C_6$-cycloalkyl, —$(CH_2)_n$-heteroaryl;

each instance of n is an integer equal to 0, 1, 2, 3, or 4;

$R^4$ is positioned at any one of the 3, 4, or 5 positions of Ring B and is selected from the group consisting of:

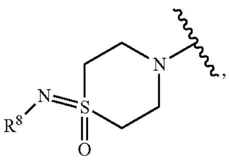,
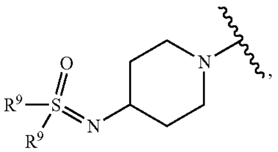,
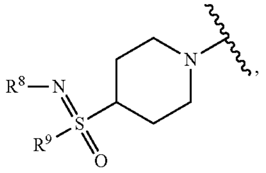,
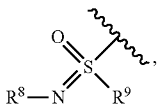,
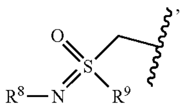,
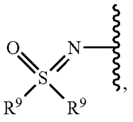, and
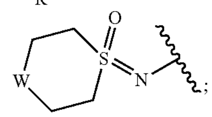;

W is selected from the group consisting of —$CH_2$—, C(O)—, —CH(OH)— and —$N(R^8)$—;

$R^8$ is selected from the group consisting of —H, optionally substituted $C_1$-$C_6$-alkyl, optionally substituted $C_1$-$C_6$-alkenyl, and —$C_3$-$C_6$-cycloalkyl;

each instance of $R^9$ is independently selected from the group consisting of optionally substituted $C_1$-$C_6$-alkyl, optionally substituted $C_1$-$C_6$-alkenyl, and $C_3$-$C_6$-cycloalkyl; and each optionally substituted alkyl or optionally substituted alkenyl can optionally be substituted with hydroxy, halogen, $C_1$-$C_3$-alkoxy, $C_1$-$C_3$-alkylthio, —CN, $C_3$-$C_6$-cycloalkyl, $C_1$-$C_3$-hydroxyalkyl, $C_2$-$C_6$ alkenyl, $C_2$-$C_6$-alkynyl, —$CF_3$, —$OCF_3$, or —$NR_7R_8$.

Aspect 2. The compound of Aspect 1 or a pharmaceutically acceptable salt thereof, further represented by Formula (IA):

(IA)

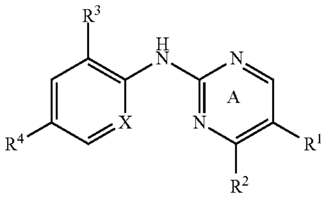

where $R^1$ is selected from the group consisting of —H, -Me, —F, —Cl, —Br, —CN, and —$CF_3$;

X is selected from —CH—;

$R^3$ is selected from the group consisting of —H, —F, —Cl, —Br, —$CF_3$, $C_1$-$C_3$-alkyl, —$OR^6$, —$N(R^7)_2$, —NHCO—($C_1$-$C_6$-alkyl), —NHCOCH═$CH_2$, and —NHCOCH═$CHCH_2N(Me)_2$;

$R^5$ is independently selected from the group consisting of —F, —Cl, —$OR^6$, —$N(R^7)_2$, —CN, —$CF_3$, —$OCF_3$, —NHCO—($C_1$-$C_3$-alkyl), —NHCOCH═$CH_2$, —NHCOCH═$CHCH_2N(Me)_2$, —$CH_2$NHCOCH═$CH_2$, and —$CH_2$NHCOCH═$CHCH_2N(Me)_2$;

each instance of $R^6$ is selected from the group consisting of —H, $C_1$-$C_6$-alkyl, $C_1$-$C_6$-alkenyl, —$(CH_2)_n$—$C_3$-$C_6$-cycloalkyl, and —$(CH_2)_n$heteroaryl;

each instance of $R^7$ is independently selected from the group consisting of —H, —$C_1$-$C_6$-alkyl, —$(CH_2)_n$—$C_3$-$C_6$-cycloalkyl, —$(CH_2)_n$-heteroaryl;

each instance of n is an integer equal to 0, 1, 2, 3, or 4;

$R^4$ is selected from the group consisting of:

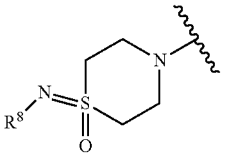

and

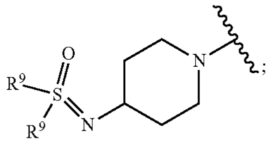

;

$R^8$ is selected from the group consisting of —H, optionally substituted $C_1$-$C_6$-alkyl, optionally substituted $C_1$-$C_6$-alkenyl, and —$C_3$-$C_6$-cycloalkyl; and each instance of $R^9$ is independently selected from the group consisting of optionally substituted $C_1$-$C_6$-alkyl, optionally substituted $C_1$-$C_6$-alkenyl, and $C_3$-$C_6$-cycloalkyl.

Aspect 3. The compound of Aspect 1 or a pharmaceutically acceptable salt thereof further represented by one of the following structures:

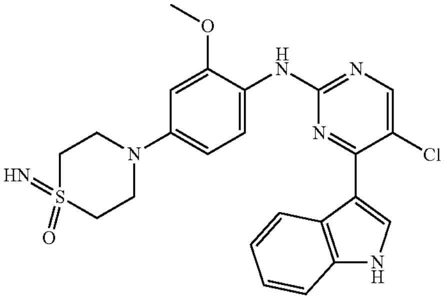

-continued

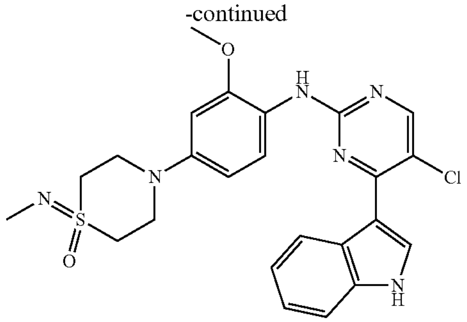

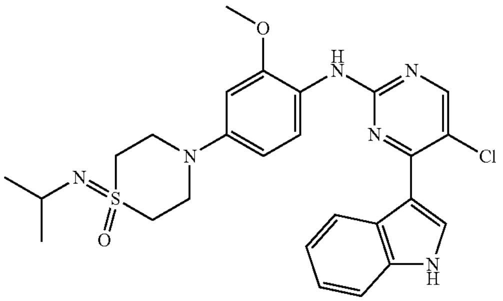

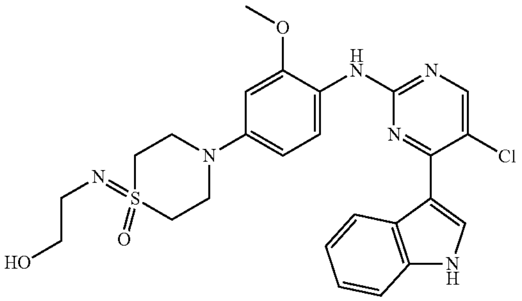

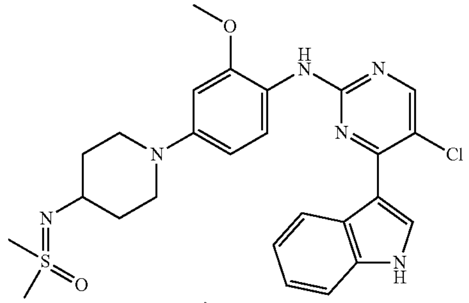

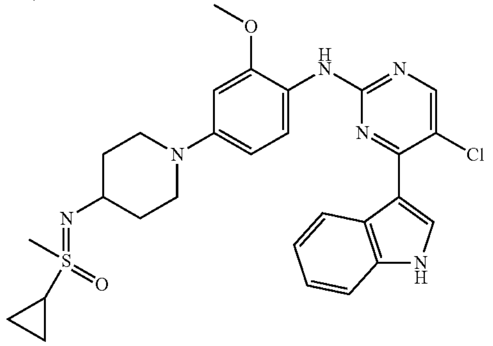

-continued
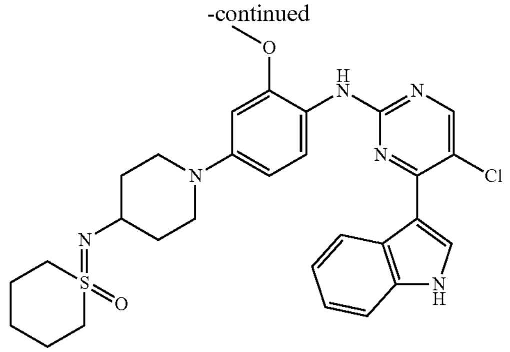
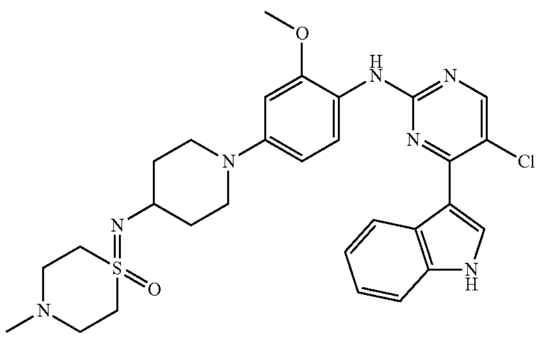
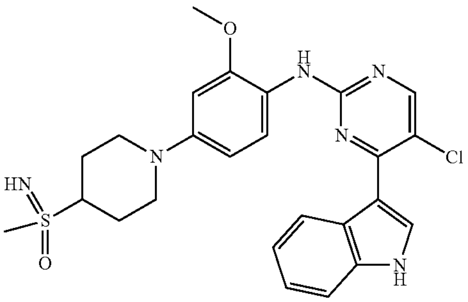
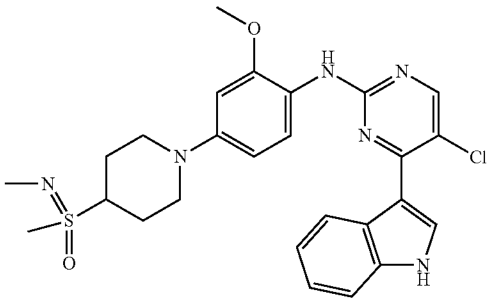
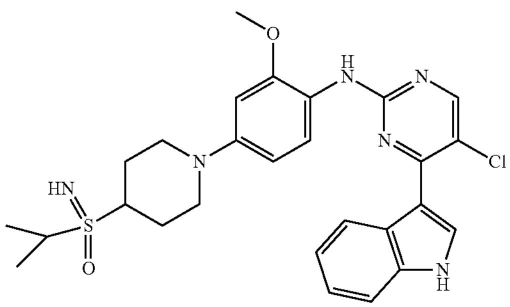
-continued
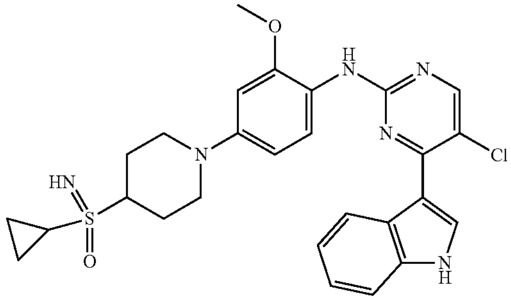
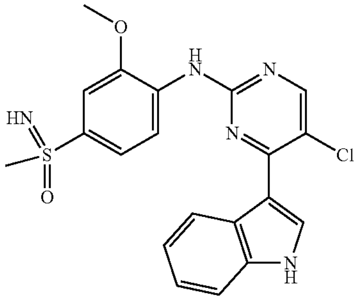
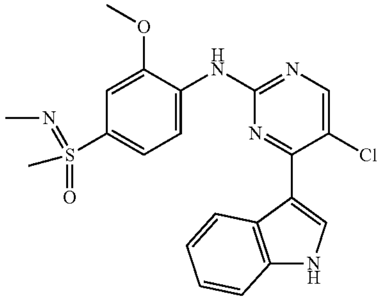
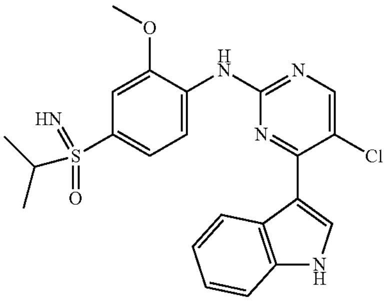
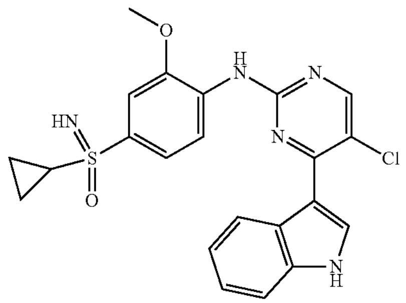

-continued
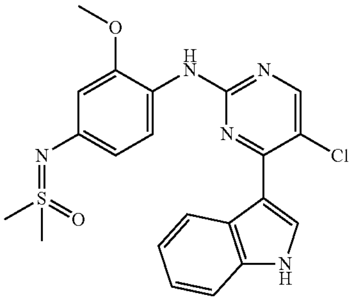
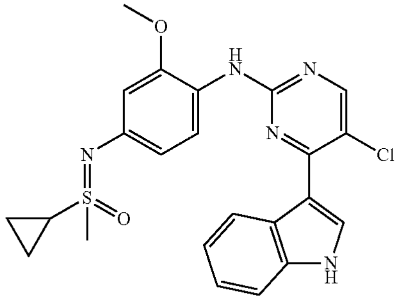
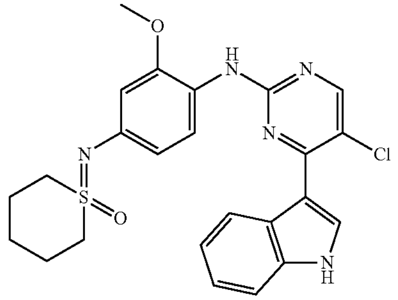
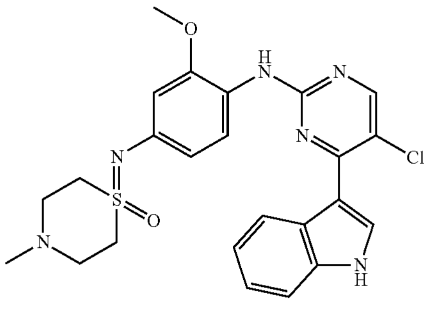
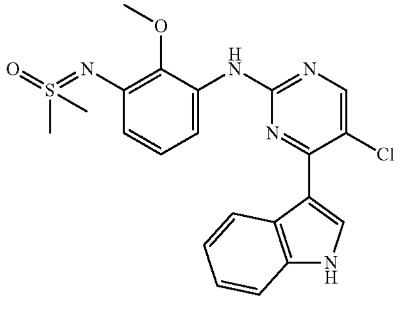
-continued
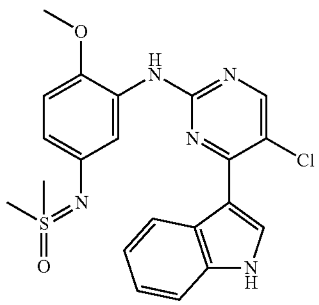
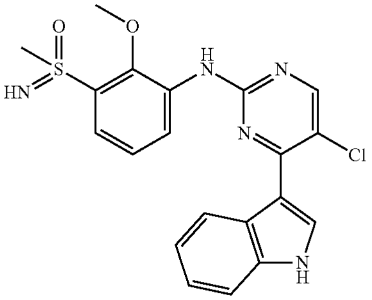
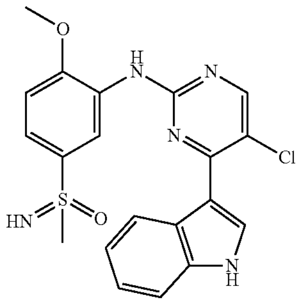
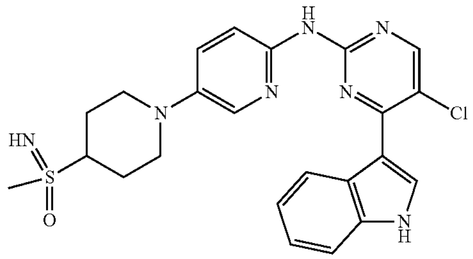
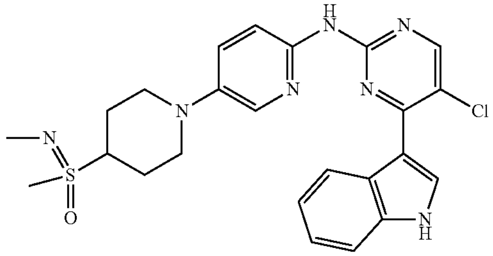
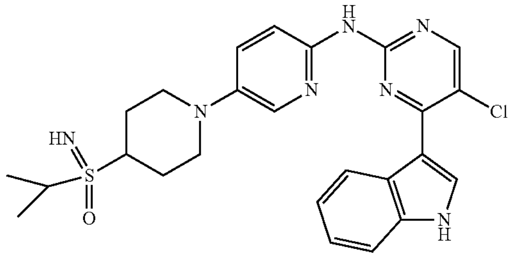

-continued
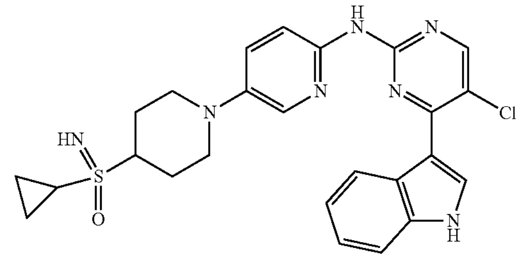
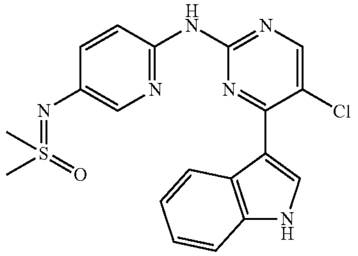
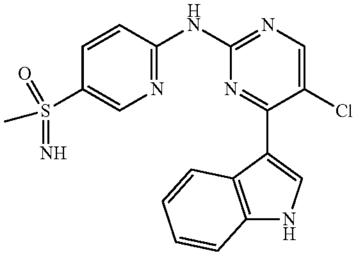
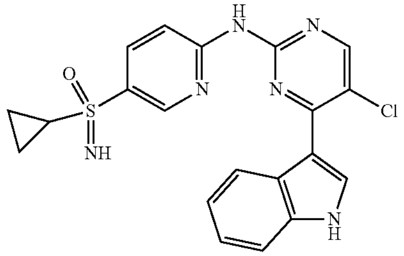
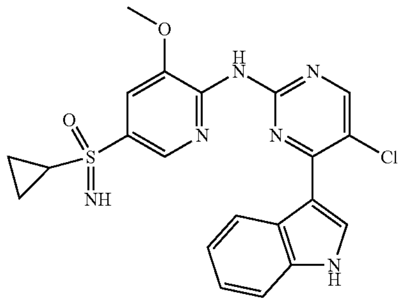
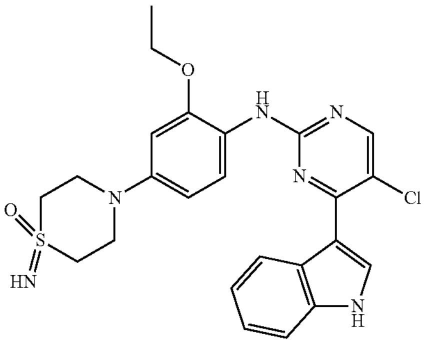
-continued
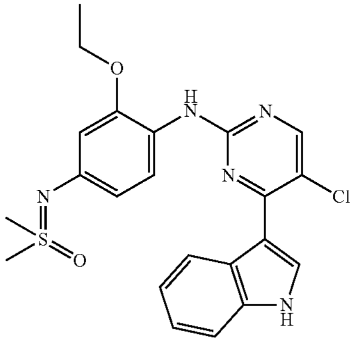
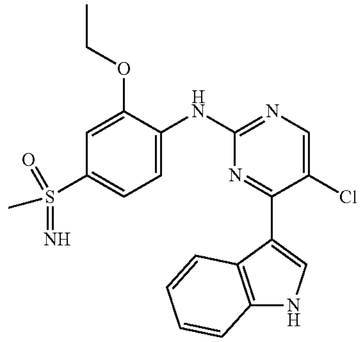
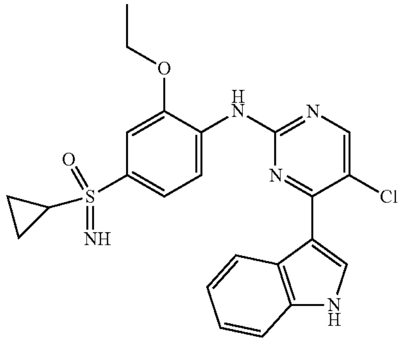
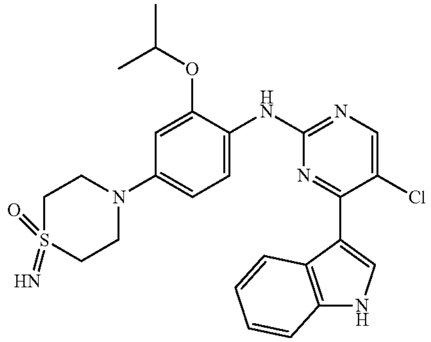
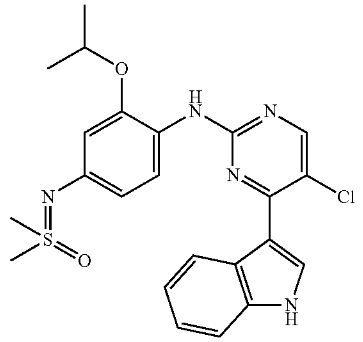

-continued
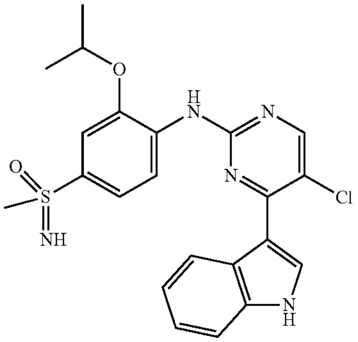
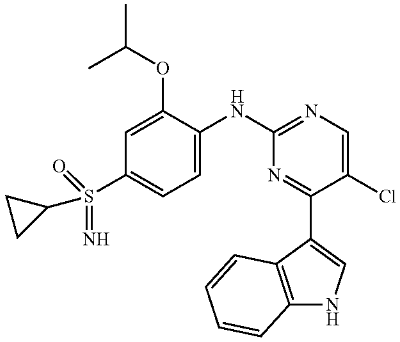
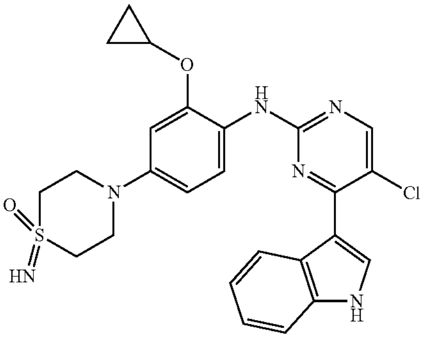
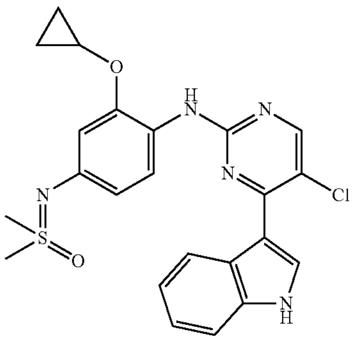
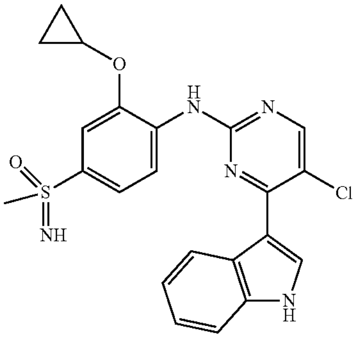
-continued
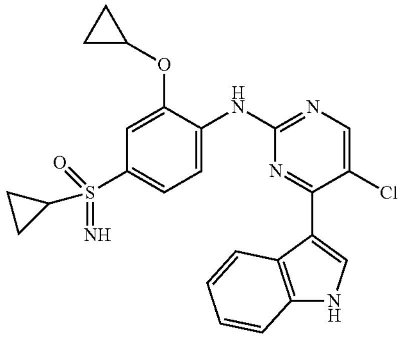
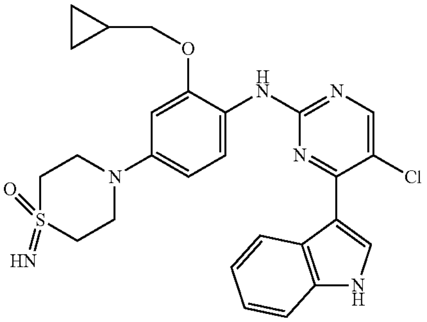
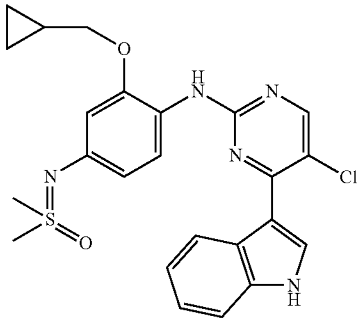
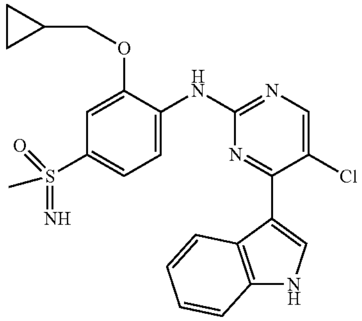
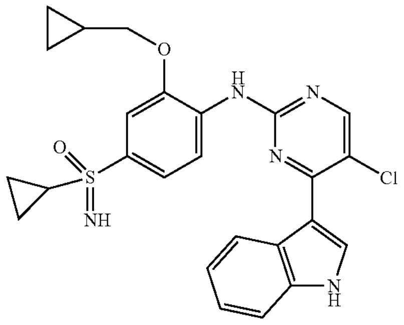

-continued
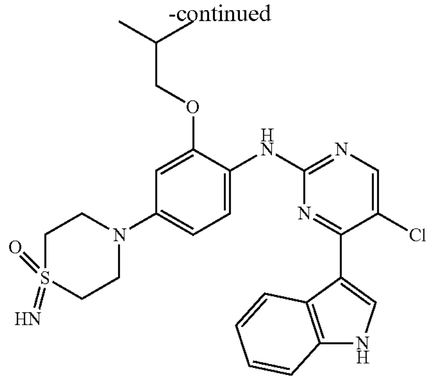
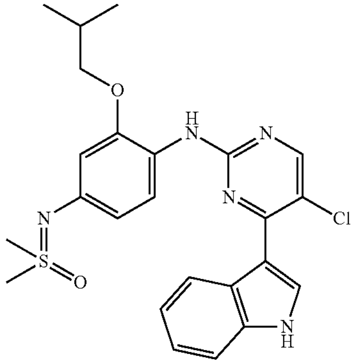
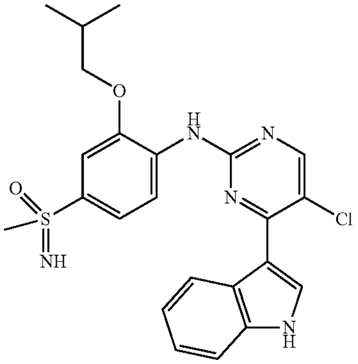
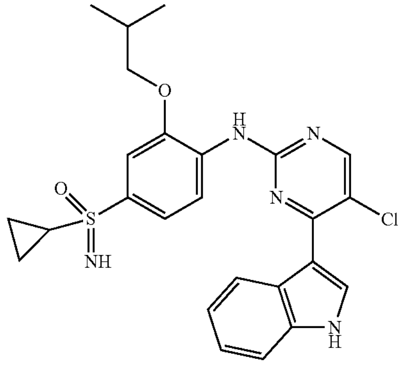
-continued
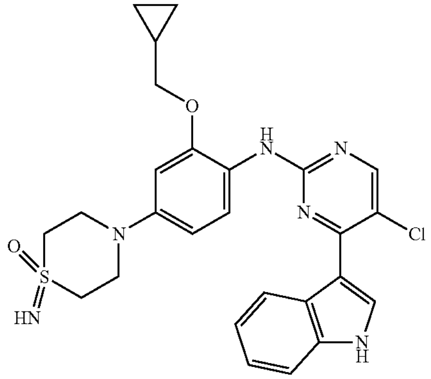
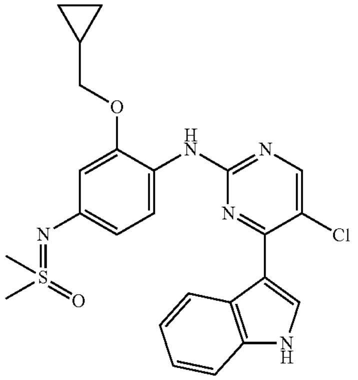
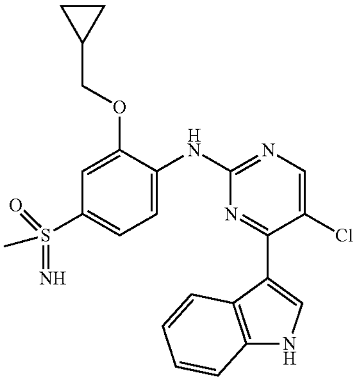
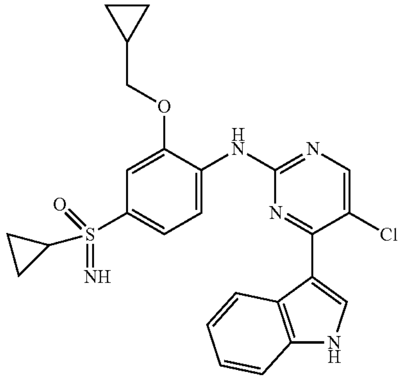

-continued
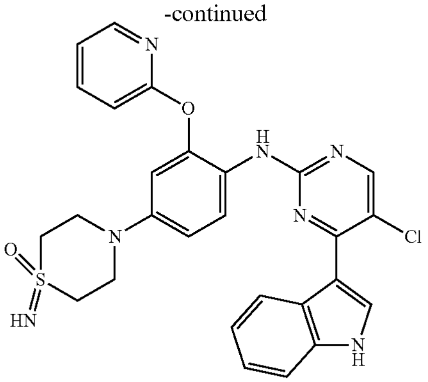
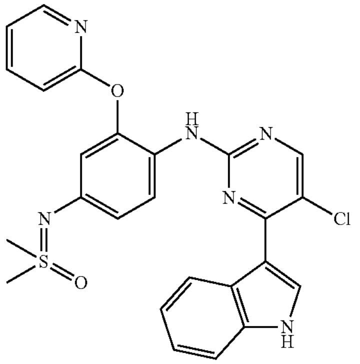
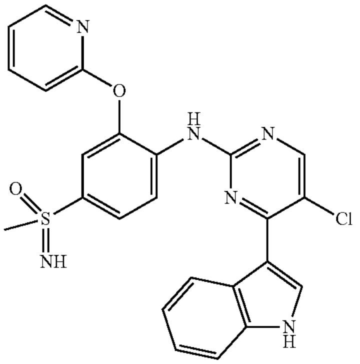
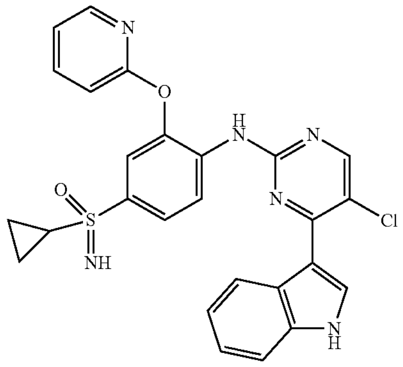
-continued
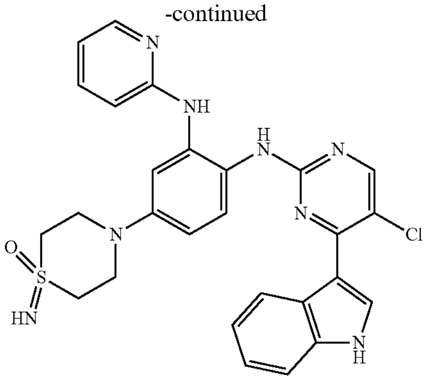
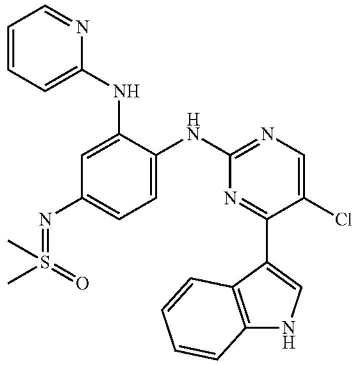
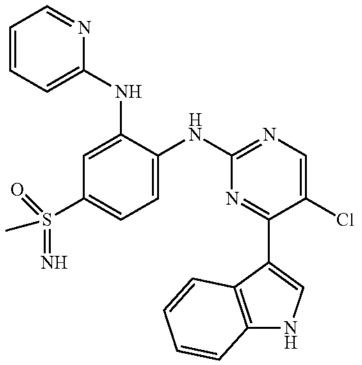
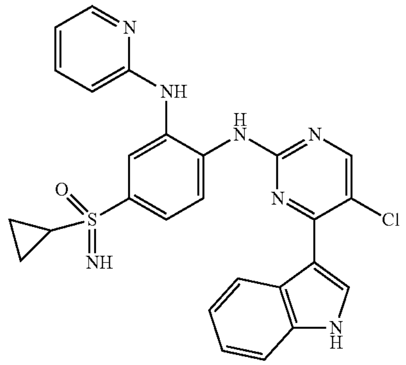

-continued
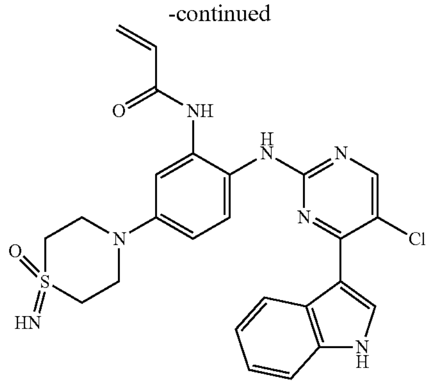
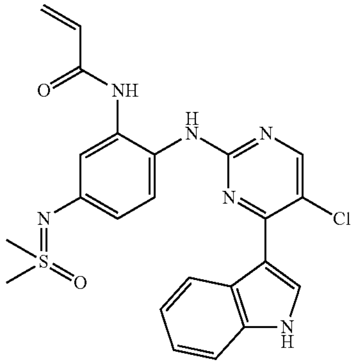
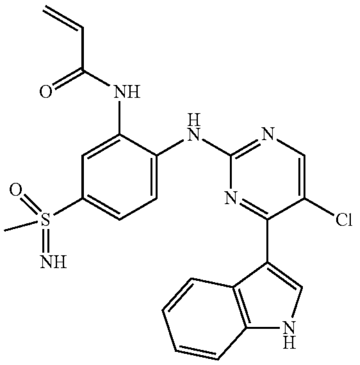
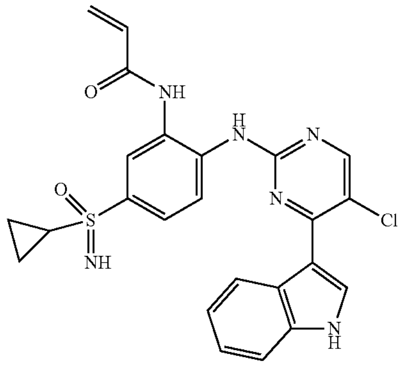
-continued
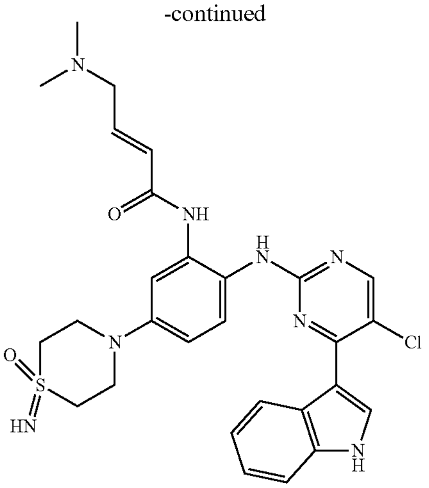
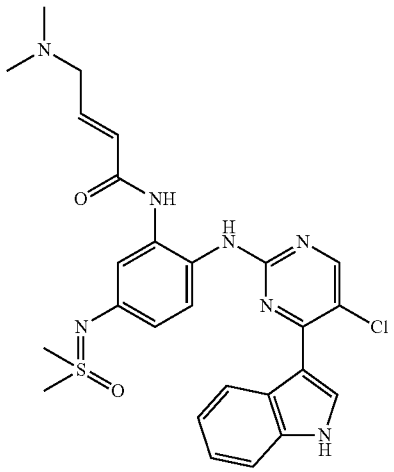
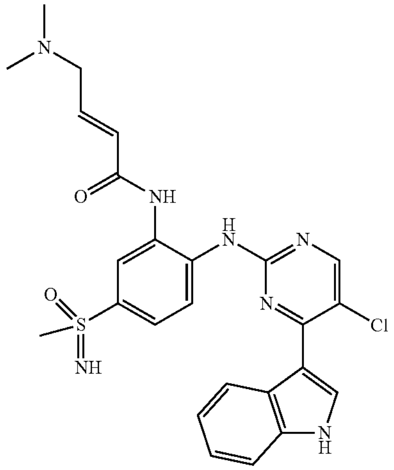

-continued
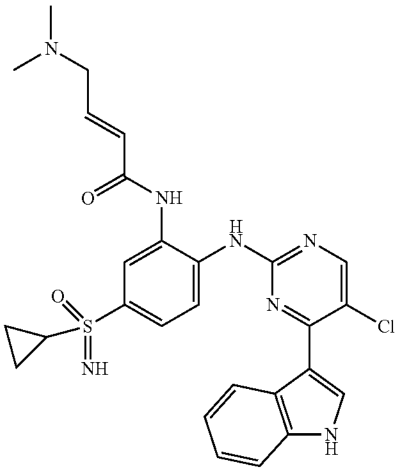
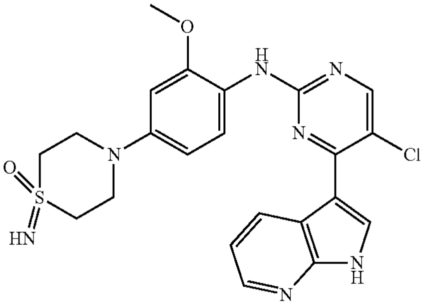
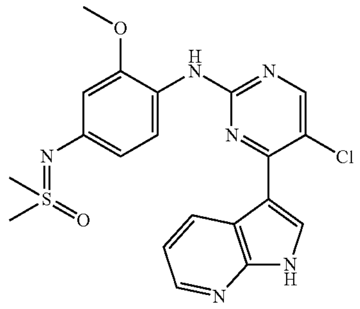
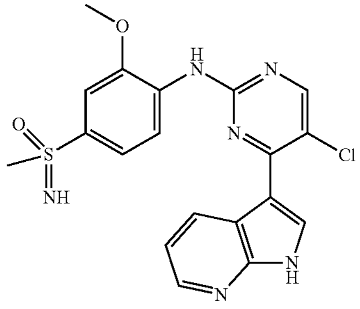
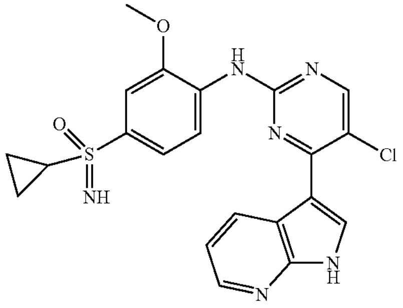
-continued
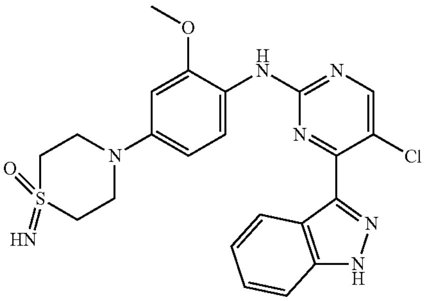
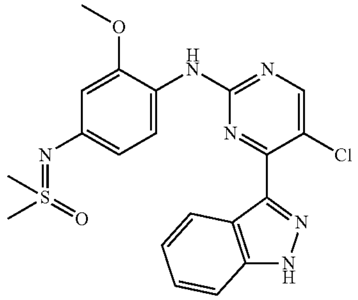
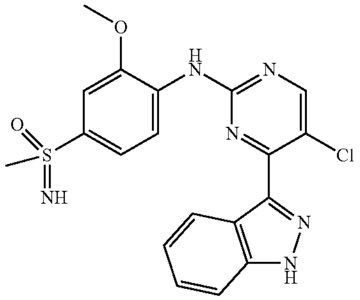
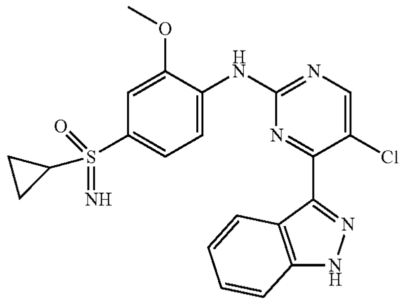
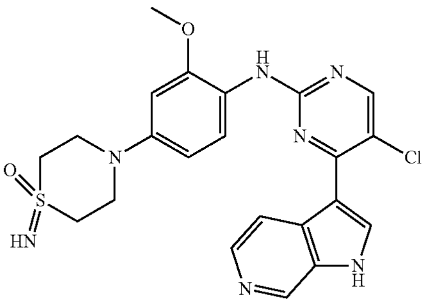

-continued
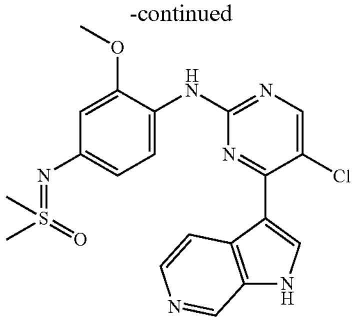
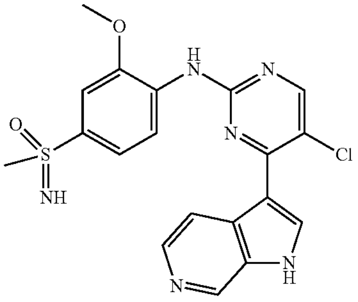
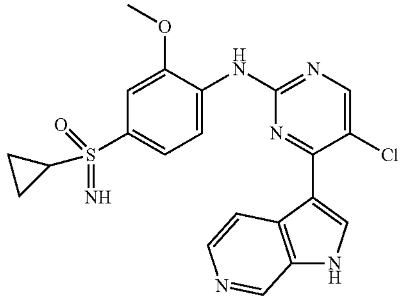
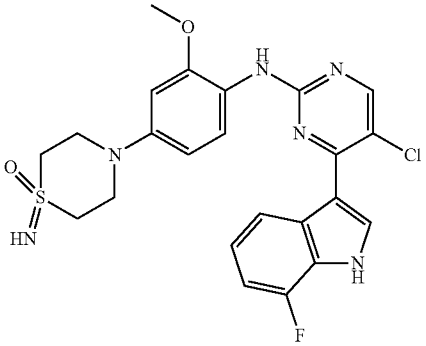
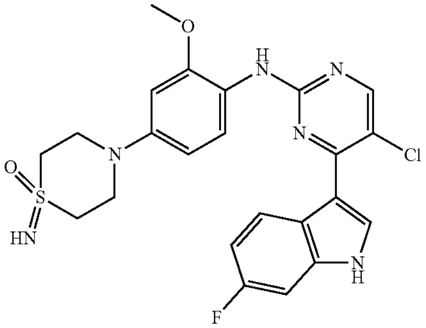
-continued
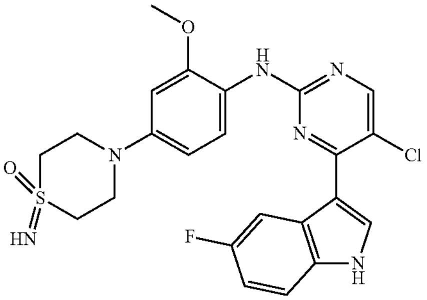
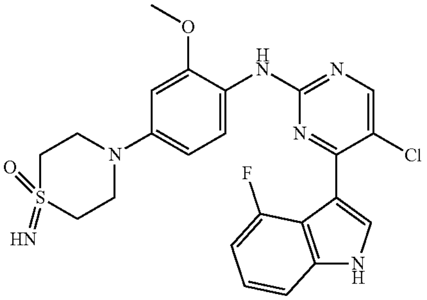
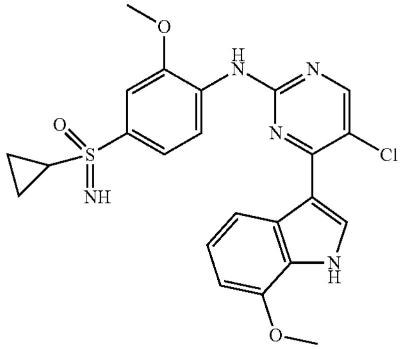
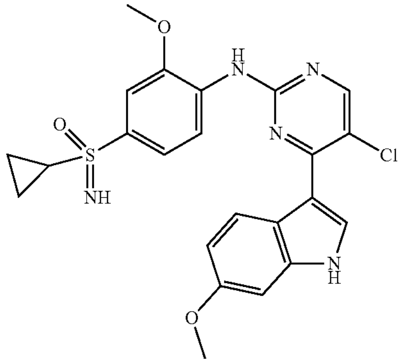
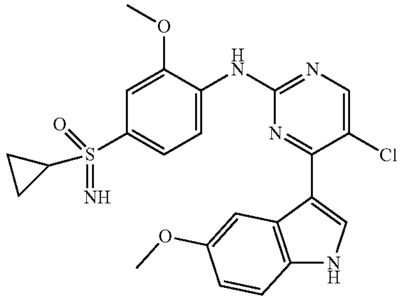

-continued
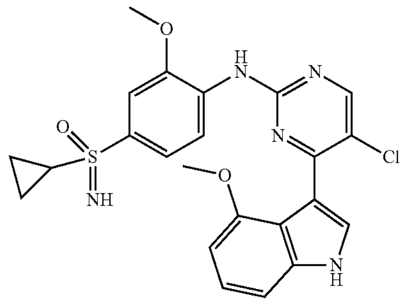
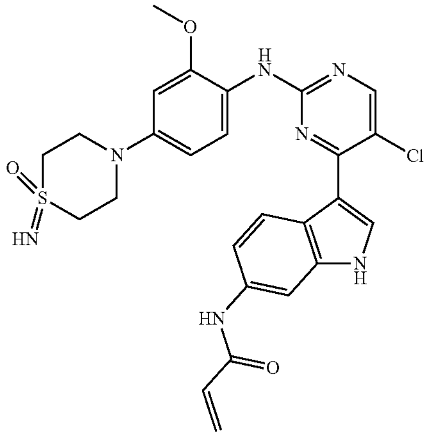
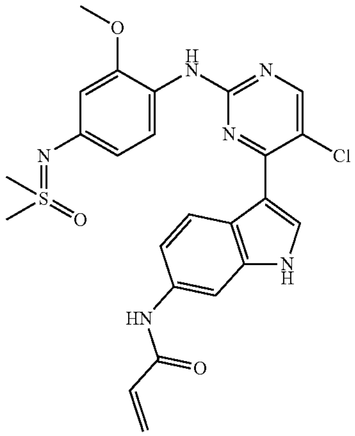
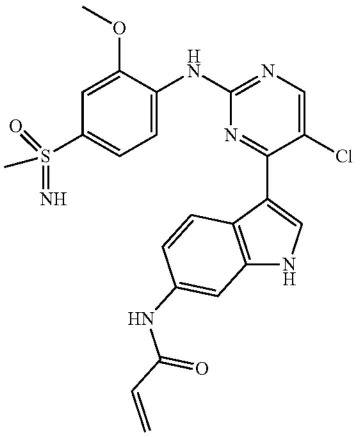
-continued
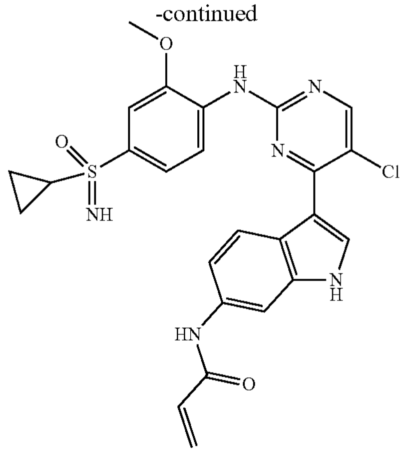
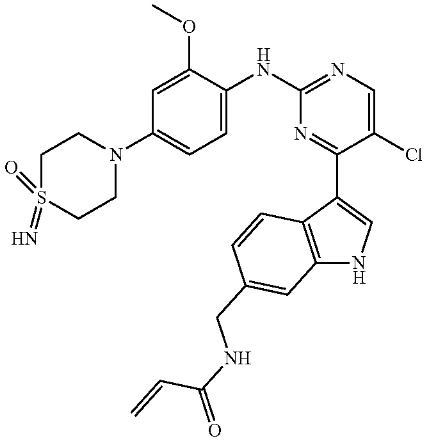
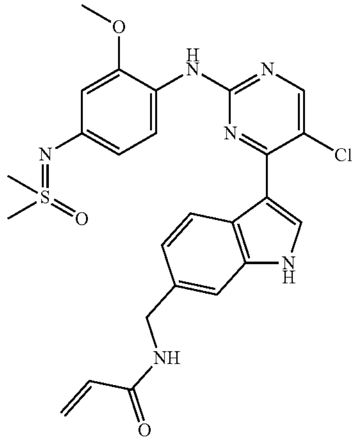

-continued
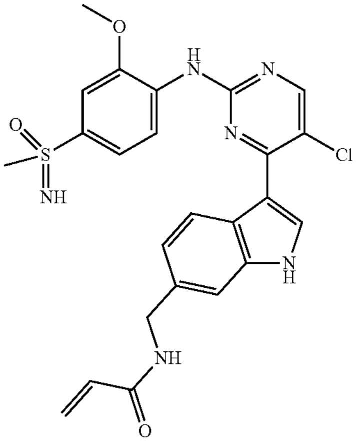
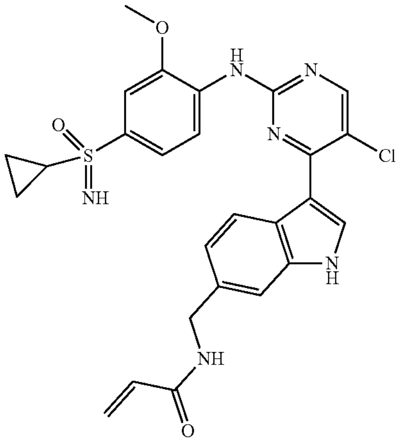
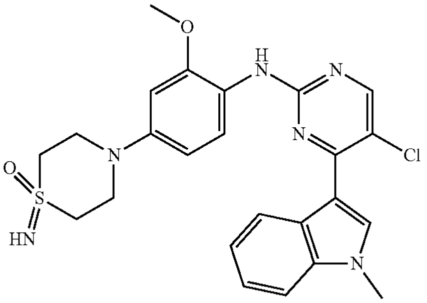
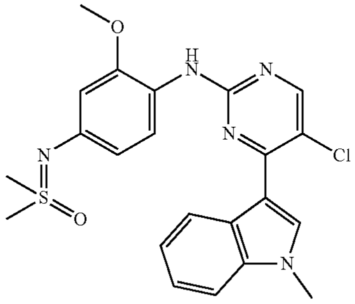
-continued
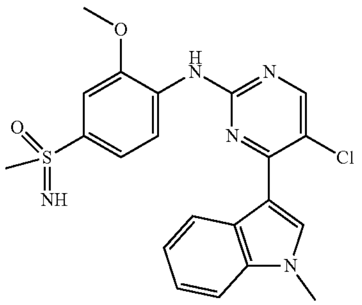
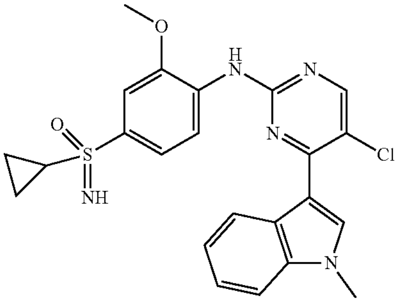
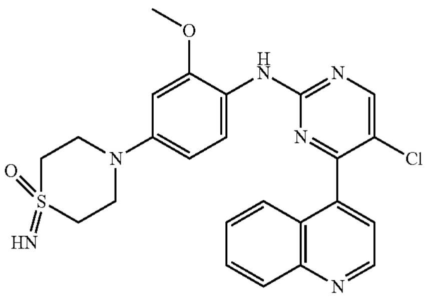
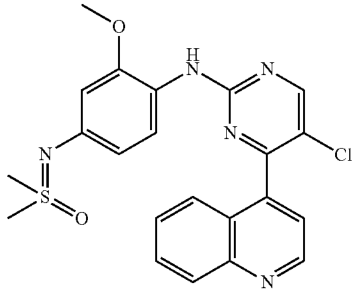
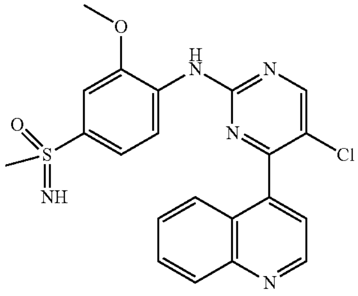

-continued
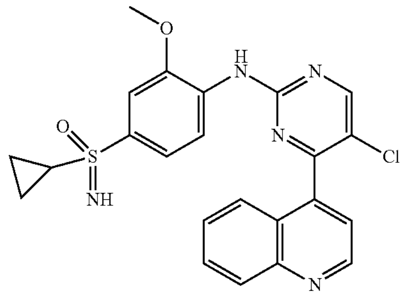
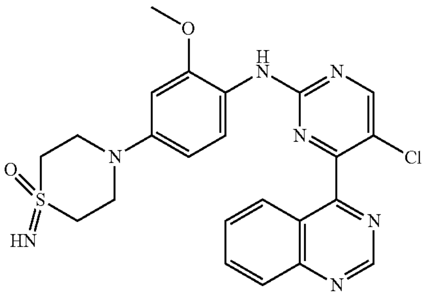
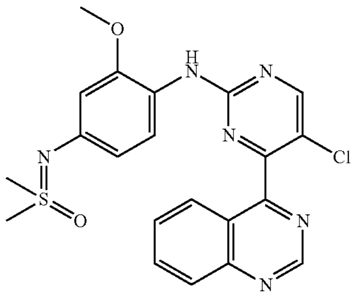
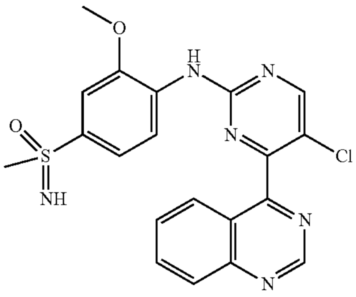
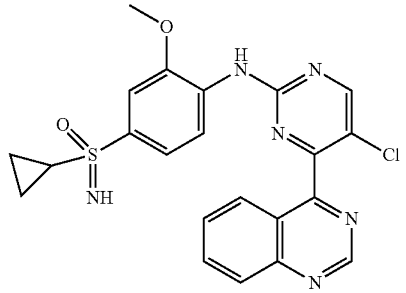
-continued
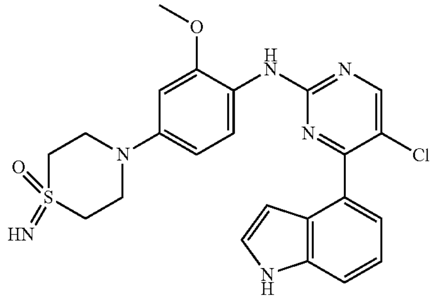
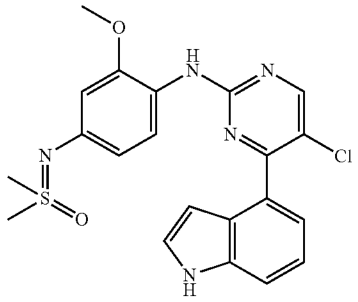
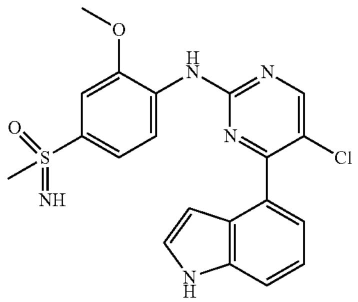
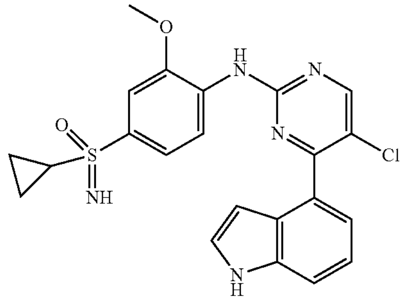
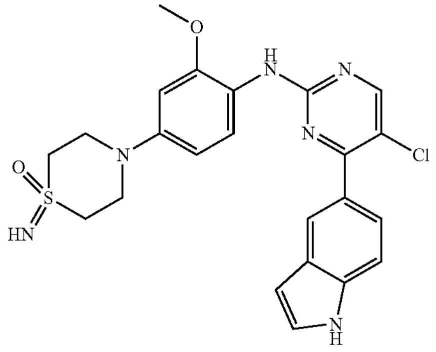

-continued
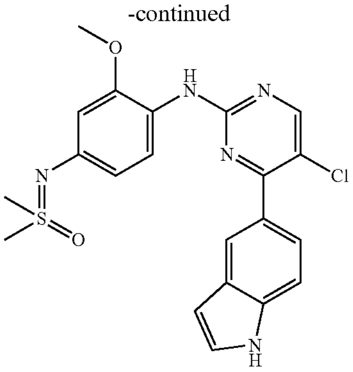
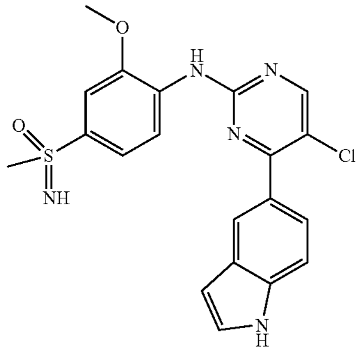
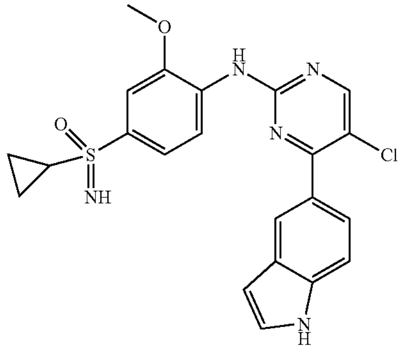
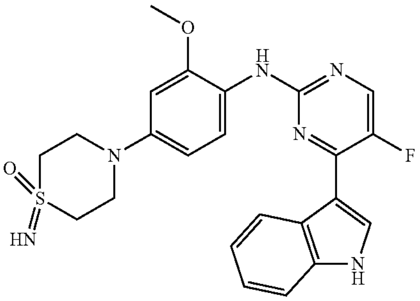
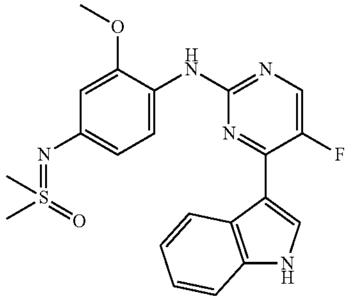
-continued
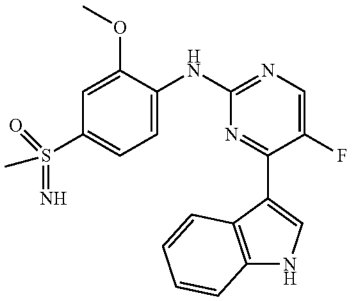
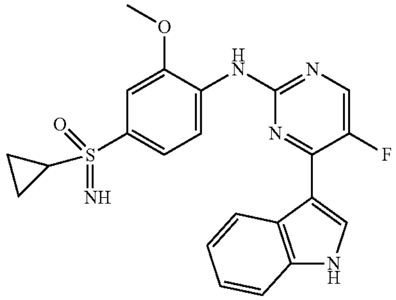
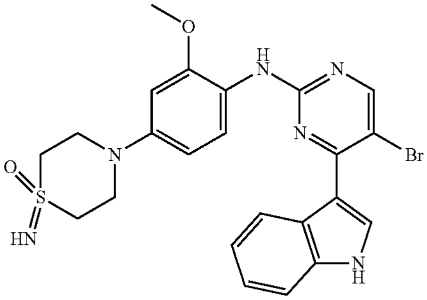
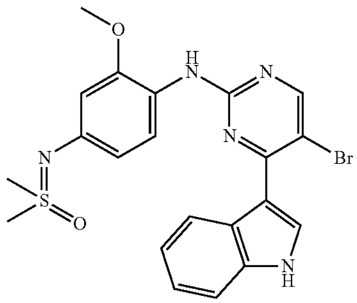
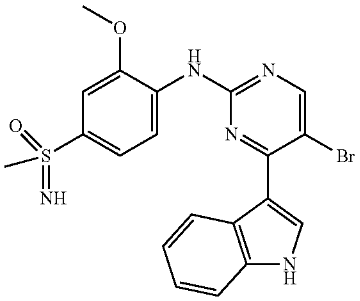

-continued
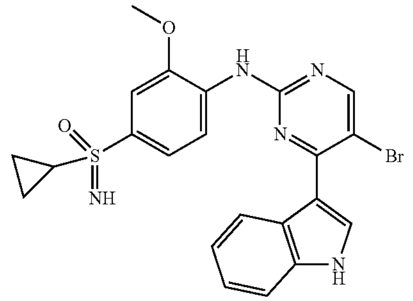
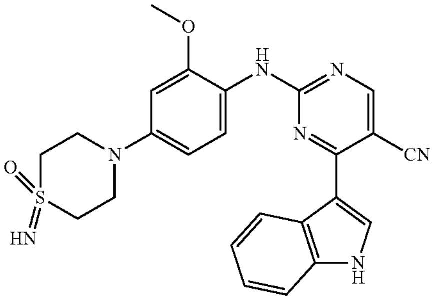
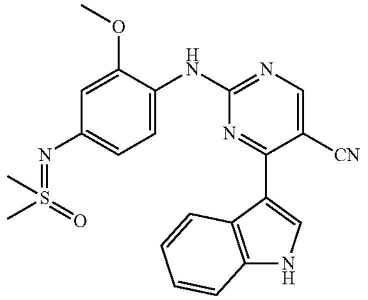
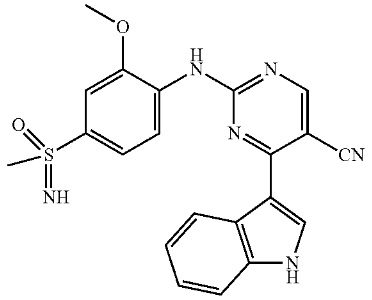
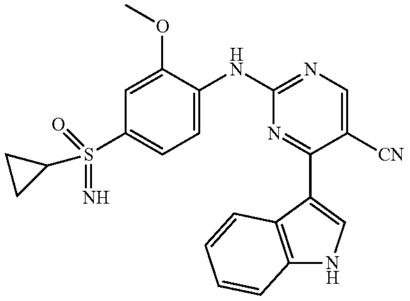
-continued
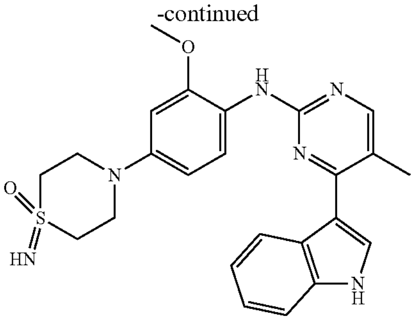
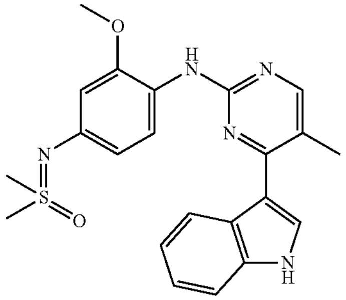
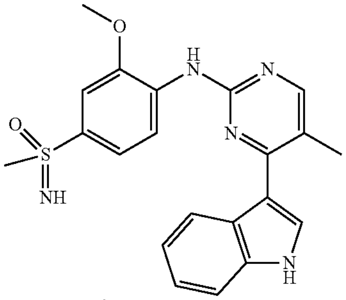
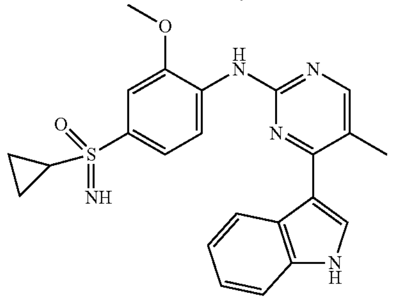
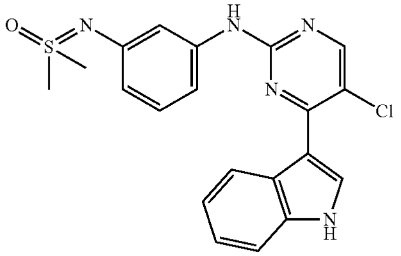
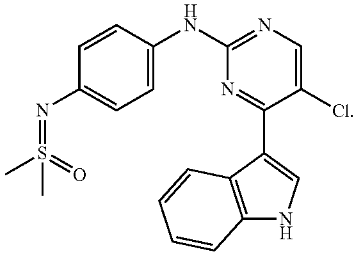

Aspect 4. A method of treating a cancer, the method comprising:

in response to a determination of the presence of a FGFR mutant polypeptide or a FGFR mutant polynucleotide in a sample from a subject, administering to the subject an effective amount the compound of any one of Aspects 1 to 3 thereby treating the cancer in the subject.

Aspect 5. A formulation comprising or consisting essentially of the compounds of any one of Aspects 1 to 3.

What is claimed is:

1. A compound of the formula IA, IB, II, or IIA, or a pharmaceutically acceptable salt thereof:

(IA)

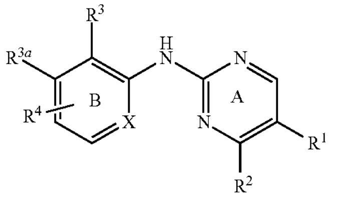

(IB)

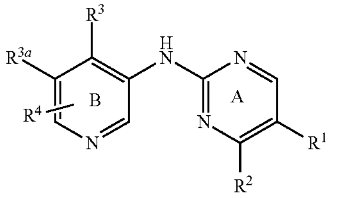

(II)

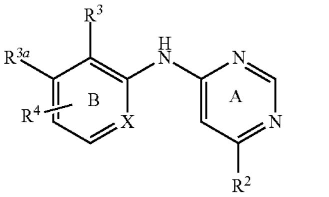

(IIA)

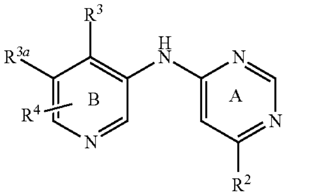

wherein $R^1$ is H, F, Cl, Br, $C_{1-6}$alkyl, CN, $C_{1-6}$haloalkyl, —C(O)$NH_2$, —C(O)$NHC_{1-6}$alkyl, or —C(O)N($C_{1-6}$alkyl)$_2$;

$R^2$ is a heteroaryl comprising 5-10 atoms optionally substituted with 1, 2, 3, or 4 independently selected $R^5$;

X is selected from —CH— and N;

$R^3$ is H, F, Cl, Br, $OC_{1-6}$alkyl, $C_{1-6}$alkyl, $C_{3-6}$cycloalkyl, $C_{1-6}$haloalkyl, $OC_{1-6}$haloalkyl, $NO_2$, $NH_2$, —NHCO—($C_1$-$C_6$-alkyl), $C_{1-6}$alk-NHC(O)$CR^{10}$═$CHR^{10}$, NHC(O)$CR^{10}$═$CHR^{10}$, —NHCOCH═$CHCH_2N(Me)_2$, $NHSO_2CR^{10}$═$CHR^{10}$, or O($C_{1-6}$alk) heterocycloalkyl;

$R^{3a}$ is H, F, Cl, $OC_{1-6}$alkyl, $C_{1-6}$alkyl, $C_{3-6}$cycloalkyl, $C_{1-6}$haloalkyl, $OC_{1-6}$haloalkyl, $NO_2$, $NH_2$, —NHCO—($C_1$-$C_6$-alkyl), $C_{1-6}$alk-NHC(O)$CR^{10}$═$CHR^{10}$, NHC(O)$CR^{10}$═$CHR^{10}$, —NHCOCH═$CHCH_2N(Me)_2$, $NHSO_2CR^{10}$═$CHR^{10}$, or O($C_{1-6}$alk) heterocycloalkyl;

$R^5$ is F, Cl, Br, $C_{1-6}$alkyl, $C_{3-6}$cycloalkyl, $OC_{1-6}$alkyl, C(O)$C_{1-6}$alkyl, hydroxy$C_{1-6}$alkyl, $NH_2$, $C_{1-6}$alk-NHC(O)$CR^{10}$═$CHR^{10}$, NHC(O)$CR^{10}$═$CHR^{10}$, NHC(O)CH═CH—$C_{1-6}$alk-$NH_2$, NHC(O)CH═CH—$C_{1-6}$alk-$NHC_{1-6}$alkyl, NHC(O)CH═CH—$C_{1-6}$alk-N($C_{1-6}$alkyl)$_2$, $NHSO_2CR^{10}$═$CHR^{10}$, NHC(O)$C_{1-6}$alkyl, or NHC(O)$C_{3-6}$cycloalkyl;

each $R^{10}$ is independently H, F, Cl, $C_{1-6}$alkyl, $C_{1-6}$haloalkyl, $C_{1-6}$alkoxy, or $C_{1-6}$hydroxyalkyl;

$R^4$ is selected from the group consisting of:

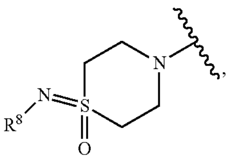,
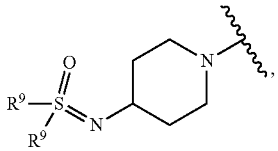,
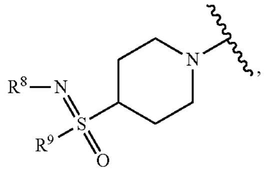,
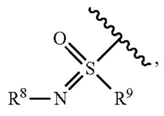,
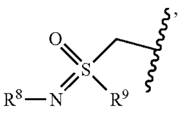,
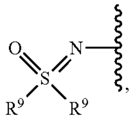, and
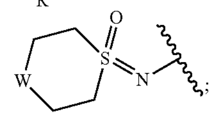;

W is selected from the group consisting of —$CH_2$—, C(O)—, —CH(OH)— and —N($R^8$)—;

$R^8$ is selected from the group consisting of —H, optionally substituted $C_1$-$C_6$-alkyl, optionally substituted $C_1$-$C_6$-alkenyl, and —$C_3$-$C_6$-cycloalkyl;

each instance of $R^9$ is independently selected from the group consisting of optionally substituted $C_1$-$C_6$-alkyl, optionally substituted $C_1$-$C_6$-alkenyl, and $C_3$-$C_6$-cycloalkyl; and each optionally substituted alkyl or optionally substituted alkenyl, when substituted, is substituted with one or more independently selected hydroxy, halogen, $C_1$-$C_3$-alkoxy, $C_1$-$C_3$-alkylthio, —CN, $C_3$-$C_6$-cycloalkyl, $C_1$-$C_3$-hydroxyalkyl, $C_2$-$C_6$ alkenyl, $C_2$-$C_6$-alkynyl, —$CF_3$, —$OCF_3$, $NH_2$, $NHC_{1-6}$alkyl, N($C_{1-6}$alkyl)$_2$.

2. The compound of claim 1 that is a compound of formula IA.

3. The compound of claim 1 that is a compound of formula IB.

4. The compound of claim 1 that is a compound of formula II.

5. The compound of claim 1 that is a compound of formula IIA.

6. The compound of claim 1 wherein X is CH.

7. The compound of claim 1, wherein X is N.

8. The compound of claim 1, wherein $R^3$ is H and $R^{3a}$ is F, Cl, $OC_{1-6}$alkyl, $C_{1-6}$alkyl, $C_{3-6}$cycloalkyl, $C_{1-6}$haloalkyl, $OC_{1-6}$haloalkyl, $NO_2$, $NH_2$, —NHCO—($C_1$-$C_6$-alkyl), $C_{1-6}$alk-NHC(O)$CR^{10}$=$CHR^{10}$, NHC(O)$CR^{10}$=$CHR^{10}$, —NHCOCH=$CHCH_2N(Me)_2$, $NHSO_2CR^{10}$=$CHR^{10}$, or O($C_{1-6}$alk)heterocycloalkyl.

9. The compound of claim 1, wherein $R^{3a}$ is H and $R^3$ is F, Cl, $OC_{1-6}$alkyl, $C_{1-6}$alkyl, $C_{3-6}$cycloalkyl, $C_{1-6}$haloalkyl, $OC_{1-6}$haloalkyl, $NO_2$, $NH_2$, —NHCO—($C_1$-$C_6$-alkyl), $C_{1-6}$alk-NHC(O)$CR^{10}$=$CHR^{10}$, NHC(O)$CR^{10}$=$CHR^{10}$, —NHCOCH=$CHCH_2N(Me)_2$, $NHSO_2CR^{10}$=$CHR^{10}$, or O($C_{1-6}$alk)heterocycloalkyl.

10. The compound of claim 1, wherein $R^3$ is H and $R^{3a}$ is H.

11. The compound of claim 1, wherein $R^4$ is

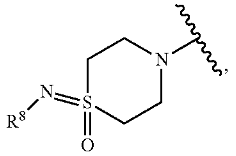

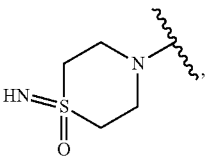

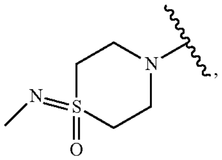

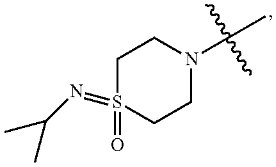

or

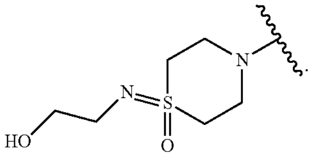

12. The compound of claim 1, wherein $R^4$ is

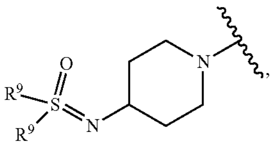

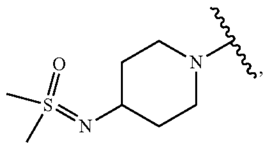

or

-continued

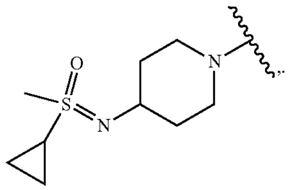

13. The compound of claim 1, wherein $R^4$ is

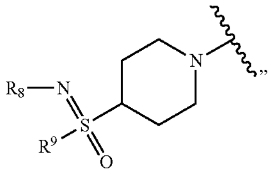

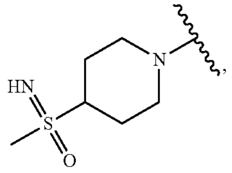

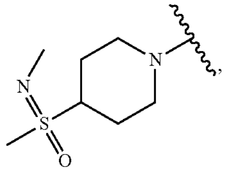

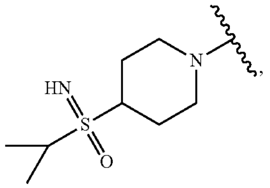

or

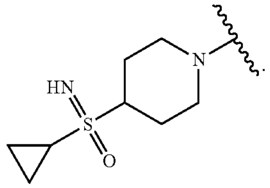

14. The compound of claim 1, wherein $R^4$ is

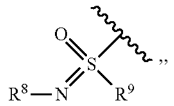

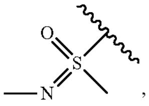

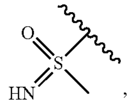

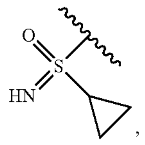

or

-continued

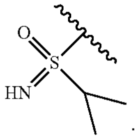

.

15. The compound of claim 1, wherein $R^4$ is

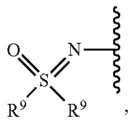

,

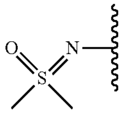

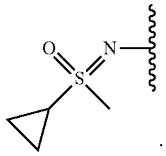

.

16. The compound of claim 1, wherein $R^4$ is

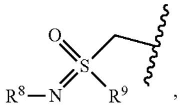

,

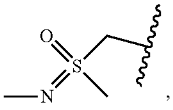

,

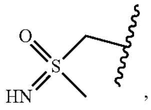

,

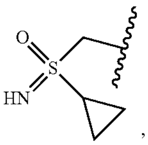

, or

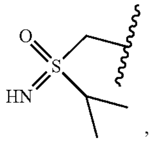

,

17. The compound of claim 1, wherein $R^4$ is

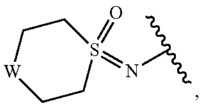

,

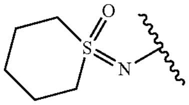

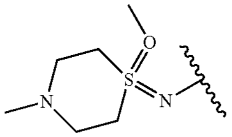

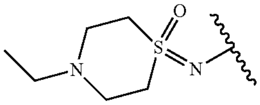

or

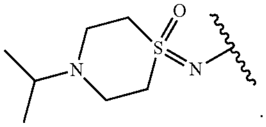

.

18. A pharmaceutically acceptable salt of a compound of claim 1.

19. A pharmaceutical composition comprising a compound of claim 1 and a pharmaceutically acceptable excipient.

20. A method of treating cancer in a subject comprising administering to the subject a therapeutically effective amount of a compound of claim 1, or a pharmaceutically acceptable salt thereof.

21. The method of claim 20, wherein the cancer is urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, or a sarcoma.

22. The method of claim 20, wherein the subject has an intrahepatic cholangiocarcinoma.

23. The method of claim 20, wherein the cancer is an FGFR-mutant cancer.

* * * * *